(12) United States Patent
Wang et al.

(10) Patent No.: US 10,280,163 B2
(45) Date of Patent: May 7, 2019

(54) 5 OR 8-SUBSTITUTED IMIDAZO[1, 5-A] PYRIDINES AS INDOLEAMINE AND/OR TRYPTOPHANE 2, 3-DIOXYGENASES

(71) Applicant: BeiGene, Ltd., Camana Bay, Grand Cayman (KY)

(72) Inventors: Hexiang Wang, Beijing (CN); Guoliang Zhang, Beijing (CN); Yunhang Guo, Beijing (CN); Bo Ren, Beijing (CN); Zhiwei Wang, Beijing (CN); Changyou Zhou, Princeton, NJ (US)

(73) Assignee: BEIGENE, LTD., Grand Cayman (KY)

( * ) Notice: Subject to any disclaimer, the term of this patent is extended or adjusted under 35 U.S.C. 154(b) by 0 days.

(21) Appl. No.: 15/564,666

(22) PCT Filed: Apr. 8, 2016

(86) PCT No.: PCT/CN2016/078787
§ 371 (c)(1),
(2) Date: Oct. 5, 2017

(87) PCT Pub. No.: WO2016/161960
PCT Pub. Date: Oct. 13, 2016

(65) Prior Publication Data
US 2018/0072716 A1 Mar. 15, 2018

(30) Foreign Application Priority Data
Apr. 10, 2015 (WO) ............... PCT/CN2015/076296

(51) Int. Cl.
| C07D 401/02 | (2006.01) |
| C07D 401/10 | (2006.01) |
| A61K 31/437 | (2006.01) |
| A61K 31/4353 | (2006.01) |
| C07D 471/04 | (2006.01) |

(52) U.S. Cl.
CPC .................. C07D 471/04 (2013.01)

(58) Field of Classification Search
CPC .. C07D 401/02; C07D 401/10; A61K 31/437; A61K 31/4353
USPC ......................................... 514/300; 546/121
See application file for complete search history.

(56) References Cited

FOREIGN PATENT DOCUMENTS

| CN | 102532144 A | 7/2012 |
| CN | 103547579 A | 1/2014 |
| JP | 09071586 | * 9/1997 |
| WO | WO 2008/110523 | 9/2008 |
| WO | WO 2014/159248 | 10/2014 |
| WO | WO 2016/161960 | 10/2016 |

OTHER PUBLICATIONS

Blatcher et al., Tetrahedron Letters (1980), 21(22), 2195-6.*
International Search Report and Written Opinion for International Application No. PCT/CN2016/078787, dated Jun. 30, 2016, 12 pages.
Blatcher, P. et al., "A direct method for the substitution of imidazo[1,5-a]pyridines at position 5," Tetrahedron Letters, 1980, vol. 21, Issue 22, pp. 2195-2196.
Tojo, S. et al., "Crystal structures and structure activity relationships of imidazothiazole derivatives as IDO1 inhibitors," ACS Medicinal Chemistry Letters, 2014, vol. 5, Issue 10, pp. 1119-1123.

* cited by examiner

Primary Examiner — Niloofar Rahmani
(74) Attorney, Agent, or Firm — Cooley LLP

(57) ABSTRACT

Disclosed herein are 5 or 8-substituted imidazo[1,5-a]pyridines and pharmaceutical compositions comprising at least one such 5 or 8-substituted imidazo[1,5-a]pyridines, processes for the preparation thereof, and the use thereof in therapy. Disclosed herein are certain 5 or 8-substituted imidazo[1,5-a]pyridines that can be useful for inhibiting indoleamine 2,3-dioxygenase and/or tryptophane 2,3-dioxygenase and for treating diseases or disorders mediated thereby.

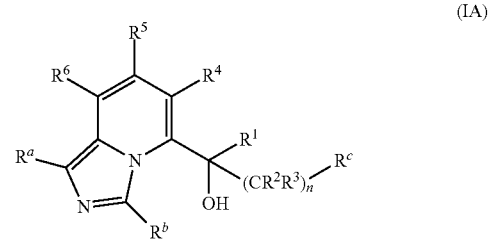

(IA)

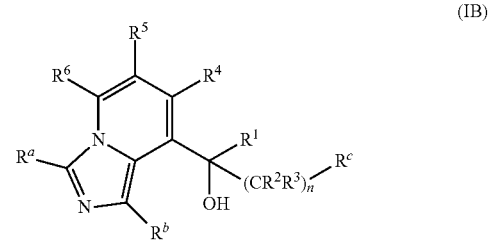

(IB)

30 Claims, 1 Drawing Sheet

5 OR 8-SUBSTITUTED IMIDAZO[1, 5-A] PYRIDINES AS INDOLEAMINE AND/OR TRYPTOPHANE 2, 3-DIOXYGENASES

CROSS-REFERENCE TO RELATED APPLICATION

This application is a U.S. National Stage Application under 35 U.S.C. § 371 of International Application No. PCT/CN2016/078787, filed on Apr. 8, 2016, and entitled "NOVEL 5 OR 8-SUBSTITUTED IMIDAZO[1,5-a]PYRIDINES AS INDOLEAMINE AND/OR TRYPTOPHANE 2,3-DIOXYGENASES", which claims the benefit of International Application No. PCT/CN2015/076296, filed Apr. 10, 2015.

FIELD OF THE INVENTION

Disclosed herein are 5 or 8-substituted imidazo[1,5-a] pyridines and pharmaceutical compositions comprising at least one such 5 or 8-substituted imidazo[1,5-a]pyridines, processes for the preparation thereof, and the use thereof in therapy. In particular, disclosed herein are certain 5 or 8-substituted imidazo[1,5-a]pyridines that can be useful for inhibiting indoleamine 2,3-dioxygenase and/or tryptophane 2,3-dioxygenase and for treating diseases or disorders mediated thereby.

BACKGROUND OF THE INVENTION

Indoleamine 2,3-dioxygenase 1 (IDO1, EC 1.13.11.42, also known as indoleamine 2,3-dioxygenase) is the first and rate-limiting enzyme in the tryptophan-kynurenine pathway that degrades the essential amino acid L-tryptophan (L-Trp) to N-formal-kynurenine, which can be subsequently metabolized through a series of steps to form NAD. IDO1 enzyme is expressed in the placenta, the mucosal and lymphoid tissues, and in inflammatory lesions (Yamazaki F, et. al., *Biochem J.* 1985; 230:635-8; Blaschitz A, et. al., *PLoS ONE*. 2011; 6:e21774). In the latter two, it is expressed primarily by antigen-presenting cells (APC), mainly dendritic cells (DC) and macrophages, and in cells exposed to interferon-gamma (IFNγ) and other pro-inflammatory stimuli. In human cells, the depletion of L-Trp resulting from IDO1 activity as well as the production of a series of immunoregulatory metabolites, collectively known as "kynurenines", can suppress the proliferation and differentiation of effector T cells [Frumento G, et. al., (2002), *Journal of Experimental Medicine* 196: 459-468], and markedly enhance the suppressor activity of regulatory T cells [Sharma M D, et al. (2009), *Blood* 113: 6102-6111]. As a result, IDO1 controls and fine-tunes both innate and adaptive immune responses [Grohmann U, et al. (2002), *Nature Immunology* 3: 1097-1101] under a variety of conditions, including pregnancy [Munn D H, et al. (1998), *Science* 281: 1191-1193], transplantation [Palafox D, et al. (2010), *Transplantation Reviews* 24: 160-165], infection [Boasso A, et al. (2009), *Amino Acids* 37: 89-89], chronic inflammation [Romani L, et al. (2008), *Nature* 451: 211-U212], autoimmunity [Platten M, et al. (2005), Science 310: 850-855], neoplasia, and depression [Maes M, et. al., Life Sci. 2002 6; 71(16): 1837-48; Myint A M, et. al., (2012), Journal of Neural Transmission 119: 245-251].

Several lines of evidence suggest that IDO is involved in induction of immune tolerance. The immunosuppressive effect of IDO1 was demonstrated first in a mouse model of fetal protection against maternal immune rejection. Treatment of pregnant mice with a tryptophan analog that inhibits IDO1, which is constitutively expressed in the placenta, resulted in T cell-mediated rejection of allogeneic embryos [Munn D H, et al. (1998), *Science* 281: 1191-1193]. Subsequent studies developed this concept as a mechanism to defeat immune surveillance in cancer (reviewed in [Prendergast GC (2008), Oncogene 27(28):3889-3900; Munn D H, et. al., (2007), J Clin Invest 117(5):1147-1154]). Indoleamine 2,3-dioxygenase is widely overexpressed in tumor cells where it is has been associated predominantly with poor prognosis [Uyttenhove C, et. al., (2003), Nat Med 9(10):1269-1274; Liu X, et. al., (2009), Curr Cancer Drug Targets 9(8):938-95]. Expression of IDO by immunogenic mouse tumor cells prevents their rejection by preimmunized mice [Uyttenhove C. et. al., Nat Med. 2003 October; 9(10): 1269-74. Epub 2003 Sep. 21]. IDO activity is shown to suppress T cells [Fallarino F, et. al., (2002), Cell Death Differ 9:1069-1077; Frumento G, et. al., (2002), J Exp Med 196(4):459-468; Terness P, et. al., (2002), J Exp Med 196(4):447-457] and NK cells [Della Chiesa M, et. al., (2006), Blood 108(13):4118-4125], and also that IDO was critical to support the formation and activity of Tregs [Fallarino F, et. al., (2003), Nat Immunol 4(12):1206-1212] and myeloid-derived suppressor cells (MDSCs) [Smith C, et. al., (2012), Cancer Discovery 2(8):722-735]. It has been suggested that the efficacy of therapeutic vaccination of cancer patients might be improved by concomitant administration of an IDO inhibitor [Uyttenhove C. et. al., Nat Med. 2003 October; 9(10):1269-74. Epub 2003 Sep. 21]. It has been shown that the IDO inhibitor, 1-MT, can synergize with chemotherapeutic agents to reduce tumor growth in mice, suggesting that IDO inhibition may also enhance the antitumor activity of conventional cytotoxic therapies [Muller A J, et. al., Nat Med. 2005 March; 11(3):312-9]. It has been shown that IDO inhibitors can synergize with anti-CTLA-4 antibody or anti-PDL-1 antibody in inhibiting tumor growth in mouse models [Holmgaard R B, et. al., J Exp Med. 2013 Jul. 1; 210(7):1389-402; Spranger S, et. al., J Immunother Cancer. 2014, 2:3].

It has been proposed that IDO is induced chronically by HIV infection, and is further increased by opportunistic infections, and that the chronic loss of Trp initiates mechanisms responsible for cachexia, dementia and diarrhea and possibly immunosuppression of AIDS patients [Brown, et al., 1991, Adv. Exp. Med. Biol., 294: 425-35]. To this end, it has recently been shown that IDO inhibition can enhance the levels of virus-specific T cells and, concomitantly, reduce the number of virally infected macrophages in a mouse model of HIV [Portula et al., 2005, Blood, 106:2382-90]. Simian Immunodeficiency Virus (SIV) is very similar to Human Immunodeficiency Virus (HIV) and it is used to study the condition in animal models. In both HIV and SIV, the level of virus in the blood, or 'viral load', is important because when the viral load is high, the disease progresses and it depletes the patient's immune system. This eventually leads to the onset of Acquired Immune Deficiency Syndrome (AIDS), where the patient cannot fight infections which would be innocuous in healthy individuals. It has also been reported that monkeys with the simian form of HIV treated with an IDO inhibitor, called D-1 mT alongside Anti-Retroviral Therapy (ART), reduced their virus levels in the blood to undetectable levels, therefore when combined with ARTs, IDO inhibitors may help HIV patients not responding to treatment in the future [Adriano Boasso, et. al., J. Immunol., April 2009; 182: 4313-4320].

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis) and depression, therapeutic agents aimed at suppression of tryptophan degradation by inhibiting IDO activity are of interests. Inhibitors of IDO can be used as effective cancer therapy as they could reverse the immunosuppressive effects of tumor microenvironment and activate anti-tumor activity of T cells. IDO inhibitors could also be useful in activation of immune responses in HIV infection. Inhibition of IDO may also be an important treatment strategy for patients with neurological or neuropsychiatric diseases or disorders such as depression. The compounds, compositions and methods herein help meet the current need for IDO modulators.

Tryptophan 2,3-dioxygenase (TDO, EC 1.13.11.11) catalyzes the same Trp degradation reaction as IDO1. TDO is primarily expressed in the liver in humans, where acts as the main regulator of systemic tryptophan levels. More recently, TDO was also found to be expressed in the brain, where it may regulate the production of neuroactive tryptophan metabolites such as kynurenic acid and quinolinic acid [Kanai M, et. al., Mol Brain 2009; 2:8]. Two recent studies [Opitz C A, et. al., Nature 2011; 478:197-203; Pilotte L, et. al., Proc Natl Acad Sci USA. 2012, 109(7):2497-502] point to the significance of TDO activity in certain cancers where it is expressed constitutively (particularly malignant glioma, hepatocellular carcinoma, melanoma, and bladder cancer). Functional studies in human tumors indicate that constitutive TDO enzymatic activity is sufficient to sustain biologically relevant tryptophan catabolism that is capable of suppressing antitumor immune responses [Opitz C A, et. al., Nature 2011; 478:197-203; Pilotte L, et. al., Proc Natl Acad Sci USA. 2012, 109(7):2497-502]. TDO expression by tumors is reported to prevent rejection by immunized mice. A specific TDO inhibitor is shown to restore the ability of mice to reject TDO-expressing tumors without causing significant toxicity [Pilotte L, et. al., Proc Natl Acad Sci USA. 2012, 109(7):2497-502]. Therefore, inhibitors of TDO can potentially be used as a single agent or in combination with other anti-cancer therapies to treat a variety of human cancers.

Small molecule inhibitors of IDO are being developed to treat or prevent IDO-related diseases such as those described above. Fox example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo(b)thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds have indoleamine-2,3-dioxygenase (IDO) inhibitory activity are further reported in WO 2004/094409; WO 2006/122150; WO 2009/073620; WO 2009/132238; WO 2011/056652; WO 2012/142237; WO 2013/107164; WO 2014/066834; WO 2014/081689; WO 2014/141110; WO 2014/150646; WO 2014/150677; WO 2015006520; WO 2015/067782; WO 2015/070007; WO 2015/082499; WO 2015/119944; WO 2015/121812; WO 2015/140717; WO 2015/173764; WO2015/188085; WO 2016/026772; US 2015328228 and US 2015266857. In particular, the compounds of WO 2012/142237 and WO 2014/159248 encompass a series of tricyclic imidazoisoindoles with potent IDO inhibitory activity.

Some substituted imidazo[1,5-a] pyridines are known in the literatures. For example, WO 2008110523 A1 (published on Sep. 18, 2008) has disclosed imidazo[1,5-a] pyridines as glutaminyl cyclase inhibitors; GB2174094A (published on Oct. 29, 1986) discloses imidazo [1,5-a] pyridine derivatives as thromboxane synthetase inhibitors; and JP1997071586A (published on Mar. 18, 1997) discloses imidazo[1,5-a] pyridines as inhibitors of the aldosterone biosynthetic enzyme cytochrome P450C18 for the treatment of primary or secondary aldosteronism, renal hypertension and so on.

However, no imidazo[1,5-a] pyridine has been reported as an IDO/TDO inhibitor. Disclosed herein are novel 5 or 8-substituted imidazo[1,5-a]pyridines exhibiting IDO, in particular IDO1, TDO, or IDO/TDO dual inhibitory activity. The inventors of the present application have unexpectedly found that substitution of hydroxyl group on the chiral α-carbon atom attached to position 5 or 8 of the imidazo [1,5-a]pyridine structure and/or ortho or meta substitution in relation to the hydroxyl-substituted chiral α-carbon atom on the pyridine moiety of the imidazo[1,5-a]pyridine structure impart unexpected enzymatic and cellular activity to the novel 5 or 8-substituted imidazo[1,5-a]pyridines disclosed herein.

SUMMARY OF THE INVENTION

Provided is a compound selected from 5 or 8-substituted imidazo[1,5-a]pyridines of Formulas (IA) and/or (IB)

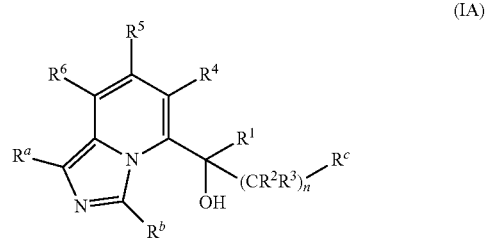

(IA)

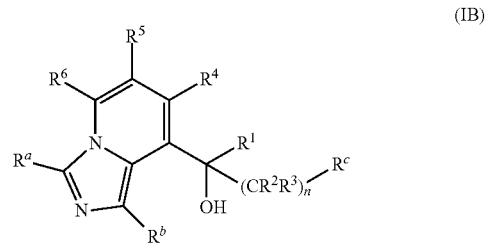

(IB)

or a stereoisomer thereof, or a pharmaceutically acceptable salt thereof,
wherein:
n=0, 1, 2, 3, or 4;
$R^a$ and $R^b$ are each independently selected from hydrogen, halogen, $C_{1-8}$ alkyl, $C_{1-8}$ haloalkyl, $C_{2-8}$ alkenyl, $C_{2-8}$ alkynyl, $C_{3-8}$ cycloalkyl, heterocyclyl, aryl, and heteroaryl;
$R^1$ is selected from hydrogen, halogen, $C_{1-8}$ alkyl and $C_{1-8}$ haloalkyl;
$R^2$ and $R^3$ are each independently selected from hydrogen, halogen, $OR^7$, $NR^7R^8$, $COR^7$, $SO_2R^7$, $C(=O)OR^7$, $C(=O)NR^7R^8$, $C_{1-8}$ alkyl, $C_{2-8}$ alkenyl, $C_{2-8}$ alkynyl, $C_{3-8}$ cycloalkyl, heterocyclyl, aryl, and heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^9$;
$R^4$, $R^5$ and $R^6$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, —CN, —OR$^7$, and —SR$^7$, wherein said C$_{1-8}$ alkyl, C$_{2-8}$ alkenyl, C$_{2-8}$ alkynyl, C$_{3-8}$ cycloalkyl, C$_{1-8}$ haloalkyl, aryl, heterocyclyl, and heteroaryl are each independently optionally substituted with at least one substituted R$^9$, provided that at least one of R$^4$ and R$^5$ is not hydrogen;

R$^C$ is selected from C$_{3-10}$ cycloalkyl, heterocyclyl or heteroaryl, each optionally substituted with at least one substituent R$^9$;

R$^7$ and R$^8$ are each independently selected from hydrogen, C$_{1-8}$ alkyl, C$_{1-8}$ haloalkyl, C$_{3-8}$ cycloalkyl, heterocyclyl, aryl, and heteroaryl optionally substituted with at least one substituent R$^9$; or R$^7$ and R$^8$ together with the nitrogen atom to which they are attached form a heterocyclyl or heteroaryl ring which optionally comprises a further hetero atom selected from nitrogen, oxygen and sulfur atom, and is optionally substituted with at least one substituent R$^9$;

R$^9$ is selected from hydrogen, halogen, C$_{1-4}$ haloalkyl, C$_{1-4}$ alkyl, C$_{2-8}$ alkenyl, C$_{3-6}$ cycloalkyl, aryl, heteroaryl, heterocyclyl, alkynyl, oxo, —C$_{1-4}$ alkyl-NR'R", —CN, —OR', —NR'R", —COR', —CO$_2$R', —CONR'R", —C(=NR')NR"R''', nitro, —NR'COR", —NR'CONR'R", —NR'CO$_2$R", —SO$_2$R', —SO$_2$aryl, —NR'SO$_2$NR"R''', NR'SO$_2$R", and —NR'SO$_2$aryl, wherein said C$_{1-4}$ alkyl, C$_{1-4}$ haloalkyl, C$_{3-6}$ cycloalkyl, aryl, heteroaryl, or heterocyclyl group are each independently optionally substituted by one, two or three substituents selected from halo, hydroxyl, C$_{1-4}$ alkyl and C$_{1-4}$ haloalkyl, wherein R', R", and R''' are each independently selected from H, C$_{1-4}$ haloalkyl, C$_{1-4}$ alkyl, C$_{2-4}$ alkenyl, C$_{2-4}$ alkynyl, C$_{3-6}$ cycloalkyl, heterocyclyl, aryl, and heteroaryl, each of which is optionally substituted by one or more halogen, C$_{1-4}$ haloalkyl and C$_{1-4}$ alkyl, or (R' and R"), and/or (R" and R''') together with the atoms to which they are attached, form a ring selected from heterocyclyl optionally substituted by halogen, C$_{1-4}$ haloalkyl and C$_{1-4}$ alkyl and heteroaryl rings optionally substituted by halogen, C$_{1-4}$ haloalkyl and C$_{1-4}$ alkyl.

Also provided is a pharmaceutical composition comprising at least one pharmaceutically acceptable carrier and a compound selected from compounds of Formulas (IA) and/or (IB), or a stereoisomer thereof, or a pharmaceutically acceptable salt thereof described herein.

Also provided is a method of treating cancer responsive to inhibition of IDO and/or TDO comprising administering to a subject in need of treating for such cancer an amount of a compound selected from compounds of Formulas (IA) and/or (IB), or a stereoisomer thereof, or a pharmaceutically acceptable salt thereof described herein effective to treat the cancer.

Also provided is a use of a compound selected from compounds of Formulas (IA) and/or (IB), or a stereoisomer thereof, or a pharmaceutically acceptable salt thereof described herein in manufacture of a medicament for treatment of the disorders or diseases above.

Also provided is a use of a compound selected from compounds of Formulas (IA) and/or (IB), or a stereoisomer thereof, or a pharmaceutically acceptable salt thereof described herein in manufacture of a medicament for inhibition of IDO and/or TDO.

Also provided is a use of a compound selected from compounds of Formulas (IA) and/or (IB), or a stereoisomer thereof, or a pharmaceutically acceptable salt thereof described herein in the manufacture of a medicament for treating cancer.

DETAILED DESCRIPTION OF THE INVENTION

Figure 1:
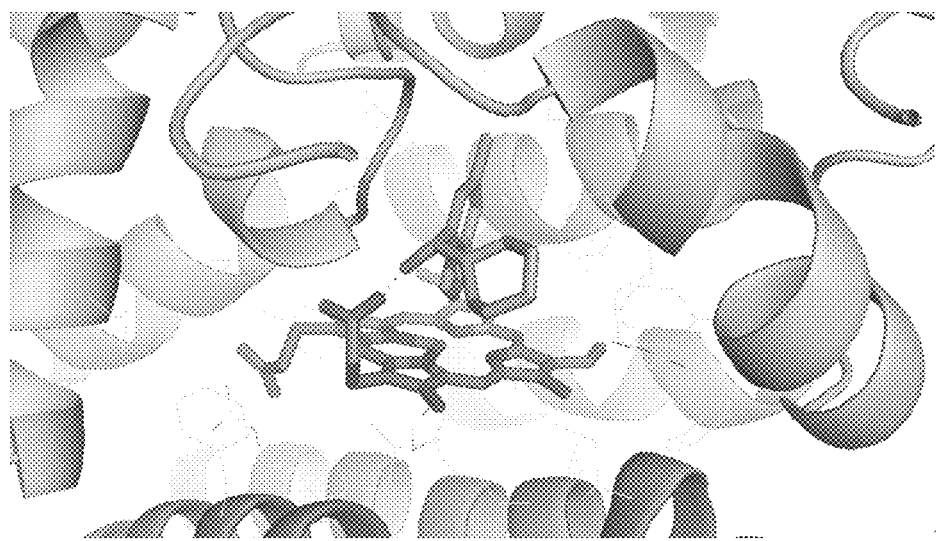
FIG. 1 shows A101a/IDO1 cocrystal structure (Resolution=50.00-2.90 Å).

As used herein, the following words, phrases and symbols are generally intended to have the meanings as set forth below, except to the extent that the context in which they are used indicates otherwise.

The following abbreviations and terms have the indicated meanings throughout:

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., C$_{1-6}$ alkyl) include, but not limited to methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$) and 3,3-dimethyl-2-butyl (—CH(CH$_3$)C(CH$_3$)$_3$) groups.

The term "alkyloxy" herein refers to an alkyl group as defined above bonded to oxygen, represented by -Oalkyl. Examples of an alkyloxy, e.g., C$_{1-6}$ alkyloxy or C$_{1-4}$ alkyloxy includes, but not limited to, methoxy, ethoxyl, isopropoxy, propxoy, n-butoxy, tert-butoxy, pentoxy and hexoxy and the like.

The term "haloalkyl" herein refers to an alkyl group in which one or more hydrogen is/are replaced by one or more halogen atoms such as fluoro, chloro, bromo, and iodo. Examples of the haloalkyl include C$_{1-6}$haloalkyl or C$_{1-4}$haloalkyl, but not limited to F$_3$C—, ClCH$_2$—, CF$_3$CH$_2$—, CF$_3$CCl$_2$—, and the like.

The term "alkenyl" herein refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., C$_{2-6}$ alkenyl, include, but not limited to ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., C$_{2-6}$ alkynyl, include, but not limited to ethynyl (—C≡CH), 1-propynyl (—C≡CCH$_3$), 2-propynyl (propargyl, —CH$_2$C≡CH), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, examples of the cycloalkyl group, e.g., $C_{3-8}$ cycloalkyl, include, but not limited to cyclopropyl, cyclobutyl, cyclopentyl, cyclohexyl, cycloheptyl, and cyclooctyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further examples of the bicyclic cycloalkyl groups include those arranged as a bicyclic ring selected from [5,6] and [6,6] ring systems, such as

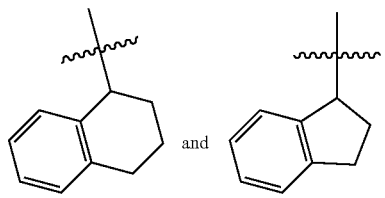 [SMILES: *C1CCCc2ccccc21 ; *C1CCc2ccccc21]

and and wherein the wavy lines indicate the points of attachment. The ring may be saturated or have at least one double bond (i.e., partially unsaturated), but is not fully conjugated, and is not aromatic, as aromatic is defined herein.

The term "Aryl" herein refers to a group selected from:

5- and 6-membered carbocyclic aromatic rings, for example, phenyl;

bicyclic ring systems such as 7 to 12 membered bicyclic ring systems wherein at least one ring is carbocyclic and aromatic, selected, for example, from naphthalene, and indane; and tricyclic ring systems such as 10 to 15 membered tricyclic ring systems wherein at least one ring is carbocyclic and aromatic, for example, fluorene.

For example, the aryl group is selected from 5 and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" herein refers to F, Cl, Br or I.

The term "heteroaryl" herein refers to a group selected from:

5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e., partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

Compounds described herein may contain an asymmetric center and may thus exist as enantiomers. Where the compounds described herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formulas (IA) and/or (IB), and salts of the stereoisomers of at least one compound of Formulas (IA) and/or (IB), such as salts of enantiomers, and/or salts of diastereomers.

"Treating," "treat," or "treatment" or "alleviation" refers to administering at least one compound and/or at least one stereoisomer thereof, and/or at least one pharmaceutically acceptable salt thereof disclosed herein to a subject in recognized need thereof that has, for example, cancer.

The term "effective amount" refers to an amount of at least one compound and/or at least one stereoisomer thereof, and/or at least one pharmaceutically acceptable salt thereof disclosed herein effective to "treat," as defined above, a disease or disorder in a subject.

The term "at least one substituent" disclosed herein includes, for example, from 1 to 4, such as from 1 to 3, further as 1 or 2, substituents, provided that the valence allows. For example, "at least one substituent $R^9$" disclosed herein includes from 1 to 4, such as from 1 to 3, further as 1 or 2, substituents selected from the list of $R^9$ as described herein.

In the first aspect, provided is a compound selected from 5 or 8-substituted imidazo[1,5-a]pyridines of Formulas (IA) and/or (IB):

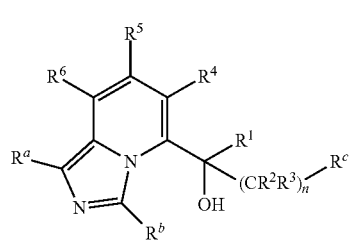

(IA)

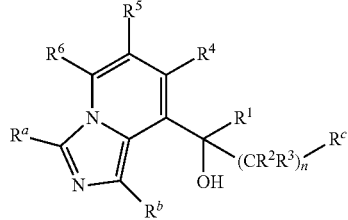

(IB)

or a stereoisomer thereof, or a pharmaceutically acceptable salt thereof,
wherein:
n=0, 1, 2, 3, or 4;
$R^a$ and $R^b$ are each independently selected from hydrogen, halogen, $C_{1-8}$ alkyl, $C_{1-8}$ haloalkyl, $C_{2-8}$ alkenyl, $C_{2-8}$ alkynyl, $C_{3-8}$ cycloalkyl, heterocyclyl, aryl, and heteroaryl;
$R^1$ is selected from hydrogen, halogen, $C_{1-8}$ alkyl and $C_{1-8}$ haloalkyl;
$R^2$ and $R^3$ are each independently selected from hydrogen, halogen, $OR^7$, $NR^7R^8$, $COR^7$, $SO_2R^7$, $C(=O)OR^7$, $C(=O)NR^7R^8$, $C_{1-8}$ alkyl, $C_{2-8}$ alkenyl, $C_{2-8}$ alkynyl, $C_{3-8}$ cycloalkyl, heterocyclyl, aryl, and heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^9$;
$R^4$, $R^5$ and $R^6$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, —CN, —$OR^7$, and —$SR^7$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituent $R^9$,
provided that at least one of $R^4$ and $R^5$ is not hydrogen;
$R^C$ is selected from $C_{3-10}$ cycloalkyl, heterocyclyl or heteroaryl, each optionally substituted with at least one substituent $R^9$;
$R^7$ and $R^8$ are each independently selected from hydrogen, $C_{1-8}$ alkyl, $C_{1-8}$ haloalkyl, $C_{3-8}$ cycloalkyl, heterocyclyl, aryl, and heteroaryl optionally substituted with at least one substituent $R^9$; or $R^7$ and $R^8$ together with the nitrogen atom to which they are attached form a heterocyclyl or heteroaryl ring which optionally comprises a further hetero atom selected from nitrogen, oxygen and sulfur atom, and is optionally substituted with at least one substituent $R^9$;
$R^9$ is selected from hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-NR'R", —CN, —OR', —NR'R", —COR', —$CO_2R'$, —CONR'R", —C(=NR')NR"R"', nitro, —NR'COR", —NR'CONR'R", —$NR'CO_2R"$, —$SO_2R'$, —$SO_2$aryl, —$NR'SO_2NR"R"'$, $NR'SO_2R"$, and —$NR'SO_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein R', R", and R"' are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl, or (R' and R"), and/or (R" and R"') together with the atoms to which they are attached, form a ring selected from heterocyclyl optionally substituted by halogen, $C_{1-4}$ haloalkyl and $C_{1-4}$ alkyl and heteroaryl rings optionally substituted by halogen, $C_{1-4}$ haloalkyl and $C_{1-4}$ alkyl.

In the second aspect, provided is 5-substituted imidazo[1,5-a]pyridines of Formula (IA):

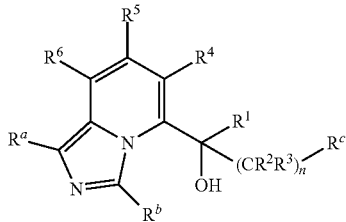

(IA)

or a stereoisomer thereof, or a pharmaceutically acceptable salt thereof,
wherein:
n=0, 1, 2, 3, or 4;
$R^a$ and $R^b$ are each independently selected from hydrogen, halogen, $C_{1-8}$ alkyl, $C_{1-8}$ haloalkyl, $C_{2-8}$ alkenyl, $C_{2-8}$ alkynyl, $C_{3-8}$ cycloalkyl, heterocyclyl, aryl, and heteroaryl;
$R^1$ is selected from hydrogen, halogen, $C_{1-8}$ alkyl and $C_{1-8}$ haloalkyl;
$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, heterocyclyl, aryl, and heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^9$;
$R^4$, $R^5$ and $R^6$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, and —$OR^7$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituted $R^9$,
provided that at least one of $R^4$ and $R^5$ is not hydrogen;
$R^C$ is $C_{3-10}$ cycloalkyl optionally substituted with at least one substituent $R^9$;
$R^7$ is selected from hydrogen, $C_{1-8}$ alkyl, $C_{1-8}$ haloalkyl, $C_{3-8}$ cycloalkyl, heterocyclyl, aryl, and heteroaryl optionally substituted with at least one substituent $R^9$;
$R^9$ is selected from hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-NR'R'', —CN, —OR', —NR'R'', —COR', —$CO_2R'$, —CONR'R'', nitro, —NR'COR'', —NR'CONR'R'', —NR'$CO_2R''$, —$SO_2R'$, —$SO_2$aryl, NR'$SO_2R''$, and —NR'$SO_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein R' and R'' are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl.

In some embodiment, for compound of Formula (IA), n is 0. In another embodiment, for compound of Formula (IA), n is 1. In yet another embodiment, for compound of Formula (IA), n is 2.

In some embodiment, for compound of Formula (IA), $R^a$ and $R^b$ are each independently selected from hydrogen, halogen, $C_{1-6}$ alkyl, or $C_{1-6}$ haloalkyl; preferably are each independently selected from hydrogen, halogen, $C_{1-4}$ alkyl, or $C_{1-4}$ haloalkyl; more preferably are each independently hydrogen.

In some embodiment, for compound for Formula (IA), $R^1$ is selected from hydrogen, halogen, $C_{1-6}$ alkyl and $C_{1-6}$ haloalkyl; preferably is selected from hydrogen, halogen, $C_{1-6}$ alkyl and $C_{1-6}$ haloalkyl; more preferably is selected from hydrogen and $C_{1-6}$ alkyl.

In some embodiment, for compound for Formula (IA), $R^2$ and $R^3$ are each independently selected from hydrogen, halogen, $C_{1-6}$ alkyl, and $C_{1-6}$ haloalkyl; preferably are each independently selected from hydrogen and $C_{1-6}$ alkyl.

In some embodiment, for compound of Formula (IA), $R^4$ is not hydrogen, $R^5$ is hydrogen, and $R^6$ is hydrogen. In another embodiment, for compound of Formula (IA), $R^4$ is not hydrogen, $R^5$ is hydrogen, and $R^6$ is not hydrogen.

In some embodiment, for compound of Formula (IA), $R^4$ is hydrogen, $R^5$ is not hydrogen, and $R^6$ is hydrogen. In another embodiment, for compound of Formula (IA), $R^4$ is hydrogen, $R^5$ is not hydrogen, and $R^6$ is not hydrogen.

In some embodiment, for compound of Formula (IA), $R^4$ is not hydrogen, $R^5$ is not hydrogen, and $R^6$ is hydrogen. In another embodiment, for compound of Formula (IA), $R^4$ is not hydrogen, $R^5$ is not hydrogen, and $R^6$ is not hydrogen.

For compound of Formula (IA), in case that $R^4$ is not hydrogen, $R^4$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, and —$OC_{1-6}$ alkyl, wherein said aryl or heteroaryl is independently optionally substituted with at least one $R^9$ independently selected from halogen, $C_{1-4}$ haloalkyl, and $C_{1-4}$ alkyl; preferably, $R^4$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl (such as fluoro substituted $C_{1-6}$ alkyl), phenyl optionally substituted with halogen, $C_{1-4}$ alkyl or $C_{1-4}$ haloalkyl, heteroaryl (such as isoxazolyl) optionally substituted with halogen, $C_{1-4}$ alkyl or $C_{1-4}$ haloalkyl, and —$OC_{1-6}$ alkyl; more preferably, $R^4$ is selected from F, Cl, Br, I, methyl, isopropyl, propenyl (such as prop-1-en-2-yl), ethynyl, cyclopropyl, $CF_3$, phenyl, dimethylisoxazolyl and methoxy.

For compound of Formula (IA), in case that $R^5$ is not hydrogen, $R^5$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, and —$OC_{1-6}$ alkyl, wherein said aryl or heteroaryl is independently optionally substituted with at least one $R^9$ independently selected from halogen, $C_{1-4}$ haloalkyl, and $C_{1-4}$ alkyl; preferably, $R^5$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl (such as fluoro substituted $C_{1-6}$ alkyl) and —$OC_{1-6}$ alkyl; more preferably, $R^5$ is selected from F, Cl, Br, I, cyclopropyl, $CF_3$ and methoxy.

For compound of Formula (IA), in case that $R^6$ is not hydrogen, $R^6$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, and —$OC_{1-6}$ alkyl, wherein said aryl or heteroaryl is independently optionally substituted with at least one $R^9$ independently selected from halogen, $C_{1-4}$ haloalkyl, and $C_{1-4}$ alkyl; preferably, $R^6$ is halogen, $C_{1-6}$ alkyl, or $C_{1-6}$ haloalkyl.

In some embodiment, for compound of Formula (IA), $R^C$ is $C_{3-8}$ cycloalkyl optionally substituted with at least one substituent $R^9$. In other embodiment, for compound of Formula (IA), $R^C$ is $C_{3-8}$ cycloalkyl optionally substituted with a phenyl group.

In some embodiment, for compound of Formula (IA), $R^C$ is $C_{3-10}$ cycloalkyl, preferably $C_{3-8}$ cycloalkyl optionally substituted with halogen, $C_{1-4}$ haloalkyl, $C_{1-4}$ alkyl and —NR'COR", wherein said $C_{1-4}$ haloalkyl and $C_{1-4}$ alkyl are optionally substituted with one or more halo or hydroxyl; wherein R' and R" are each independently selected from H, $C_{1-4}$ haloalkyl, $C_{1-4}$ alkyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl; preferably, $R^C$ is $C_{3-8}$ cycloalkyl optionally substituted with $C_{1-4}$ alkyl and —NR'COR", wherein said $C_{1-4}$ alkyl is optionally substituted with hydroxyl; wherein R' is hydrogen, and R" is aryl which is phenyl substituted with halogen (such as fluoro and chloro).

In other embodiment, for compound of Formula (IA), $R^C$ is unsubstituted $C_{3-10}$ cycloalkyl; preferably, unsubstituted $C_{3-8}$ cycloalkyl; more preferably $R^C$ is unsubstituted cyclohexyl. In yet another embodiment, for compound of Formula (IA), $R^C$ is cyclopropyl, cyclobutyl, cyclopentyl, or cycloheptyl.

In some embodiment, for compound of Formula (IA), n is zero, and $R^C$ is unsubstituted cyclohexyl. In other embodiment, for compound of Formula (IA), n is 1, and $R^C$ is unsubstituted cyclohexyl. In another embodiment, for compound of Formula (IA), n is 2, and $R^C$ is unsubstituted cyclohexyl.

In some embodiment, for compound of Formula (IA), n is zero, and $R^C$ is unsubstituted cyclopentyl. In other embodiment, for compound of Formula (IA), n is 1, and $R^C$ is unsubstituted cyclopentyl. In another embodiment, for compound of Formula (IA), n is 2, and $R^C$ is unsubstituted cyclopentyl.

In some embodiment, for compound of Formula (IA), n is zero, and $R^C$ is unsubstituted bicyclo[2.2.1]heptan-2-yl.

In some embodiment, for compound of Formula (IA), n is zero, and $R^C$ is 4-phenyl substituted cyclohexyl.

In some embodiment, for compound of Formula (IA), the chiral α-carbon atom attached to the imidazo[1,5-a]pyridine structure is in S- or R-configuration. Preferably, for compound of Formula (IA), the chiral α-carbon atom attached to the imidazo[1,5-a]pyridine structure is in a S-configuration.

In the third aspect, provided is 8-substituted imidazo[1,5-a]pyridines of Formula (IB):

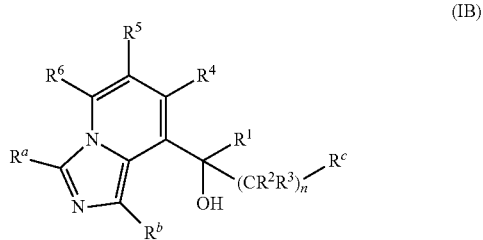

(IB)

or a stereoisomer thereof, or a pharmaceutically acceptable salt thereof,
wherein:
n=0, 1, 2, 3, or 4;
$R^a$ and $R^b$ are each independently selected from hydrogen, halogen, $C_{1-8}$ alkyl, $C_{1-8}$ haloalkyl, $C_{2-8}$ alkenyl, $C_{2-8}$ alkynyl, $C_{3-8}$ cycloalkyl, heterocyclyl, aryl, and heteroaryl;
$R^1$ is selected from hydrogen, halogen, $C_{1-8}$ alkyl and $C_{1-8}$ haloalkyl;
$R^2$ and $R^3$ are each independently selected from hydrogen, halogen, $C_{1-8}$ alkyl, $C_{2-8}$ alkenyl, $C_{2-8}$ alkynyl, $C_{3-8}$ cycloalkyl, heterocyclyl, aryl, and heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^9$;

$R^4$, $R^5$ and $R^6$ are each independently selected from hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, and —$OR^7$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituted $R^9$,
provided that $R^4$ is not hydrogen;
$R^C$ is $C_{3-10}$ cycloalkyl optionally substituted with at least one substituent $R^9$;
$R^7$ is selected from hydrogen, $C_{1-8}$ alkyl, $C_{1-8}$ haloalkyl, $C_{3-8}$ cycloalkyl, heterocyclyl, aryl, and heteroaryl optionally substituted with at least one substituent $R^9$;
$R^9$ is selected from hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-NR'R", —CN, —OR', —NR'R", —COR', —$CO_2$R', —CONR'R", nitro, —NR'COR", —NR'CONR'R", —NR'$CO_2$R", —$SO_2$R', —$SO_2$aryl, NR'$SO_2$R", and —NR'$SO_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl, wherein R' and R" are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl.

In some embodiment, for compound of Formula (IB), n is 0. In another embodiment, for compound of Formula (IB), n is 1. In yet another embodiment, for compound of Formula (IB), n is 2.

In some embodiment, for compound of Formula (IB), $R^a$ and $R^b$ are each independently selected from hydrogen, halogen, $C_{1-6}$ alkyl, or $C_{1-6}$ haloalkyl; preferably are each independently selected from hydrogen, halogen, $C_{1-4}$ alkyl, or $C_{1-4}$ haloalkyl; more preferably are each independently hydrogen.

In some embodiment, for compound for Formula (IB), $R^1$ is selected from hydrogen, halogen, $C_{1-6}$ alkyl and $C_{1-6}$ haloalkyl; preferably is selected from hydrogen, halogen, $C_{1-6}$ alkyl and $C_{1-6}$ haloalkyl; more preferably is selected from hydrogen and $C_{1-6}$ alkyl.

In some embodiment, for compound for Formula (IB), $R^2$ and $R^3$ are each independently selected from hydrogen, halogen, $C_{1-6}$ alkyl, and $C_{1-6}$ haloalkyl; preferably are each independently selected from hydrogen and $C_{1-6}$ alkyl.

In some embodiment, for compound for Formula (IB), $R^4$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, and —$OC_{1-6}$ alkyl; preferably, $R^4$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl (such as fluoro substituted $C_{1-6}$ alkyl) and —$OC_{1-6}$ alkyl; more preferably, $R^4$ is selected from F, Cl, Br, I, methyl, isopropyl, and cyclopropyl.

In some embodiment, for compound of Formula (IB), $R^5$ is hydrogen, and $R^6$ is hydrogen. In another embodiment, for compound of Formula (IB), $R^5$ is hydrogen, and $R^6$ is not hydrogen.

In some embodiment, for compound of Formula (IB), $R^5$ is not hydrogen, and $R^6$ is hydrogen. In another embodiment, for compound of Formula (IB), $R^5$ is not hydrogen, and $R^6$ is not hydrogen.

For compound of Formula (IB), in case that $R^5$ is not hydrogen, $R^5$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, and —$OC_{1-6}$ alkyl, wherein said aryl or heteroaryl is independently optionally substituted with at least one $R^9$ independently selected from halogen, $C_{1-4}$ haloalkyl, and $C_{1-4}$ alkyl; preferably, $R^5$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl (such as fluoro substituted $C_{1-6}$ alkyl) and —$OC_{1-6}$ alkyl; more preferably, $R^5$ is selected from F, Cl, Br, I, cyclopropyl, $CF_3$ and methoxy.

For compound of Formula (IB), in case that $R^6$ is not hydrogen, $R^6$ is selected from halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, and —$OC_{1-6}$ alkyl, wherein said aryl or heteroaryl is independently optionally substituted with at least one $R^9$ independently selected from halogen, $C_{1-4}$ haloalkyl, and $C_{1-4}$ alkyl; preferably, $R^6$ is halogen, $C_{1-6}$ alkyl, or $C_{1-6}$ haloalkyl; more preferably, $R^6$ is halogen.

In some embodiment, for compound of Formula (IB), $R^C$ is $C_{3-8}$ cycloalkyl optionally substituted with at least one substituent $R^9$. In other embodiment, for compound of Formula (IB), $R^C$ is $C_{3-8}$ cycloalkyl optionally substituted with a phenyl group.

In some embodiment, for compound of Formula (IB), $R^C$ is $C_{3-10}$ cycloalkyl, preferably $C_{3-8}$ cycloalkyl optionally substituted with halogen, $C_{1-4}$ haloalkyl, $C_{1-4}$ alkyl and —NR'COR", wherein said $C_{1-4}$ haloalkyl and $C_{1-4}$ alkyl are optionally substituted with one or more halo or hydroxyl; wherein R' and R" are each independently selected from H, $C_{1-4}$ haloalkyl, $C_{1-4}$ alkyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl; preferably, $R^C$ is $C_{3-8}$ cycloalkyl optionally substituted with $C_{1-4}$ alkyl and —NR'COR", wherein said $C_{1-4}$ alkyl is optionally substituted with hydroxyl; wherein R' is hydrogen, and R" is aryl which is phenyl substituted with halogen (such as fluoro and chloro).

In other embodiment, for compound of Formula (IB), $R^C$ is unsubstituted $C_{3-10}$ cycloalkyl; preferably, unsubstituted $C_{3-8}$ cycloalkyl; more preferably, $R^C$ is unsubstituted cyclohexyl. In yet another embodiment, for compound of Formula (IB), $R^C$ is cyclopropyl, cyclobutyl, cyclopentyl, or cycloheptyl.

In some embodiment, for compound of Formula (IB), n is zero, and $R^C$ is unsubstituted cyclohexyl. In other embodiment, for compound of Formula (IB), n is 1, and $R^C$ is unsubstituted cyclohexyl. In another embodiment, for compound of Formula (IB), n is 2, and $R^C$ is unsubstituted cyclohexyl.

In some embodiment, for compound of Formula (IB), n is zero, and $R^C$ is unsubstituted cyclopentyl. In other embodiment, for compound of Formula (IB), n is 1, and $R^C$ is unsubstituted cyclopentyl. In another embodiment, for compound of Formula (IB), n is 2, and $R^C$ is unsubstituted cyclopentyl.

In some embodiment, for compound of Formula (IB), n is zero, and $R^C$ is unsubstituted bicyclo[2.2.1]heptan-2-yl.

In some embodiment, for compound of Formula (IB), n is zero, and $R^C$ is 4-phenyl substituted cyclohexyl.

In some embodiment, for compound of Formula (IB), the chiral α-carbon atom attached to the imidazo[1,5-a]pyridine structure is in S- or R-configuration. Preferably, for compound of Formula (IB), the chiral α-carbon atom attached to the imidazo[1,5-a]pyridine structure is in a S-configuration.

Also provided herein is a compound selected from the following compounds, or a stereoisomer thereof or a pharmaceutically acceptable salt thereof:

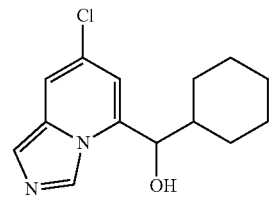

Example A101

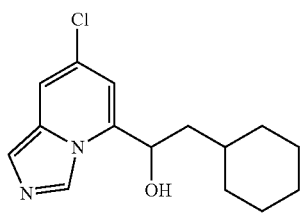

Example A102

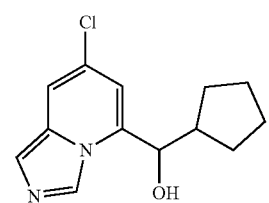

Example A103

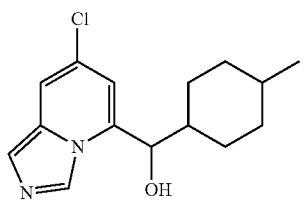

Example A104

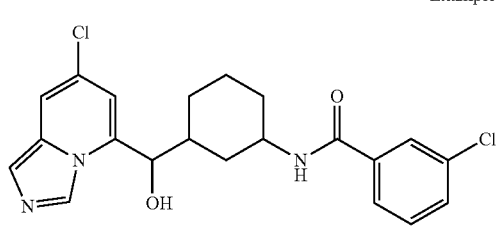

Example A105

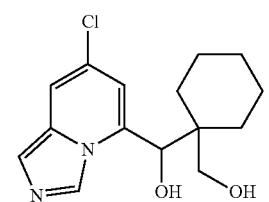

Example A106

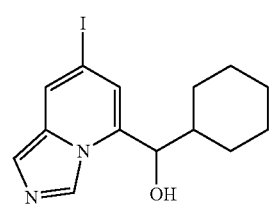

Example A107

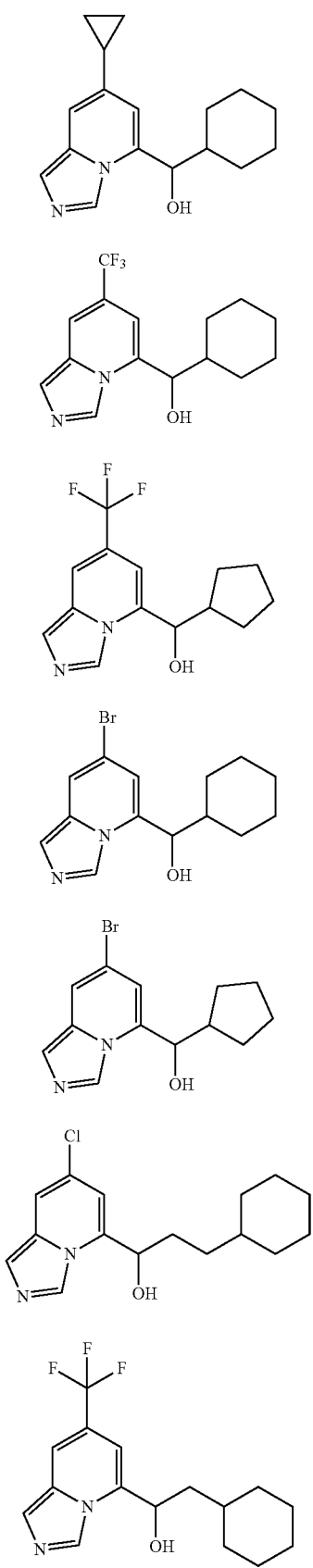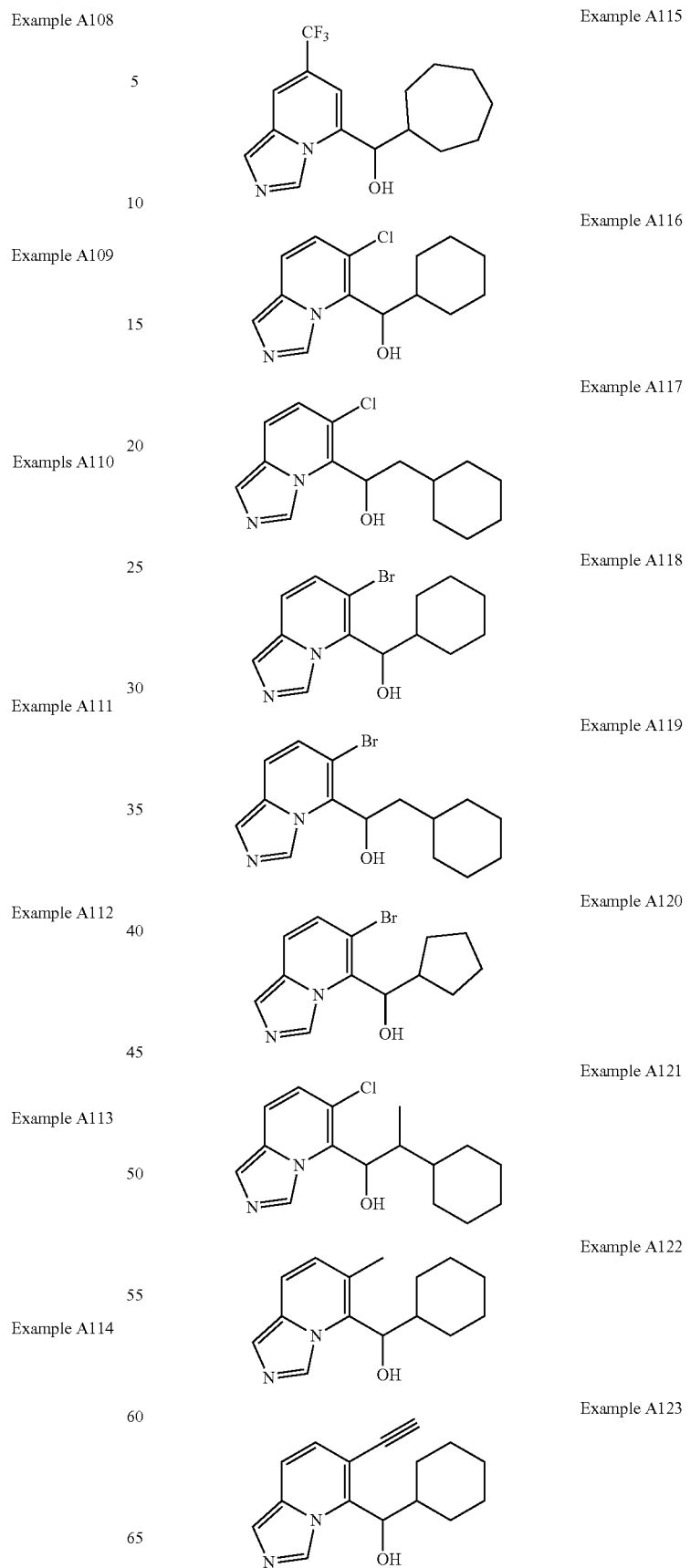

Example A124

Example A125

Example A126

Example A127

Example A128

Example A129

Example A130

Example A131

Example A132

Example A133

Example A134

Example A135

Example A136

Example A137

Example A138

Example A139

Example A140
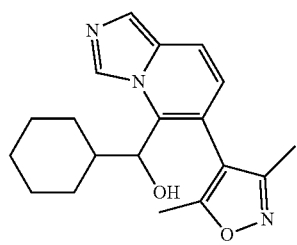
Example A141
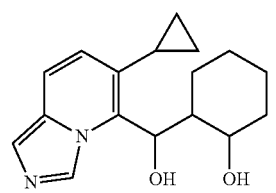
Example A142
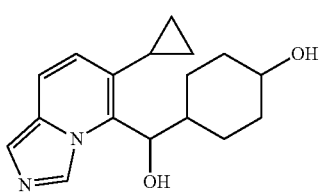
Example A143
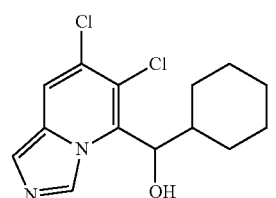
Example A144
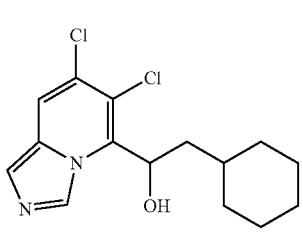
Example A145
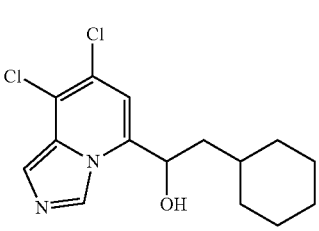
Example A146
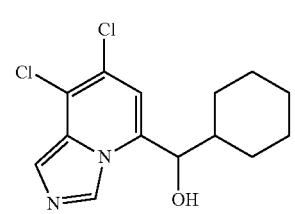
Example A147
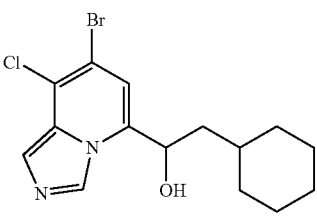
Example A148
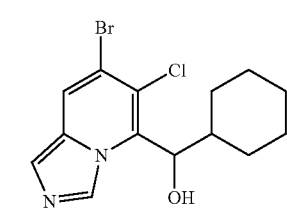
Example A149
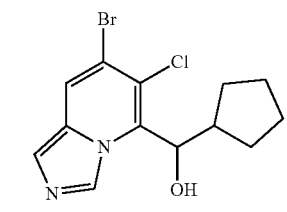
Example A150
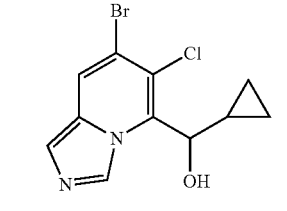
Example A151
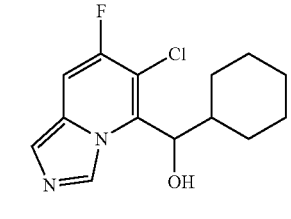
Example A152
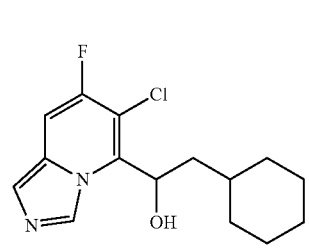
Example A153
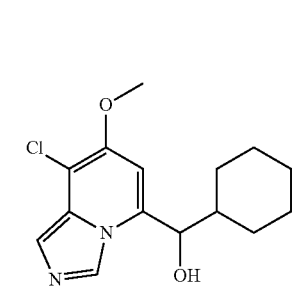

Example A154
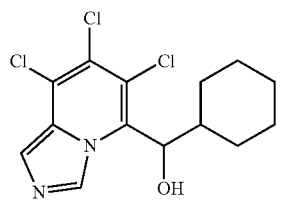
Example A155
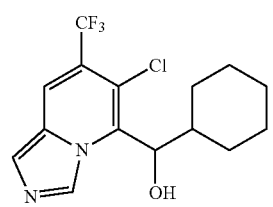
Example A156
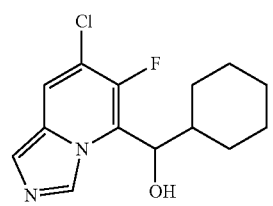
Example A157
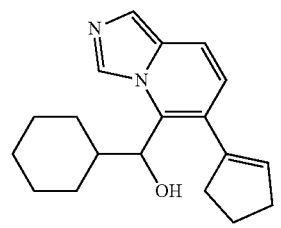
Example A158
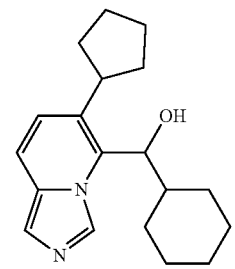
Example A159
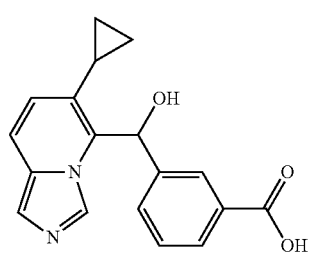
Example A160
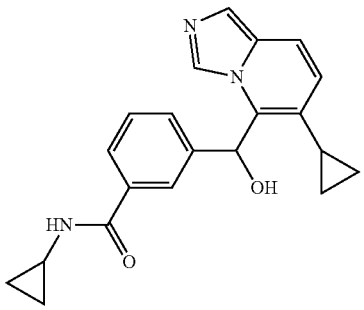
Example A161
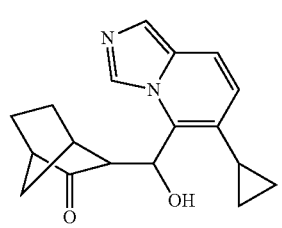
Example A162
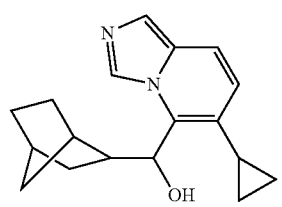
Example A163
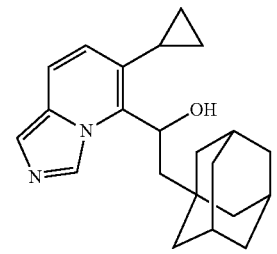
Example A164
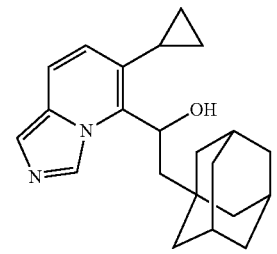
Example A165
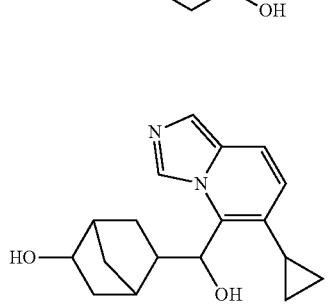

Example B101
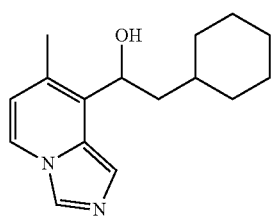
Example B102
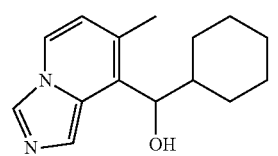
Example B103
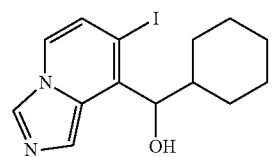
Example B104
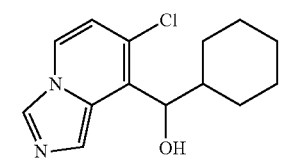
Example B105
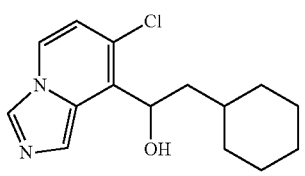
Example B106
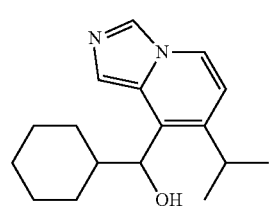
Example B107
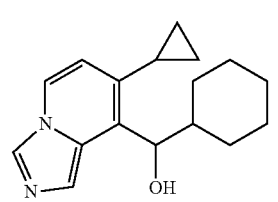
Example B108
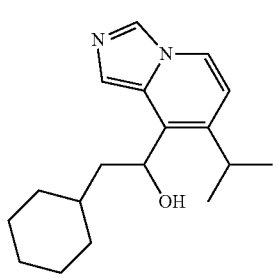
Example B109
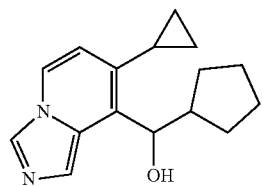
Example B110
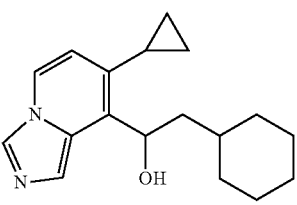
Example B111
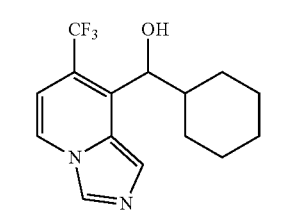
Example B112
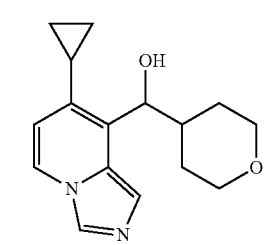
Example B113
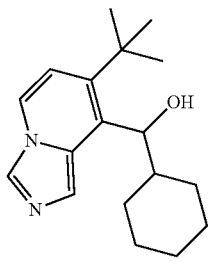
Example B114
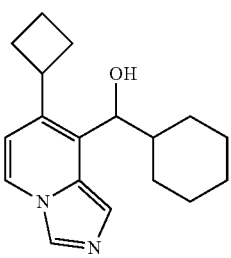
Example B115
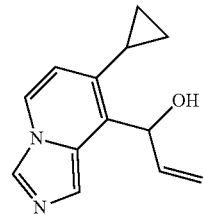

Example B116
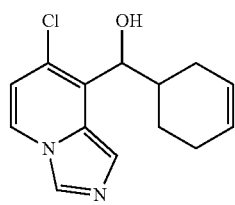
Example B117
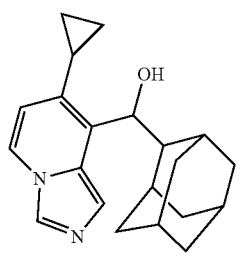
Example B118
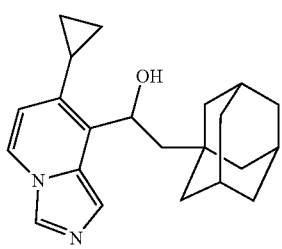
Example B119
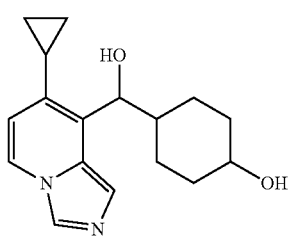
Example B120
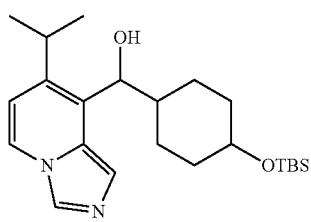
Example B121
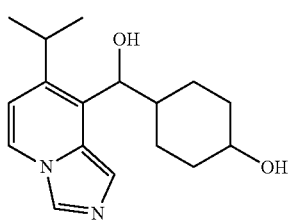
Example B122
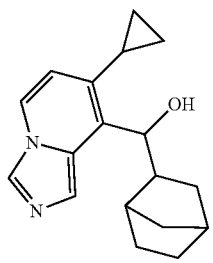
Example B123
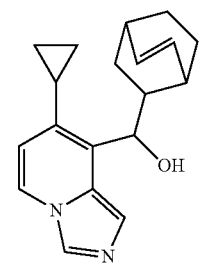
Example B124
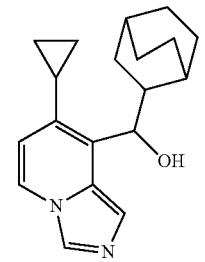
Example B125
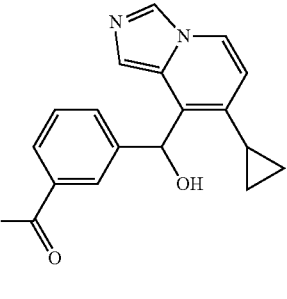
Example B126
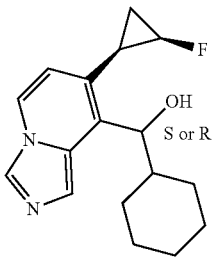
Example B127
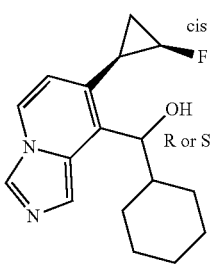

Example B128
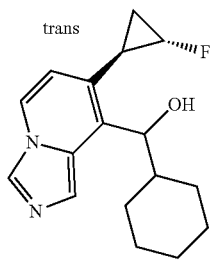
Example B129
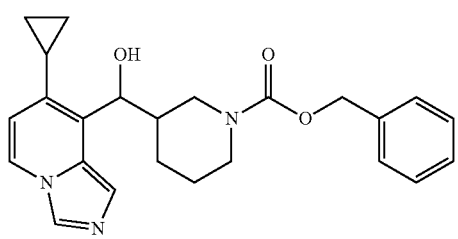
Example B130
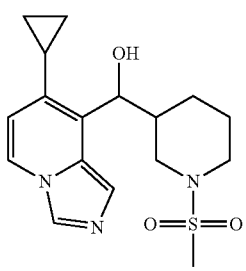
Example B131
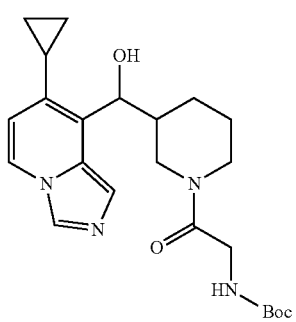
Example B132
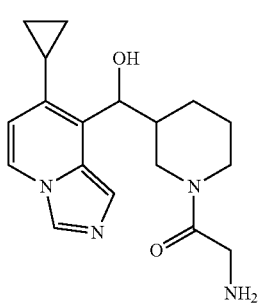
Example B133
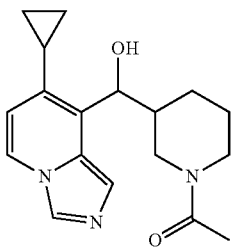
Example B134
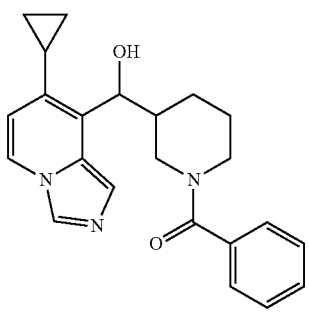
Example B135
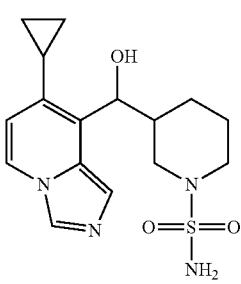
Example B136
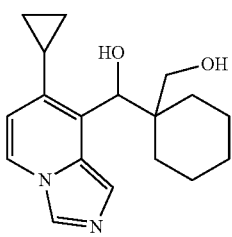
Example B137
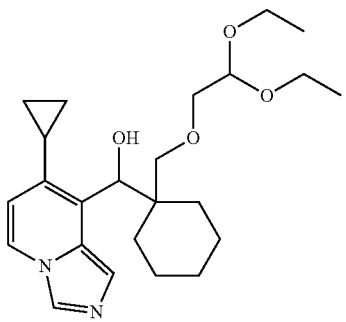

Example B138

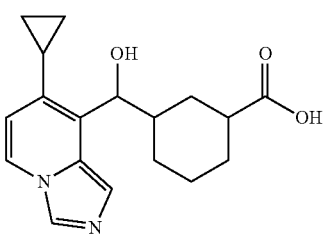

Example B139

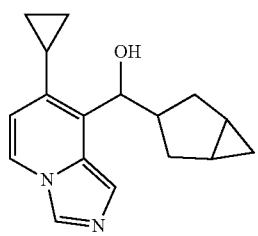

Example B140

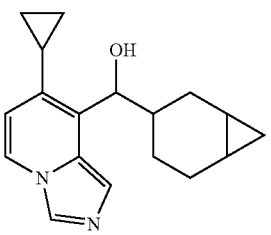

Example B141

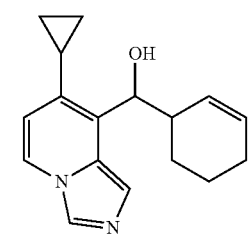

Example B142

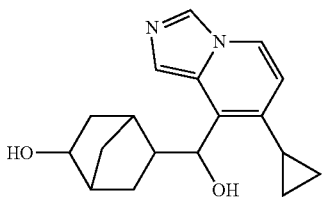

Example B143

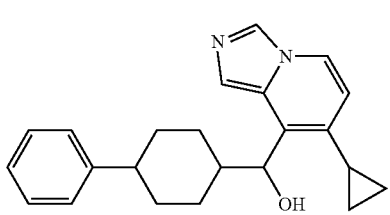

Also provided herein is a compound selected from the following compounds showing the following stereochemistry:

Example A101a

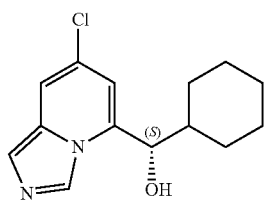

Fast isomer in chiral IC HPLC
Eluting reagent: $CO_2$/MeOH = 75/25(V/V)

Example A101b

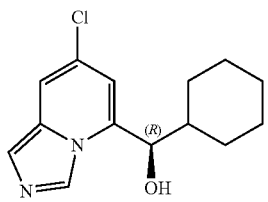

Slow isomer in chiral IC HPLC
Eluting reagent: $CO_2$/MeOH = 75/25(V/V)

Example A102a

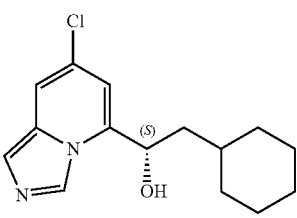

Fast isomer in chiral AD HPLC
Eluting reagent: MeOH = 100%

Example A102b

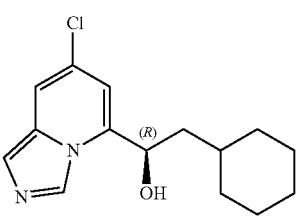

Slow isomer in chiral AD HPLC
Eluting reagent: MeOH = 100%

Example A109a

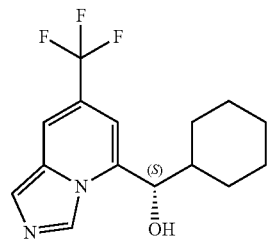

Fast isomer in chiral IC HPLC
Eluting reagent: Hexane/IPA = 90/10(V/V)

-continued

Example A109b

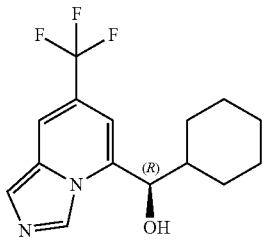

Slow isomer in chiral IC HPLC
Eluting reagent: Hexane/IPA = 90/10(V/V)

Example A114a

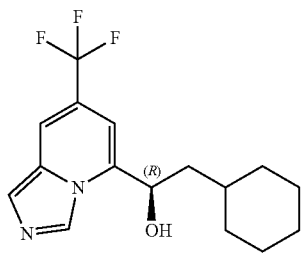

Fast isomer in chiral AD HPLC
Eluting reagent: Hexane/IPA = 90/10(V/V)

Example A114b

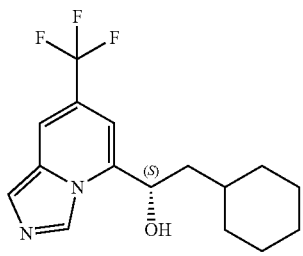

Slow isomer in chiral AD HPLC
Eluting reagent: Hexane/IPA = 90/10(V/V)

Example A116a

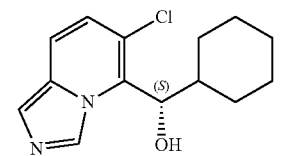

Fast isomer in chiral OD HPLC
Eluting reagent: Hexane/IPA/TEA = 70/30/0.1

Example A116b

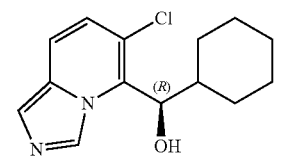

Slow isomer in chiral OD HPLC
Eluting reagent: Hexane/IPA/TEA = 70/30/0.1

Example A117a

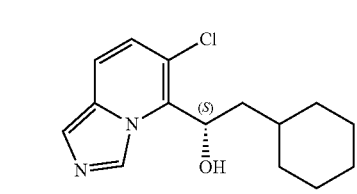

Fast isomer in chiral AS HPLC
Eluting reagent: Hexane/EtOH/TEA = 90/10/0.1(V/V/V)

-continued

Example A117b

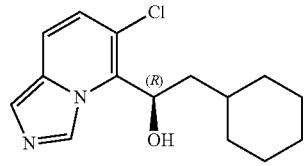

Slow isomer in chiral AS HPLC
Eluting reagent: Hexane/EtOH/TEA = 90/10/0.1(V/V/V)

Example A118a

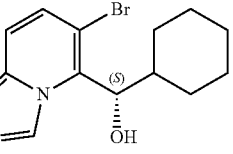

Fast isomer in chiral OD HPLC
Eluting reagent: Hexane/EtOH/ = 80/20(V/V)

Example A118b

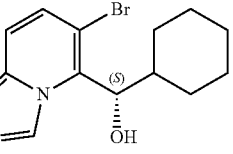

Slow isomer in chiral OD HPLC
Eluting reagent: Hexane/EtOH/ = 80/20(V/V)

Example A119a

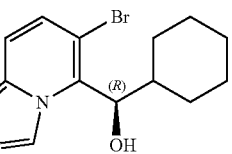

Fast isomer in chiral OD HPLC
Eluting reagent: Hexane/EtOH/ = 80/20(V/V)

Example A119b

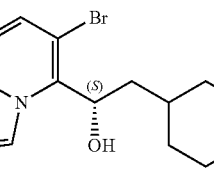

Slow isomer in chiral OD HPLC
Eluting reagent: Hexane/EtOH/ = 80/20(V/V)

Example A124a

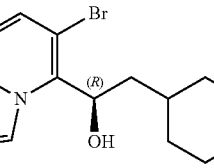

Fast isomer in chiral OD HPLC
Eluting reagent: $CO_2$/EtOH = 80/20(/V/V)

Example A124b

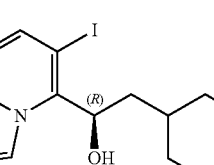

Slow isomer in chiral OD HPLC
Eluting reagent: $CO_2$/EtOH = 80/20(/V/V)

Example A125a

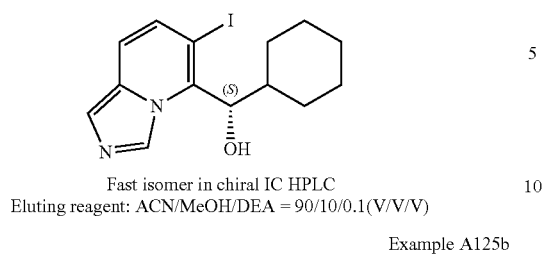

Fast isomer in chiral IC HPLC
Eluting reagent: ACN/MeOH/DEA = 90/10/0.1(V/V/V)

Example A125b

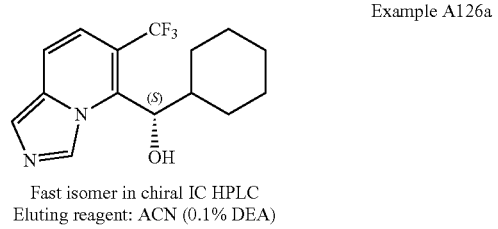

Slow isomer in chiral IC HPLC
Eluting reagent: ACN/MeOH/DEA = 90/10/0.1(V/V/V)

Example A126a

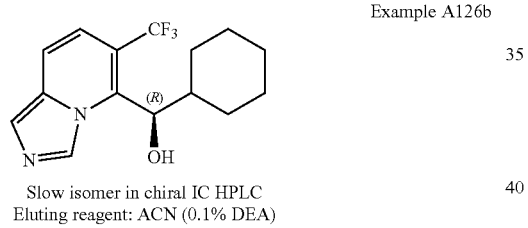

Fast isomer in chiral IC HPLC
Eluting reagent: ACN (0.1% DEA)

Example A126b

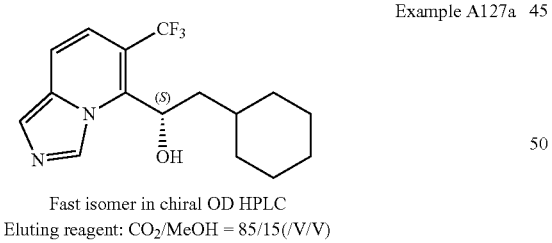

Slow isomer in chiral IC HPLC
Eluting reagent: ACN (0.1% DEA)

Example A127a

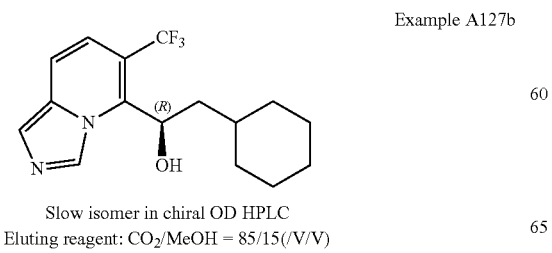

Fast isomer in chiral OD HPLC
Eluting reagent: $CO_2$/MeOH = 85/15(/V/V)

Example A127b

Slow isomer in chiral OD HPLC
Eluting reagent: $CO_2$/MeOH = 85/15(/V/V)

Example A129a

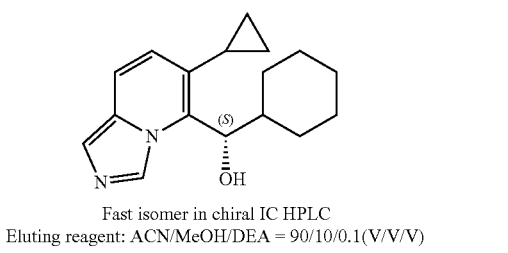

Fast isomer in chiral IC HPLC
Eluting reagent: ACN/MeOH/DEA = 90/10/0.1(V/V/V)

Example A129b

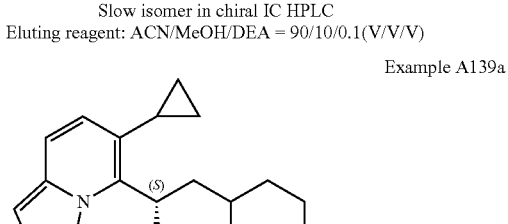

Slow isomer in chiral IC HPLC
Eluting reagent: ACN/MeOH/DEA = 90/10/0.1(V/V/V)

Example A139a

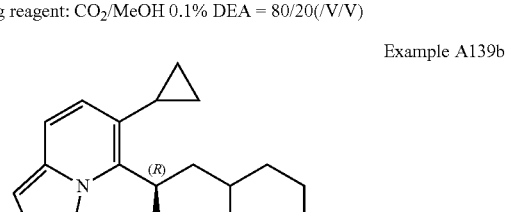

Fast isomer in chiral AD HPLC
Eluting reagent: $CO_2$/MeOH 0.1% DEA = 80/20(/V/V)

Example A139b

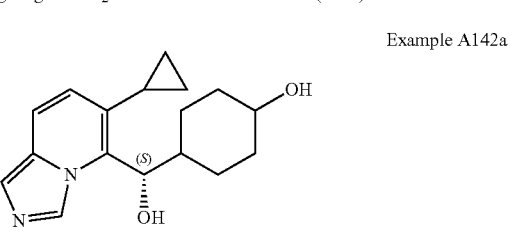

Slow isomer in chiral AD HPLC
Eluting reagent: $CO_2$/MeOH 0.1% DEA = 80/20(/V/V)

Example A142a

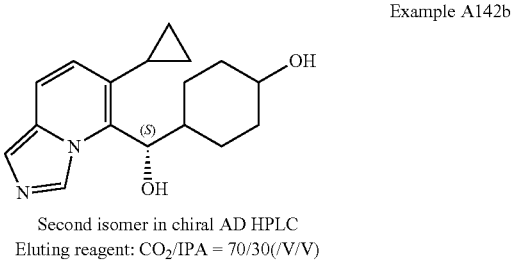

First isomer in chiral AD HPLC
Eluting reagent: $CO_2$/IPA = 70/30(/V/V)

Example A142b

Second isomer in chiral AD HPLC
Eluting reagent: $CO_2$/IPA = 70/30(/V/V)

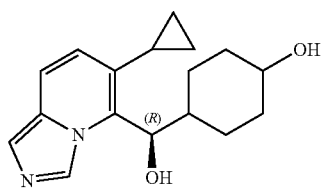

Third isomer in chiral AD HPLC
Eluting reagent: CO$_2$/IPA = 70/30(/V/V)

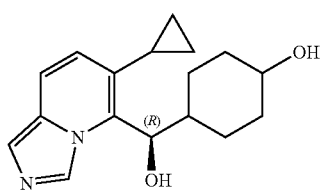

Forth isomer in chiral AD HPLC
Eluting reagent: CO$_2$/IPA = 70/30(/V/V)

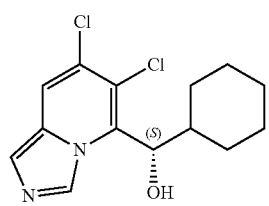

Fast isomer in chiral OZ HPLC
Eluting reagent: Hexane/IPA = 80/20(V/V)

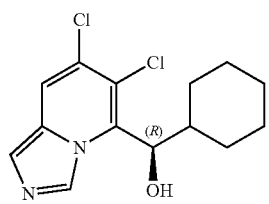

Slow isomer in chiral OZ HPLC
Eluting reagent: Hexane/IPA = 80/20(V/V)

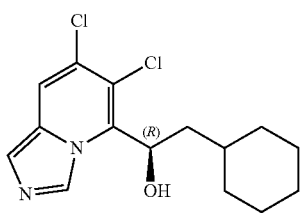

Fast isomer in chiral AS HPLC
Eluting reagent: Hexane/EtOH = 90/10(V/V)

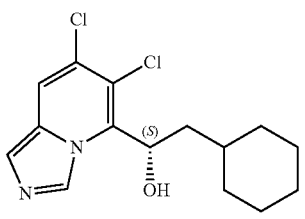

Slow isomer in chiral AS HPLC
Eluting reagent: Hexane/EtOH = 90/10(V/V)

Example A142c

Example A142d

Example A143a

Example A143b

Example A144a

Example A144b

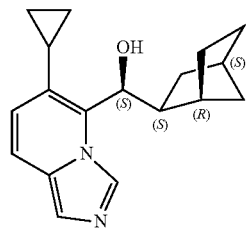

Fast isomer in chiral AC HPLC
Eluting reagent: Hexane/EtOH = 90/10(V/V)

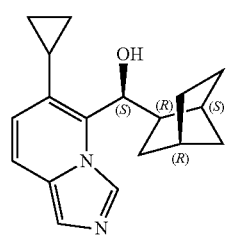

Slow isomer in chiral AC HPLC
Eluting reagent: Hexane/EtOH = 90/10(V/V)

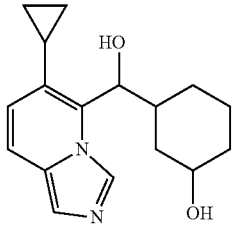

First isomer on normal HPLC
Two isomers

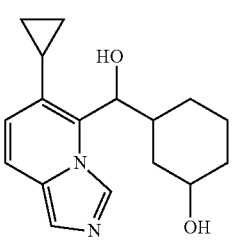

Second isomer on normal HPLC
Four isomers

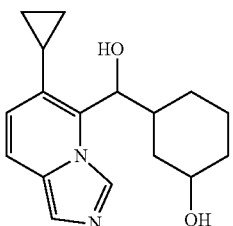

Third isomer on normal HPLC
Two isomers

Example A162a

Example A162b

Example A164a

Example A164b

Example A164c

Example B102a

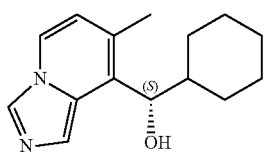

Fast isomer in chiral AS HPLC
Eluting reagent: CO$_2$/MeOH(0.1% DEA) = 80/20(/V/V)

Example B102b

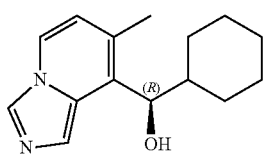

Slow isomer in chiral AS HPLC
Eluting reagent: CO$_2$/MeOH(0.1% DEA) = 80/20(/V/V)

Example B106a

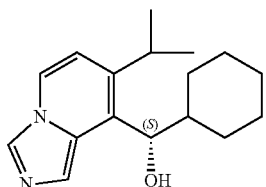

Fast isomer in chiral AS HPLC
Eluting reagent: CO$_2$/MeOH(0.1% DEA) = 80/20(/V/V)

Example B106b

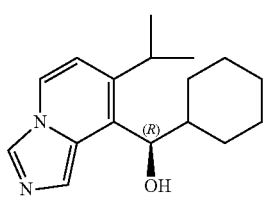

Slow isomer in chiral AS HPLC
Eluting reagent: CO$_2$/MeOH(0.1% DEA) = 80/20(/V/V)

Example B107a

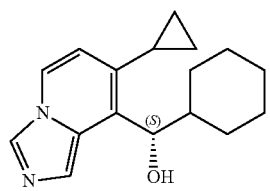

Fast isomer in chiral AY HPLC
Eluting reagent: CO$_2$/EtOH 0.1% DEA = 75/25(/V/V)

Example B107b

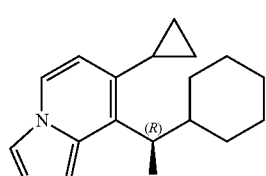

Slow isomer in chiral AY HPLC
Eluting reagent: CO$_2$/EtOH 0.1% DEA = 75/25(/V/V)

Example B110a

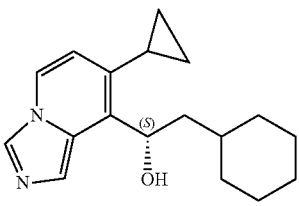

Fast isomer in chiral AS HPLC
Eluting reagent: CO$_2$/MeOH = 80/20(/V/V)

Example B110b

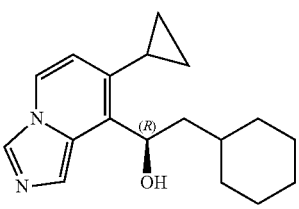

Slow isomer in chiral AS HPLC
Eluting reagent: CO$_2$/MeOH = 80/20(/V/V)

Example B119a

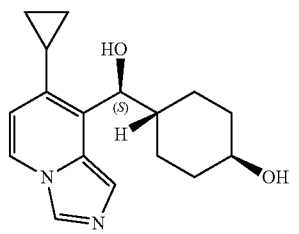

Fast trans isomer in chiral OJ HPLC
Eluting reagent: EtOH (100%)

Example B119b

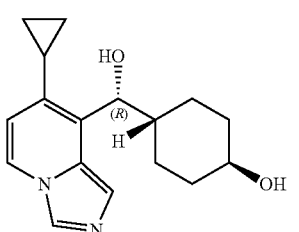

Slow trans isomer in chiral OJ HPLC
Eluting reagent: EtOH (100%)

Example B119c

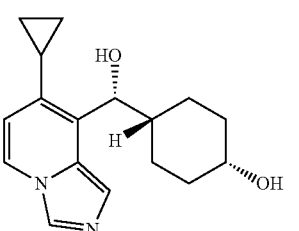

Fast cis isomer in chiral AD HPLC
Eluting reagent: EtOH/DEA = 100/0.1 (V/V)

-continued

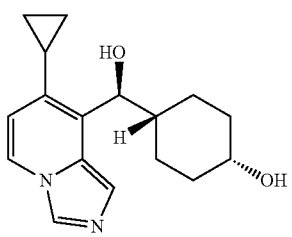

Example B119d

Slow cis isomer in chiral AD HPLC
Eluting reagent: EtOH/DEA = 100/0.1 (V/V)

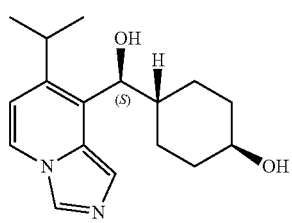

Example B121a

Fast trans isomer in chiral OJ HPLC
Eluting reagent: CO$_2$/MeOH = 80/20 (/V/V)

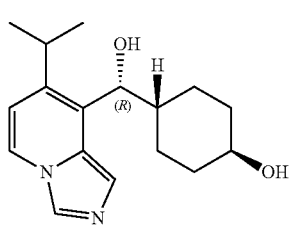

Example B121b

Slow trans isomer in chiral OJ HPLC
Eluting reagent: CO$_2$/MeOH = 80/20 (/V/V)

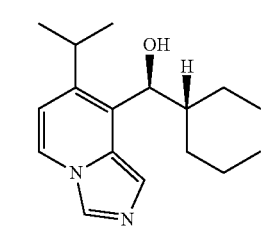

Example B121c

Fast cis isomer in chiral AD HPLC
Eluting reagent: CO$_2$/MeOH 0.1% DEA = 75/25 (V/V)

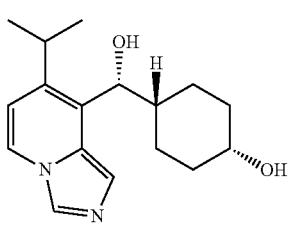

Example B121d

Slow cis isomer in chiral AD HPLC
Eluting reagent: CO$_2$/MeOH 0.1% DEA = 75/25 (V/V)

-continued

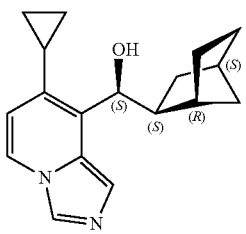

Example B122a

Second isomer in chiral AC HPLC
Eluting reagent: Hexane/EtOH = 90/10(/V/V)

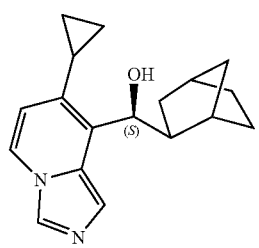

Example B122b

First isomer in chiral AC HPLC
Eluting reagent: Hexane/EtOH = 90/10(/V/V)

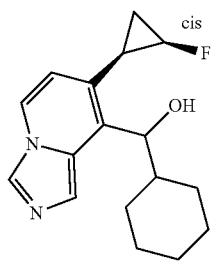

Example B126a

Fast isomer in normal HPLC
Two isomers

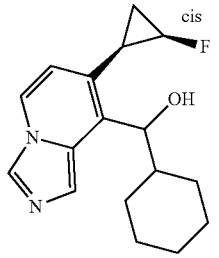

Example B126b

Slow isomer in normal HPLC
Two isomers

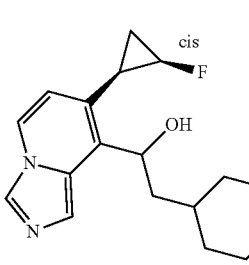

Example B127a

Fast isomer in normal HPLC
Two isomers

Example B127b

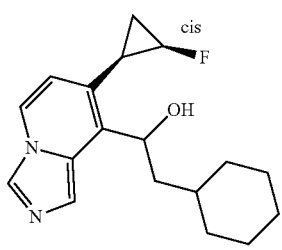

Slow isomer in normal HPLC
Two isomers

Example B128a

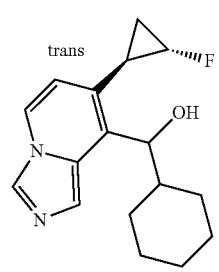

First trans isomer in chiral AS HPLC
Eluting reagent: CO2/EtOH 0.1% DEA = 60/40 (/V/V)
Two isomers Example B128b

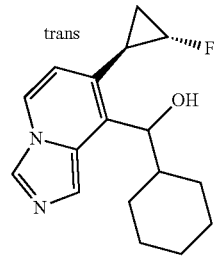

Second trans isomer in chiral AS HPLC
Eluting reagent: CO2/EtOH 0.1% DEA = 60/40 (/V/V)
single isomer Example B128c

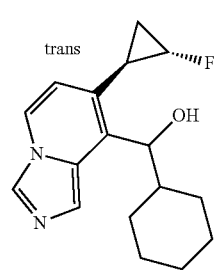

Third trans isomer in chiral AS HPLC
Eluting reagent: CO2/EtOH 0.1% DEA = 60/40 (/V/V)
single isomer Example B130a

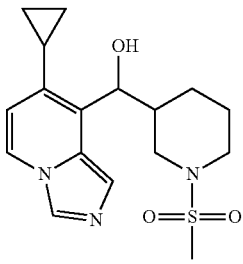

Fast isomer in normal HPLC
Two isomers

Example B130b

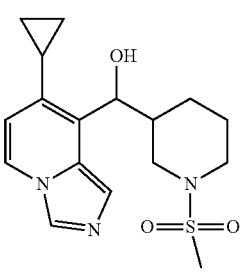

Slow isomer in normal HPLC
Two isomers

Example B133a

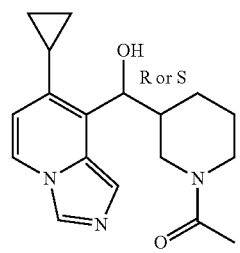

Fast isomer in normal HPLC
Two isomers

Example B133b

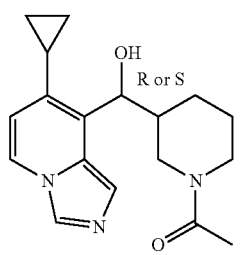

Slow isomer in normal HPLC
Two isomers

Example B135a

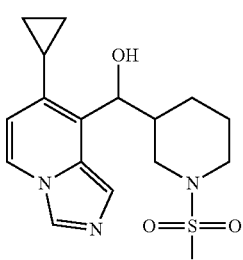

Fast isomer in normal HPLC
Two isomers

-continued

Example B135b

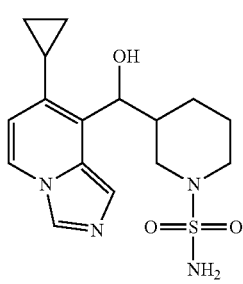

Slow isomer in normal HPLC
Two isomers

Example B143a

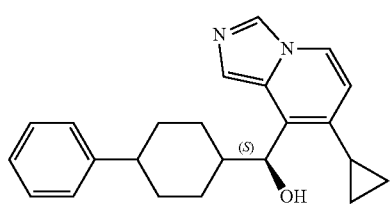

(trans or cis-phenyl)

Example B143b

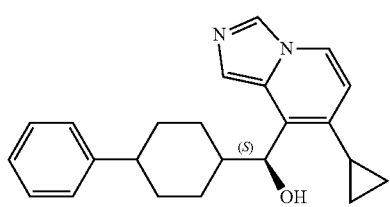

(cis or trans-phenyl)

or a pharmaceutically acceptable salt thereof.

The results of the "biological assays" part of the description have demonstrated that substitution of hydroxyl group on the chiral α-carbon atom attached to position 5 or 8 of the imidazo[1,5-a]pyridine structure and/or ortho or meta substitution in relation to the hydroxyl-substituted chiral α-carbon atom on the pyridine moiety of the imidazo[1,5-a]pyridine structure impart both unexpected enzymatic and cellular activity to the novel 5 or 8-substituted imidazo[1,5-a]pyridines disclosed herein. For example, each of Examples A101 to A165 and Examples B101 to B143 exhibited activity of inhibiting both IDO1 and TDO with $IC_{50}$ values ranging from 0.1 nM to 10 µM as well as activity of inhibiting Hela Cell-Based IDO1 with $EC_{50}$ values ranging less than 10000 nM.

The results also demonstrated that 5-substituted imidazo[1,5-a]pyridines having hydroxyl-substituted chiral α-carbon atom at position 5 and further ortho substitution on the pyridine moiety of the imidazo[1,5-a]pyridine structure and 8-substituted imidazo[1,5-a]pyridines having hydroxyl-substituted chiral α-carbon atom at position 8 and further ortho substitution on the pyridine moiety of the imidazo[1,5-a]pyridine structure exhibit selective inhibition of IDO1 over TDO. For example, Example A119 exhibited an enzymatic $IC_{50}$ value to IDO1 of 22 nM and an enzymatic $IC_{50}$ value to TDO of 12000 nM; Example A117 exhibited an enzymatic $IC_{50}$ value to IDO1 of 28 nM and an enzymatic $IC_{50}$ value to TDO of 9700 nM; and Example B105 exhibited an enzymatic $IC_{50}$ value to IDO1 of 33 nM and an enzymatic $IC_{50}$ value to TDO of 4900 nM.

In the fourth aspect, provided herein is the process for preparing the compounds of formula (IA) or (IB) disclosed herein.

The compounds disclosed herein, and/or the pharmaceutically acceptable salts thereof, can be synthesized from commercially available starting materials taken together with the disclosure herein.

Compounds of Formula (IA and IB) may be prepared by the exemplary processes described in the working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Greene, T. W. et al., eds., *Protecting Groups in Organic Synthesis*, 3$^{rd}$ Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Reactions, Mechanisms, and Structure.* 4$^{th}$ Edition, Wiley & Sons, New York, N.Y. (1992); Katritzky, A. R. et al., eds., *Comprehensive Organic Functional Groups Transformations*, 1$^{st}$ Edition, Elsevier Science Inc., Tarrytown, N.Y. (1995); Larock, R. C., *Comprehensive Organic Transformations*, VCH Publishers, Inc., New York, N.Y. (1989), and references therein. Compounds of the invention (IA) may be prepared according to the following schemes utilizing chemical transformations familiar to anyone of ordinary proficiency in the art of organic/medicinal chemistry. References to many of these transformations can be found in March's Advanced Organic Chemistry Reactions, Mechanisms, and Structure, Fifth Edition by Michael B. Smith and Jerry March, Wiley-Interscience, New York, 2001, or other standard texts on the topic of synthetic organic chemistry.

Scheme A

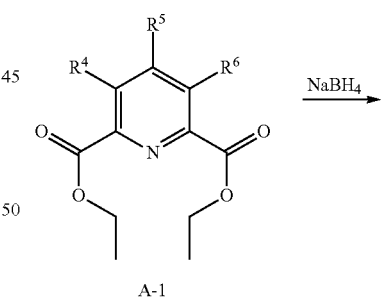

A-1

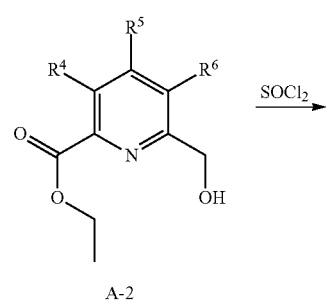

A-2

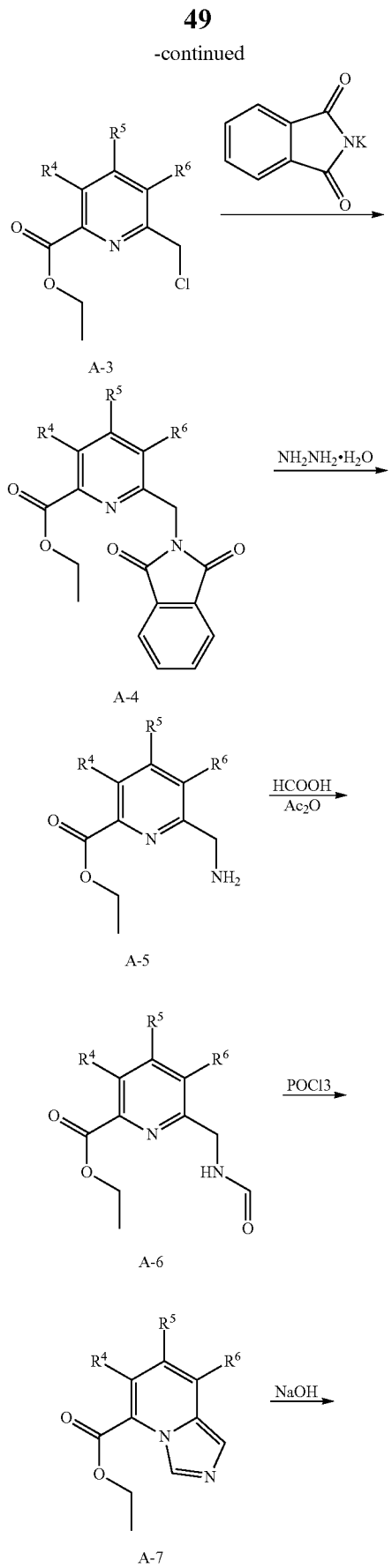

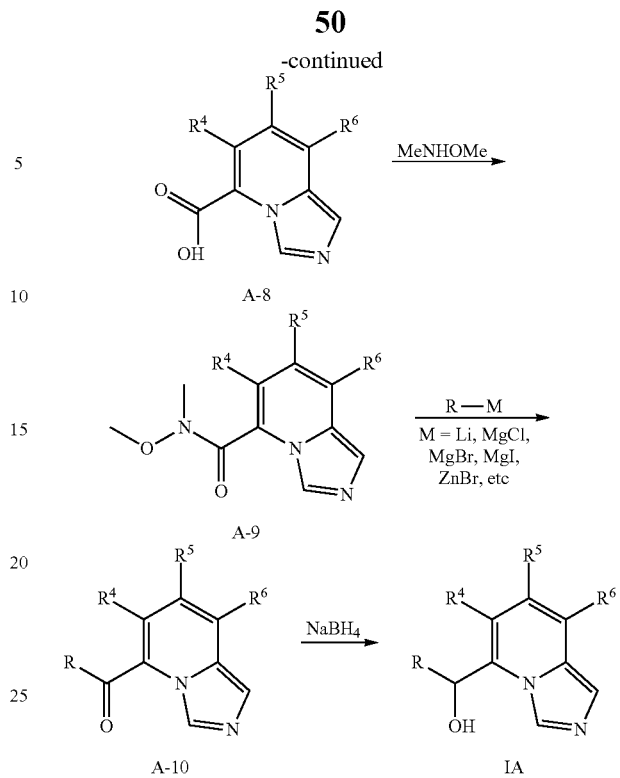

wherein R corresponds to —(CR²R³)ₙ—R^C in the case that R¹ is hydrogen

In this scheme, Compound A-1 (wherein R⁴, R⁵ and R⁶ are defined as above) are commercially available or can be easily prepared utilizing chemical transformations familiar to anyone of ordinary proficiency in the art of organic/medicinal chemistry. Treatment of Compound A-1 with a reducing agent, for example, sodium borohydride, in an alcoholic solvent, gives Compound A-2 which is then converted into the chloride A-3 by thionyl chloride. Treatment of a chloride with, a protecting agent, such as potassium phthalimide in a solvent such as THF, DMF, NMP or DMSO affords Compound A-4. Deprotection of the phthalimide protecting group by heating with hydrazine gives a free base A-5. The formamide formation of Compound A-5 is accomplished by treatment with a mixture of formic acid and acetic acid to give Compound A-6 which is cyclized into imidazo[1,5-a]pyridine ester A-7 by heating with POCl₃ in an inert solvent such as toluene. Hydrolysis of Compound A-7 undergoes using a base such as sodium hydroxide in a solvent such as water or alcohol or a mixture of both. The resulting acid A-8 is converted into Weinreb amide A-9 by reacting it with N,O-dimethyl hydroxylamine under a typical coupling reaction condition. A typical Grignard reaction of Weinreb amide A-9 gives the ketone A-10. Reduction of the ketone A-10 can be performed to give diasteromeric mixture (IA) with a reducing agent such as sodium borohydride in an alcoholic solvent. The final chiral HPLC separation affords single enatiodiastereomers. It should be noted that single enantiomers or diastereomers can also be prepared by using chiral reducing agents. The optical purity can be improved by other typical chiral resolution methods reported in the various literatures.

Scheme B

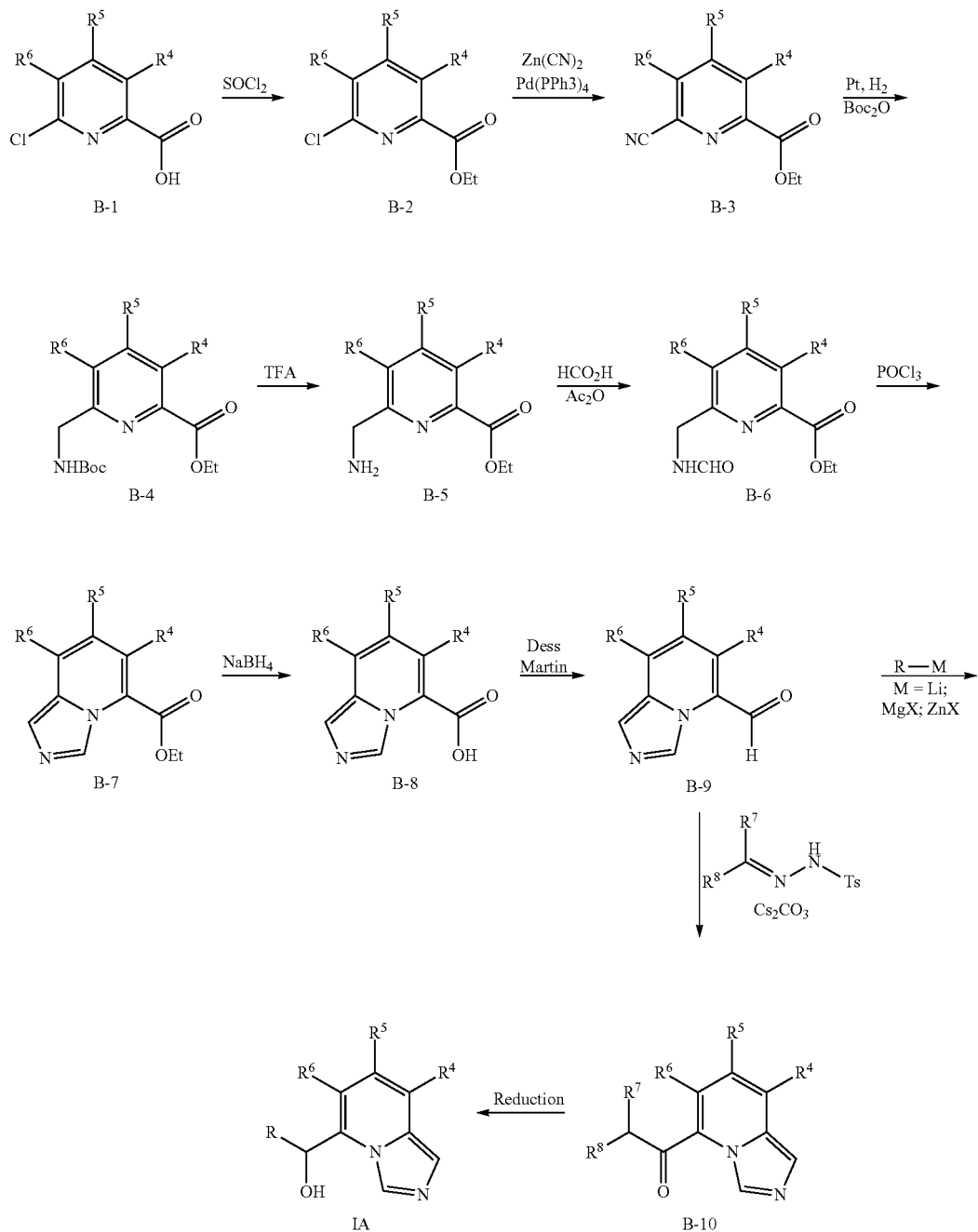

wherein R corresponds to —(CR²R³)ₙ—R^C in the case that R¹ is hydrogen

Compounds 1A (R⁴, R⁵, R⁶, R⁷ and R⁸ are defined as above) can also be prepared by a slightly modified procedure. The commercially available Compound B-1 is converted into the 2-chloro-6-carboxylate ester B-2 first. After replacement of chloro atom by cyano group, the resulting 2-cyano-6-carboxylate ester pyridine B-3 is hydrogenated to 2-Boc-aminomethyl-6-carboxylate ester pyridine B-4 in the simultaneous presence of Boc₂O and platinum catalyst. The following de-protection of Boc produces the free amine B-5 which is converted into formamide B-6. Further cyclization into imidazo[1,5-a]pyridine ester B-7 is effected by treatment of POCl₃. Reduction of Compound B-7 gives the alcohol B-8 which undergoes Dess Martin or other oxidation reaction to yield the aldehyde B-9. Addition of Grignard reagent to the aldehyde gives the final alcohol (IA). Alternatively the ketone B-10 is firstly prepared by treatment of the aldehyde with the hydrozone in the presence of a base such as cesium carbonate under reflux condition. Reduction of the ketone B-10 with a reducing agent gives a racemic mixture of the alcohol (IA). Further chiral separation yields single enantiomers.

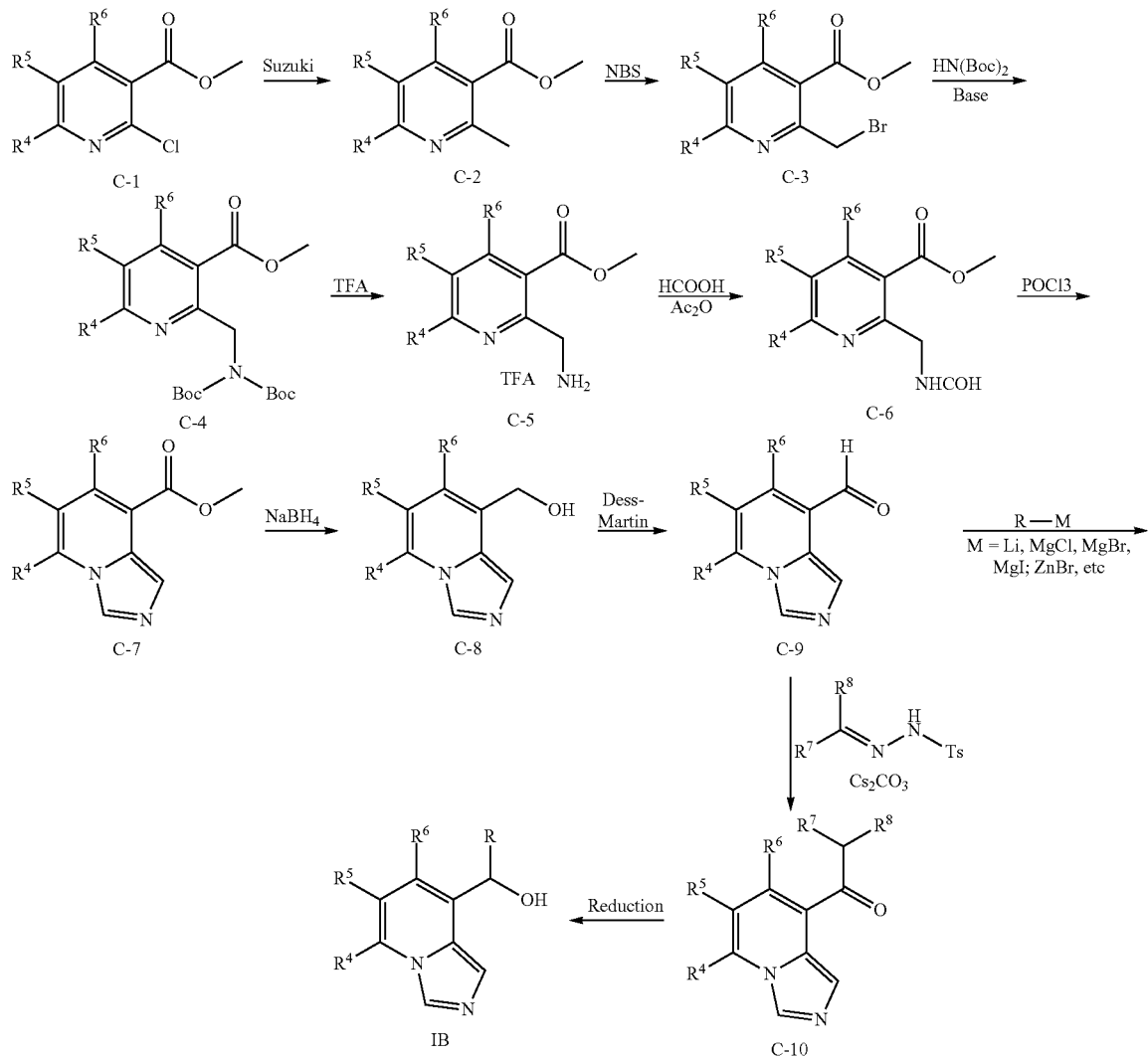

Scheme C wherein R corresponds to —(CR²R³)ₙ—Rᶜ in the case that R¹ is hydrogen

Compounds IB (R⁴, R⁵ and R⁶ are defined as above) can be prepared by a similar procedure. The commercially available Compound C-1 is converted into the 2-methyl-3-carboxylate ester C-2. Radical catalyzed bromo substitution at alpha position gives bromomethyl pyridine ester C-3. After replacement of bromo atom by bis-(Boc)amide, the resulting 2-bis(Boc)aminomethyl-3-carboxylate ester pyridine C-4 is treated with TFA to give the aminomethyl pyridine TFA salt C-5. The formamide C-6 is then prepared and further converted into imidazo[1,5-a]pyridine ester C-7 effected by treatment of POCl₃. Reduction of Compound C-7 gives the alcohol C-8 which undergoes Dess Martin or other oxidation reaction to yield the aldehyde C-9. Addition of Grignard reagent to the aldehyde gives the final alcohol (IB). Further chiral separation yields single enantiomers. Alternatively the ketone C-10 is firstly prepared by treatment of the aldehyde with the hydrozone in the presence of a base such as cesium carbonate under reflux condition. Reduction of the ketone C-10 with a reducing agent gives a racemic mixture of the alcohol (IIA). Further chiral separation yields single enantiomers.

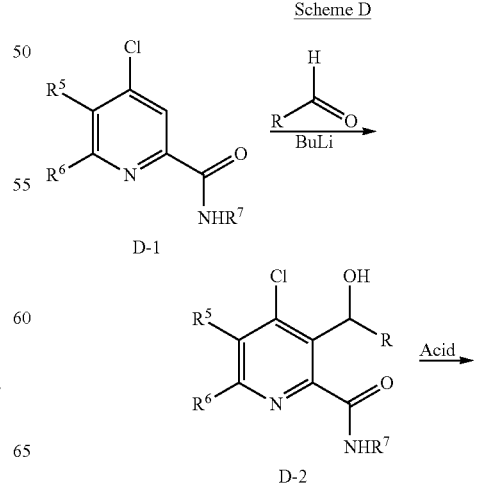

Scheme D

-continued

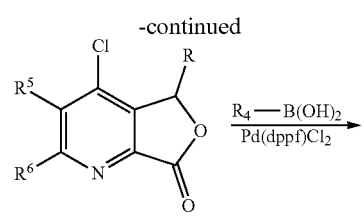

D-3

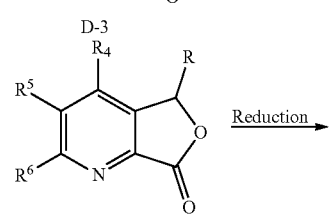

D-4

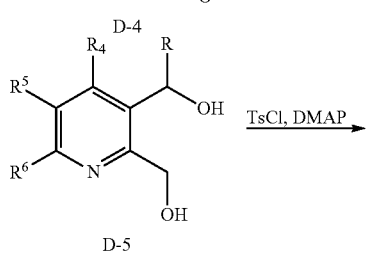

D-5

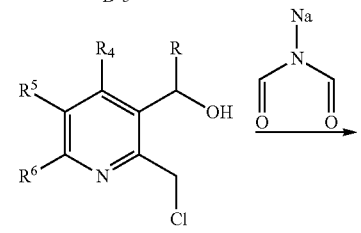

D-6

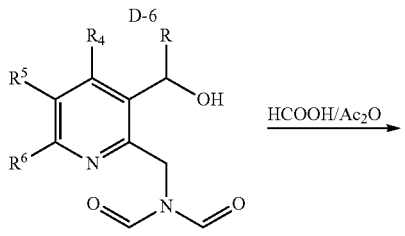

D-7

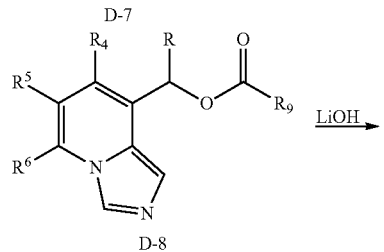

D-8

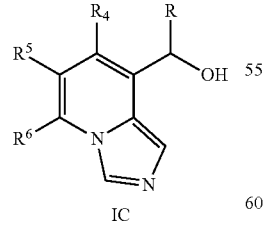

IC wherein
R[7] is a conventional amino protecting group;
R corresponds to —(CR$^2$R$^3$)$_n$—R$^C$ in the case that R$^1$ is hydrogen Compounds IC(R$^4$, R$^5$, and R$^6$ are defined as above) can be prepared by a similar procedure. The commercially available Compound D-1 is converted into the hydroxyl-methyl-4-chloro-amide D-2. Acid catalyzed cyclization lactone D-3. After replacement of chloride atom by alkyl or ring, the resulting lactone D-4 is treated with AlLiH$_4$ to give diol D-5. The primary alcohol was replaced with chloride to give D-6, and which was treated with sodium diformamide to give N-formylformamide compound D-7. The formamide D-7 is then cyclized with formic acid and acetic anhydride solvent to give D-8. The ester was hydrolysis with lithium hydrate to give racemic IC, which was separated with chiral HPLC or chiral acid to give single enantiomers.

Scheme E

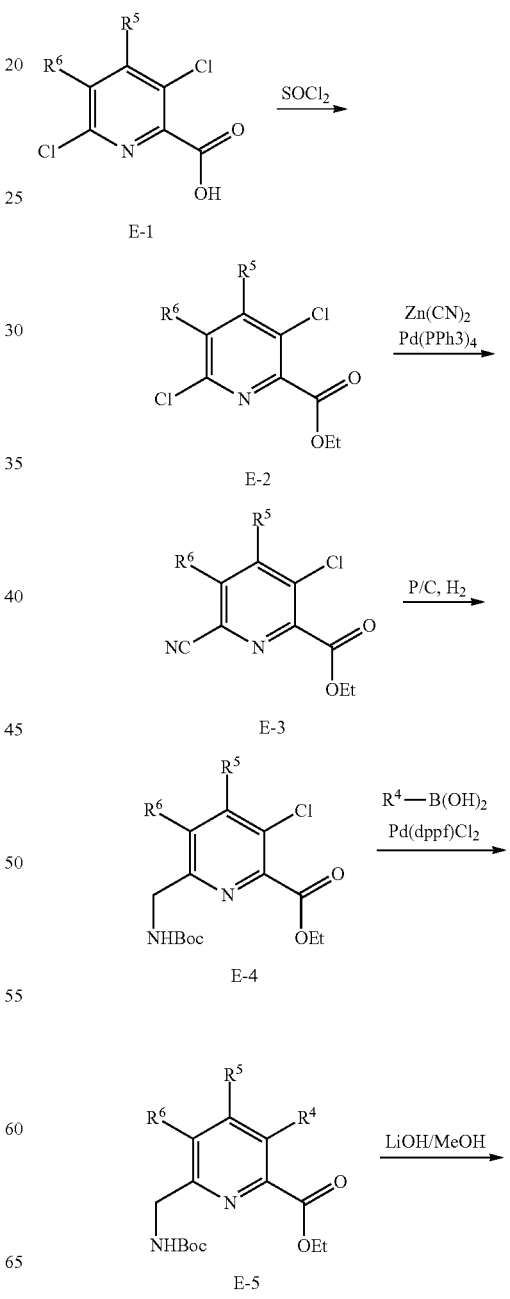

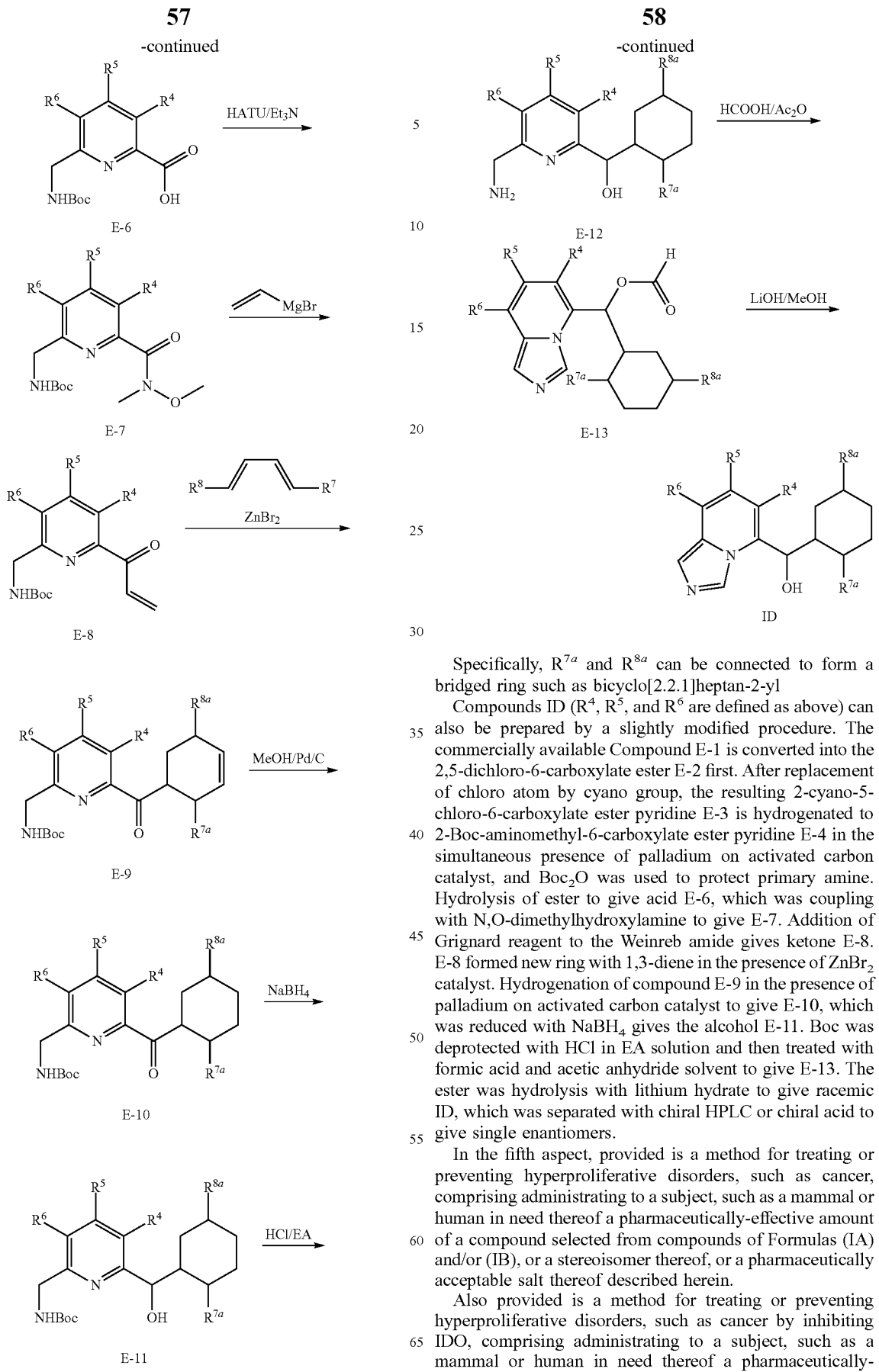

Specifically, $R^{7a}$ and $R^{8a}$ can be connected to form a bridged ring such as bicyclo[2.2.1]heptan-2-yl Compounds ID ($R^4$, $R^5$, and $R^6$ are defined as above) can also be prepared by a slightly modified procedure. The commercially available Compound E-1 is converted into the 2,5-dichloro-6-carboxylate ester E-2 first. After replacement of chloro atom by cyano group, the resulting 2-cyano-5-chloro-6-carboxylate ester pyridine E-3 is hydrogenated to 2-Boc-aminomethyl-6-carboxylate ester pyridine E-4 in the simultaneous presence of palladium on activated carbon catalyst, and $Boc_2O$ was used to protect primary amine. Hydrolysis of ester to give acid E-6, which was coupling with N,O-dimethylhydroxylamine to give E-7. Addition of Grignard reagent to the Weinreb amide gives ketone E-8. E-8 formed new ring with 1,3-diene in the presence of $ZnBr_2$ catalyst. Hydrogenation of compound E-9 in the presence of palladium on activated carbon catalyst to give E-10, which was reduced with $NaBH_4$ gives the alcohol E-11. Boc was deprotected with HCl in EA solution and then treated with formic acid and acetic anhydride solvent to give E-13. The ester was hydrolysis with lithium hydrate to give racemic ID, which was separated with chiral HPLC or chiral acid to give single enantiomers.

In the fifth aspect, provided is a method for treating or preventing hyperproliferative disorders, such as cancer, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof described herein.

Also provided is a method for treating or preventing hyperproliferative disorders, such as cancer by inhibiting IDO, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof described herein.

Also provided is a method for treating or preventing cancer including but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof described herein.

Also provided is a method for treating or preventing HIV/AIDS, comprising administrating to a subject, such as a mammal or human in need thereof a pharmaceutically-effective amount of a compound selected from compounds of Formulas (IA) and/or (IB), or a stereoisomer thereof, or a pharmaceutically acceptable salt thereof described herein.

Also provided is a method for enhancing the effectiveness of an anti-retroviral therapy, comprising administrating to a subject, such as a mammal or human in need thereof an anti-retroviral agent and a pharmaceutically-effective amount of a compound selected from compounds of Formulas (IA) and/or (IB), or a stereoisomer thereof, or a pharmaceutically acceptable salt thereof described herein.

Also provided herein is a method of treating cancer responsive to inhibition of IDO and/or TDO comprising administering to a subject, such as a mammal or human, in need of treating for the cancer a pharmaceutically-effective amount of a compound selected from compounds of (IA) or (IB), or a stereoisomer thereof, or a pharmaceutically acceptable salt thereof described herein, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma.

Also provided herein is a use of a compound selected from compounds of (IA) or (IB), or a stereoisomer thereof, or a pharmaceutically acceptable salt thereof described herein in the manufacture of a medicament for the treatment of cancer responsive to inhibition of IDO and/or TDO, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma.

Also provided herein is a compound selected from compounds of (IA) or (IB), or a stereoisomer thereof, or a pharmaceutically acceptable salt thereof described herein for use in the treatment of cancer responsive to inhibition of IDO and/or TDO, wherein the cancer includes but not limiting to, for example, melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of Billary Tract, Non-small-cell-lung cancer, endometrium cancer, blood cancer, large intestinal colon carcinoma, histiocytic lymphoma, lung adenocarcinoma.

The compound selected from compounds of Formulas (IA) and/or (IB), or a stereoisomer thereof, or a pharmaceutically acceptable salt thereof may be employed alone or in combination with at least one other therapeutic agent for treatment. In some embodiments, the compound selected from compounds of Formulas (IA) and/or (IB), or a stereoisomer thereof, or a pharmaceutically acceptable salt thereof can be used in combination with at least one additional therapeutic agent. The at least one additional therapeutics agent can be, for example, selected from anti-hyperproliferative, anti-cancer, and chemotherapeutic agents. The at least one compound and/or at least one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the at least one compound and/or at least one pharmaceutically acceptable salt disclosed herein.

A "chemotherapeutic agent" is a chemical compound useful in the treatment of cancer, regardless of mechanism of action. Chemotherapeutic agents include compounds used in "targeted therapy" and conventional chemotherapy. Suitable chemotherapeutic agents can be, for example, selected from: agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g., interferons, such as IFN-α and interleukins, such as IL-2); adoptive immunotherapy agents; hematopoietic growth factors; agents that induce tumor cell differentiation (e.g., all-trans-retinoic acid); gene therapy reagents; antisense therapy reagents and nucleotides; tumor vaccines; and inhibitors of angiogenesis.

Examples of chemotherapeutic agents include Erlotinib (TARCEVA®, Genentech/OSI Pharm.); Bortezomib (VELCADE®, Millennium Pharm.); Fulvestrant (FASLODEX®, AstraZeneca); Sunitinib (SUTENT®, Pfizer); Letrozole (FEMARA®, Novartis); Imatinib mesylate (GLEEVEC®, Novartis); PTK787/ZK 222584 (Novartis); Oxaliplatin (Eloxatin®, Sanofi); 5-FU (5-fluorouracil); Leucovorin; Rapamycin (Sirolimus, RAPAMUNE®, Wyeth); Lapatinib (TYKERB®, GSK572016, Glaxo Smith Kline); Lonafarnib (SCH 66336); Sorafenib (NEXAVAR®, Bayer); Irinotecan (CAMPTOSAR®, Pfizer) and Gefitinib (IRESSA®, AstraZeneca); AG1478, AG1571 (SU 5271, Sugen); Trametinib (GSK1120212); Selumetinib (AZD6244); Binimetinib (MEK162); Pimasertib; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines such as altretamine, triethylenemelamine, triethylenephosphoramide, triethylenethiophosphoramide and trimethylomelamine; acetogenins (such as bullatacin and bullatacinone); a camptothecin (such as the synthetic analog topotecan); bryostatin; callystatin; CC-1065 and its adozelesin, carzelesin and bizelesin synthetic analogs; cryptophycins (such as cryptophycin 1 and cryptophycin 8); dolastatin; duocarmycin and the synthetic analogs thereof, such as KW-2189 and CB1-TM1; eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, such as calicheamicin gammaII and calicheamicin omegaII (Angew Chem. Intl. Ed. Engl. (1994) 33:183-186); dynemicin, such as dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; and rogens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminol evulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ib and ronate; CPT-11; topoisomerase inhibitor RFS 2000; difluoromethylornithine (DMFO); retinoids such as retinoic acid; and pharmaceutically acceptable salts, acids and derivatives of any of the above.

The "chemotherapeutic agent" can also be selected, for example, from: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY 117018, onapristone, and FARESTON® (toremifine citrate); (ii) aromatase inhibitors that inhibit the enzyme aromatase, which regulates estrogen production in the adrenal gl and s, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti- and rogens such as flutamide, nilutamide, bicalutamide, leuprolide, and goserelin; as well as troxacitabine (a 1,3-dioxolane nucleoside cytosine analog); (iv) protein kinase inhibitors such as MEK1/2 inhibitors, for example, trametinib, selumetinib, pimasertib and GDC-0973; (v) lipid kinase inhibitors; (vi) antisense oligonucleotides, such asthose which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and $HER^2$ expression inhibitors; (viii) anti-retroviral protease inhibitors, such as lopinavir, indinavir, nelfinavir, amprenavir, darunavir and atazanavir; (ix) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (x) anti-angiogenic agents such as bevacizumab (AVASTIN®, Genentech); and (xi) pharmaceutically acceptable salts, acids and derivatives of any of the above.

The "chemotherapeutic agent" can also be selected, for example, from therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the compound selected from compounds of Formulas (IA) and/or (IB) or (IV), stereoisomers thereof, and pharmaceutically acceptable salt thereofmay, for example, be selected from: alemtuzumab, apolizumab, aselizumab, atlizumab, bapineuzumab, bevacizumab, BGB-A317, BGB-A333, bivatuzumab mertansine, cantuzumab mertansine, cedelizumab, certolizumab pegol, cidfusituzumab, cidtuzumab, daclizumab, eculizumab, efalizumab, elotuzumab, epratuzumab, erlizumab, felvizumab, fontolizumab, gemtuzumab ozogamicin, inotuzumab ozogamicin, ipilimumab, labetuzumab, lintuzumab, mpdl3280A, matuzumab, medi4736, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, Pembroluzima, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tremelizumab, tucotuzumab celmoleukin, tucusituzumab, umavizumab, urtoxazumab, and visilizumab.

In the sixth aspect, provided is a pharmaceutical composition comprising a compound selected from compounds of Formulas (IA) and/or (IB), or a stereoisomer thereof, or a pharmaceutically acceptable salt thereof described herein and pharmaceutically-acceptable carriers, diluents, or adjuvants.

Also provided herein is a composition comprising a compound selected from compounds of Formulas (IA) and/or (IB), or a stereoisomer thereof, or a pharmaceutically acceptable salt thereof, and at least one pharmaceutically acceptable carrier.

The composition comprising a compound selected from compounds of Formulas (IA) and/or (IB), or a stereoisomer thereof, or a pharmaceutically acceptable salt thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The compound selected from Formulas (IA) and/or (IB), or a stereoisomer thereof, or a pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The compound selected from compounds of Formulas (IA) and/or (IB), or a stereoisomer thereof, or a pharmaceutically acceptable salt thereof disclosed herein can also be administered parenterally, in sterile liquid dosage forms, such as dispersions, suspensions or solutions. Other dosages forms that can also be used to administer the compound selected from Formulas (IA) and/or (IB), or a stereoisomer thereof, or a pharmaceutically acceptable salt thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the at least one compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene gycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in Remington's Pharmaceutical Sciences, A. Osol, a standard reference text in the art.

The compound selected from compounds of Formulas (IA) and/or (IB), or a stereoisomer thereof, or a pharmaceutically acceptable salt thereof disclosed herein can further be examined for efficacy in treating cancer by in vivo assays. For example, the at least one compound and/or the at least one pharmaceutically acceptable salts thereof disclosed herein can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the compound selected from compounds of Formulas (IA) and/or (IB), or a stereoisomer thereof, or a pharmaceutically acceptable salt thereof disclosed herein may be conveniently delivered in the form of an aerosol spray presentation from pressurized packs or nebulisers. The compound selected from compounds of Formulas (IA) and/or (IB), or a stereoisomer thereof, or a pharmaceutically acceptable salt thereof disclosed herein may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of a compound selected from compounds of Formulas (IA) and/or (IB), or a stereoisomer thereof, or a pharmaceutically acceptable salt thereof disclosed herein in at least one suitable propellant, selected, for example, from fluorocarbons and hydrocarbons.

For ocular administration, an ophthalmic preparation may be formulated with an appropriate weight percentage of a solution or suspension of the compound selected from compounds of Formulas (IA) and/or (IB), or a stereoisomer thereof, or a pharmaceutically acceptable salt thereof disclosed herein in an appropriate ophthalmic vehicle, such that the compound selected from compounds of Formulas (IA) and/or (IB), stereoisomers thereof, and at least one pharmaceutically acceptable salts thereof disclosed herein is maintained in contact with the ocular surface for a sufficient time period to allow the compound to penetrate the corneal and internal regions of the eye.

Useful pharmaceutical dosage-forms for administration of the compound selected from compounds of Formulas (IA) and/or (IB), or a stereoisomer thereof, or a pharmaceutically acceptable salt thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the compound selected from compounds of Formulas (IA) and/or (IB), stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound selected from compounds of Formulas (IA) and/or (IB), or a stereoisomer thereof, or a pharmaceutically acceptable salt thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound selected from compounds of Formulas (IA) and/or (IB), or a stereoisomer thereof, or a pharmaceutically acceptable salt thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the at least one compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided a compound selected from compounds of Formulas (IA) and/or (IB), or a stereoisomer thereof, or a pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound selected from compounds of Formulas (IA) and/or (IB), or a stereoisomer thereof, or a pharmaceutically acceptable salt thereof are administered stepwise or in conjunction with at least one other therapeutic agent. When drugs are administered in physical combination, the dosage form and administration route should be selected depending on the compatibility of the combined drugs. Thus the term "coadministration" is understood to include the administration of at least two agents concomitantly or sequentially, or alternatively as a fixed dose combination of the at least two active components.

The compound selected from compounds of Formulas (IA) and/or (IB), stereoisomers thereof, and pharmaceutically acceptable salt thereof disclosed herein can be administered as the sole active ingredient or in combination with at least one second active ingredient, selected, for example, from other active ingredients known to be useful for treating cancers in a patient.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^1$H NMR spectra were recorded on a Varian instrument operating at 400 MHz. $^1$H-NMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_2CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz). All compound names except the reagents were generated by ChemDraw version 12.0.

In the following examples, the abbreviations below are used:

AcOH Acetic acid
Aq Aqueous
Brine Saturated aqueous sodium chloride solution
Bn Benzyl
BnBr Benzyl Bromide
$CH_2Cl_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol Et₂O or ether Diethyl ether
g Grams
h or hr Hour
HATU O-(7-Azabenzotriazol-1-yl)-N,N,N',N'-tetramethyluronium hexafluorophosphate
HCl Hydrochloric acid
HPLC High-performance liquid chromatography
IPA 2-propanol
i-PrOH Isopropyl alcohol
mg Milligrams
mL Milliliters
Mmol Millimole
MeCN Acetonitrile
MeOH Methanol
Min Minutes
ms or MS Mass spectrum
Na₂SO₄ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THF Tetrahydrofuran
TLC thin layer chromatography
μL Microliters Example A: Synthesis of 5-Substituted imidazo[1,5-a]pyridines Example A001: Cyclohexyl(imidazo[1,5-a]pyridine-5-yl)methanol

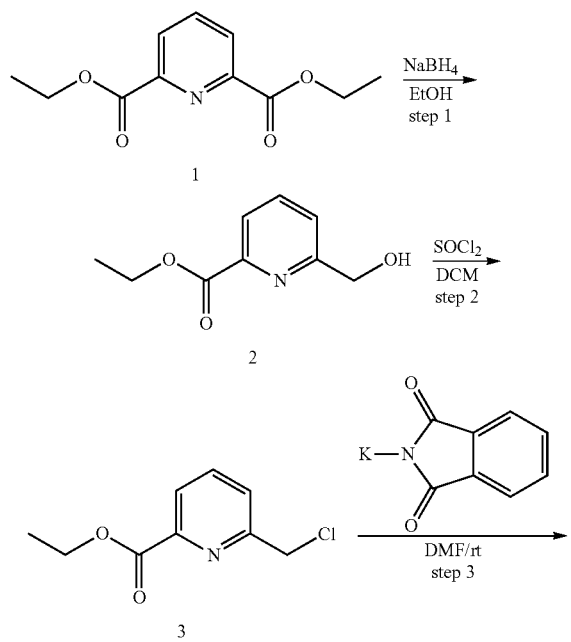

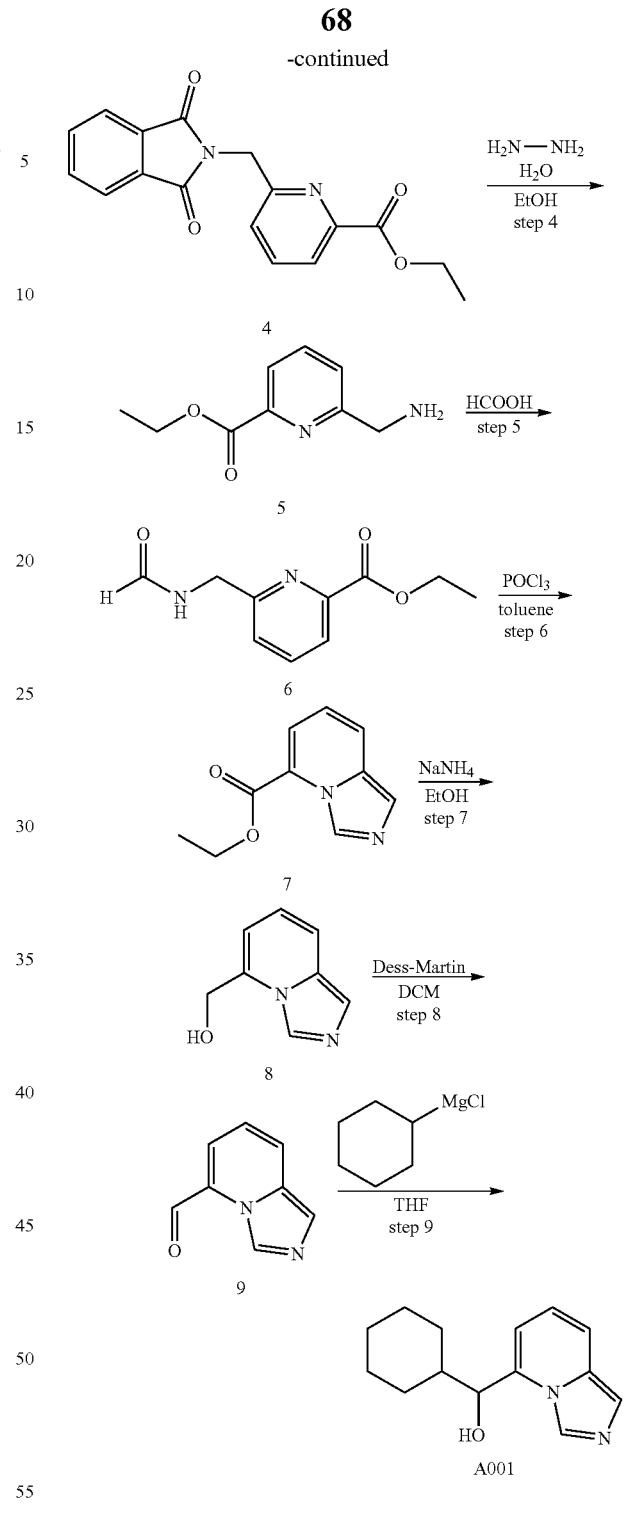

Step 1: Ethyl 6-(hydroxymethyl)picolinate 2,6-Pyridine dicarboxylic acid diethyl eater (27.9 g, 0.125 mol) and NaBH₄ (3.8 g, 0.1 mol) were dissolved in dry THF (250 mL) and refluxed for 2 h under moisture protection. The solvent was removed and water (50 mL) was added. After stirring for 10 min, the mixture was extracted with EA (200 mL*2). The organic phases were combined and dried over MgSO₄, and the solvent was evaporated under reduced pressure. The residue was purified by flash chromatography on silica gel with PE/EA=1:1 to give the product as colorless solid (28 g in 41% yield). $^1$H NMR (DMSO-$d_6$) 8.00 (t, 1H, J=7.6 Hz), 7.91 (d, 1H, J=7.2 Hz), 7.71 (d, 1H, J=7.6 Hz), 5.56 (t, 1H, J=6.0 Hz), 4.62 (d, 2H, J=6.0 Hz), 4.34 (q, 2H, J=7.2 Hz), 1.33 (d, 3H, J=7.2 Hz).

Step 2: Ethyl 6-(chloromethyl)picolinate

Thoroughly dried 6-(hydroxymethyl) pyridine-2-carboxylic acid ethyl ester (28 g, 154 mmol) was dissolved in DCM (400 mL) was added dropwise of $SOCl_2$ (56 mL) at 0° C. After 90 min the solution was allowed to reach room temperature and the excess of $SOCl_2$ was removed under reduced pressure without heating. DCM (500 mL) was added to the oily residue, and the solution was washed with saturated aqueous of $NaHCO_3$ and dried over $Na_2SO_4$. Evaporation of the solvent afforded 2-(chloromethyl)pyridine-6-carboxylic acid ethyl ester (31 g in 100% yield) as an orange oil. $^1$H NMR (DMSO-$d_6$) 8.01-8.08 (m, 2H), 7.81 (d, 1H, J=7.2 Hz), 4.86 (s, 2H), 4.37 (q, 2H, J=6.0 Hz), 1.34 (t, 3H, J=7.2 Hz).

Step 3: Ethyl 6-((1,3-dioxoisoindolin-2-yl)methyl)picolinate 2-(Chloromethyl)pyridine-6-carboxylic acid ethyl ester (59 g, 270 mmol) in anhydrous DMF (210 mL) was slowly added sodium phthalimide (54 g, 320 mmol) at room temperature and the mixture was stirred overnight. Then the reaction mixture was centrifuged, the solvent was removed under reduced pressure, and the residue was suspended in $H_2O$ (200 mL) and EA (300 mL), then filtered to give crude product as a white solid. (74 g in 88% yield). $^1$H NMR (DMSO-$d_6$) δ 7.88-7.96 (m, 6H), 7.64 (dd, 1H, J=7.2 Hz), 4.98 (s, 2H), 4.24 (q, 2H, J=6.4 Hz), 1.17 (t, 3H, J=7.2 Hz).

Step 4: Ethyl 6-(aminomethyl)picolinate

To a solution of ethyl 6-((1,3-dioxoisoindolin-2-yl) methyl) picolinate (80 g, 258 mmol) in EtOH (1000 mL) was added Hydrazine hydrate (13 mL, 98%) at room temperature and the mixture was heated at 80° C. for 2 h. Then cooled to room temperature, filtered to remove the white precipitate and HCOOH (400 mL) was added to the filtrate, filtered again to remove white precipitate and the filtrate was evaporated under reduced pressure to give crude product as an oil containing HCOOH, and this crude product was used for next step without further purification.

Step 5: Ethyl 6-(formamidomethyl)picolinate

A solution of crude ethyl 6-(aminomethyl)picolinate (258 mmol) in HCOOH (500 mL) was heated at 80° C. for 4 hours. Then cooled to room temperature and evaporated the solvent under reduced pressure before HCl (500 mL, 1N) was added to the residue. Then extracted with EA (200 mL), the aqueous layer was adjust pH=7-8 with saturated aqueous of NaOH, then extracted with EA (500 mL*2), combined the organic layer, dried over $Na_2SO_4$, the filtered to remove $Na_2SO_4$, evaporated the solvent under reduced pressure to give a crude product as yellow oil (23 g in 40% yield for last two steps). And this crude product was used for next step without further purification.

Step 6: Ethyl imidazo[1,5-a]pyridine-5-carboxylate

To a solution of ethyl 6-(formamidomethyl)picolinate (23 g, 110 mmol) in toluene (400 mL) was added $POCl_3$ (23 mL) at room temperature and the mixture was heated at 80° C. for 2 hours. Then cooled to room temperature and evaporated the solvent under reduced pressure before HCl (400 mL, 1N) was added to the residue, extracted with EA (200 mL*2), isolated the aqueous layer, adjusted pH=7-8 with saturated aqueous of NaOH before extracted with EA (400 mL*2), combined the organic layers, evaporated the solvent under reduced pressure to give crude solid (13 g in 62% yield) as a brown solid. $^1$H NMR (DMSO-$d_6$) δ 9.13 (s, 1H), 7.98 (d, 1H, J=8.8 Hz), 7.67 (s, 1H), 7.64 (dd, 1H, J=6.8 Hz), 4.24 (q, 2H, J=6.4 Hz), 1.39 (t, 3H, J=7.2 Hz).

Step 7: Imidazo[1,5-a]pyridin-5-ylmethanol

To a solution of ethyl imidazo[1,5-a]pyridine-5-carboxylate (36 g, 189 mmol) in EtOH (1 L) was added batch wise of $NaBH_4$ (14.3 g, 379 mmol) at 80° C. and the mixture was stirred at 80° C. for 1 h. Then evaporated the solvent under reduced pressure and water (100 mL) was added to the residue, extracted with EA (400 mL*2), combined the organic layer, dried over $Na_2SO_4$, filtered to remove the solid, the filtrate was evaporated under reduced pressure to give crude product (27.9 g) and this crude product was used for next step without further purification. $^1$H NMR (DMSO-$d_6$) δ 8.33 (s, 1H), 7.53 (d, 1H, J=8.8 Hz), 7.79-6.83 (m, 1H), 6.68 (dd, 1H, J=6.4 Hz), 5.73 (s, 1H), 4.76 (s, 2H).

Step 8: Imidazo[1,5-a]pyridin-5-ylmethanol

To a solution of imidazo[1,5-a]pyridin-5-ylmethanol (17 g, 115 mmol) in DCM (1 L) was added portion of Dess-Martin (59 g, 1.2 eq) at room temperature and the mixture was stirred for 5 hours before saturated aqueous of $NaHCO_3$ was added slowly to adjust pH=6-7, isolated the organic layer, $H_2O$ (500 mL) was added, followed by addition of conc.HCl to adjust pH=2-3, isolated the aqueous layer, $Na_2CO_3$ was added to adjust to pH=7-8, extracted with EA (500 mL*2), combined the organic layer, evaporated the solvent under reduced pressure to give a crude product, 10 g in 60% yield. $^1$H NMR (DMSO-$d_6$) δ 9.95 (s, 1H), 9.32 (s, 1H), 8.11 (d, 1H, J=9.2 Hz), 7.78 (dd, 1H, J=6.4 Hz), 7.75 (s, 1H), 7.10 (dd, 1H, J=8.8 Hz).

Step 9: Cyclohexyl(imidazo[1,5-a]pyridin-5-yl) methanol

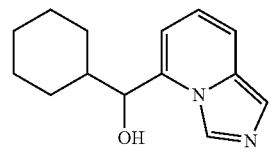 [SMILES: OC(c1cccc2cncn12)C1CCCCC1]

To a solution of imidazo[1,5-a]pyridine-5-carbaldehyde (1.46 g, 10 mmol) in dry THF (200 mL) was added drop wise of cyclohexylmagnesium chloride (10 mL, 2M) at 0° C. under $N_2$ air balloon protected. And the mixture was stirred warmed to room temperature slowly for 2 hours. Water (100 mL) was added to the mixture and extracted with EA (100 mL*2), combined the organic layers and dried over $Na_2SO_4$, filtered to remove $Na_2SO_4$ and the filtrate was concentrated, the crude product was purified by column chromatography (PE/EA=3:2 as eluent) to give 1.4 g in 61% yield. $^1$H NMR (DMSO-$d_6$) δ 8.48 (s, 1H), 7.48 (d, 1H, J=6.8 Hz), 7.40 (s, 1H), 6.78 (dd, 1H, J=8.8 Hz), 6.60 (d, 1H, J=6.4 Hz), 5.71

(d, 1H, J=4.4 Hz), 4.61 (dd, 1H, J=6.8 Hz), 1.87 (m, 2H), 1.70 (m, 1H), 1.60 (m, 2H), 1.87 (m, 2H), 1.31 (m, 1H), 1.11 (m, 5H).

Examples A001a and A001b: (S)-cyclohexyl(imidazo[1,5-a]pyridin-5-yl)methanol compound and (R)-cyclohexyl(imidazo[1,5-a]pyridin-5-yl)methanol

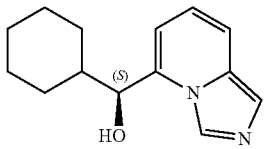

A001a

Fast isomer in chiral AD HPLC
Eluting reagent: CO$_2$/MeOH = 75/25 (V/V)

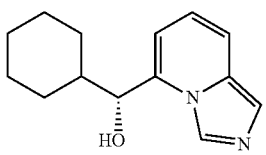

A001b

Slow isomer in chiral AD HPLC
Eluting reagent: CO$_2$/MeOH = 75/25 (V/V)

Each enantiomer of racemic A001a and A001b was separated using preparative HPLC on a Chiralpak AD with 25% Methanol/Carbon dioxide as an eluent. The enantiomeric excesses were determined by using HPLC on a Chiralpak AD with 25% Methanol/Carbon dioxide as an eluent at a flow rate of 2.0 mL/min. The first one enantiomer eluted at the retention time of 4.8 min, and the other enantiomer eluted at the retention time of 6.9 min. The spectral properties of the title compounds were identical with those of 1.1. The absolute configurations of A001a and A001b are tentatively assigned as (S) and (R) respectively based on assumption that the binding model of the more potent isomer A001a is the same as that of A101a with IDO1 enzyme.

Examples A002 to A008 were synthesized from imidazo[1,5-a]pyridine-5-carbaldehyde and the corresponding Grignard reagent by following the procedures similar to those as described in Example A001.

Example A002: cyclopentyl(imidazo[1,5-a]pyridin-5-yl)methanol

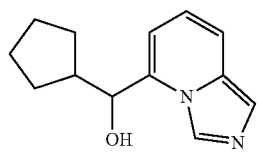 [SMILES: OC(c1cccc2cncn12)C1CCCC1]

$^1$H NMR (DMSO-d$_6$) δ 8.52 (s, 1H), 7.51 (d, 1H, J=9.2 Hz), 7.43 (s, 1H), 6.82 (m, 1H), 6.67 (d, 1H, J=6.4 Hz), 5.75 (d, 1H, J=5.2 Hz), 4.64 (dd, 1H, J=5.2 Hz), 1.02-1.73 (m, 9H).

Example A003: cyclopropyl(imidazo[1,5-a]pyridin-5-yl)methanol

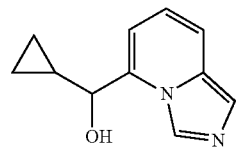 [SMILES: OC(c1cccc2cncn12)C1CC1]

$^1$H NMR (DMSO-d$_6$) δ 8.52 (s, 1H), 7.55 (d, 1H, J=8.8 Hz), 7.44 (s, 1H), 6.81 (m, 2H), 5.73 (d, 1H, J=5.6 Hz), 4.33 (dd, 1H, J=6.0 Hz), 1.42 (m, 1H), 0.61 (m, 1H), 0.48 (m, 2H), 0.36 (m, 1H).

Example A004: 1-(imidazo[1,5-a]pyridin-5-yl)-2,2-dimethylpropan-1-ol

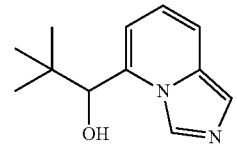

$^1$H NMR (DMSO-d$_6$) δ 8.68 (s, 1H), 7.46-7.48 (m, 1H), 7.37 (s, 1H), 6.78-6.81 (m, 1H), 6.59-6.61 (m, 1H), 5.73-5.74 (m, 1H), 4.81-4.82 (m, 1H), 0.93 (s, 9H). MS (ESI) m/e [M+1]$^+$205.

Example A005: 1-(imidazo[1,5-a]pyridin-5-yl)-2-methylpropan-1-ol

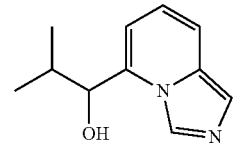

$^1$H NMR (DMSO-d$_6$) δ 8.53 (s, 1H), 7.48-7.50 (m, 1H), 7.41 (s, 1H), 6.77-6.79 (m, 1H), 6.63-6.64 (m, 1H), 5.82-5.83 (m, 1H), 4.65-4.68 (m, 1H), 3.75-3.80 (m, 2H), 3.17-3.20 (m, 1H), 2.10-2.12 (m, 1H), 1.68-1.72 (m, 1H), 1.32-1.38 (m, 1H), 1.12-1.16 (m, 1H). MS (ESI) m/e [M+1]$^+$233.

Example A006: 1-(imidazo[1,5-a]pyridin-5-yl)prop-2-yn-1-ol

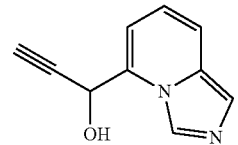

$^1$H NMR (DMSO-d$_6$) 8.45 (s, 1H), 7.60 (d, 1H, J=8.8 Hz), 7.48 (s, 1H), 6.88 (m, 2H), 6.59 (d, 1H, J=6.0 Hz), 5.82 (m, 1H), 3.68 (s, 1H).

Example A007: imidazo[1,5-a]pyridin-5-yl(phenyl)methanol

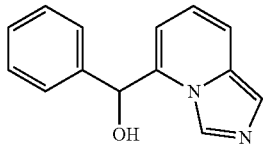 [SMILES: OC(c1ccccc1)c1cccc2cncn12]

$^1$H NMR (DMSO-d$_6$) δ 8.27 (s, 1H), 7.49-7.55 (m, 3H), 7.30-7.39 (m, 5H), 6.85 (t, 1H, J=7.2 Hz), 6.69 (d, 1H, J=6.0 Hz), 6.48 (d, 1H, J=4.4 Hz), 6.08 (d, 1H, J=4.4 Hz).

Example A008: (4-fluorophenyl)(imidazo[1,5-a]pyridin-5-yl)methanol

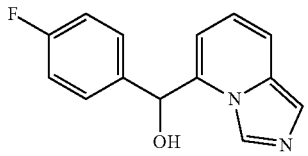 [SMILES: OC(c1ccc(F)cc1)c1cccc2cncn12]

$^1$H NMR (DMSO-d$_6$) δ 8.29 (s, 1H), 7.52-7.56 (m, 3H), 7.41 (s, 1H), 7.19 (t, 2H, J=8.8 Hz), 6.84 (dd, 1H, J=8.8 Hz), 6.66 (d, 1H, J=6.4 Hz), 6.57 (m, 1H), 6.09 (d, 1H, J=4.4 Hz).

Example A009: Cycloheptyl(imidazo[1,5-a]pyridin-5-yl)methanol

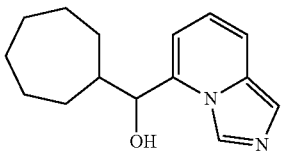 [SMILES: OC(c1cccc2cncn12)C1CCCCCC1]

Under N$_2$ atmosphere, Mg (2.4 g, 10 mmol) and I$_2$ (100 mg) was suspended on THF was dropwisely bromocycloheptane (1.0 mmol), when reaction caused, dropwisely bromocy cloheptane (9.0 mmol) under 50° C., the mixture was stirred at RT for 2 hours to give cycloheptylmagnesium bromide.

To a solution of imidazo[1,5-a]pyridine-5-carbaldehyde (146 mg, 1 mmol) in THF (20 mL) was added dropwise cycloheptylmagnesium bromide (4 mmol) at 0° C. for 10 minutes. The mixture was quenched with aqueous NH$_4$Cl (50 mL) and EA (50 mL), washed with brine (50 mL), dried over Na$_2$SO$_4$ and concentrated. The residue was purified by Pre-TLC to give yellow solid (W=20 mg). $^1$H NMR (DMSO-d$_6$) δ 8.46 (s, 1H), 7.48-7.50 (m, 1H), 7.41 (s, 1H), 6.78-6.82 (m, 1H), 6.63-6.65 (m, 1H), 5.71-5.72 (m, 1H), 4.63-4.66 (m, 1H), 1.98-2.02 (m, 1H), 1.32-1.79 (m, 13H). MS (ESI) m/e [M+1]$^+$245.

Example A010: imidazo[1,5-a]pyridin-5-yl(tetrahydro-2H-pyran-4-yl)methanol

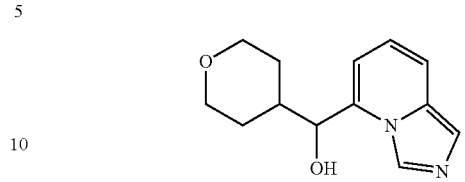

Example A010 was synthesized from imidazo[1,5-a]pyridine-5-carbaldehyde and 4-bromotetrahydro-2H-pyran by following the procedures similar to those in Example A009.
$^1$H NMR (DMSO-d$_6$) δ 8.46 (s, 1H), 7.48-7.50 (m, 1H), 7.41 (s, 1H), 6.78-6.82 (m, 1H), 6.63-6.64 (m, 1H), 5.71-5.72 (m, 1H), 4.59-4.61 (m, 1H), 2.14-2.19 (m, 1H), 0.95 (d, 3H, J=6.4 Hz), 0.84 (d, 3H, J=6.4 Hz). MS (ESI) m/e [M+1]$^+$ 191.

Example A013: Imidazo[1,5-a]pyridin-5-yl(piperidin-4-yl)methanol hydrochloride

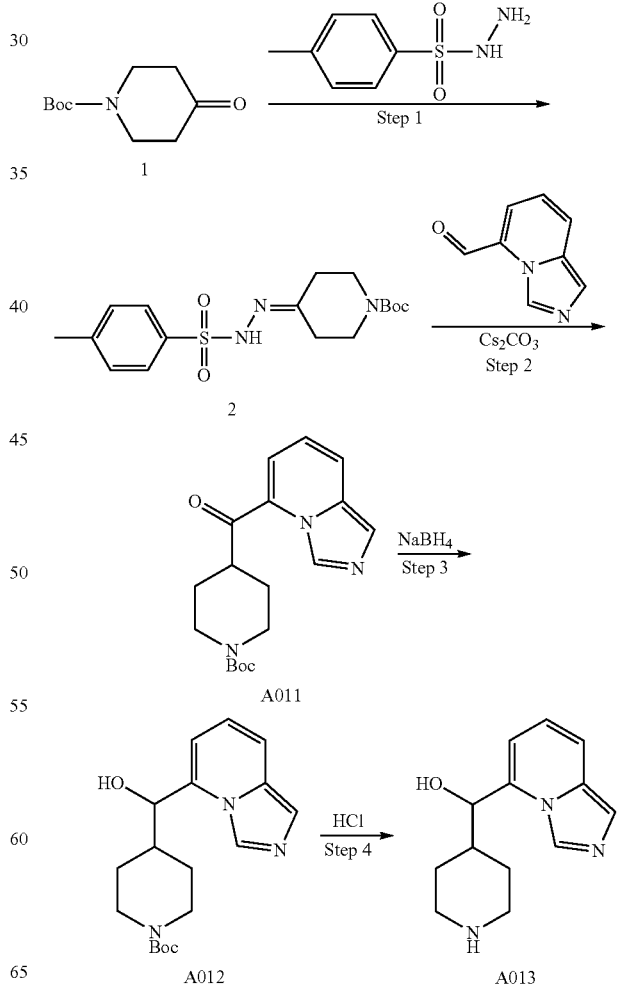

Step 1. Tert-butyl 4-(2-tosylhydrazono)piperidine-1-carboxylate

Tert-butyl 4-oxopiperidine-1-carboxylate (3.98 g, 20 mmol) and 4-methylbenzenesulfono-hydrazide (3.92 g, 20 mmol) were suspended on MeOH (50 mL), the mixture was stirred at RT for overnight. Then the solvent was removed by reduce pressure to give white solid as product without any purification. (W=7.4 g). MS (ESI) m/e [M+1]$^+$368

Step 2. Tert-butyl 4-(imidazo[1,5-a]pyridine-5-carbonyl)piperidine-1-carboxylate 1-(Imidazo[1,5-a]pyridin-5-yl)-2-methylpropan-1-ol (146 mg, 1 mmol), tert-butyl 4-(2-tosylhydrazono)piperidine-1-carboxylate (367 mg, 1 mmol) and Cs$_2$CO$_3$ (487.5, 1.5 mmol) were suspended on 1,4-dioxane (100 mL), the mixture was refluxed for 5 hours, then the mixture was quenched with EA (100 mL) and brine (50 mL), the organic layer was dried over Na$_2$SO$_4$ and concentrated. The residue was purified by chromatography on silica gel (elute with EA/petroleum ether=1:10 to 1:0) to give Example A011 (yellow oil, w=80 mg). $^1$H NMR (DMSO-d$_6$) δ 9.42 (s, 1H), 8.05-8.08 (m, 2H), 7.69 (s, 1H), 6.98-7.01 (m, 1H), 4.00-4.04 (m, 2H), 3.74-3.77 (m, 1H), 2.93 (m, 2H), 1.81-1.84 (m, 2H), 1.38-1.50 (m, 12H). MS (ESI) m/e [M+1]$^+$330

Step 3. Tert-butyl 4-(hydroxy(imidazo[1,5-a]pyridin-5-yl)methyl)piperidine-1-carboxylate To a solution of tert-butyl 4-(imidazo[1,5-a]pyridine-5-carbonyl)piperidine-1-carboxylate (75.80 mg, 0.23 mmol) in MeOH (5 mL) was added NaBH$_4$ (44 mg, 1.15 mmol), the mixture was stirred at RT for 3 hours, The solvent was removed by reduce pressure. The residue was purified by Pre-TLC to give Example A012 (W=60 mg). $^1$H NMR (DMSO-d$_6$) 8.51 (s, 1H), 7.48-7.50 (m, 1H), 741 (s, 1H), 6.77-6.79 (m, 1H), 6.63-6.64 (m, 1H), 4.66-4.69 (m, 1H), 3.90-4.02 (m, 2H), 2.50-2.51 (m, 2H), 1.99-2.04 (m, 1H), 1.75 (m, 1H), 1.20-1.38 (m, 12H). MS (ESI) m/e [M+1]$^+$332

Step 4. Imidazo[1,5-a]pyridin-5-yl(piperidin-4-yl)methanol hydrochloride

Tert-butyl 4-(hydroxy(imidazo[1,5-a]pyridin-5-yl)methyl)piperidine-1-carboxylate (50 mg) was suspended on HCl (gas)/EtOH, then stirred at RT for 3 hours, then the solvent was removed by reduce pressure to give Example A013 (w=41 mg). $^1$H NMR (CD$_3$OD-d$_4$) δ 9.69 (s, 1H), 8.09 (s, 1H), 7.08 (m, 1H), 7.17-7.29 (m, 2H)), 4.8 (m, 1H), 3.28-3.31 (m, 2H), 2.87-2.95 (m, 2H), 2.18-2.33 (m, 2H), 1.63-1.67 (m, 3H). MS (ESI) m/e [M+1]$^+$232.

Example A014: Imidazo[1,5-a]pyridin-5-yl(1-methylpiperidin-4-yl)methanol

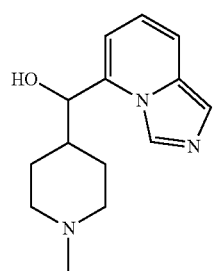

Imidazo[1,5-a]pyridin-5-yl(piperidin-4-yl)methanol hydrochloride (30 mg, 0.13 mmol) and 40% aqueous HCHO (0.1 mL) was suspended on THF/Et$_3$N (5 mL/0.1 mL), the mixture was stirred at RT for overnight. Then Sodium triacetoxyborohydride (49 mg, 0.26 mmol) was added, the mixture was stirred at RT for 3 hours. The mixture was quenched with EA/H$_2$O (50 mL/50 mL) the organic layer was dried over Na$_2$SO$_4$ and concentrated. The residue was purified by Pre-TLC to give Example A014 (w=6.0 mg). $^1$H NMR (CD$_3$OD-d$_4$) δ 8.77 (s, 1H), 7.48-7.49 (m, 2H), 6.73-6.88 (m, 2H)), 4.8 (m, 1H), 3.20-3.35 (m, 2H), 2.73-2.89 (m, 2H), 2.45 (s, 3H), 1.92-2.08 (m, 2H), 0.81-1.75 (m, 4H). MS (ESI) m/e [M+1]$^+$246.

Example A015: 5-(cyclohexylmethyl)imidazo[1,5-a]pyridine

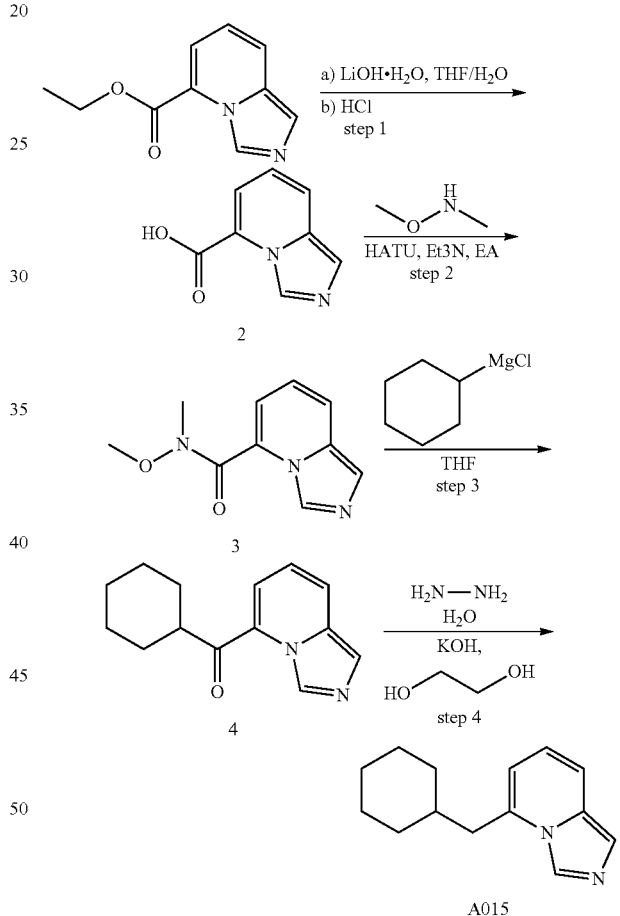

Step 1: imidazo[1,5-a]pyridine-5-carboxylic acid

To a solution of ethyl imidazo[1,5-a]pyridine-5-carboxylate (2.0 g, 10.5 mmol, Compound of Step 6 in Example A001) in a mixture of THF (20 mL) and water (5 mL) was added lithium hydroxide hydrate (881 mg, 2 eq) at room temperature and the mixture was stirred overnight. Evaporated the solvent under reduced pressure and water (80 mL) was added to the residue and adjust pH=6-7 with HCl (4 N) and the yellow precipitate was collected by filtration to give 1.1 g in 65% yield. ¹H NMR (DMSO-d₆) δ 9.20 (s, 1H), 7.90 (d, 1H, J=9.2 Hz), 7.61 (s, 1H), 7.57 (dd, 1H, J=6.8 Hz), 6.90 (dd, 1H, J=9.2 Hz).

Step 2: N-methoxy-N-methylimidazo[1,5-a]pyridine-5-carboxamide

To a solution of imidazo[1,5-a]pyridine-5-carboxylic acid (0.5 g, 3.1 mmol) in EA (250 mL) and added Et₃N (1.26 g, 4 eq), HATU (2.4 g, 2 eq) and the mixture was stirred for 15 minutes before N,O-dimethylhydroxylamine (302 mg, 1 eq) was added and the mixture was stirred overnight. Water (50 mL) was added and isolated the organic layer, washed with brine (50 mL*3), dried over Na₂SO₄, filtered to remove Na₂SO₄ and the filtrate was evaporated under reduced pressure to give crude product and the crude product was used for next step without further purification. ¹H NMR (DMSO-d₆) δ 8.35 (s, 1H), 7.71 (d, 1H, J=9.2 Hz), 7.50 (s, 1H), 7.01 (dd, 1H, J=6.8 Hz), 6.85 (d, 1H, J=9.2 Hz), 3.62 (s, 3H), 3.38 (s, 3H).

Step 3: cyclohexyl(imidazo[1,5-a]pyridin-5-yl)methanone

To a solution of N-methoxy-N-methylimidazo[1,5-a]pyridine-5-carboxamide (150 mg, 0.73 mmol) in dry THF (20 mL) was added drop wise of cyclohexylmagnesium chloride (1.5 mL, 2 M) at −70° C. under N₂ air balloon protected and the mixture was stirred for 2 hours before water (20 mL) was added and extracted with EA (20 mL*2), combined the organic layers, dried over Na₂SO₄, filtered to remove Na₂SO₄ and the filtrate was evaporated under reduced pressure to give crude product, further purification by Pre-TLC (PE/EA=3:1) to give compound 4 (30 mg in 18% yield). ¹H NMR (DMSO-d₆) δ 9.44 (s, 1H), 8.00-8.05 (m, 2H), 7.68 (s, 1H), 6.97-7.00 (m, 1H), 3.53 (s, 1H), 1.69-1.86 (m, 5.5H), 1.43-1.51 (m, 4.5H).

Step 4: 5-(cyclohexylmethyl)imidazo[1,5-a]pyridine

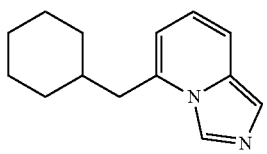 [SMILES: c1cc(CC2CCCCC2)n2cncc2c1]

To a solution of cyclohexyl(imidazo[1,5-a]pyridin-5-yl)methanone (30 mg, 0.13 mmol) in ethane-1,2-diol (10 mL) was added hydrazine hydrate (1 mL) and KOH (30 mg, 1.0 eq) and the mixture was heated at 130° C. for 4 hours. Then water (20 mL) was added and extracted with EA (20 mL*3), combined the organic layers, dried over Na₂SO₄, filtered to remove Na₂SO₄ and the filtrate was evaporated under reduced pressure to give crude product, further purification by Pre-HPLC to give 5.06 mg in 18% yield. ¹H NMR (DMSO-d₆) δ 8.39 (s, 1H), 7.45 (d, 1H, J=9.2 Hz), 7.40 (s, 1H), 6.76 (dd, 1H, J=9.2 Hz), 6.46 (d, 1H, J=6.4 Hz), 2.82 (d, 2H, J=7.2 Hz), 1.62-1.81 (m, 4H), 1.02-1.23 (m, 5H).

Example A016: 1-cyclohexyl-1-(imidazo[1,5-a]pyridin-5-yl)ethan-1-ol

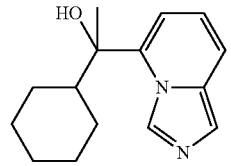 [SMILES: CC(O)(c1cccc2cncn12)C1CCCCC1]

To a solution of cyclohexyl(imidazo[1,5-a]pyridin-5-yl)methanone (50 mg, 0.22 mmol) in dry THF (15 mL) was added drop wise of methyllithium (0.3 mL, 1.6 M) at −70° C. and the mixture was stirred for 15 minutes. Then saturated aqueous of NH₄Cl (15 mL) was added and extracted with EA (20 mL*3), combined the organic layers, dried over Na₂SO₄, filtered to remove Na₂SO₄ and the filtrate was evaporated under reduced pressure to give crude product, further purification by Pre-TLC to give 4.36 mg in 8% yield. ¹H NMR (DMSO-d₆) δ 8.86 (s, 1H), 7.49 (d, 1H, J=8.8 Hz), 7.43 (s, 1H), 6.78 (dd, 1H, J=8 Hz), 6.57 (d, 1H, J=6.8 Hz), 5.64 (s, 1H), 2.03-2.09 (m, 1H), 1.91-1.94 (m, 4H), 1.72-1.76 (m, 1H), 1.53-1.58 (m, 5H), 0.93-1.23 (m, 6H).

Examples A017 to A019 were synthesized from imidazo[1,5-a]pyridine-5-carbaldehyde and the corresponding Grignard reagent by following the procedures similar to those as described in Example A001.

Example A017: 1-(imidazo[1,5-a]pyridin-5-yl)ethan-1-ol

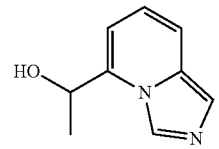

¹H NMR (DMSO-d₆) δ 8.47 (s, 1H), 7.50 (d, 1H, J=8.8 Hz), 7.43 (s, 1H), 6.81 (dd, 1H, J=8.4 Hz), 6.67 (d, 1H, J=6.8 Hz), 5.85 (d, 1H, J=5.6 Hz), 5.08 (m, 1H), 1.52 (d, 3H, J=6.8 Hz). Example A018: cyclobutyl(imidazo[1,5-a]pyridin-5-yl)methanol

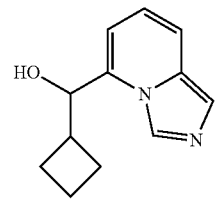 [SMILES: OC(c1cccc2cncn12)C1CCC1]

¹H NMR (DMSO-d₆) δ 8.48 (s, 1H), 7.48 (d, 1H, J=9.2 Hz), 7.40 (s, 1H), 6.76 (dd, 1H, J=8.8 Hz), 6.55 (d, 1H, J=6.8 Hz), 5.79 (m, 1H), 4.80 (t, 1H, J=6.8 Hz), 2.87-2.93 (m, 1H), 1.97-2.06 (m, 2H), 1.78-1.87 (m, 4H).

Example A019: 1-(imidazo[1,5-a]pyridin-5-yl)-2-phenylethan-1-ol

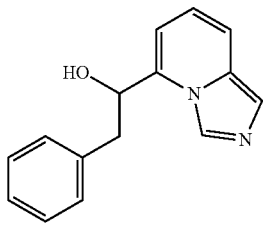 [SMILES: OC(Cc1ccccc1)c1cccc2cncn12]

¹H NMR (DMSO-d₆) 8.53 (s, 1H), 7.49 (d, 1H, J=9.2 Hz), 7.43 (s, 1H), 7.18-7.23 (m, 5H), 6.75 (d, 1H, J=8.8 Hz), 6.59 (d, 1H, J=6.4 Hz), 5.94 (s, 1H), 5.11-5.13 (m, 1H), 3.09-3.21 (m, 2H).

Example A020: 7-chloro-5-((4,4-difluorocyclohexyl)fluoromethyl)imidazo[1,5-a]pyridine

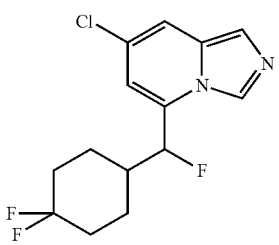 [SMILES: FC(c1cc(Cl)cc2cncn12)C1CCC(F)(F)CC1]

To a solution of 4-((7-chloroimidazo[1,5-a]pyridin-5-yl)(hydroxy)methyl)cyclohexan-1-one (30 mg, 0.1 mmol) in DCM (10 mL) was added DAST (32 mg, 2 eq) at 0° C. and the mixture was stirred for 4 hours. Then saturated aqueous of NaHCO₃ (10 mL) was added and extracted with DCM (20 mL*3), combined the organic layers, dried over Na₂SO₄, filtered to remove Na₂SO₄ and the filtrate was evaporated under reduced pressure to give crude product, and this crude product was purified by Pre-HPLC to give 4.2 mg in 14% yield. ¹H NMR (DMSO-d₆) δ 8.52 (s, 1H), 7.83 (s, 1H), 7.48 (s, 1H), 6.86 (s, 1H), 5.78-5.91 (m, 1H), 2.00-2.07 (m, 4H), 1.81-1.90 (m, 2H), 1.43-1.51 (m, 3H).

Example A021: 7-chloro-5-(cyclohexylfluoromethyl)imidazo[1,5-a]pyridine

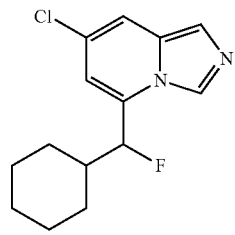 [SMILES: FC(c1cc(Cl)cc2cncn12)C1CCCCC1]

¹H NMR (DMSO-d₆) δ 8.52 (s, 1H), 7.82 (s, 1H), 7.47 (s, 1H), 6.82 (s, 1H), 5.70 (dd, 1H, J=8.0 Hz), 1.90-1.92 (m, 1H), 1.73-1.76 (m. 1H), 1.60-1.67 (s, 2H), 1.09-1.34 (m, 7H).

Example A022: cyclohexyl(8-fluoroimidazo[1,5-a]pyridin-5-yl)methanol

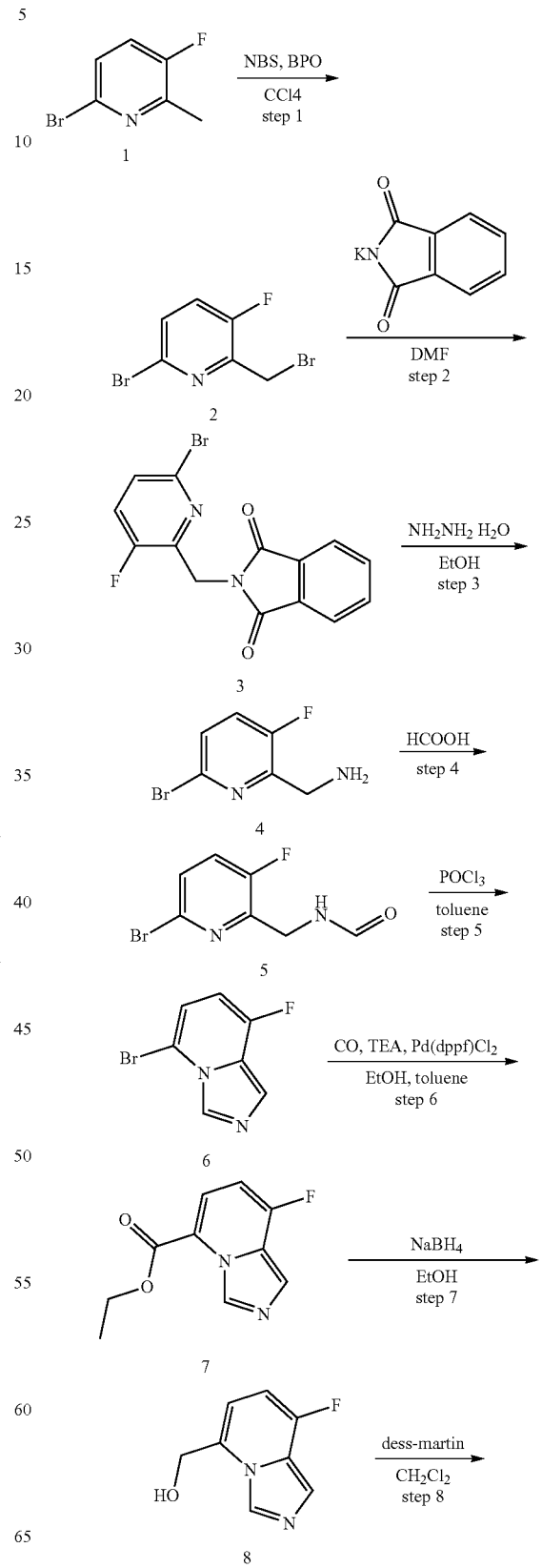

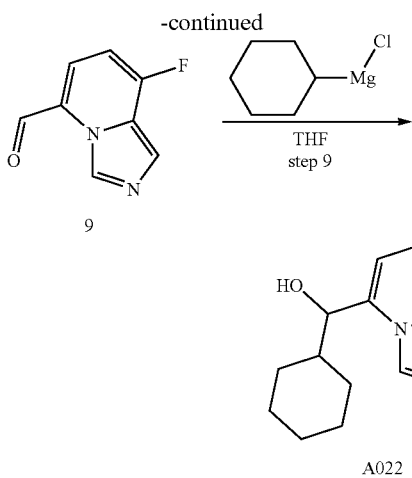

Step 1: 6-bromo-2-(bromomethyl)-3-fluoropyridine

To a suspension of 6-bromo-3-fluoro-2-methylpyridine (1.9 g, 10 mmol) and N-bromosuccinimide (NBS, 1.98 g, 11.15 mmol) in $CCl_4$ (40 mL) was added benzoyl peroxide (BPO, 0.12 g, 0.5 mmol). The resulting mixture was stirred at reflux for 4 hrs. The mixture was cooled to room temperature. A precipitate was formed and the solid was filtered. The filtrate was concentrated to give a brown solid (3 g, 100%) which used directly for next step without further purification. MS: M/e 270 $(M+2)^+$

Step 2: 2-((6-bromo-3-fluoropyridin-2-yl)methyl)isoindoline-1,3-dione

To a solution of the product of step 1 (3 g, 10 mmol) in DMF (20 mL) was added potassium 1,3-dioxoisoindolin-2-ide (1.85 g, 10 mmol). The reaction mixture was stirred at rt for one hour. To the mixture was added water (40 mL) and a white precipitate was formed. Then the solid was filtered, washed with water (20 ml) and PE (20 mL), dried to give the desired product (2.2 g, 65% for 2 steps) as a white solid. $^1H$ NMR (400 MHz, $CDCl_3$) δ 7.93-7.88 (m, 2H), 7.78-7.74 (m, 2H), 7.36 (dd, J=8.4, 3.6 Hz, 1H), 7.29-7.23 (m, 1H), 5.05 (d, J=1.6 Hz, 2H). ppm. MS: M/e 335 $(M+1)^+$

Step 3: (6-bromo-3-fluoropyridin-2-yl)methylamine

To a solution of the product of step 2 (2.2 g, 6.59 mmol) in EtOH (20 mL) was added a solution of hydrazine hydrate (0.3 g, 6.59 mmol). The solution was stirred at reflux for 3 hrs. The mixture was cooled to rt. The solid was filtered and the filtrate was concentrated. To the residue was added a solution of EA/PE (20 mL/20 mL). The resulting residue was filtered and the filtrate was concentrated to get the desired product (1.2 g, 89% for crude yield) as yellow oil. MS: M/e 205 $(M+1)^+$

Step 4: N-((6-bromo-3-fluoropyridin-2-yl)methyl)formamide

A solution of the product of step 3 (1.2 g, 5.88 mmol) in formic acid (10 mL) was stirred at 100° C. for 56 hrs. The reaction was quenched with water (40 mL), extracted with EA (40 mL*2). The organic layer was washed by saturated $NaHCO_3$ aqueous solution followed by saturated brine solution, dried over $Na_2SO_4$, filtered and concentrated to get crude product (0.7 g, 51%) as a solid, which was used in next step directly. MS: M/e 233 $(M+1)^+$

Step 5: 5-bromo-8-fluoroimidazo[1,5-a]pyridine

To a solution of the product of step 4 (0.7 g, 3 mmol) in toluene (10 mL) was added $POCl_3$ (450 mg, 3 mmol). The mixture was stirred at 90° C. for 30 min. The reaction was cooled to room temperature, quenched with saturated $NaHCO_3$ aqueous solution, extracted with (30 mL×2). The organic layer was washed with saturated brine solution, dried over $Na_2SO_4$, filtered and concentrated. The residue was purified by silica gel column chromatography eluting with PE:EA=3:1 to get the desired product (0.4 g, 62%) as a yellow solid. MS: M/e 215 $(M+1)^+$

Step 6: ethyl 8-fluoroimidazo[1,5-a]pyridine-5-carboxylate

To a solution of the product of step 5 (0.3 g, 1.4 mmol) in EtOH (8 mL) and toluene (1 mL) was added TEA (0.28 g, 2.8 mmol) and $Pd(dppf)Cl_2$ (0.1 g, 0.14 mmol). The resulting mixture was stirred at 100° C. for 8 hrs under CO (about 0.5 MPa). The resulting solution was concentrated. The residue was purified by silica gel column chromatography eluting with PE:EA=3:1 to get the desired product (0.2 g, 69%) as a yellow solid. MS: M/e 209 $(M+1)^+$

Step 7: (8-fluoroimidazo[1,5-a]pyridin-5-yl)methanol

To a mixture of the product of step 6 (0.2 g, 1 mmol) in EtOH (5 mL) was added $NaBH_4$ (76 mg, 2 mmol). The resulting mixture was stirred at 80° C. for 2 hrs. The reaction was quenched with acetone (2 mL). The resulting solution was concentrated. The residue was washed by water, extracted with EA (30 mL*2). The combined organic layer was washed by brine, dried over sodium sulfate anhydrous then concentrated to give the desired product (160 mg, crude) as a white solid. MS: M/e 167 $(M+1)^+$

Step 8: 8-fluoroimidazo[1,5-a]pyridine-5-carbaldehyde

To a solution of the product of step 7 (160 mg, crude) in $CH_2Cl_2$ (10 mL) was added Dess-Martin reagent (424 mg, 1 mmol). The solution was stirred at rt for 0.5 h. The solution was washed by water, extracted with $CH_2Cl_2$ (30 mL). The combined organic layer was washed by brine, dried over sodium sulfate anhydrous then concentrated and purified by silica gel column chromatography eluting with PE:EA=3:1 to get the desired product (150 mg, 100%) as a yellow solid. $^1H$ NMR (400 MHz, DMSO-$d_6$) δ 9.93 (s, 1H), 9.41 (d, J=3.2 Hz, 1H), 7.90-7.85 (m, 2H), 7.04 (dd, J=10.0, 7.6 Hz, 1H). ppm. MS: M/e 165 $(M+1)^+$

Step 9: cyclohexyl(8-fluoroimidazo[1,5-a]pyridin-5-yl)methanol

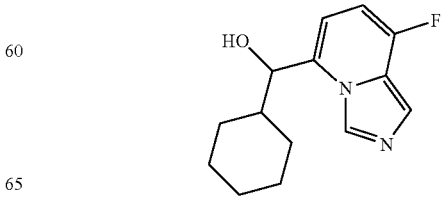

To the solution of the product of step H (33 mg, 0.2 mmol) in THF (3 mL) was added a solution of cyclohexylmagnesium chloride in THF (0.17 mL, 1.3 mol/L). The solution was stirred at rt for 0.5 h. The solution was washed by water, extracted with EA (30 mL). The organic layer was washed by brine, dried over sodium sulfate anhydrous then concentrated and purified by prep-TLC (EA:PE=1:1) to give the desired product (1.7 mg) as a white solid. $^1$H NMR (400 MHz, DMSO-$d_6$) δ 8.63 (d, J=3.2 Hz, 1H), 7.56 (s, 1H), 6.70-6.55 (m, 2H), 5.75 (d, J=4.0 Hz, 1H), 4.62 (dd, J=7.2, 3.6 Hz, 1H), 1.91-1.58 (m, 5H), 1.35-1.03 (m, 6H) ppm. MS: M/e 249 (M+1)$^+$ Example A023: (8-bromoimidazo[1,5-a]pyridin-5-yl)(cyclohexyl)methanol

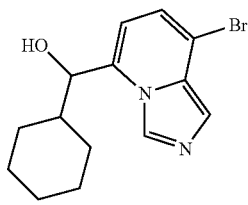 [SMILES: OC(c1ccc(Br)c2cncn12)C1CCCCC1]

Example A023 was prepared according to the similar procedures described for Example A118 using ethyl 5-bromo-6-(hydroxymethyl)picolinate (the by-product of step 4 in synthesis of Example A118) as the starting material under appropriate conditions that could be recognized by one skilled in the art. $^1$H NMR (400 MHz, DMSO-$d_6$) δ 8.96 (s, 1H), 7.68 (s, 1H), 7.26 (d, J=7.2 Hz, 1H), 6.68 (d, J=7.2 Hz, 1H), 4.66 (d, J=6.8 Hz, 1H), 1.86 (m, 2H), 1.65 (m, 4H), 1.32 (d, J=8.8 Hz, 1H), 1.11 (m, 6H) ppm. MS: M/e 309/311 (M+1)$^+$.

Example A024: (8-chloroimidazo[1,5-a]pyridin-5-yl)(cyclohexyl)methanol

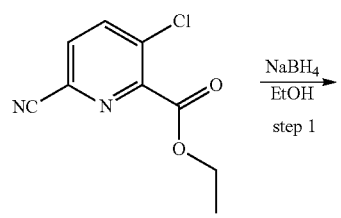

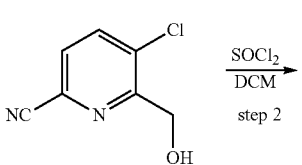

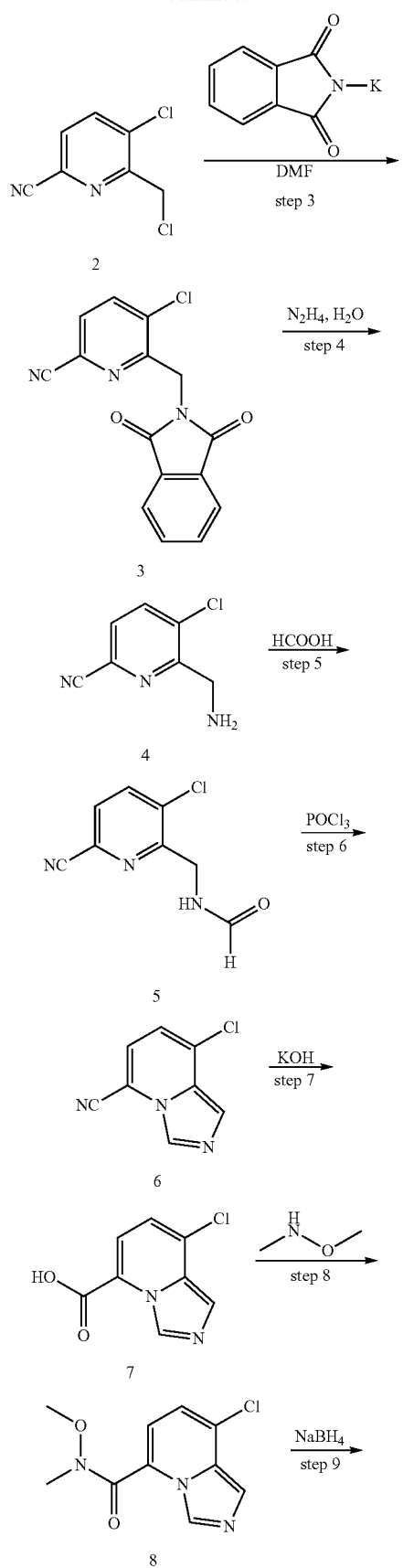

-continued

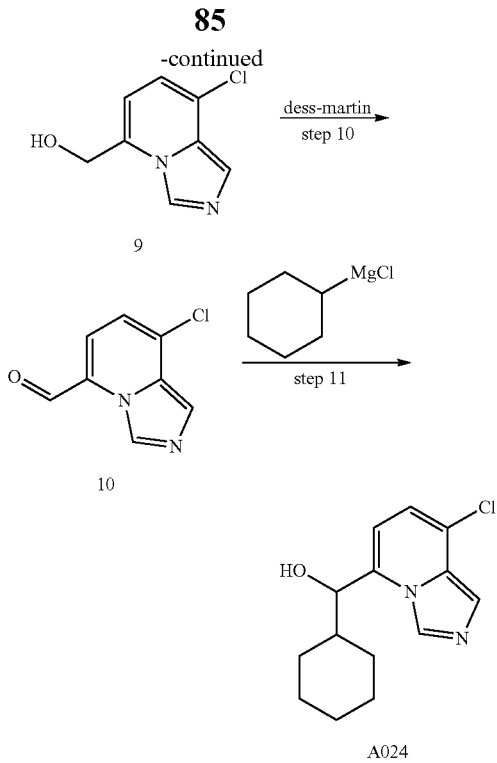

Step 1: 5-chloro-6-(hydroxymethyl)picolinonitrile

To a stirred solution of ethyl 3-chloro-6-cyanopicolinate (6 g, 28.6 mmol) in EtOH:THF=2:1 (30 mL) was added NaBH$_4$ (1.13 g, 30 mmol) was stirred at room temperature for 1.5 h under moisture protection. The solvent was removed and water (50 mL) was added. After stirring for 10 min, the mixture was extracted with EA (20 ml×3). The combined organic layers were dried over Na$_2$SO$_4$, filtered and concentrated to give crude product. The crude was purified by silica gel chromatography (PE:EA=20:1-4:1) to give product (2 g, 20%) as a yellow solid. $^1$H NMR (400 MHz, DMSO) δ 8.20 (d, J=8.2 Hz, 1H), 8.03 (d, J=8.2 Hz, 1H), 4.67 (s, 2H). LC-MS (M+H)$^+$=169

Step 2: 5-chloro-6-(chloromethyl)picolinonitrile

To a stirred solution of 5-chloro-6-(hydroxymethyl)picolinonitrile (4.5 g, 26.6 mmol) in DCM (40 mL) was added drop-wise of SOCl$_2$ (6.37 g) at 0° C. After 90 min the solution was allowed to reach room temperature and the excess of SOCl$_2$ was removed under reduced pressure without heating. DCM (50 mL) was added to the oily residue, and the solution was washed with saturated aqueous of NaHCO$_3$ and dried over Na$_2$SO$_4$. Evaporation of the solvent afforded product (5.1 g, 98%) as orange oil. LC-MS (M+H)$^+$=187.

Step 3: 5-chloro-6-((1,3-dioxoisoindolin-2-yl)methyl)picolinonitrile

A mixture of 5-chloro-6-(chloromethyl)picolinonitrile (4.3 g, 23 mmol) in anhydrous DMF (40 mL) was slowly added sodium phthalimide (4.04 g, 21.85 mmol) at room temperature and the mixture was stirred overnight. Then the reaction mixture was centrifuged, the solvent was removed under reduced pressure, and the residue was suspended in H$_2$O (20 mL) and EA (30 mL), then filtered to give product (6.8 g, 86%) as a white solid. $^1$H NMR (400 MHz, DMSO) δ 8.30 (d, J=8.2 Hz, 1H), 8.05 (d, J=8.2 Hz, 1H), 7.98-7.88 (m, 4H), 5.06 (s, 2H). LC-MS (M+H)$^+$=298

Step 4: 6-(aminomethyl)-5-chloropicolinonitrile

To a solution of 5-chloro-6-((1,3-dioxoisoindolin-2-yl)methyl)picolinonitrile (6.8 g, 23 mmol) in EtOH (40 mL) was added Hydrazine hydrate (4.04 g, 98%) at room temperature and the mixture was heated at 80° C. for 2 h. Then cooled to room temperature, filtered to remove the white precipitate and HCOOH (100 mL) was added to the filtrate, filtered again to remove white precipitate and the filtrate was evaporated to give crude product as an oil containing HCOOH, and this crude product was used for next step without further purification. LC-MS (M+H)$^+$=168.

Step 5: N-((3-chloro-6-cyanopyridin-2-yl)methyl)formamide

A mixture of 6-(aminomethyl)-5-chloropicolinonitrile (3.0 g, 17.86 mmol) in HCOOH (40 mL) was heated at 80° C. for 4 hours. Cooled to room temperature and evaporated the solvent before HCl (50 mL, 1N) was added to the residue. The aqueous layer was adjust pH=7-8 with saturated aqueous of NaOH, the extracted with EA (20 ml×3), combined the organic layer, dried over Na$_2$SO$_4$, the filtered to remove Na$_2$SO$_4$, evaporated the solvent to give a crude product as yellow oil (1.5 g). And this crude product was used for next step without further purification. LC-MS (M+H)$^+$=196.

Step 6: 8-chloroimidazo[1,5-a]pyridine-5-carbonitrile

To a stirred solution of N-((3-chloro-6-cyanopyridin-2-yl)methyl)formamide (1.8 g, 9.2 mmol) in toluene (20 mL) was added POCl$_3$ (28 g) at room temperature and the mixture was heated at 80° C. for 2 hours. Then cooled to room temperature and evaporated the solvent before HCl (40 mL, 1N) was added to the residue, extracted with EA (20 ml×3), isolated the aqueous layer, adjusted pH=7-8 with saturated aqueous of NaOH before extracted with EA (20 ml×3), combined the organic layers, evaporated the solvent to give product (1.1 g, 67.9%) as a brown solid. $^1$H NMR (400 MHz, DMSO) δ 8.72 (s, 1H), 7.78 (s, 1H), 7.67 (d, J=7.4 Hz, 1H), 7.16 (d, J=7.4 Hz, 1H). LC-MS (M+H)$^+$=178.

Step 7: 8-chloroimidazo[1,5-a]pyridine-5-carboxylic acid

A mixture of compound 9 (0.2 g, 1.13 mmol) and KOH (0.19 g, 3.39 mmol) in EtOH (20 ml) was stirred at 90° C. for 2 h. TLC (DCM:MeOH=5:1, R$_f$=0.2) showed the reaction was completed. Cooled to room temperature and evaporated the solvent before HCl (20 mL, 1N) was added to the residue. The aqueous layer was adjust pH=7-8, the solvent was removed under reduced pressure to give crude compound 7 (0.3 g, 90%) as a yellow solid. And this crude product was used for next step without further purification. LC-MS (M+H)+=197

Step 8: 8-chloro-N-methoxy-N-methylimidazo[1,5-a]pyridine-5-carboxamide

To a stirred solution of compound 10 (0.2 g, 1.02 mmol), HOBT (0.165 g, 1.22 mmol), EDCI (0.234 g, 1.22 mmol), Et₃N (0.2 g, 2.04 mmol), and N,O-dimethylhydroxylamine (0.12 g, 1.22 mmol) at room temperature for 4 h. TLC (PE:EA=1:1, R_f=0.2) showed the reaction was completed. The solvent was evaporated under reduced pressure. The mixture was add saturated NH₄Cl (20 ml) and extracted with EA (20 ml×3). The combined organic layer were dried over Na₂SO₄. filtered and concentrated to give compound 8 (0.29 g, 90%) as a gray solid. LC-MS (M+H)⁺=240.

Step 9: 8-chloroimidazo[1,5-a]pyridine-5-carbaldehyde

To a stirred solution of compound 8 (0.29 g, 1.2 mmol) in EtOH (10 mL) was added NaBH₄ (68 mg, 1.8 mmol) was stirred at room temperature for 2 h under moisture protection. The solvent was removed and water (10 mL) was added. After stirring for 10 min, the mixture was extracted with EA (20 ml×3). The combined organic layer were dried over Na₂SO₄, filtered and concentrated to give compound 9 (92 mg, 42%) as a yellow solid. LC-MS (M+H)+=183.

Step 10: 8-chloroimidazo[1,5-a]pyridine-5-carbaldehyde

To a solution of compound 9 (92 m g, 0.52 mmol) in DCM (10 ml) was added portion of Dess-Martin (424 m g, 1 mmol) at room temperature and the mixture was stirred for 2 hours before saturated aqueous of NaHCO₃ was added slowly to adjust pH=6-7, isolated the organic layer, H₂O (50 mL) was added, followed by addition of conc. HCl to adjust pH=2-3, isolated the aqueous layer, Na₂CO₃ was added to adjust to pH=7-8, extracted with EA (10 mL×2), combined the organic layer, evaporated the solvent to give a product (50 mg, 50%) as a as a yellow solid. LC-MS (M+H)⁺=181.

Step 11: (8-chloroimidazo[1,5-a]pyridin-5-yl)(cyclohexyl)methanol

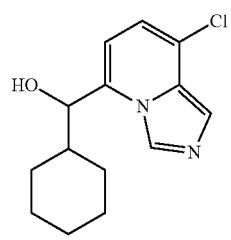 [SMILES: OC(c1ccc(Cl)c2cncn12)C1CCCCC1]

To a solution of imidazo[1,5-a]pyridine-5-carbaldehyde (146 mg, 1.0 mmol) in dry THF (15 mL) was added dropwise of phenylmagnesium chloride (1.0 mL, 2M) at 0° C. under N₂ air balloon was protected. And the mixture was stirred warmed to room temperature slowly for 2 hours. Water (20 mL) was added to the mixture and extracted with EA (20 mL×3), combined the organic layers and dried over Na₂SO₄, filtered to remove Na₂SO₄ and the filtrate was concentrated, the crude product was purified by Pre-TLC (DCM/MeOH=9:1 as eluent) to give 5.25 mg in 4% yield. ¹H NMR (400 MHz, CD₃OD) δ 8.53 (s, 1H), 7.42 (s, 2H), 6.80 (d, J=7.2 Hz, 1H), 6.51 (d, J=7.2 Hz, 1H), 4.51 (d, J=7.8 Hz, 1H), 1.96 (d, J=12.8 Hz, 1H), 1.90-1.78 (m, 1H), 1.69 (dd, J=12.9, 2.4 Hz, 1H), 1.60-1.49 (m, 3H), 1.29-1.01 (m, 4H), 0.86-0.68 (m, 2H).

Example A025: 1-(8-chloroimidazo[1,5-a]pyridin-5-yl)-2-cyclohexylethan-1-ol

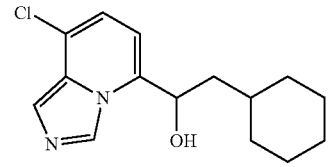 [SMILES: OC(CC1CCCCC1)c1ccc(Cl)c2cncn12]

Example A025 was prepared according to the procedures described for Example A024 using 8-chloroimidazo[1,5-a]pyridine-5-carbaldehyde and (cyclohexylmethyl)magnesium chloride as the starting material under appropriate conditions that could be recognized by one skilled in the art. ¹H NMR (400 MHz, CD₃OD-d₄) δ 8.45 (d, J=0.8 Hz, 1H), 7.43 (d, J=0.8 Hz, 1H), 6.32 (d, J=7.2 Hz, 1H), 6.57 (d, J=7.2 Hz, 1H), 4.95 (dd, J=8.8, 4.8 Hz, 1H), 1.38-1.62 (m, 7H), 1.09-1.21 (m, 4H), 0.89-0.96 (m, 2H). MS: M/e 309/311 (M+1)⁺.

Example A026: 7-chloro-5-(cyclohexylmethyl)imidazo[1,5-a]pyridine

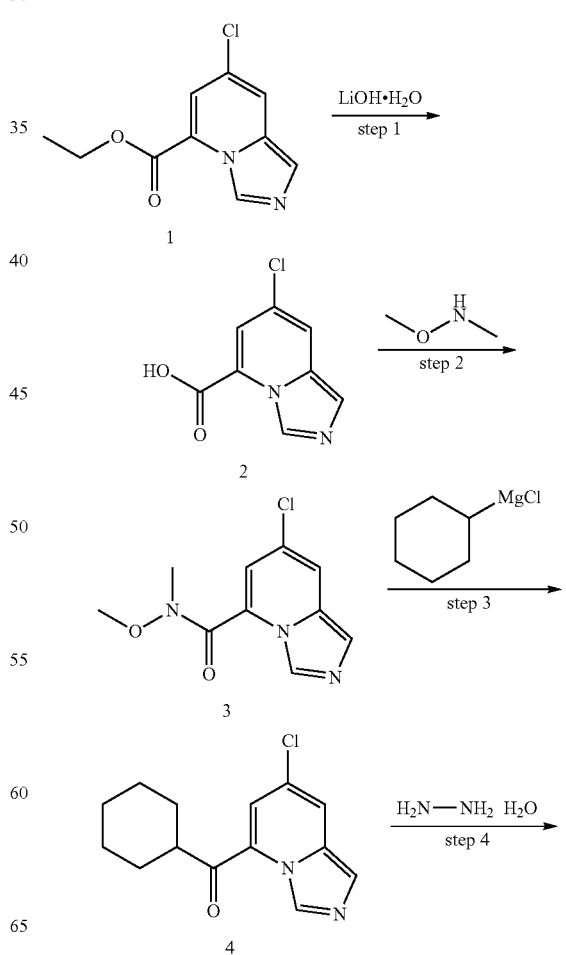

89

-continued

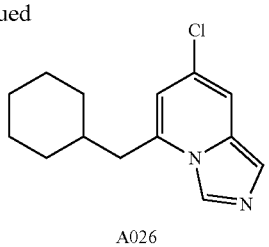

A026

Step 1: 7-chloroimidazo[1,5-a]pyridine-5-carboxylic acid

To a solution of ethyl 7-chloroimidazo[1,5-a]pyridine-5-carboxylate (0.5 g, 2.2 mmol) in a mixture of THF (15 mL) and water (5 mL) was added lithium hydroxide hydrate (370 mg, 4 eq) at room temperature and the mixture was stirred overnight. Evaporated the solvent under reduced pressure and water (10 mL) was added to the residue and adjust pH=6-7 with HCl (4 N) and the yellow precipitate was collected by filtration to give 256 mg in 59% yield. $[M+H]^+=197$.

Step 2: 7-chloro-N-methoxy-N-methylimidazo[1,5-a]pyridine-5-carboxamide

To a solution of 7-chloroimidazo[1,5-a]pyridine-5-carboxylic acid (256 mg, 1.3 mmol) in DMF (15 mL) and added Et$_3$N (265 mg, 2 eq), HATU (494 mg, 1 eq) and the mixture was stirred for 15 minutes before N,O-dimethylhydroxylamine (127 mg, 1 eq) was added and the mixture was stirred overnight. Water (35 mL) was added and isolated the organic layer, washed with brine (20 mL*3), dried over Na$_2$SO$_4$, filtered to remove Na$_2$SO$_4$ and the filtrate was evaporated under reduced pressure to give crude product and the crude product was used for next step without further purification. $[M+H]^+=240$.

Step 3: (7-chloroimidazo[1,5-a]pyridin-5-yl)(cyclohexyl)methanone

To a solution of 7-chloro-N-methoxy-N-methylimidazo[1,5-a]pyridine-5-carboxamide (311 mg, 1.3 mmol) in dry THF (20 mL) was added drop wise of cyclohexylmagnesium chloride (2.6 mL, 2 M) at −70° C. under N$_2$ air balloon protected and the mixture was stirred for 2 hours before water (20 mL) was added and extracted with EA (20 mL*2), combined the organic layers, dried over Na$_2$SO$_4$, filtered to remove Na$_2$SO$_4$ and the filtrate was evaporated under reduced pressure to give crude product, further purification by Pre-TLC (PE/EA=1:1) to give 30 mg in 18% yield. $[M+H]^+=263$.

Step 4: 7-chloro-5-(cyclohexylmethyl)imidazo[1,5-a]pyridine

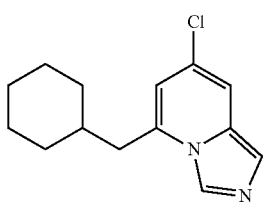 [SMILES: Clc1cc(CC2CCCCC2)n2cncc2c1]

90

To a solution of (7-chloroimidazo[1,5-a]pyridin-5-yl)(cyclohexyl)methanone (30 mg, 0.13 mmol) in ethane-1,2-diol (10 mL) was added hydrazine hydrate (1 mL) and KOH (30 mg, 1.0 eq) and the mixture was heated at 130° C. for 4 hours. Then water (20 mL) was added and extracted with EA (20 mL*3), combined the organic layers, dried over Na$_2$SO$_4$, filtered to remove Na$_2$SO$_4$ and the filtrate was evaporated under reduced pressure to give crude product, further purification by Pre-HPLC to give 4.6 mg in 18% yield. $^1$H NMR (DMSO-d) δ 8.46 (s, 1H), 7.64 (d, 1H, J=2.0 Hz), 7.39 (s, 1H), 6.55 (d, 1H, J=2.0 Hz), 2.84 (d, 2H, J=7.2 Hz), 1.78-1.79 (m, 1H), 1.62-1.81 (m, 5H), 1.02-1.23 (m, 5H).

Example A101: (7-chloroimidazo[1,5-a]pyridin-5-yl)(cyclohexyl)methanol

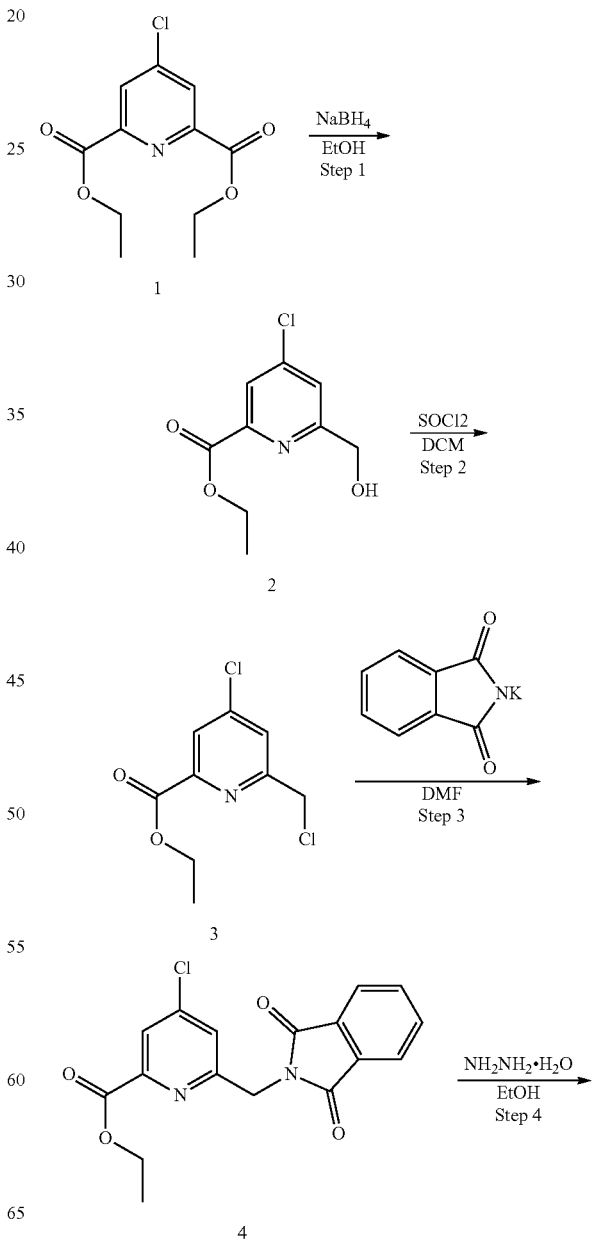

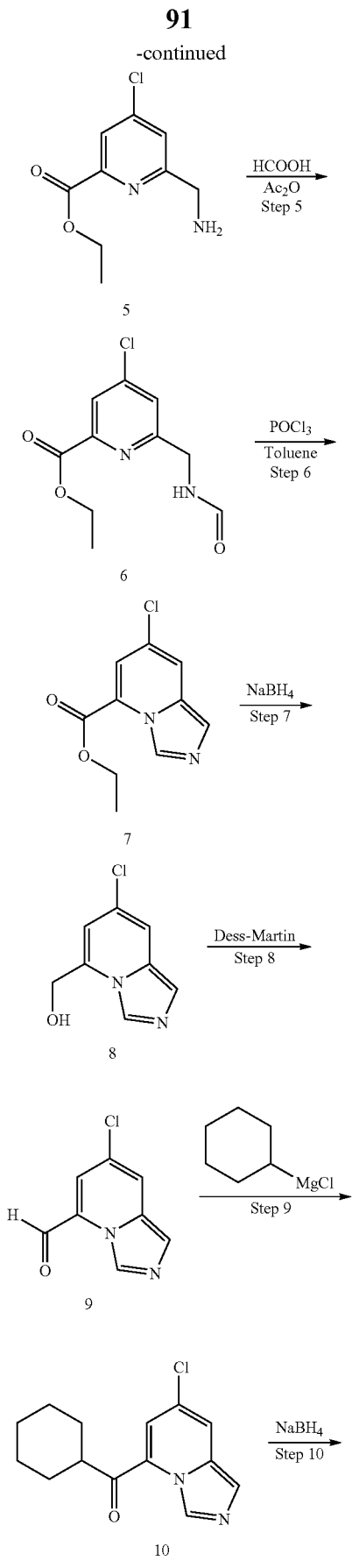

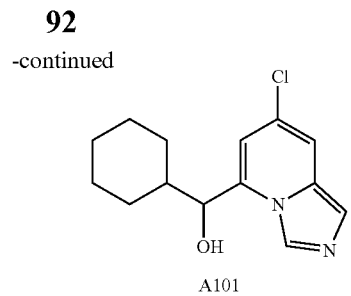

A101

Step 1: Ethyl 4-chloro-6-(hydroxymethyl)picolinate

Diethyl 4-chloropyridine-2,6-dicarboxylate (32 g, 123 mmol) and NaBH$_4$ (2.4 g, 62 mmol) were EtOH (100 mL) and refluxed for 2 h under moisture protection. The solvent was removed and water (100 mL) was added. After stirring for 10 min, the mixture was extracted with EA (100 mL*3). The organic phases were combined and dried over Na$_2$SO$_4$, and the solvent was evaporated under reduced pressure. The residue was purified by flash chromatography on silica gel with PE/EA=1:1 to give the product as white solid (11 g in 41% yield).

Step 2: Ethyl 4-chloro-6-(chloromethyl)picolinate

To a solution of ethyl 4-chloro-6-(hydroxymethyl)picolinate (11 g, 51 mmol) in DCM (80 mL) was added dropwise of SOCl$_2$ (11 mL) at r.t. After 3 h the solution was allowed to reach room temperature and the excess of SOCl$_2$ was removed under reduced pressure without heating. The residue was adjusted the pH>7 with saturated aqueous of NaHCO$_3$ and extracted with EtOAc (100 mL×2). The organic layer was dried over with Na$_2$SO$_4$. Evaporation of the solvent afforded 2-(chloromethyl)pyridine-6-carboxylic acid ethyl ester (12.3 g) as a brown oil which was used next step without further purification. MS (ESI) m/e [M+1]$^+$234.

Step 3: Ethyl 4-chloro-6-((1,3-dioxoisoindolin-2-yl)methyl)picolinate

To a solution of ethyl 4-chloro-6-(chloromethyl)picolinate (12.3 g, 53 mmol) in DMF (80 mL) was slowly added sodium phthalimide (12 g, 63.6 mmol) at room temperature and the mixture was stirred overnight. The solid was filtered and washed with H$_2$O (200 mL). The residue solid was suspended in Et$_{2O}$, filtered and dried under vacuum to give the product (10 g, 56%) as a white solid. $^1$H NMR (CDCl$_3$) δ 7.99 (d, J=1.6 Hz, 1H), 7.9-7.94 (m, 2H), 7.76-7.81 (m, 2H), 7.34 (d, J=1.6 Hz), 5.11 (s, 2H), 4.42 (q, J=7.2 Hz, 2H), 1.34 (t, J=7.2 Hz, 3H). MS (ESI) m/e [M+1]$^+$345.

Step 4: Ethyl 6-(aminomethyl)-4-chloropicolinate

To a solution of ethyl 4-chloro-6-((1,3-dioxoisoindolin-2-yl)methyl)picolinate (10 g, 29 mmol) in EtOH (60 mL) was added Hydrazine hydrate (1.5 g, 29 mmol) at room temperature and the mixture was heated at 90° C. for 2 h. Then cooled to room temperature, filtered to remove the white precipitate and HCOOH (70 mL) was added to the filtrate, filtered again to remove white precipitate and the filtrate was evaporated to give crude product containing HCOOH (9 g) as a brown oil, and this crude product was used for next step without further purification. MS (ESI) m/e [M+1]$^+$215.

Step 5: Ethyl 4-chloro-6-(formamidomethyl)picolinate

A solution of crude ethyl 6-(aminomethyl)-4-chloropicolinate (9 g, 42 mmol) in HCOOH (100 mL) was heated at 90° C. for 2 hours. Cooled to room temperature and evaporated the solvent before HCl (500 mL, 1 mmol/mL) was added to the residue. Then extracted with EA (80 mL*3). The organic layer was dried over with $Na_2SO_4$, filtered and concentrated to give a mixture of solid and liquid. To the mixture was added EtOAc (30 ml), the solid was filtered and the filtrate was concentrated to give the product (4.7 g, 47%) as a brown solid which was used next step without further purification.

Step 6: Ethyl 7-chloroimidazo[1,5-a]pyridine-5-carboxylate

To a solution of ethyl 4-chloro-6-(formamidomethyl)picolinate (4.7 g, 19.3 mmol) in toluene (30 mL) was added $POCl_3$ (4.7 mL) at room temperature and the mixture was heated at 80° C. for 2 hours. Then cooled to room temperature and evaporated the solvent before HCl (10 mL, con.) and $H_2O$ (20 ml) was added to the residue, extracted with EA (50 mL*2), isolated the aqueous layer, adjusted pH=7-8 with saturated aqueous of NaOH before extracted with EA (100*2), combined the organic layers, evaporated the solvent to give crude solid which was further purified by column chromatography, on silica (100 g), eluting with EtOAc (500 mL) to give the product (2.25 g, 52%) as a yellow solid. MS (ESI) m/e [M+1]$^+$225.

Step 7: (7-chloroimidazo[1,5-a]pyridin-5-yl)methanol

To a solution of ethyl 7-chloroimidazo[1,5-a]pyridine-5-carboxylate (2.25 g, 10 mmol) in EtOH (50 mL) was added batch wise of $NaBH_4$ (0.5 g, 12 mmol) at r.t. and the mixture was stirred at 90° C. for 2 h. Then evaporated the solvent and $H_2O$ (100 mL) was added to the residue. The solid was filtered and dried to give the product (2.1 g, 117%) as a yellow solid which was used next step without further purification. MS (ESI) m/e [M+1]$^+$183.

Step 8: 7-chloroimidazo[1,5-a]pyridine-5-carbaldehyde

To a solution of imidazo[1,5-a]pyridin-5-ylmethanol (2 g, 11 mmol) in DCM (60 mL) and THF (40 mL) was added portion of Dess-Martin (9.3 g, 22 mmol) at room temperature and the mixture was stirred overnight. To the resulting mixture was added $H_2O$ (30 mL) and HCl (6 mL). The aqueous layer was extracted with EtOAc (20 ml*2) and adjusted the pH>8 with $Na_2CO_3$. The aqueous layer was extracted with EtOAc (50 mL*3). The organic layer was dried over with $Na_2SO_4$, filtered and concentrated to give the product (770 mg, 39%) as a brown solid which was used next step without further purification. MS (ESI) m/e [M+1]$^+$ 181.

Step 9: (7-chloroimidazo[1,5-a]pyridin-5-yl)(cyclohexyl)methanol

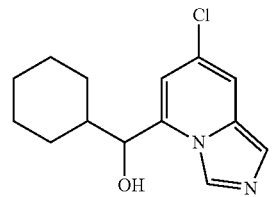 [SMILES: OC(c1cc(Cl)cc2cncn12)C1CCCCC1]

To a solution of 7-chloroimidazo[1,5-a]pyridine-5-carbaldehyde in dry THF (15 mL) was added dropwise of cyclohexylmagnesium chloride (1.3 mL, 1.3M) at 0° C. under $N_2$ air balloon was protected. And the mixture was stirred warmed to room temperature slowly for 30 mins. Water (10 mL) was added to the mixture and extracted with EA (20 mL*2), combined the organic layers and dried over $Na_2SO_4$, filtered to remove $Na_2SO_4$ and the filtrate was concentrated, the crude product was purified by pre-HPLC (PE/EA=1:1 as eluent) to give the compound of Example A101 (Compound 2.1) (18 mg, 12% yield). $^1$H NMR (DMSO-$d_6$) δ 8.53 (s, 1H), 7.67 (s, 1H), 7.40 (s, 1H), 6.64 (s, 1H), 5.85 (d, 1H, J=4.0 Hz), 4.65-4.68 (m, 1H), 3.07-3.10 (m, 3H), 1.57-1.83 (m, 5H) and 1.11-1.40 (m, 2H). MS (ESI) m/e [M+1]$^+$265.

Examples A101a and A101b: (S)-(7-chloroimidazo[1,5-a]pyridin-5-yl)(cyclohexyl)methanol compound and (R)-(7-chloroimidazo[1,5-a]pyridin-5-yl)(cyclohexyl)methanol

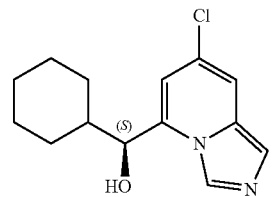

A101a

Fast isomer in chiral IC HPLC
Eluting reagent: $CO_2$/MeOH = 75/25 (V/V)

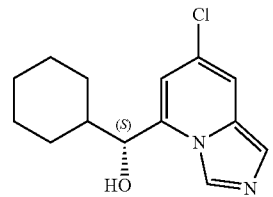

A101b

Slow isomer in chiral IC HPLC
Eluting reagent: $CO_2$/MeOH = 75/25 (V/V)

Each enantiomer of racemic A101a and A101b was separated using preparative HPLC on a Chiralpak IC with 25% Methanol/Carbon dioxide as an eluent. The enantiomeric excesses were determined by using HPLC on a Chiralpak AD with 25% Methanol/Carbon dioxide as an eluent at a flow rate of 2.0 mL/min. The first one enantiomer eluted at the retention time of 4.1 min, and the other enantiomer eluted at the retention time of 6.2 min. The spectral properties of the title compounds were identical with those of A101.

The absolute stereochemistry of the more potent compound A101a in enzymatic and cellular assays is assigned as (S)-configuration on the chiral α-carbon atom based on its cocrystal structure with IDO1 enzyme (FIG. 1).

Example A102: 1-(7-chloroimidazo[1,5-a]pyridin-5-yl)-2-cyclohexylethan-1-ol

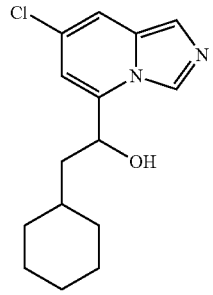 [SMILES: OC(CC1CCCCC1)c1cc(Cl)cc2cncn12]

Example A012 was synthesized from 7-chloroimidazo[1,5-a]pyridine-5-carbaldehyde and (cyclohexylmethyl)magnesium bromide as described in Example A101. $^1$H NMR (DMSO-d$_6$) δ 8.42 (s, 1H), 7.68 (d, 1H, J=2.0 Hz), 7.41 (s, 1H), 6.67 (s, 1H), 5.96 (d, 1H, J=3.2 Hz), 4.97-5.02 (m, 1H), 1.87-1.90 (m, 1H), 1.55-1.73 (m, 7H), 1.11-1.23 (m, 3H), 0.91-0.99 (m, 2H).

Examples A102a and A102b: (S)-1-(7-chloroimidazo[1,5-a]pyridin-5-yl)-2-cyclohexylethan-1-ol compound and (R)-1-(7-chloroimidazo[1,5-a]pyridin-5-yl)-2-cyclohexylethan-1-ol 102a
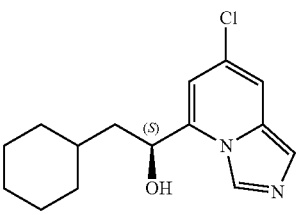
Fast isomer in chiral AD HPLC
Eluting reagent: MeOH = 100%

102b
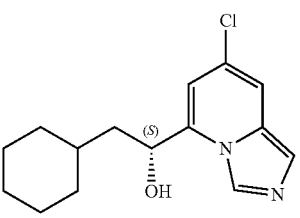
Slow isomer in chiral AD HPLC
Eluting reagent: MeOH = 100%

Each enantiomer of racemic A102a and A102b was separated using preparative HPLC on a Chiralpak AD with 100% Methanol as an eluent. The enantiomeric excesses were determined by using HPLC on a Chiralpak AD with 100% Methanol as an eluent at a flow rate of 2.0 mL/min. The first one enantiomer eluted at the retention time of 3.15 min, and the other enantiomer eluted at the retention time of 4.85 min. The spectral properties of the title compounds were identical with those of A102. The absolute configurations of A102a and A102b are tentatively assigned as (S) and (R) respectively based on assumption that the binding model of the more potent isomer A102a is the same as that of A101a with IDO1 enzyme.

Example A103: (7-chloroimidazo[1,5-a]pyridin-5-yl)(cyclopentyl)methanol

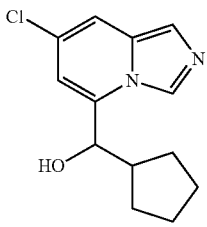 [SMILES: OC(c1cc(Cl)cc2cncn12)C1CCCC1]

Example A103 was synthesized from 7-chloroimidazo[1,5-a]pyridine-5-carbaldehyde and cyclopentylmagnesium bromide as described in Example A101. $^1$H NMR (DMSO-d$_6$) δ 8.55 (s, 1H), 7.67 (s, 1H), 7.40 (s, 1H), 6.68 (s, 1H), 5.88 (d, 1H, J=5.2 Hz), 4.68-4.72 (m, 1H), 3.30 (s, 1H), 2.45-2.51 (m, 1H) and 1.15-1.68 (m, 7H). MS (ESI) m/e [M+1]$^+$251.

Example A104: (7-chloroimidazo[1,5-a]pyridin-5-yl)(4-methylcyclohexyl)methanol

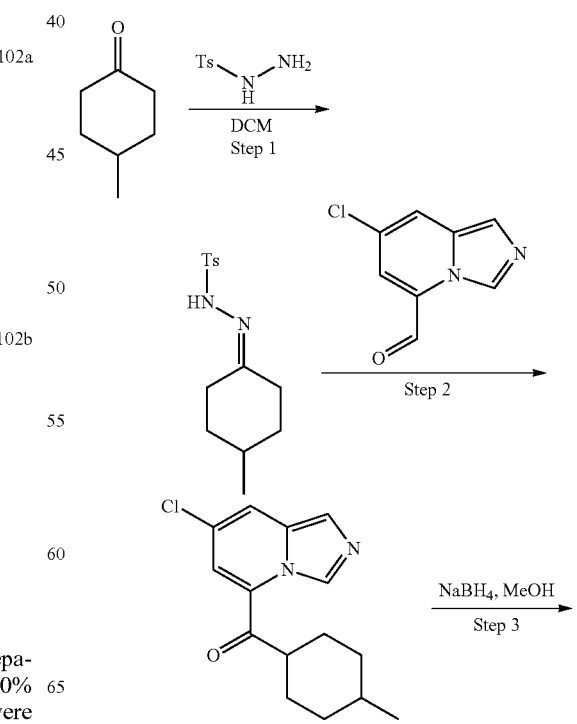

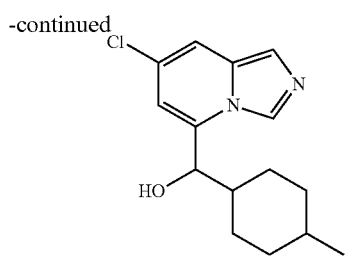

Step 1: 4-methyl-N'-(4-methylcyclohexylidene)benzenesulfonohydrazide

To a solution of 4-methylcyclohexan-1-one (2.0 g, 17.85 mmol) in MeOH (10 mL) was added 4-methylbenzenesulfonohydrazide (3.32 g, 17.85 mmol) at room temperature and the mixture was stirred overnight. After concentrated to dryness, the crude was added MeOH 5 mL and sonicated for 5 minutes, there were some white solid separated out, filtered and concentrated to dryness get a white solid 2.99 g in 60.69% yield. $^1$H NMR (CDCl$_3$) δ 7.85 (d, 2H, J=8.0 Hz), 7.44 (s, 1H, NH), 7.30 (d, 2H, J=8.0 Hz), 2.64 (m, 1H), 2.42 (m, 4H), 2.11 (m, 1H), 1.83 (m, 3H), 1.62 (m, 1H), 1.12 (m, 1H), 0.92 (d, 2H, J=8.0 Hz).

Step 2: (7-chloroimidazo[1,5-a]pyridin-5-yl)(4-methylcyclohexyl)methanone

To a solution of (E)-N'-(dihydro-2H-pyran-3(4H)-ylidene)-4-methylbenzenesulfono-hydrazide (181 mg, 1.00 mmol) in 1,4-dioxane (15 mL) was added 4-methyl-N'-(4-methylcyclohexylidene)benzenesulfonohydrazide (276 mg, 1.00 mmol) and Cs$_2$CO$_3$ (487 mg, 1.50 mmol) at room temperature and the mixture was stirred at 110° C. under N$_2$ air balloon was protected for overnight. After concentrated to dryness, the crude was added water 20 mL and extracted with EA (20 mL*3), combined the organic layer, dried over Na$_2$SO$_4$, filtered and concentrated, the crude product was purified by Pre-TLC (DCM/MeOH=15:1 as eluent) to give 56 mg in 20.2% yield. ESI-MS m/z 277.1 ([M+H]$^+$).

Step 3: (7-chloroimidazo[1,5-a]pyridin-5-yl)(4-methylcyclohexyl)methanol

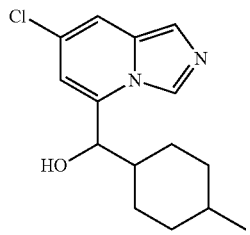 [SMILES: CC1CCC(C(O)c2cc(Cl)cc3cncn23)CC1]

To a solution of (7-chloroimidazo[1,5-a]pyridin-5-yl)(4-methylcyclohexyl)methanone (56 mg, 0.2 mmol) in MeOH (5 mL) was added NaBH$_4$ (15 mg, 0.4 mmol) at room temperature and the mixture was sonicated for 5 minutes. After quenched with water 0.5 mL and concentrated to dryness, the crude product was purified by Pre-TLC (EA/PE=1:1 as eluent), get a pale yellow solid 9.78 mg in 17.6% yield. $^1$H NMR (DMSO-d$_6$) δ 8.53 (s, 1H), 7.67 (d, 1H, J=1.6 Hz), 7.40 (s, 1H), 6.63 (d, 1H, J=1.6 Hz), 5.85 (d, 1H, J=1.6 Hz), 4.67 (m, 1H), 1.59-1.84 (m, 4H), 1.12-1.34 (m, 4H), 0.81-0.94 (m, 5H).

Example A105: 3-chloro-N-(3-((7-chloroimidazo[1,5-a]pyridin-5-yl)(hydroxy)methyl) cyclohexyl)benzamide

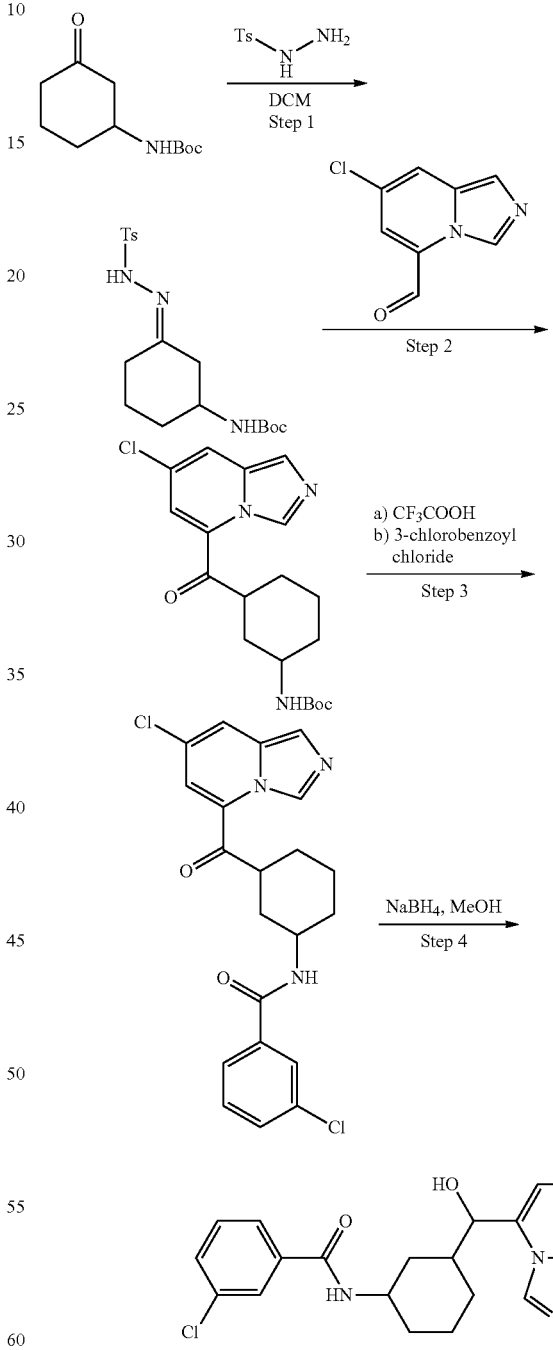

Step 1: Synthesis of tert-butyl (E)-(3-(2-tosylhydrazono)cyclohexyl)carbamate To a solution of tert-butyl (3-oxocyclohexyl)carbamate (8.4 g, 39 mmol) in MeOH (50 mL) was added 4-methylbenzenesulfonohydrazide (7.3 g, 39 mmol). The mixture was stirred overnight at r.t. After the reaction was completed, the solvent was removed under vacuum to give the product (15.7 g, 100%) as a white solid which was used next step without further purification.

Step 2: Synthesis of tert-butyl (3-(7-chloroimidazo[1,5-a]pyridine-5-carbonyl)cyclohexyl) carbamate To a solution of 7-chloroimidazo[1,5-a]pyridine-5-carbaldehyde (1.5 g, 8.2 mmol) in 1,4-dioxane (50 mL) was added $Cs_2CO_3$ (5.3 g, 16.4 mmol) and tert-butyl (E)-(3-(2-tosylhydrazono)cyclohexyl)carbamate (6.2 g, 16.4 mmol). The mixture was stirred overnight at 110° C. under $N_2$. The solid was filtered and the filtrate was concentrated to give crude product which was further purified by column chromatography, on silica (100 g), eluting with EA:PE=1:1 to give the product (1.2 g, 39%) as a brown oil. MS (ESI) m/e [M+1]$^+$378.

Step 3: Synthesis of 3-chloro-N-(3-(7-chloroimidazo[1,5-a]pyridine-5-carbonyl)cyclohexyl)-benzamide To a solution of tert-butyl (3-(7-chloroimidazo[1,5-a]pyridine-5-carbonyl)cyclohexyl)-carbamate (500 mg, 1.3 mmol) in DCM (50 ml) was added $CF_3COOH$ (3 ml). The mixture was stirred overnight at r.t. After the reaction was completed, the mixture was concentrated to give (3-aminocyclohexyl)(7-chloroimidazo[1,5-a]pyridin-5-yl)methanone which was used to the next step without further purification.

To a solution of (3-aminocyclohexyl)(7-chloroimidazo[1,5-a]pyridin-5-yl)methanone in THF (30 ml) was added $Et_3N$ (3 ml) and 3-chlorobenzoyl chloride (0.2 ml). The mixture was stirred for 5 h at r.t. After the reaction was completed. To the mixture was added $NaHCO_3$ (saturate, 20 ml) and extracted with EtOAc (50 ml×3). The organic layer was dried over with $Na_2SO_4$, filtered and concentrated to give the product (500 mg, 92%) as brown oil which was used next step without further purification. MS (ESI) m/e [M+1]$^+$416.

Step 4: Synthesis of 3-chloro-N-(3-((7-chloroimidazo[1,5-a]pyridin-5-yl)(hydroxy)methyl)-cyclohexyl)benzamide

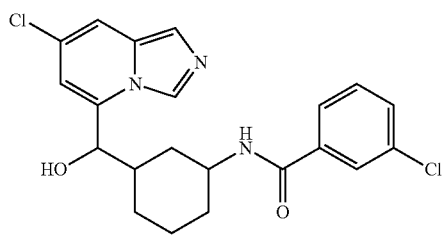 [SMILES: O=C(NC1CCCC(C(O)c2cc(Cl)cc3cncn23)C1)c1cccc(Cl)c1]

To a solution of 3-chloro-N-(3-(7-chloroimidazo[1,5-a]pyridine-5-carbonyl)cyclohexyl)-benzamide (500 mg, 1.2 mmol) in EtOH (30 ml) was added $NaBH_4$ (91 mg, 2.4 mmol). The mixture was stirred for 30 mins at r.t. The mixture was concentrated and to the residue was added $H_2O$ (30 ml) and extracted with EA (30 ml×3). The organic layer was dried over with $Na_2SO_4$, filtered and concentrated to give the crude product which was further purified by pre-HPLC to give the product (3 mg, 0.6%) as a white solid. $^1$H NMR (DMSO-$d_6$) 8.71 (s, 1H), 8.37-8.42 (m, 1H), 7.71-7.88 (m, 3H), 7.46-7.60 (m, 3H), 6.72 (s, 1H), 5.98 (s, 1H), 4.74-4.84 (m, 2H), 3.76-3.79 (m, 2H), 1.94-2.03 (m, 3H), and 1.31-1.78 (m, 4H). MS (ESI) m/e [M+1]$^+$418.

Example A106: (7-chloroimidazo[1,5-a]pyridin-5-yl)(1-(hydroxymethyl)cyclohexyl)methanol

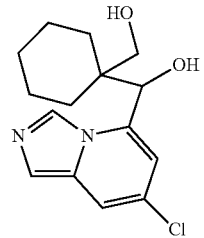 [SMILES: OCC1(C(O)c2cc(Cl)cc3cncn23)CCCCC1]

To a solution of 1-((7-chloroimidazo[1,5-a]pyridin-5-yl)(hydroxy)methyl)cyclohexane-1-carboxylate (50 mg, 0.15 mmol) in ether (5 mL) was added lithium aluminum hydride (11 mg, 0.3 mmol) and the mixture was stirred at room temperature for 24 hours, after the mixture reaction was concentrated to dryness. The crude was added water 20 mL, and extracted with EA (20 mL*3), the water layer was concentrated to dryness, the crude product was purified by Pre-TLC (EA/PE=1:1 as eluent) to give 5 mg in 11.3% yield. $^1$H NMR (DMSO-$d_6$) δ 8.68 (s, 1H), 7.54 (d, 1H, J=1.6 Hz), 7.36 (d, 1H, J=0.4 Hz), 6.68 (d, 1H, J=1.6 Hz), 5.10 (s, 1H), 4.84 (s, 1H), 3.83 (d, 1H, J=11.2 Hz), 3.58 (d, 1H, J=11.2 Hz), 1.0-1.71 (m, 10H).

Example A107: cyclohexyl(7-iodoimidazo[1,5-a]pyridin-5-yl)methanol 2,2,2-trifluoroacetate

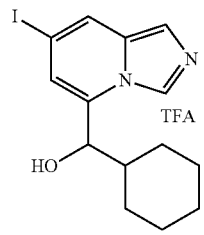 [SMILES: OC(c1cc(I)cc2cncn12)C1CCCCC1]

$^1$H NMR (DMSO-$d_6$) δ 9.08 (s, 1H), 8.17 (s, 1H), 7.71 (s, 1H), 7.04 (s, 1H), 4.67 (m, 1H), 4.40 (s, 1H), 1.60-1.82 (m, 5H), 1.10-1.31 (m, 6H). MS (ESI) m/e [M+1]$^+$357.

Example A108: cyclohexyl(7-cyclopropylimidazo[1,5-a]pyridin-5-yl)methanol 2,2,2-trifluoroacetate

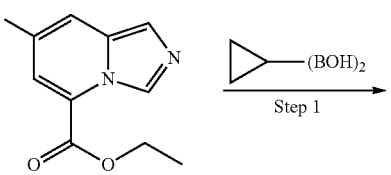

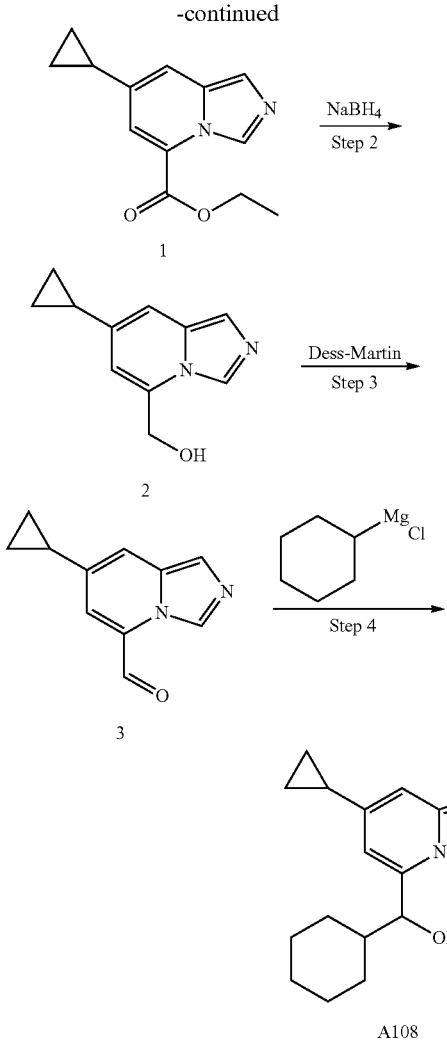

Step 1: ethyl 7-cyclopropylimidazo[1,5-a]pyridine-5-carboxylate

Ethyl 7-iodoimidazo[1,5-a]pyridine-5-carboxylate (948 mg, 3 mmol), cyclopropylboronic acid (387 mg, 5 mmol), 4,5-BIS-DIPHENYLPHOSPHANYL-9,9-DIMETHYL-9H-XANTHENE (174 mg, 0.3 mmol), Tris(dibenzylideneacetone)dipalladium (275 mg, 0.3 mmol) and $K_2CO_3$ (1251 mg, 9.0 mmol) were suspended on toluene (50 mL), the mixture was heated to 110° C. for 5 hours under $N_2$ atmosphere, The mixture was quenched with $H_2O$ (150 mL) and EA (150 mL), washed with brine (150 mL), dried over $Na_2SO_4$ and concentrated. The residue was purified by chromatography on silica gel (elute with EA/petroleum ether=1:5-1:1) to give yellow solid (w=600 mg). MS (ESI) m/e $[M+1]^+231$.

Step 2: (7-cyclopropylimidazo[1,5-a]pyridin-5-yl) methanol

Ethyl 7-cyclopropylimidazo[1,5-a]pyridine-5-carboxylate (400 mg, 1.74 mmol) was suspended on EtOH (20 mL), then $NaBH_4$ (198 mg, 5.22 mmol) was added at room temperature. The mixture was stirred at room temperature for 4 hours. The mixture was quenched with EA (100 mL) and $H_2O$ (100 mL), the organic layer was washed with brine (100 mL), dried over $Na_2SO_4$ and concentrated. The residue was purified chromatography on silica gel (elute with EA/petroleum ether=1:5-1:0) to give yellow oil (w=280 mg). MS (ESI) m/e $[M+1]^+189$ Step 3: 7-cyclopropylimidazo[1,5-a]pyridine-5-carbaldehyde To a solution of (7-cyclopropylimidazo[1,5-a]pyridin-5-yl)methanol (140 mg, 0.76 mmol) in DCM (10 mL) was added Dess-Martin reagent (647 mg, 1.53 mmol) at room temperature. The mixture was stirred at room temperature for 4 hours. The mixture was quenched with EA (100 mL) and $H_2O$ (50 mL), the organic layer was washed with brine (100 mL), dried over $Na_2SO_4$ and concentrated. The residue was purified by chromatography on silica gel (elute with EA/petroleum ether=1:10-1:1) to give yellow solid (w=60 mg). MS (ESI) m/e $[M+1]^+187$.

Step 4: cyclohexyl(7-cyclopropylimidazo[1,5-a]pyridin-5-ylmethanol 2,2,2-trifluoroacetate

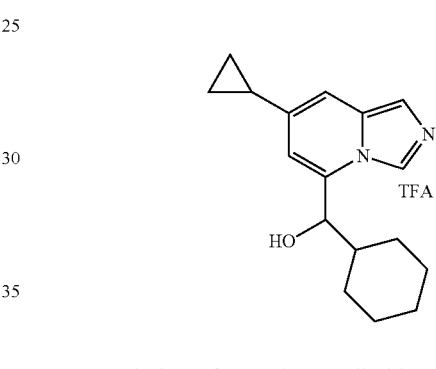

To a solution of 7-cyclopropylimidazo[1,5-a]pyridine-5-carbaldehyde (60 mg, 0.32 mmol) in THF (6 mL) was added dropwise cyclohexylmagnesium chloride (0.5 mmol, 1.3N in toluene) under $N_2$ atmosphere at room temperature for 0.5 hour. The mixture was stirred at RT for 0.5 hour. The mixture was quenched with aqueous $NH_4Cl$ (50 mL) and EA (50 mL), washed with brine (50 mL), dried over $Na_2SO_4$ and concentrated. The residue was purified by Pre-HPLC to give white solid (W=3.0 mg). $^1H$ NMR (DMSO-$d_6$) δ 9.50 (s, 1H), 7.81 (s, 1H), 7.42 (s, 1H), 6.80 (s, 1H), 4.67 (m, 1H), 4.40 (s, 1H), 1.67-2.01 (m, 5H), 0.81-0.88 (m, 10H). MS (ESI) m/e $[M+1]^+271$.

Example A109: cyclohexyl(7-(trifluoromethyl)imidazo[1,5-a]pyridin-5-yl)methanol

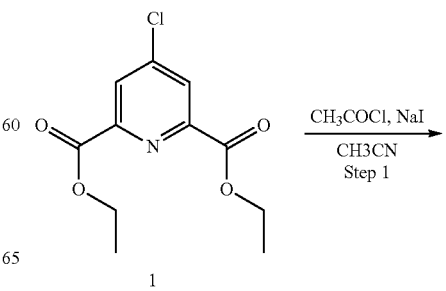

103
-continued
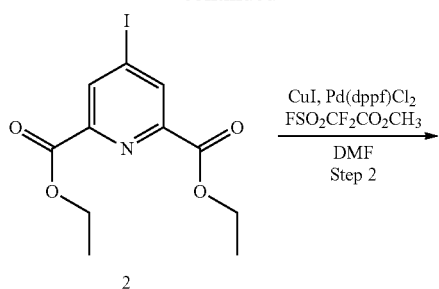
2
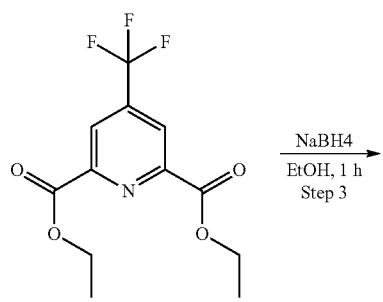
3
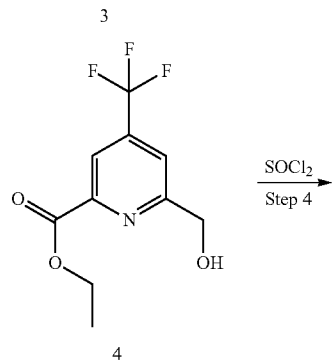
4
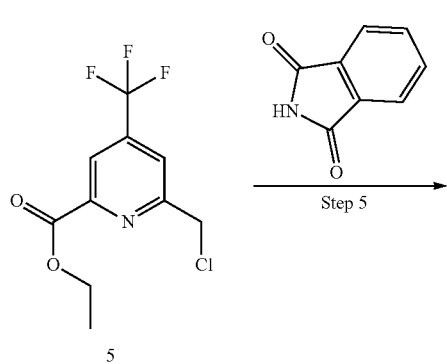
5
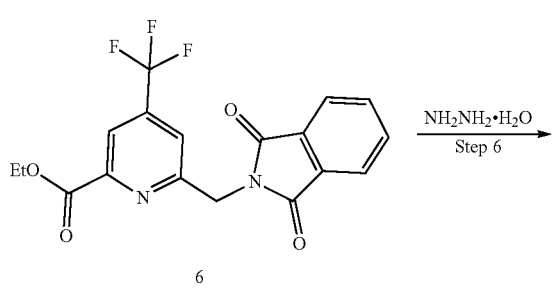
6
104
-continued
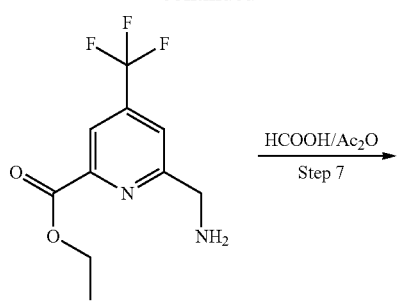
7
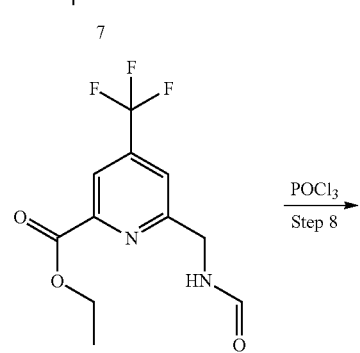
8
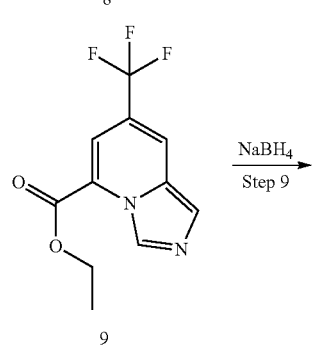
9
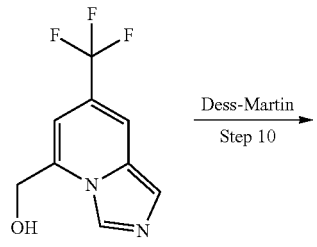
10
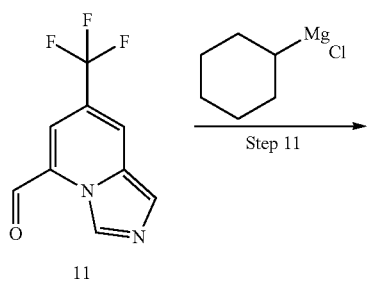
11

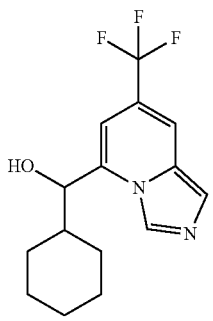 [SMILES: OC(c1cc(C(F)(F)F)cc2cncn12)C1CCCCC1]

A109

Step 1: Synthesis of diethyl 4-iodopyridine-2,6-dicarboxylate

To a solution of diethyl 4-chloropyridine-2,6-dicarboxylate (70 g, 266 mmol) in CH$_3$CN (570 mL) was added acetyl chloride (56 mL) and NaI (280 g, 1862 mmol) at r.t. Then the mixture was stirred overnight at 65° C. The solid was filtered and the filtrate was concentrated under vacuum. To the residue was added Na$_2$CO$_3$ (aq) to adjusted the pH>7 and extracted with EtOAc (500 mL*3). The organic layer was dried over with Na$_2$SO$_4$, filtered and concentrated to give crude product which was further purified by column chromatography, eluting with EA: PE=1:1 to give the product (59.5 g, 64%) as a brown solid. $^1$H NMR (DMSO-d$_6$) δ 8.56 (s, 2H), 4.40 (q, 4H, J=7.2 Hz), 1.35 (t, 6H, J=7.2 Hz). MS (ESI) m/e [M+1]$^+$350.

Step 2: Synthesis of diethyl 4-(trifluoromethyl)pyridine-2,6-dicarboxylate

To a solution of diethyl 4-iodopyridine-2,6-dicarboxylate (6.5 g, 19 mmol) in DMF (50 mL) was added Cu (7.3 g, 38 mmol), Pd(dppf)Cl$_2$ (0.7 g, 0.95 mmol) and FSO$_2$CF$_2$CO$_2$CH$_3$ (9.1 g, 47.5 mmol). The mixture was stirred overnight at 100° C. under N$_2$. The solid was filtered and the filtrate was poured into H$_2$O (150 mL) and extracted with EtOAc (50 mL*3). The organic layer was dried over with Na$_2$SO$_4$, filtered and concentrated to give crude product which was further purified by column chromatography, eluting with EA:PE=1:1 to give the product (2.8 g, 51%) as a brown solid.

Step 3: Synthesis of ethyl 6-(hydroxymethyl)-4-(trifluoromethyl)picolinate

To a solution of diethyl 4-(trifluoromethyl)pyridine-2,6-dicarboxylate (2.8 g, 9.6 mmol) in EtOH (20 mL) was added NaBH$_4$ (182 mg, 4.8 mmol). The mixture was stirred for 1 h at 90° C. The solution was removed under vacuum. To the residue was added H$_2$O (50 mL) and extracted with EtOAc (50 mL*3). The organic layer was dried over with Na$_2$SO$_4$, filtered and concentrated to give the product (1.6 g, 67%) as a brown solid which was used next step without further purification.

Step 4: Synthesis of ethyl 6-(chloromethyl)-4-(trifluoromethyl)picolinate

To a solution of ethyl 6-(hydroxymethyl)-4-(trifluoromethyl)picolinate (1.6 g, 6.4 mmol) in DCM (20 mL) was added dropwise of SOCl$_2$ (2 mL) at r.t. After 3 h at room temperature and the excess of SOCl$_2$ was removed under reduced pressure without heating. The residue was adjusted the pH>7 with saturated aqueous of NaHCO$_3$ and extracted with EtOAc (30 mL*2). The organic layer was dried over with Na$_2$SO$_4$. Evaporation of the solvent afforded ethyl 6-(chloromethyl)-4-(trifluoromethyl)picolinate (1.8 g), which was used to the next step without further purification.

Step 5: Ethyl 6-((1,3-dioxoisoindolin-2-yl)methyl)-4-(trifluoromethyl)picolinate To a solution of ethyl 6-(chloromethyl)-4-(trifluoromethyl)picolinate (1.8 g, 6.7 mmol) in DMF (30 mL) was added sodium phthalimide (1.5 g, 8.04 mmol) at room temperature and the mixture was stirred overnight at r.t. Then solid was filtered and the filtrate was poured into water (50 mL) and extracted with EtOAc (50 mL*3). The organic layer was purified by column chromatography, on silica, eluting with EA:PE=1:1 to give the product (1.4 g). MS (ESI) m/e [M+1]$^+$379.

Steps 6 and 7: Ethyl 6-(formamidomethyl)-4-(trifluoromethyl)picolinate

To a solution of ethyl 6-((1,3-dioxoisoindolin-2-yl) methyl)-4-(trifluoromethyl)picolinate (1.4 g, 3.7 mmol) in EtOH (80 mL) was added hydrazine hydrate (222 mg). The mixture was stirred for 3.5 h at 90° C. Then cooled to room temperature, filtered to remove the white precipitate and HCOOH (20 mL) was added to the filtrate, filtered again to remove white precipitate and the filtrate was evaporated to give crude product containing HCOOH as a brown oil, and this crude product ethyl 6-(aminomethyl)-4-(trifluoromethyl)picolinate was used for next step without further purification. The crude product ethyl 6-(aminomethyl)-4-(trifluoromethyl)picolinate was dissolved in HCOOH (60 mL) Ac$_2$O (20 mL) and stirred for 2 h at 50° C. Cooled to room temperature and evaporated the solvent before HCl (30 mL, 0.5N) was added to the residue. Then extracted with EA (30 mL*3). The organic layer was dried over with Na$_2$SO$_4$, filtered and concentrated to give product (880 mg, 86% (by two steps)) which was used next step without further purification. MS (ESI) m/e [M+1]$^+$277.

Step 8: Ethyl 7-(trifluoromethyl)imidazo[1,5-a]pyridine-5-carboxylate

To a solution of ethyl 6-(formamidomethyl)-4-(trifluoromethyl)picolinate (0.88 g, 3.2 mmol) in toluene (30 mL) was added POCl$_3$ (1.5 mL) at room temperature and the mixture was heated at 80° C. for 2 hours. Then cooled to room temperature and evaporated the solvent before HCl (5 mL, con.) and H$_2$O (20 ml) was added to the residue, extracted with EA (20 mL*2), isolated the aqueous layer, adjusted pH=7-8 with saturated aqueous of NaOH before extracted with EA (100 mL*2), combined the organic layers, evaporated the solvent to give the product (480 mg, 58%) as a brown oil. MS (ESI) m/e [M+1]$^+$259.

Step 9: (7-(trifluoromethyl)imidazo[1,5-a]pyridin-5-yl)methanol

To a solution of ethyl 7-(trifluoromethyl)imidazo[1,5-a] pyridine-5-carboxylate (480 mg, 1.9 mmol) in EtOH (50 mL) was added batch wise of NaBH$_4$ (144 mg, 3.8 mmol) at r.t. and the mixture was stirred at 90° C. for 2 h. The solvent was removed under vacuum. To the residue was added H₂O (20 mL) and HCl (37%, 5 mL), then extracted with EtOAc (30 mL*2). The aqueous layer was adjusted with Na₂CO₃ (solid) to pH>8 and extracted with EtOAc (30 mL*3). The organic layer was dried over with Na₂SO₄, filtered and concentrated to give the product (230 mg, 56%) as a brown solid.

Step 10: 7-(trifluoromethyl)imidazo[1,5-a]pyridine-5-carbaldehyde

To a solution of (7-(trifluoromethyl)imidazo[1,5-a]pyridin-5-yl)methanol (230 mg, 1.1 mmol) in DCM (50 mL) was added portion of Dess-Martin (932 mg, 2.2 mmol) at room temperature and the mixture was stirred overnight. To the resulting mixture was added H₂O (20 mL) and HCl (5 mL). The aqueous layer was extracted with DCM (20 ml*2) and adjusted the pH>8 with Na₂CO₃. The aqueous layer was extracted with EtOAc (50 mL*3). The organic layer was dried over with Na₂SO₄, filtered and concentrated to give the product (130 mg, 55%) as a brown solid which was used next step without further purification. MS (ESI) m/e [M+1]⁺ 215.

Step 11: Cyclohexyl(7-(trifluoromethyl)imidazo[1,5-a]pyridin-5-yl)methanol

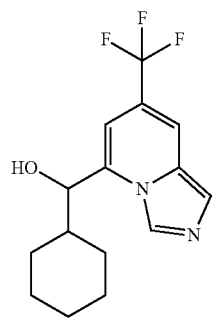

To a solution of 7-(trifluoromethyl)imidazo[1,5-a]pyridine-5-carbaldehyde (50 mg, 0.23 mmol) in dry THF (20 mL) was added dropwise of cyclohexylmagnesium chloride (0.29 mL, 1.6M) at 0° C. under N₂ air balloon was protected. And the mixture was stirred warmed to room temperature slowly for 30 mins. Water (20 mL) was added to the mixture and extracted with EA (30 mL*3), combined the organic layers and dried over Na₂SO₄, filtered to remove Na₂SO₄ and the filtrate was concentrated, the crude product was purified by pre-TLC (PE/EA=1:1 as eluent) to give 20 mg in 28% yield. ¹H NMR (DMSO-d₆) δ 8.70 (s, 1H), 8.08 (s, 1H), 7.73 (s, 1H), 6.80 (s, 1H), 5.89 (d, 1H, J=4.0 Hz), 4.76 (q, 1H, J=4.8 Hz), 1.59-1.81 (m, 5H), 1.23-1.32 (m, 1H) and 1.11-1.16 (m, 6H). MS (ESI) m/e [M+1]⁺299.

Examples A109a and A109b: (S)-cyclohexyl(7-(trifluoromethyl)imidazo[1,5-a]pyridin-5-yl)methanol and (R)-cyclohexyl(7-(trifluoromethyl)imidazo[1,5-a]pyridin-5-yl)methanol

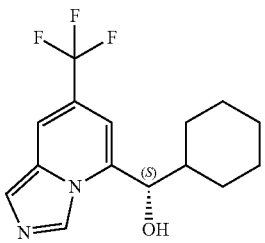

A109a

Fast isomer in chiral IC HPLC
Eluting reagent: Hexane/IPA = 90/10(V/V)

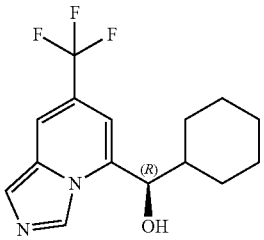

A109b

Slow isomer in chiral IC HPLC
Eluting reagent: Hexane/IPA = 90/10(V/V)

Each enantiomer of racemic A109a and A109b was separated using preparative HPLC on a Chiralpak IC with Eluting reagent: Hexane/IPA=90/10 (V/V) as an eluent. The enantiomeric excesses were determined by using HPLC on a Chiralpak IC with Hexane/IPA=90/10 (V/V) as an eluent at a flow rate of 2.0 mL/min. The first one enantiomer eluted at the retention time of 4.17 min, and the other enantiomer eluted at the retention time of 5.84 min. The spectral properties of the title compounds were identical with those of A109. The absolute configurations of A109a and A109b are tentatively assigned as (S) and (R) respectively based on assumption that the binding model of the more potent isomer A109a is the same as that of A101a with IDO1 enzyme.

Example A110: Cyclopentyl(7-(trifluoromethyl)imidazo[1,5-a]pyridin-5-yl)methanol

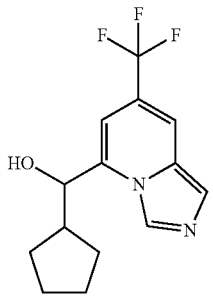 [SMILES: OC(c1cc(C(F)(F)F)cc2cncn12)C1CCCC1]

Example A110 was synthesized from 7-(trifluoromethyl)imidazo[1,5-a]pyridine-5-carbaldehyde and cyclopentylmagnesium chloride by following the procedures similar to those in Example A109. ¹H NMR (DMSO-d₆) δ 8.72 (s, 1H), 8.09 (s, 1H), 7.73 (s, 1H), 6.84 (s, 1H), 5.92 (d, 1H, J=6.0 Hz), 4.80 (q, 1H, J=4.8 Hz) and 1.44-1.63 (m, 9H). MS (ESI) m/e [M+1]⁺285.

Examples A111 and A112 were synthesized following similar procedures under appropriate conditions that could be recognized by one skilled in the art.

Example A111: (7-bromoimidazo[1,5-a]pyridin-5-yl)(cyclohexyl)methanol

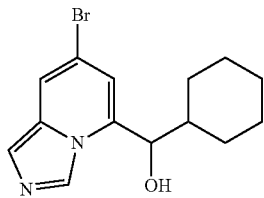 [SMILES: OC(c1cc(Br)cc2cncn12)C1CCCCC1]

¹H NMR (400 MHz, CDCl₃) δ 9.64 (t, J=3.6 Hz, 1H), 7.80 (s, 1H), 7.76 (s, 1H), 6.98 (s, 2H), 4.75 (d, J=2.0 Hz, 1H), 2.31-1.65 (m, 5H), 1.41-1.02 (m, 6H) ppm. MS: M/e 309 (M+1)⁺

Example A112: (7-bromoimidazo[1,5-a]pyridin-5-yl)(cyclopentyl)methanol

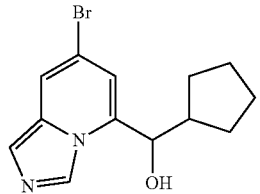 [SMILES: OC(c1cc(Br)cc2cncn12)C1CCCC1]

¹H NMR (400 MHz, CD₃OD) δ 8.68 (s, 1H), 7.74 (s, 1H), 7.45 (s, 1H), 6.80 (s, 1H), 4.63 (d, J=8.4 Hz, 1H), 2.60-2.40 (m, 1H), 2.16-1.75 (m, 2H), 1.71-1.40 (m, 6H) ppm. MS: M/e 295 (M+1)⁺

Examples A113 and A114 were synthesized with the corresponding aldehyde and Grignard reagent following the procedures similar to those in Example A109.

Example A113: 1-(7-chloroimidazo[1,5-a]pyridin-5-yl)-3-cyclohexylpropan-1-ol

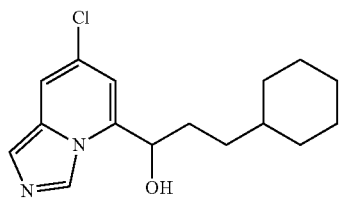 [SMILES: OC(CCC1CCCCC1)c1cc(Cl)cc2cncn12]

¹H NMR (DMSO-d₆) δ 8.47 (s, 1H), 7.67 (d, J=2.0 Hz, 1H), 7.41 (s, 1H), 6.66 (d, J=2.0 Hz, 1H), 5.83 (d, J=4.2 Hz, 1H), 4.86-4.90 (m, 1H), 2.49-2.51 (m, 2H), 1.74-1.75 (m, 5H), 1.12-1.20 (m, 6H), 0.81-0.85 (m, 2H).

Example A114: 2-cyclohexyl-1-(7-(trifluoromethyl)imidazo[1,5-a]pyridin-5-yl)ethan-1-ol

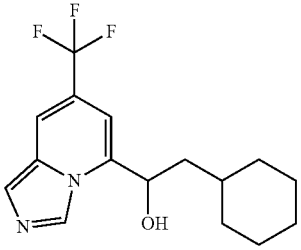 [SMILES: OC(CC1CCCCC1)c1cc(C(F)(F)F)cc2cncn12]

¹H NMR (DMSO-d₆) δ 8.56 (s, 1H), 8.10 (s, 1H), 7.74 (s, 1H), 6.84 (s, 1H), 5.86 (d, 1H, J=5.6 Hz), 5.05-5.10 (m, 1H), 1.59-1.91 (m, 7H), 0.89-1.23 (m, 6H).

Examples A114a and A114b: (R)-2-cyclohexyl-1-(7-(trifluoromethyl)imidazo[1,5-a]pyridin-5-yl)ethan-1-ol and (S)-2-cyclohexyl-1-(7-(trifluoromethyl)imidazo[1,5-a]pyridin-5-yl)ethan-1-ol

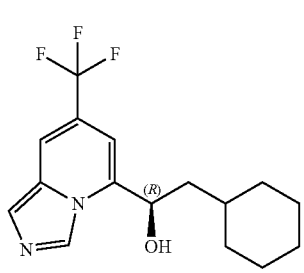

A114a

Fast isomer in chiral AD HPLC
Eluting reagent: Hexane/IPA = 90/10(V/V)

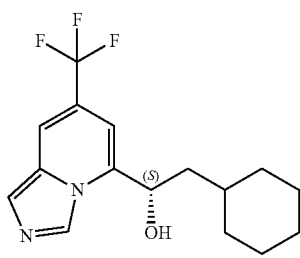

A114b

Slow isomer in chiral AD HPLC
Eluting reagent: Hexane/IPA = 90/10(V/V)

Each enantiomer of racemic A114a and A114b was separated using preparative HPLC on a Chiralpak AD with Eluting reagent (Hexane/IPA=90/10 (V/V)) as an eluent. The enantiomeric excesses were determined by using HPLC on a Chiralpak AD with Hexane/IPA (90/10, (V/V)) as an eluent at a flow rate of 2.0 mL/min. The first one enantiomer eluted at the retention time of 3.81 min, ¹H NMR (DMSO-d₆) δ 8.56 (s, 1H), 8.10 (s, 1H), 7.74 (s, 1H), 6.84 (s, 1H), 5.86 (d, 1H, J=5.6 Hz), 5.05-5.10 (m, 1H), 1.59-1.91 (m, 7H), 0.89-1.23 (m, 6H). MS (ESI) m/e [M+1]⁺313; and the other enantiomer eluted at the retention time of 4.54 min, ¹H NMR (DMSO-d₆) 8.56 (s, 1H), 8.10 (s, 1H), 7.74 (s, 1H), 6.84 (s, 1H), 5.86 (d, 1H, J=5.6 Hz), 5.05-5.10 (m, 1H), 1.59-1.91 (m, 7H), 0.89-1.23 (m, 6H). MS (ESI) m/e [M+1]+ 313. The absolute configurations of A1114a and A114b are tentatively assigned as (R) and (S) respectively based on assumption that the binding model of the more potent isomer A114b is the same as that of A101a with IDO1 enzyme.

Example A115: cycloheptyl(7-(trifluoromethyl)imidazo[1,5-a]pyridin-5-yl)methanol

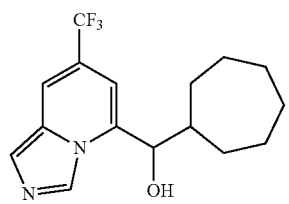 [SMILES: OC(c1cc(C(F)(F)F)cc2cncn12)C1CCCCCC1]

Example A115 was synthesized with the corresponding aldehyde and Grignard reagent following the procedures similar to those in Example A109. $^1$H NMR (DMSO-$d_6$) 8.67 (s, 1H), 8.08 (s, 1H), 7.73 (s, 1H), 6.82 (s, 1H), 5.90 (d, J=4.8 Hz, 1H), 4.68 (dd, J=4.8, 10.2 Hz, 1H), 1.99-2.01 (m, 1H), 1.02-1.67 (m, 12H). LC-MS (M+H)+=313.

Example A116: (6-chloroimidazo[1,5-a]pyridin-5-yl)(cyclohexyl)methanol

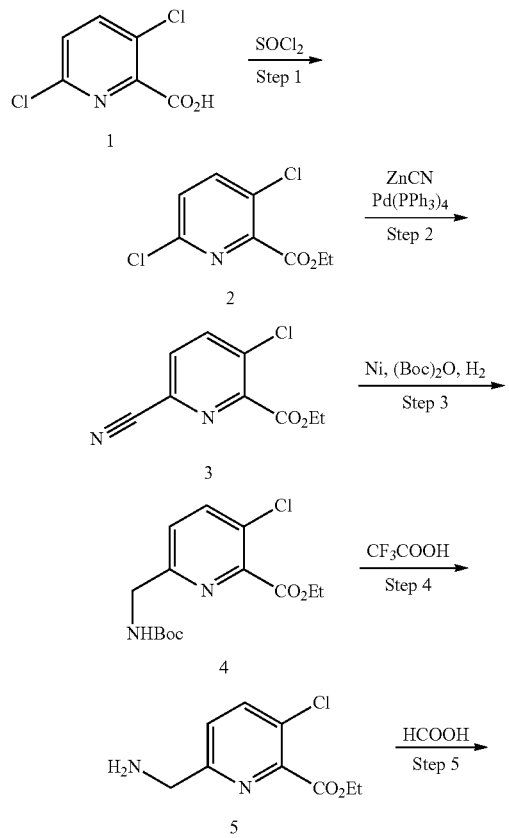

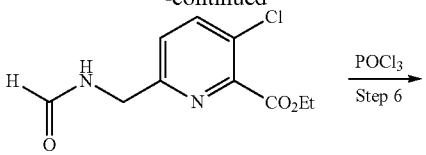

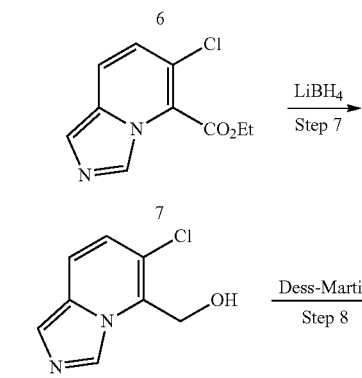

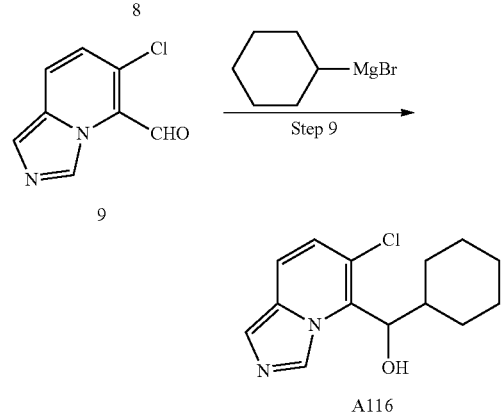

Step 1: Ethyl 3,6-dichloropicolinate

To a solution of compound 1 (100 g, 520.8 mmol) in EtOH (400 mL) was added drop-wise SOCl$_2$ (155 g, 1.3 mol) at 0° C. Then the mixture was stirred at 90° C. for 2 h. TLC (PE:EA=3:1, R$_f$=0.5) showed the reaction was completed. The solvent was evaporated under reduced pressure. The mixture was add saturated NaHCO$_3$ adjusted PH=7 and extracted with EA (200 ml*3). The combined organic layer was dried with Na$_2$SO$_4$, filtered and concentrated to give compound (120 g, 100%) as yellow oil. LC-MS (M+H)+ =220.

Step 2: ethyl 3-chloro-6-cyanopicolinate

A mixture of compound 2 (50 g, 90.816 mmol) in DMF (300 mL) was added (20 g, 170.45 mmol) and Pd(pph$_3$)$_4$ (26 g, 227.3 mol), then the mixture was stirred at 95° C. for 2 hours under N$_2$. TLC (PE:EA=3:1, R$_f$=0.5) showed the reaction was completed. The solvent was added H$_2$O (100 ml) filtered to remove the white precipitate and extracted with EA (200 ml*3). The combined organic layer was dried over Na$_2$SO$_4$, filtered and concentrated to give crude product. The crude was purified by silica gel chromatography (PE:EA=20:1-8:1) to give compound 3 (22 g, 47%) as yellow oil.

Step 3: Ethyl 6-(((tert-butoxycarbonyl)amino)methyl)-3-chloropicolinate

To a solution of compound 3 (3.6 g, 17.1 mmol) and (Boc)$_2$O (5.95 g, 34.2 mmol) in EtOH (30 mL) was added Raney-Ni (3.6 g) was stirred at room temperature for 16 h under H$_2$ at 60 psi. Then filtration, the solvent was removed under vacuum. The residue was purified by silica gel chromatography (PE:EA=5:1) to give compound 4 (4.6 g, 85.4%) as a colorless solid. LC-MS (M+H)$^+$=259, 315.

Step 4: Ethyl 6-(aminomethyl)-3-chloropicolinate

To a stirred solution of compound 4 (5.35 g, 16.98 mmol) in DCM (30 mL) was added CF$_3$COOH (15 mL) and stirred at rt for 3 h. Then the solvent was removed under reduced under vacuum to give the product, which was used for the next step without further purification. LC-MS (M+H)$^+$=215.

Step 5: Ethyl 3-chloro-6-(formamidomethyl)picolinate

A mixture of compound 5 (4.3 g) in HCOOH (30 mL) was stirred at 50° C. for 30 min. Then (AcO)$_2$O (10 mL) was added and stirred further for 2 h at 50° C. After cooling to rt, the solvent was removed under vacuum to give the crude product (3.5 g), which was used for the next step without further purification. LC-MS (M+H)$^+$=243.1

Step 6: ethyl 6-chloroimidazo[1,5-a]pyridine-5-carboxylate

A mixture of compound 6 (3.5 g, 14.5 mmol) in toluene (20 mL) was added POCl$_3$ (2 mL) and the mixture was heated at 80° C. for 2 h. Then cooled to room temperature, the solvent was removed under vacuum, the residue was added sat. aq. NaHCO$_3$ (100 mL), extracted with DCM (100 mL*2), dried with Na$_2$SO$_4$, evaporated under vacuum. The residue was purified by silica gel (PE:EA=1:5 then DCM:MEOH=100:1) to give product as a yellow solid (2.0 g, 62%). $^1$H NMR (400 MHz, DMSO-d$_6$) δ 8.63 (s, 1H), 7.84-7.86 (d, J=9.2 Hz, 1H), 7.62 (s, 1H), 6.91-6.93 (d, J=9.2 Hz, 1H), 4.49-4.55 (m, 1H), 1.37-1.41 (m, 3H). LC-MS (M+H)$^+$=225.

Step 7: (6-chloroimidazo[1,5-a]pyridin-5-yl)methanol

To a solution of compound 7 (2.0 g, 8.93 mmol) in EtOH (60 mL) was added LiBH$_4$ (0.45 g, 22.3 mmol) and stirred at rt for 4 hours. Then water (100 mL) was added, extracted with DCM (100 mL*2), dried with Na$_2$SO$_4$, the filtered to remove Na$_2$SO$_4$, evaporated the solvent to give a crude product as yellow oil (1.9 g). And this crude product was used for next step without further purification. LC-MS (M+H)$^+$=183.0.

Step 8: 6-chloroimidazo[1,5-a]pyridine-5-carbaldehyde

To a solution of compound 8 (1.9 g, 10.43 mmol) in DCM (50 mL) was added Dess-Martin (6.64 g, 15.65 mmol) at room temperature and the mixture was stirred at rt for 12 hours. Then water (80 mL) was added, extracted with DCM (75 mL*2), dried with Na$_2$SO$_4$, the filtered to remove Na$_2$SO$_4$, evaporated the solvent, the residue was purified by silica gel (PE:EA=1:5 then to =1:1) to give product as a yellow solid (1.5 g, 83%). LC-MS (M+H)$^+$=181.

Step 9: (6-chloroimidazo[1,5-a]pyridin-5-yl)(cyclohexyl)methanol (Example A116)

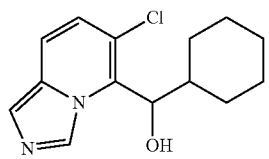 [SMILES: OC(c1c(Cl)ccc2cncn12)C1CCCCC1]

To a solution of compound 9 (0.1 g, 0.56 mmol) in THF (10 mL) was added cyclohexyl-magnesium bromide (0.6 mL, 1.12 mmol) at −60° C. and the mixture was stirred at −60° C. for 2 hours. Then water (20 mL) was added, extracted with DCM (20 mL×2), dried with Na$_2$SO$_4$, the filtered to remove Na$_2$SO$_4$, evaporated the solvent, the residue was purified pre-HPLC to give product as a white solid (25 mg, 21%). $^1$H NMR (400 MHz, CD$_3$OD) δ 9.58 (s, 1H), 7.93 (s, 1H), 7.65 (d, J=10 Hz, 1H), 7.11 (d, J=10 Hz, 1H), 5.19 (d, J=9.6 Hz, 1H), 2.16-2.19 (m, 1H), 1.98-2.03 (m, 1H), 1.72-1.76 (m, 1H). 1.57-1.61 (m, 2H), 1.03-1.24 (m, 7H). LC-MS (M+H)+=265.1.

Examples A116a and A116b: (S)-(6-chloroimidazo[1,5-a]pyridin-5-yl)(cyclohexyl)methanol compound and (R)-(6-chloroimidazo[1,5-a]pyridin-5-yl)(cyclohexyl)methanol

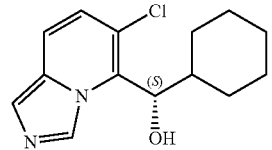

A116a

Fast isomer in chiral OD HPLC
Eluting reagent: Hexane/IPA/TEA = 70/30/0.1

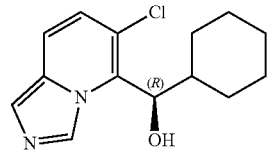

A116b

Slow isomer in chiral OD HPLC
Eluting reagent: Hexane/IPA/TEA = 70/30/0.1

Each enantiomer of racemic A116a and A116b was separated using preparative HPLC on a Chiralpak OD with Hexane/IPA/TEA=70/30/0.1 as an eluent. The enantiomeric excesses were determined by using HPLC on a Chiralpak OD with Hexane/IPA/TEA=70/30/0.1 as an eluent at a flow rate of 1.0 mL/min. The first one enantiomer eluted at the retention time of 3.42 min, and the other enantiomer eluted at the retention time of 4.65 min. The spectral properties of the title compounds were identical with those of A116. The absolute configurations of A116a and A116b are tentatively assigned as (S) and (R) respectively based on assumption that the binding model of the more potent isomer A116a is the same as that of A101a with IDO1 enzyme.

Example A117 was synthesized from 6-chloroimidazo[1,5-a]pyridine-5-carbaldehyde and the corresponding Grignard regent by following the procedures similar to those in Example A116.

Example A117: 1-(6-chloroimidazo[1,5-a]pyridin-5-yl)-2-cyclohexylethan-1-ol

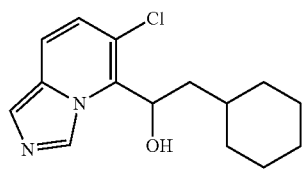

$^1$HNMR (400 MHz, DMSO-$d_6$) δ 8.71 (s, 1H), 7.54 (d, J=10 Hz, 1H), 7.47 (s, 1H), 6.79 (d, J=10 Hz, 1H), 6.03 (d, J=4 Hz, 1H), 5.48-5.52 (m, 1H), 1.96-2.01 (m, 1H), 1.47-1.77 (m, 7H), 0.88-1.25 (m, 5H). LC-MS (M+H)$^+$=279.1.

Examples A117a and A117b: (S)-1-(6-chloroimidazo[1,5-a]pyridin-5-yl)-2-cyclohexylethan-1-ol and (R)-1-(6-chloroimidazo[1,5-a]pyridin-5-yl)-2-cyclohexylethan-1-ol A117a

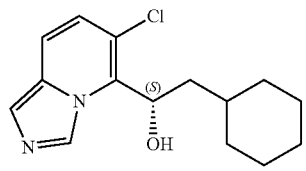 [SMILES: OC(CC1CCCCC1)c1c(Cl)ccc2cncn12]

Fast isomer in chiral AS HPLC
Eluting reagent: Hexane/EtOH/TEA = 90/10/0.1(V/V/V)

A117b

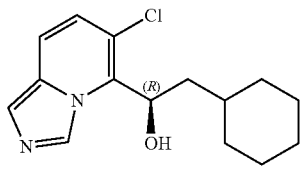

Slow isomer in chiral AS HPLC
Eluting reagent: Hexane/EtOH/TEA = 90/10/0.1(V/V/V)

Each enantiomer of racemic A117a and A117b was separated using preparative HPLC on a Chiralpak AS with Hexane/EtOH/TEA=90/10/0.1 as an eluent. The enantiomeric excesses were determined by using HPLC on a Chiralpak AS with Hexane/EtOH/TEA=90/10/0.1 as an eluent at a flow rate of 1.0 mL/min. The first one enantiomer eluted at the retention time of 5.15 min, and the other enantiomer eluted at the retention time of 7.99 min. The spectral properties of the title compounds were identical with those of A117. The absolute configurations of A117a and A117b are tentatively assigned as (S) and (R) respectively based on assumption that the binding model of the more potent isomer A117a is the same as that of A101a with IDO1 enzyme.

Example A118: 6-bromoimidazo[1,5-a]pyridin-5-yl)(cyclohexyl)methanol

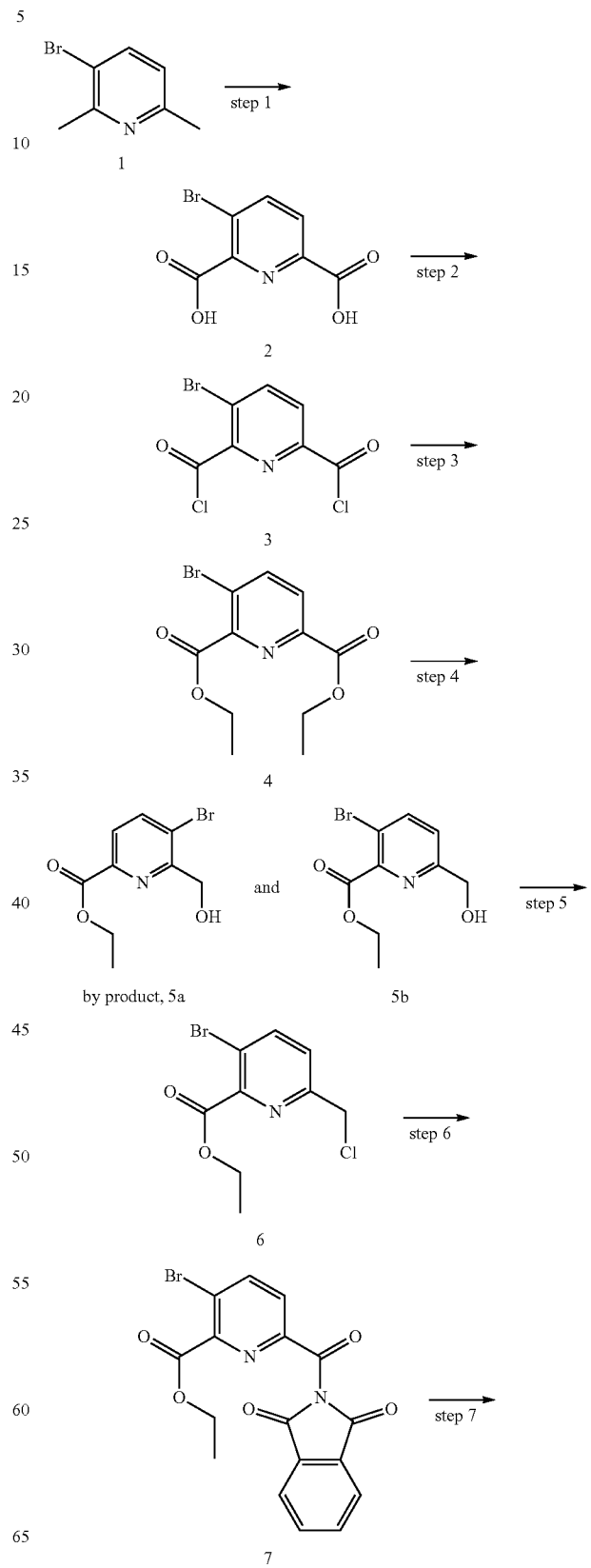

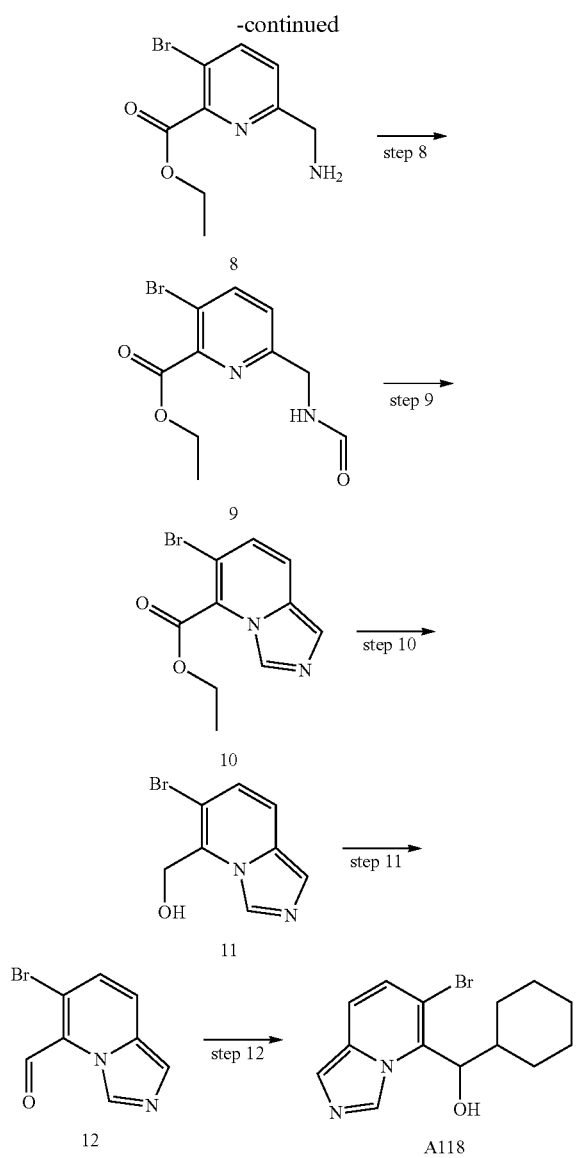

Step 1: 3-bromopyridine-2,6-dicarboxylic acid

To a solution of 3-bromo-2,6-dimethylpyridine (20 g, 0.107 mol) in $H_2O$ (300 mL) was added $KMnO_4$ (85 g, 0.537 mol) in ten portions. The first five portions were added over 5 hours at 70° C. and the second five portions over 5 hours at 90° C. After complete addition, the mixture was stirred at 90° C. for 12 hours. The reaction mixture was filtered hot and the residue was washed with hot $H_2O$ (100 mL). The filtrate was concentrated and conc. HCl (60 mL) was added, heating to 100° C. to dissolve the precipitated white solid. The mixture was allowed cool to room temperature and filtered. The cake was collected and dried to give target compound (12 g, 45.6%) as a white solid. $^1$H NMR (400 MHz, DMSO-$d_6$) δ 13.82 (s, 2H), 8.36 (t, J=18.8 Hz, 1H), 8.02 (d, J=8.4 Hz, 1H) ppm. MS: M/e 246 (M+1)$^+$.

Step 2: 3-bromopyridine-2,6-dicarbonyl dichloride

A mixture of the product of step 1 (12 g, 48.8 mmol) in $SOCl_2$ (20 mL) was stirred at 100° C. for 2 hours until complete dissolved, then concentrated to give target compound, which was directly used to the next step without further purification.

Step 3: diethyl 3-bromopyridine-2,6-dicarboxylate

A mixture of the product of step 2 (48.8 mmol) in EtOH (50 mL) and refluxed for 4 hours. Then the reaction mixture was concentrated to give target compound (14.7 g, 100%) as yellow oil. $^1$H NMR (400 MHz, CDCl$_3$) δ 8.12 (d, J=8.4 Hz, 1H), 8.05 (d, J=8.4 Hz, 1H), 4.58-4.43 (m, 4H), 1.44 (m, 6H). MS: M/e 302 (M+1)$^+$.

Step 4: ethyl 3-bromo-6-(hydroxymethyl)picolinate

To a stirred mixture of the product of step 3 (14.7 g, 48.8 mmol) in EtOH (100 mL) was added NaBH$_4$ (0.92 g, 24.4 mmol) portionwise. After the addition, the reaction mixture was stirred at 50° C. for 4 hours. Then more NaBH$_4$ (0.2 g) was added in 4 portions until the product of step C was consumed. The reaction was quenched by acetone and concentrated to give the residue, which was treated with EtOAc/H$_2$O (100 mL/100 mL). The organic layer was separated, concentrated and purified by column chromatography (petroleum ether/EtOAc=6:1-2:1) to give the target compound (4 g, 31.5%) and by-product (2 g, 15.7%) as colorless oil. The target compound (5b): $^1$H NMR (400 MHz, CDCl$_3$) δ 7.96 (d, J=8.4 Hz, 1H), 7.31 (d, J=8.4 Hz, 1H), 4.77 (s, 2H), 4.48 (q, J=7.2 Hz, 2H), 1.44 (t, J=7.2 Hz, 3H) ppm. MS: M/e 260/262 (M+1)$^+$. 5a (by-product): $^1$H NMR (400 MHz, CDCl$_3$) δ 8.01 (d, J=8.2 Hz, 1H), 7.96-7.91 (d, J=8.2 Hz, 1H), 4.81 (s, 2H), 4.48-4.42 (q, J=7.2 Hz, 2H), 4.32 (s, 1H), 1.45-1.41 (t, J=7.2 Hz, 3H) ppm. MS: M/e 260/262 (M+1)$^+$.

Step 5: ethyl 3-bromo-6-(chloromethyl)picolinate

To a stirred solution of the product of step 4 (4 g, 15.4 mmol) in CH$_2$Cl$_2$ (4 mL) was added dropwise SOCl$_2$ (3.6 g, 30.8 mmol) at 0° C. After the addition, the reaction was stirred for 4 hours at room temperature. The reaction mixture was washed with H$_2$O (20 mL). The organic layer was separated, dried over Na$_2$SO$_4$ and concentrated to give target compound (3.75 g, 87.7%) as yellow oil. MS: M/e 278/280 (M+1)$^+$.

Step 6: ethyl 3-bromo-6-((1,3-dioxoisoindolin-2-yl)methyl)picolinate

To a stirred solution of the product of step 5 (3.75 g, 13.5 mmol) in DMF (10 mL) was added potassium 1,3-dioxoisoindolin-2-ide (2.5 g, 13.5 mmol). After the addition, the reaction mixture was stirred overnight. The reaction mixture was poured into H$_2$O (50 mL) and stirred for 30 minutes, then filtered. The cake was collected, dried to give target compound (4.59 g, 87.6%) as a white solid. $^1$H NMR (400 MHz, DMSO-$d_6$) δ 8.19 (d, J=8.4 Hz, 1H), 7.91 (m, 4H), 7.55 (d, J=8.4 Hz, 1H), 4.91 (s, 2H), 4.29 (q, J=7.2 Hz, 2H), 1.19 (t, J=7.2 Hz, 3H) ppm. MS: M/e 389/391 (M+1)$^+$.

Step 7: ethyl 6-(aminomethyl)-3-bromopicolinate

To a stirred suspension of the product of step 6 (4.59 g, 11.82 mmol) in EtOH (100 mL) was added N$_2$H$_4$.H$_2$O (0.59 g, 11.82 mmol). After the addition, the reaction mixture was stirred at 90° C. for 5 hours. The reaction mixture was allowed cool to room temperature, and HCOOH (1 mL) was added and stirred for 30 min and filtered. The filtrate was concentrated to give the residue, which was treated with EtOAc (100 mL) and filtered. The filtrate was concentrated to give target compound (3 g, 100%) as yellow oil, which was directly used to the next step. MS: M/e 259/261 (M+1)$^+$.

Step 8: ethyl 3-bromo-6-(formamidomethyl)picolinate

A solution of product of step 7 (3 g, 11.82 mmol) in HCOOH (10 mL) was stirred at 100° C. overnight. The reaction mixture was poured into H$_2$O (60 mL) and extracted with EtOAc (30 mL*3). The combined organic layers were washed with brine, dried over Na$_2$SO$_4$ and concentrated under vacuum to give target compound (3.1 g, 91.3%), which was used to the next step. MS: M/e 287/289 (M+1)$^+$.

Step 9: ethyl 6-bromoimidazo[1,5-a]pyridine-5-carboxylate

To a stirred solution of the product of 8 (3.1 g, 10.8 mmol) in toluene (20 mL) was added POCl$_3$ (3 mL), then the reaction mixture was stirred at 90° C. for 3 hours. The reaction mixture was poured into H$_2$O (20 mL) and basified to pH=9~11 with aq. K$_2$CO$_3$, then extracted with EtOAc (20 mL×3). The combined organic layers were washed with brine, dried over Na$_2$SO$_4$ and concentrated to give target compound (1.95 g, 67.1%) as yellow oil. $^1$H NMR (400 MHz, DMSO-d$_6$) δ 8.55 (s, 1H), 7.74 (d, J=9.6 Hz, 1H), 7.60 (s, 1H), 7.02 (d, J=9.6 Hz, 1H), 4.52 (q, J=7.2 Hz, 3H), 1.39 (t, J=7.2 Hz, 4H) ppm. MS: M/e 269/271 (M+1)$^+$.

Step 10: (6-bromoimidazo[1,5-a]pyridin-5-yl)methanol

To a stirred solution of the product of step 9 (1.95 g, 7.5 mmol) in EtOH (20 mL) was added NaBH$_4$ (0.285 g, 7.5 mmol). Then the reaction mixture was stirred at 60° C. for 2 hours. The reaction was quenched with acetone (2 mL) and concentrated to give the residue, which was treated with EtOAc/H$_2$O (50 mL/50 mL). The organic layer was separated, washed with brine, dried over Na$_2$SO$_4$ and concentrated to give target compound (1.2 g, 70.4%) as yellow oil. MS: M/e 227/229 (M+1)$^+$.

Step 11: 6-bromoimidazo[1,5-a]pyridine-5-carbaldehyde

To a stirred solution of the product of step 10 (1.2 g, 5.28 mmol) in CH$_2$Cl$_2$ (10 mL) was added Dess-Martin periodinane (2.2 g, 5.28 mmol). After the addition, the reaction mixture was stirred for 2 hours. The reaction mixture was washed with aq. K$_2$CO$_3$, brine, dried over Na$_2$SO$_4$, concentrated and purified by column chromatography (petroleum ether/EtOAc=4:1~2:1) to give target compound (500 mg, 42%) as a yellow solid. MS: M/e 225/257 (M+1)$^+$.

Step 12: (6-bromoimidazo[1,5-a]pyridin-5-yl)(cyclohexyl)methanol

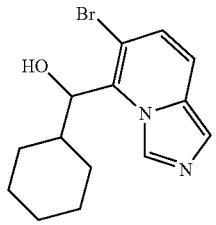 [SMILES: OC(c1c(Br)ccc2cncn12)C1CCCCC1]

To a stirred solution of product of step 11 (200 mg, 0.89 mmol) in dry THF (10 mL) was added dropwise Cyclohexylmagnesium chloride (0.67 mL, 1.34 mmol) at 0° C. After the addition, the reaction mixture was stirred for 2 hours at room temperature. The reaction was quenched with H$_2$O, extracted with EtOAc (20 mL×2). The combined organic layers were washed with brine, dried over Na$_2$SO$_4$, concentrated and purified by Prep-HPLC to give target compound. $^1$H NMR (400 MHz, DMSO-d$_6$) δ 9.16 (s, 1H), 7.81 (s, 1H), 7.61 (d, J=9.6 Hz, 1H), 7.11 (d, J=9.6 Hz, 1H), 6.23 (s, 1H), 5.10 (d, J=9.6 Hz, 1H), 2.14 (m, 2H), 1.76 (d, J=13.6 Hz, 1H), 1.59 (d, J=8.2 Hz, 2H), 1.32-0.91 (m, 6H) ppm. MS: M/e 309/311 (M+1).

Examples A118a and A118b: (S)-(6-bromoimidazo[1,5-a]pyridin-5-yl)(cyclohexyl)methanol and (R)-(6-bromoimidazo[1,5-a]pyridin-5-yl)(cyclohexyl)methanol

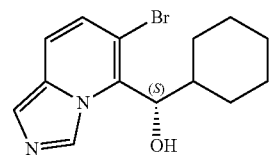

A118a

Fast isomer in chiral OD HPLC
Eluting reagent: Hexane/EtOH = 80/20(V/V)

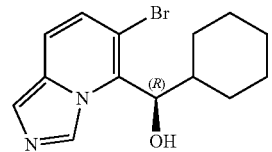

A118b

Slow isomer in chiral OD HPLC
Eluting reagent: Hexane/EtOH = 80/20(V/V)

Each enantiomer of racemic A118a and A118b was separated using preparative HPLC on a Chiralpak OD with Hexane/EtOH=80/20 as an eluent. The enantiomeric excesses were determined by using HPLC on a Chiralpak OD with Hexane/EtOH=80/20 as an eluent at a flow rate of 1.0 mL/min. The first one enantiomer eluted at the retention time of 2.32 min, and the other enantiomer eluted at the retention time of 3.15 min. The spectral properties of the title compounds were identical with those of A118. The absolute configurations of A118a and A118b are tentatively assigned as (S) and (R) respectively based on assumption that the

Example A119: 1-(6-bromoimidazo[1,5-a]pyridin-5-yl)-2-cyclohexylethan-1-ol

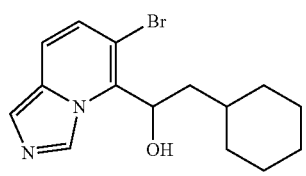

To a stirred solution of 6-bromoimidazo[1,5-a]pyridine-5-carbaldehyde (the product of Step 11 in synthesis of compound A118, 200 mg, 0.89 mmol) in dry THF (10 mL) was added dropwise (cyclohexylmethyl)magnesium bromide (7 mL, 3.56 mmol) at 0° C. After the addition, the reaction mixture was stirred for 2 hours at room temperature. The reaction was quenched with H$_2$O, extracted with EtOAc (30 mL×2). The combined organic layers were washed with brine, dried over Na$_2$SO$_4$, concentrated and purified by prep-HPLC to give target compound. $^1$H NMR (400 MHz, DMSO-d$_6$) δ 9.13 (s, 1H), 7.74 (s, 1H), 7.57 (d, J=9.6 Hz, 1H), 7.06 (d, J=9.6 Hz, 1H), 6.20 (s, 1H), 5.51 (dd, J=9.6, 4.4 Hz, 1H), 1.98 (m 1H), 1.79 (t, J=12.8 Hz, 2H), 1.67 (m, 2H), 1.52-1.43 (m, 2H), 1.30-1.08 (m, 4H), 0.94 (m, 2H) ppm. MS: M/e 323/325 (M+1)$^+$.

Examples A119a and A119b: (S)-1-(6-bromoimidazo[1,5-a]pyridin-5-yl)-2-cyclohexylethan-1-ol compound and (R)-1-(6-bromoimidazo[1,5-a]pyridin-5-yl)-2-cyclohexylethan-1-ol

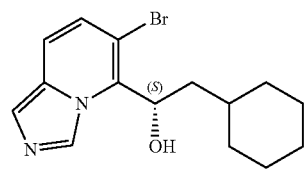

A119a

Fast isomer in chiral OD HPLC
Eluting reagent: Hexane/EtOH/ = 80/20 (V/V)

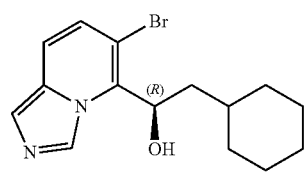 [SMILES: OC(CC1CCCCC1)c1c(Br)ccc2cncn12]

A119b

Slow isomer in chiral OD HPLC
Eluting reagent: Hexane/EtOH/ = 80/20 (V/V)

Each enantiomer of racemic A119a and A119b was separated using preparative HPLC on a Chiralpak OD with Hexane/EtOH/=80/20 (V/V) as an eluent. The enantiomeric excesses were determined by using HPLC on a Chiralpak OD with Hexane/EtOH/=80/20 (V/V) as an eluent at a flow rate of 2.0 mL/min. The first one enantiomer eluted at the retention time of 2.28 min, and the other enantiomer eluted at the retention time of 3.28 min. The spectral properties of the title compounds were identical with those of Example A119. The absolute configurations of A119a and A119b are tentatively assigned as (S) and (R) respectively based on assumption that the binding model of the more potent isomer A119a is the same as that of A101a with IDO1 enzyme.

Example A120: (6-bromoimidazo[1,5-a]pyridin-5-yl)(cyclopentyl)methanol

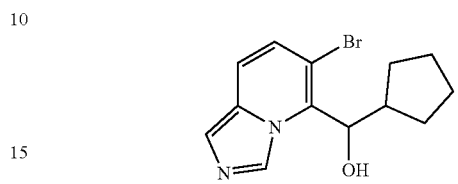

Example A120 was synthesized from 6-bromoimidazo[1,5-a]pyridine-5-carbaldehyde and cyclopentylmagnesium chloride by following the procedures similar to those in Example A118. $^1$H NMR (400 MHz, DMSO-d$_6$) δ 9.18 (s, 1H), 7.80 (s, 1H), 7.60 (d, J=9.6 Hz, 1H), 7.11 (d, J=9.6 Hz, 1H), 6.28 (br. s, 1H), 5.15 (d, J=10.4 Hz, 1H), 2.69-2.66 (m, 1H), 2.03-1.88 (m, 1H), 1.63-1.56 (m, 6H), 1.30-1.22 (m, 2H) ppm. MS: M/e 295/297 (M+1)$^+$.

Example A121: 1-(6-chloroimidazo[1,5-a]pyridin-5-yl)-2-cyclohexylpropan-1-ol

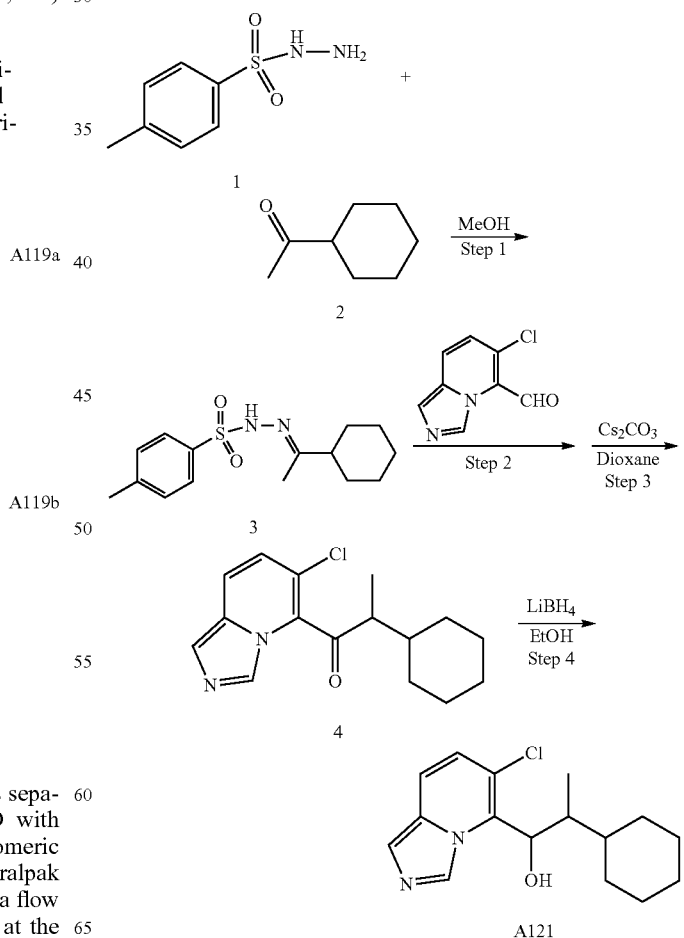

A121

Step 1: (E)-N'-(1-cyclohexylethylidene)-4-methyl-benzenesulfonohydrazide

To a solution of 4-methylbenzenesulfonohydrazide (compound 1, 2.95 g, 15.85 mmol) and 1-cyclohexylethan-1-one (compound 2, 2.0 g, 15.85 mmol) in 30 mL of MeOH was stirred at rt for 4 h. LC-MS showed the reaction was completed. The solvent was concentrated to give crude product, which was filtrated and washed with PE/EA=(2:1) to give compound 3 (4.5 g, 96.5%) as a white solid. LC-MS (M+H)$^+$=295.1.

Step 2 1-(6-chloroimidazo[1,5-a]pyridin-5-yl)-2-cyclohexylpropan-1-one

A mixture of compound 3 (0.3 g, 1.68 mmol), 6-chloroimidazo[1,5-a]pyridine-5-carbaldehyde (0.49 g, 1.68 mmol) and Cs$_2$CO$_3$ (0.81 g, 2.50 mmol) in Dioxane (30 mL) was stirred at 110° C. for 4 h under N$_2$, the solvent was removed under vacuum. The residue was purified by silica gel chromatography (PE:EA=5:1) to give compound 4 (20 mg, 4.7%) as a yellow solid. LC-MS (M+H)$^+$=291.1.

Step 3: 1-(6-chloroimidazo[1,5-a]pyridin-5-yl)-2-cyclohexylpropan-1-ol

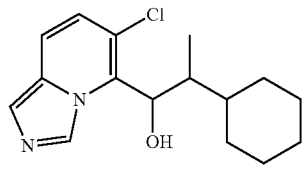 [SMILES: CC(C1CCCCC1)C(O)c1c(Cl)ccc2cncn12]

To a solution of compound 4 (20 mg, 0.07 mmol) in EtOH (10 mL) was added LiBH$_4$ (4.0 mg, 0.18 mmol) and stirred at rt for 4 hours. Then water (20 mL) was added, extracted with DCM (20 mL*2), dried with Na$_2$SO$_4$, then filtered to remove Na$_2$SO$_4$, evaporated the solvent to give a crude product as yellow oil (1.9 g). Then the crude product was purified by pre-HPLC to give the product (5 mg, 25%) as a white solid. $^1$H NMR (400 MHz, CD$_3$OD) δ 8.63 (s, 1H), 7.38 (d, J=9.6 Hz, 1H), 7.35 (s, 1H), 6.68-6.70 (d, J=9.6 Hz, 1H), 5.34-5.37 (d, J=10.4 Hz, 1H), 1.92-2.21 (m, 2H), 1.61-1.75 (m, 4H), 1.01-1.26 (m, 6H), 0.47-0.49 (d, J=7.2 Hz, 3H). LC-MS (M+H)$^+$=293.1.

Example A122: cyclohexyl(6-methylimidazo[1,5-a]pyridin-5-yl)methanol

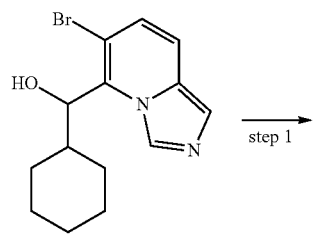

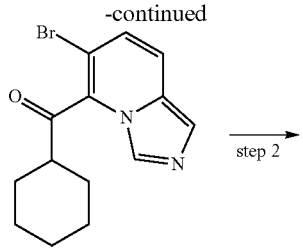

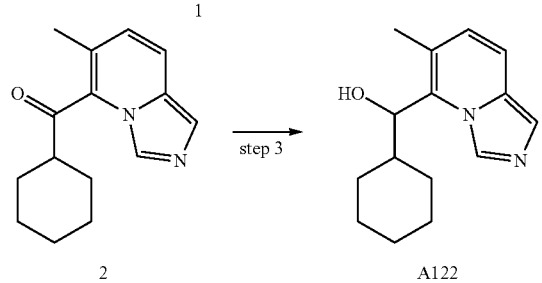

Step 1: (6-bromoimidazo[1,5-a]pyridin-5-yl)(cyclohexyl)methanone

To a stirred solution of (6-bromoimidazo[1,5-a]pyridin-5-yl)(cyclohexyl)methanol (225 mg, 0.75 mmol) in CH$_2$Cl$_2$ (10 mL) was added Dess-Martin periodinane (636 mg, 1.5 mmol). After the addition, the reaction was stirred for 2 hours. The reaction was quenched with aq. K$_2$CO$_3$ (30 mL) and the organic layer was separated and concentrated to give the residue, which was purified by column chromatography (petroleum ether/EtOAc=5:1) to give the target compound (120 mg) as yellow oil. MS: M/e 307/309 (M+1)$^+$.

Step 2: cyclohexyl(6-methylimidazo[1,5-a]pyridin-5-yl)methanone

To a stirred solution of the product of Step A (120 mg, 0.39 mmol) in dry THF (10 mL) was added MeMgBr (1 mL, 1.6 mmol). After the addition, the reaction was stirred at 45° C. for 2 hours. The reaction was quenched with H$_2$O (10 mL) and extracted with EtOAc (5 mL×2). The combined organic layers were washed with brine, dried over Na$_2$SO$_4$ and concentrated to give the residue, which was directly used to the next step. MS: M/e 243 (M+1)$^+$.

Step 3: cyclohexyl(6-methylimidazo[1,5-a]pyridin-5-yl)methanol

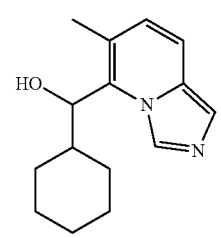 [SMILES: Cc1ccc2cncn2c1C(O)C1CCCCC1]

To a stirred solution of the product B (0.39 mmol) in MeOH (2 mL) was added NaBH$_4$ (15 mg, 0.39 mmol). After 10 minutes, the reaction was quenched with acetone (2 mL) and concentrated to give the residue, which was purified by prep-HPLC to give the target compound as a white solid. $^1$H NMR (400 MHz, DMSO-$d_6$) δ 9.48 (s, 1H), 7.99 (s, 1H), 7.65 (d, J=9.6 Hz, 1H), 7.01 (d, J=9.6 Hz, 1H), 4.88 (d, J=9.6 Hz, 1H), 2.30 (s, 3H), 2.19 (d, J=11.6 Hz, 1H), 2.02-1.99 (m, 1H), 1.74-1.71 (m, 1H), 1.57-1.51 (m, 2H), 1.21-0.94 (m, 7H) ppm. MS: M/e 245 (M+1)$^+$.

Example A123: cyclohexyl(6-ethynylimidazo[1,5-a]pyridin-5-yl)methanol

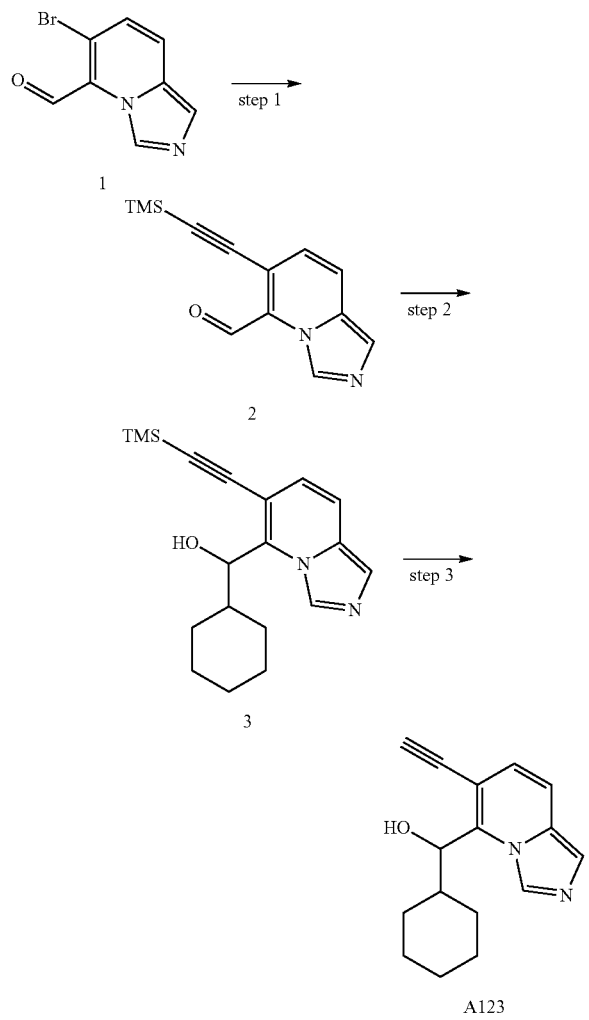

Step 1: 6-((trimethylsilyl)ethynyl)imidazo[1,5-a]pyridine-5-carbaldehyde

To a stirred solution of 6-bromoimidazo[1,5-a]pyridine-5-carbaldehyde (100 mg, 0.44 mmol) and ethynyltrimethylsilane (52 mg, 0.53 mmol) in DMF (5 mL) was added CuI (8.4 mg, 0.044 mmol), Pd(PPh)$_2$Cl$_2$ (31 mg, 0.044 mmol) and Et$_3$N (90 mg, 0.88 mmol). After the addition, the reaction was stirred for 2 hours. The reaction was poured into H$_2$O (20 mL) and extracted with EtOAc (15 mL×3). The combined organic layers were washed with brine, dried over Na$_2$SO$_4$, concentrated and purified by column chromatography (Petroleum ether/EtOAc=5:1~2:1) to give the target compound (60 mg, 56.3%) as a yellow solid. MS: M/e 243 (M+1)$^+$.

Step 2: cyclohexyl(6-((trimethylsilyl)ethynyl)imidazo[1,5-a]pyridin-5-yl)methanol To a stirred solution of the product of step A (60 mg, 0.248 mmol) in THF (10 mL) was added cyclohexylmagnesium bromide (2 M, 0.25 mL) at room temperature. After stirred for half an hour, the reaction mixture was quenched with H$_2$O (10 mL) and extracted with EtOAc (10 mL×3). The combined organic layers were washed with brine, dried over Na$_2$SO$_4$, and concentrated to give the target compound without further purification. MS: M/e 327 (M+1)$^+$.

Step 3: cyclohexyl(6-ethynyl)imidazo[1,5-a]pyridin-5-yl)methanol

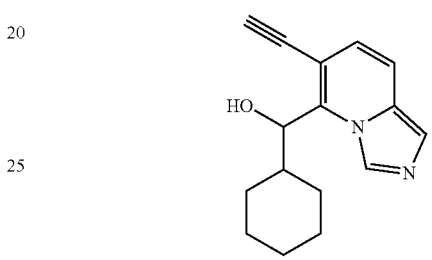

To a stirred solution of the product of step B (0.248 mmol) in DMF (5 mL) was added CsF (38 mg, 0.248 mmol). After the addition, the reaction mixture was stirred overnight. The reaction mixture was poured into H$_2$O (15 mL) and extracted with EtOAc (10 mL×3). The combined organic layers were washed with brine, dried over Na$_2$SO$_4$, concentrated and purified by prep-HPLC to give the target compound (32 mg, 50%) as a white solid. $^1$H NMR (400 MHz, DMSO-$d_6$) δ 9.26 (s, 1H), 7.82 (s, 1H), 7.68 (d, J=9.2 Hz, 1H), 7.00 (d, J=9.2 Hz, 1H), 5.14 (d, J=9.6 Hz, 1H), 4.64 (s, 1H), 2.23 (d, J=12.4 Hz, 1H), 2.05 (s, 1H), 1.76 (d, J=12.6 Hz, 1H), 1.58 (s, 2H), 1.11 (m, 7H) ppm. MS: M/e 255 (M+1)$^+$.

Example A124: 2-cyclohexyl-1-(6-iodoimidazo[1,5-a]pyridin-5-yl)ethan-1-ol

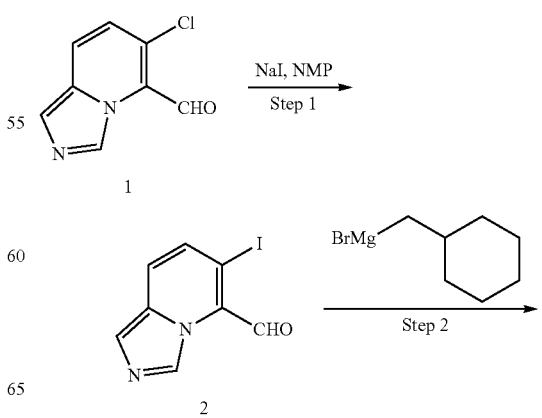

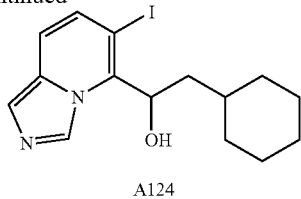

A124

Step 1: 6-iodoimidazo[1,5-a]pyridine-5-carbaldehyde

To a stirred solution of 6-chloroimidazo[1,5-a]pyridine-5-carbaldehyde (2.0 g, 11.1 mmol) in NMP (25 mL) was added NaI (12.0 g, 80.0 mmol) at rt and the resulted mixture was stirred at 130° C. for 10 hours. The mixture was added 50 mL of EA and the resulted mixture was filtered through a celite pad and the filtrate was washed with brine (50 mL×3), dried over $Na_2SO_4$, concentrated and the resulted residue was purified by column chromatography to give the title product (320 mg, 11%) as an orange solid. $^1$H NMR (400 MHz, DMSO-$d_6$) δ 10.09 (s, 1H), 9.43 (s, 1H), 7.80 (d, J=9.2 Hz, 1H), 7.74 (s, 1H), 7.37 (d, J=9.2 Hz, 1H). MS: M/e 273 (M+1)$^+$.

Step 2: 2-cyclohexyl-1-(6-iodoimidazo[1,5-a]pyridin-5-yl)ethan-1-ol

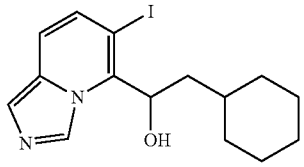 [SMILES: OC(CC1CCCCC1)c1c(I)ccc2cncn12]

To a stirred solution of 6-iodoimidazo[1,5-a]pyridine-5-carbaldehyde (100 mg, 0.37 mmol) in THF (5 mL) under $N_2$ was added a solution of (cyclohexylmethyl) magnesium bromide in THF (0.5 M, 1.5 mL) at rt in drops. The resulted mixture was stirred for 2 hrs. 5 mL of $H_2O$ was added, and the mixture was extracted with EA (5 mL*3). The combined extracts were washed with brine (10 mL*2), dried over $Na_2SO_4$, concentrated. The resulted residue was purified by prep-HPLC to give the title product (35 mg, 11%) as a light yellow solid. $^1$H NMR (400 MHz, DMSO-$d_6$) δ 9.21 (s, 1H), 7.78 (s, 1H), 7.40 (d, J=9.6 Hz, 1H), 7.24 (d, J=9.6 Hz, 1H), 6.24 (s, 1H), 5.43 (dd, J=10.0, 4.0 Hz, 1H), 1.91-1.74 (m, 2H), 1.74-1.55 (m, 5H), 1.32-1.11 (m, 4H), 1.06-0.87 (m, 2H). MS: M/e 371 (M+1)$^+$.

Examples A124a and A124b: (S)-2-cyclohexyl-1-(6-iodoimidazo[1,5-a]pyridin-5-yl)ethan-1-ol and (R)-2-cyclohexyl-1-(6-iodoimidazo[1,5-a]pyridin-5-yl)ethan-1-ol

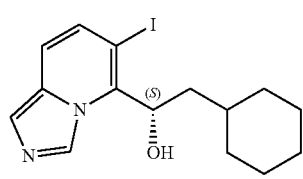

A124a

Fast isomer in chiral OD HPLC
Eluting reagent: $CO_2$/EtOH = 80/20 (/V/V)

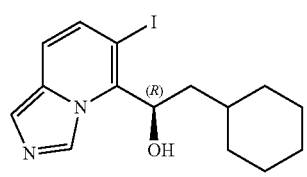

A124b

Slow isomer in chiral OD HPLC
Eluting reagent: $CO_2$/EtOH = 80/20 (/V/V)

Each enantiomer of racemic A124a and A124b was separated using preparative HPLC on a Chiralpak OD with $CO_2$/MeOH=80/20 (/V/V) as an eluent. The enantiomeric excesses were determined by using HPLC on a Chiralpak OD with $CO_2$/MeOH=80/20 (/V/V) as an eluent at a flow rate of 2.0 mL/min. The first one enantiomer eluted at the retention time of 6.94 min, and the other enantiomer eluted at the retention time of 8.62 min. The spectral properties of the title compounds were identical with those of compound A124. The absolute configurations of A124a and A124b are tentatively assigned as (S) and (R) respectively based on assumption that the binding model of the more potent isomer A124a is the same as that of A101a with IDO1 enzyme.

Example A125: cyclohexyl(6-iodoimidazo[1,5-a]pyridin-5-yl)methanol

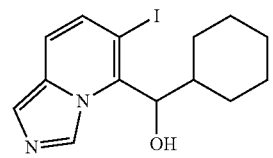 [SMILES: OC(c1c(I)ccc2cncn12)C1CCCCC1]

Example 125 was prepared according to the procedures described for Example A124 under appropriate conditions that could be recognized by one skilled in the art. $^1$H NMR (400 MHz, DMSO-$d_6$) δ 9.23 (s, 1H), 7.85 (s, 1H), 7.45 (d, J=9.6 Hz, 1H), 7.31 (d, J=9.6 Hz, 1H), 6.30 (br s, 1H), 5.07 (d, J=9.2 Hz, 1H), 2.28-2.08 (m, 2H), 1.83-1.75 (m, 1H), 1.67-1.57 (m, 2H), 1.35-1.00 (m, 6H). MS: M/e 357 (M+1)$^+$

Example A125a and 125b: (S)-cyclohexyl(6-iodoimidazo[1,5-a]pyridin-5-yl)methanol and (R)-cyclohexyl(6-iodoimidazo[1,5-a]pyridin-5-yl)methanol

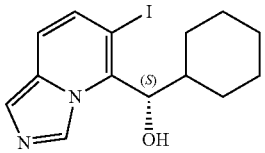

A125a

Fast isomer in chiral IC HPLC
Eluting reagent: ACN/MeOH/DEA = 90/10/0.1 (V/V/V)

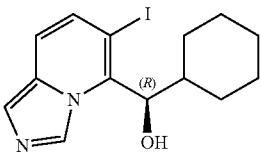

A125b

Slow isomer in chiral IC HPLC
Eluting reagent: ACN/MeOH/DEA = 90/10/0.1 (V/V/V)

Each enantiomer of racemic A125a and A125b was separated using preparative HPLC on a Chiralpak IC with ACN/MeOH/DEA=90/10/0.1 (V/V/V) as an eluent. The enantiomeric excesses were determined by using HPLC on a Chiralpak IC with ACN/MeOH/DEA=90/10/0.1 (V/V/V) as an eluent at a flow rate of 1.0 mL/min. The first one enantiomer eluted at the retention time of 3.07 min, and the other enantiomer eluted at the retention time of 4.16 min. The spectral properties of the title compounds were identical with those of compound A125. The absolute configurations of A125a and A125b are tentatively assigned as (S) and (R) respectively based on assumption that the binding model of the more potent isomer A125a is the same as that of A101a with IDO1 enzyme.

Example A126: cyclohexyl(6-(trifluoromethyl)imidazo[1,5-a]pyridine-5-yl)methanol

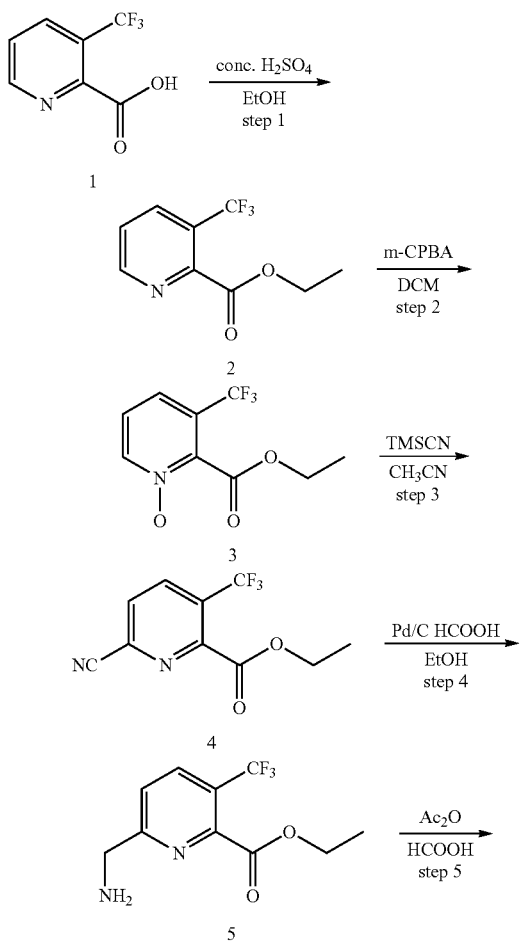

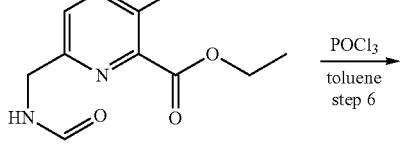

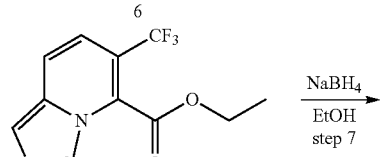

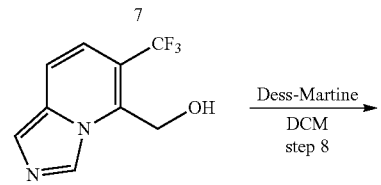

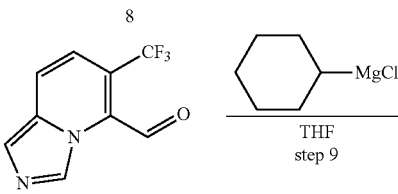

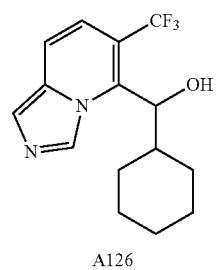

A126

Step 1: ethyl 3-(trifluoromethyl)picolinate

To a solution of 3-(trifluoromethyl)picolinic acid (3.8 g, 20 mmol) in EtOH (50 mL) was added conc.$H_2SO_4$ (3 mL). The resulting mixture was refluxed overnight. The mixture was concentrated, poured into water (40 mL) and treated with 1N NaOH to pH=8. The mixture was extracted with EA (40 mL×3), washed with saturated brine solution, dried over $Na_2SO_4$, filtered and concentrated to get the desired product (2.5 g, 57%) as oil. MS: M/e 220 (M+1)[+]

Step 2:
2-(ethoxycarbonyl)-3-(trifluoromethyl)pyridine 1-oxide

To a solution of the product of step 1 (2.5 g, 11.4 mmol) in DCM (30 mL) was added m-CPBA (3.9 g, 22.8 mmol). The reaction mixture was stirred at rt overnight. The suspension was filtered and the solid was washed with DCM (30 ml). The filtrate was diluted with saturated $NaHCO_3$ solution, extracted with DCM (40 mL×2). The organic layer was washed with 10% $NaHSO_3$ solution, brine, dried over $Na_2SO_4$, filtered and concentrated. The residue was purified by silica gel column chromatography eluting with PE:EA=1:1 to get the desired product (1.6 g, 59%) as oil. MS: M/e 236 (M+1)

Step 3: ethyl 6-cyano-3-(trifluoromethyl)picolinate

To a solution of the product of step 2 (1.6 g, 6.77 mmol) and TEA (2.7 g, 27 mmol) in CH$_3$CN (40 mL) was added TMSCN (0.8 g, 8.12 mmol) and dimethylcarbamic chloride (0.8 g, 7.45 mmol). The solution was stirred at reflux overnight. Another portion of TMSCN (0.8 g, 8.12 mmol) and dimethylcarbamic chloride (0.8 g, 7.45 mmol) was added. Then the solution was stirred at reflux for further 16 hrs. The mixture was cooled to rt, quenched with water (50 mL), extracted with EA (40 mL×3), washed with brine, dried over Na$_2$SO$_4$, filtered and concentrated. The residue was purified by silica gel column chromatography eluting with PE:EA=10:1 to get the desired product (1.3 g, 78%) as oil. $^1$H NMR (400 MHz, CDCl$_3$) δ 8.25 (d, J=8.4 Hz, 1H), 7.94 (dd, J=8.0, 0.8 Hz, 1H), 4.51 (q, J=14.4, 7.2 Hz, 2H), 1.43 (t, J=7.2 Hz, 3H). ppm. MS: M/e 245 (M+1)$^+$ Step 4: ethyl 6-(aminomethyl)-3-(trifluoromethyl)picolinate To a solution of the product of step 3 (1.3 g, 5.32 mmol) in EtOH (20 mL) and formic acid (3 mL) was added Pd/C (0.13 g, 10%). The reaction mixture was stirred at rt under H$_2$ atmosphere (balloon) overnight. The solution was filtered, washed with EtOH (20 ml), and the filtrate was concentrated to get the desired product as black oil. MS: M/e 249 (M+1)

Step 5: ethyl 6-(formamidomethyl)-3-(trifluoromethyl)picolinate

A solution of the product of step 4 (crude) in formic acid (12 mL) and acetic anhydride (4 mL) was stirred at 50° C. for 5 hrs. The reaction was quenched with water (30 mL), extracted with EA (40 mL×3). The organic layer was washed by saturated NaHCO$_3$ aqueous solution followed by saturated brine solution, dried over Na$_2$SO$_4$, filtered and concentrated to get crude product (0.6 g) as oil, which was used in next step directly. MS: M/e 277 (M+1)$^+$ Step 6: ethyl 6-(trifluoromethyl)imidazo[1,5-a]pyridine-5-carboxylate To a solution of the product of step 5 (0.6 g, crude) in toluene (10 mL) was added POCl$_3$ (0.8 g, 5.32 mmol). The mixture was stirred at 90° C. for 2 hrs. The reaction was cooled to room temperature, quenched with saturated NaHCO$_3$ aqueous solution, extracted with EA (40 mL×2). The organic layer was washed with saturated brine solution, dried over Na$_2$SO$_4$, filtered and concentrated. The residue was purified by silica gel column chromatography eluting with PE:EA=3:1 to get the desired product (0.24 g, 17.5% for 3 steps) as a yellow solid. MS: M/e 259

Step 7: (6-(trifluoromethyl)imidazo[1,5-a]pyridin-5-yl)methanol

To a mixture of the product of step 6 (0.24 g, 0.93 mmol) in EtOH (10 mL) was added NaBH$_4$ (70 mg, 1.86 mmol). The resulting mixture was stirred at 80° C. for 2 hrs. The reaction cooled to room temperature, 2/3 of EtOH was removed under reduced pressure. To the residue was added water (20 mL) and a suspension was formed. The solid was collected by filtration to give the desired product (120 mg, 60%) as a light yellow solid. MS: M/e 217 (M+1)$^+$ Step 8: 6-(trifluoromethyl)imidazo[1,5-a]pyridine-5-carbaldehyde To a solution of the product of step 7 (120 mg, 0.55 mmol) in CH$_2$Cl$_2$ (20 mL) was added Dess-Martin reagent (280 mg, 0.66 mmol). The solution was stirred at rt for 0.5 h. Then another portion of Dess-Martin reagent (100 mg, 0.23 mmol) was added and the reaction was stirred at rt for 20 min. The solution was washed by water, extracted with CH$_2$Cl$_2$ (50 mL). The combined organic layer was washed by brine, dried over sodium sulfate anhydrous then concentrated and purified by silica gel column chromatography eluting with PE:EA=2:1 to get the desired product (90 mg, 75%) as a yellow solid. MS: M/e 215 (M+1)$^+$ Step 9: cyclohexyl(6-(trifluoromethyl)imidazo[1,5-a]pyridin-5-yl)methanol

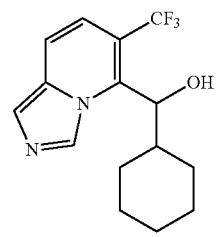 [SMILES: OC(c1c(C(F)(F)F)ccc2cncn12)C1CCCCC1]

To the solution of the product of step 8 (45 mg, 0.2 mmol) in THF (4 mL) was added a solution of cyclohexylmagnesium chloride in THF (0.15 mL, 2 mol/L). The solution was stirred at rt for 0.5 h. The solution was washed by water, extracted with EA (30 mL). The organic layer was washed by brine, dried over sodium sulfate anhydrous then concentrated and purified by prep-TLC (EA:PE=1:1) to give the desired product (15 mg) as a white solid. $^1$H NMR (400 MHz, DMSO-d$_6$) δ 8.84 (s, 1H), 7.70 (d, J=9.2 Hz, 1H), 7.55 (s, 1H), 6.97 (d, J=9.2 Hz, 1H), 6.34 (d, J=4.0 Hz, 1H), 4.83 (dd, J=9.2, 4.0 Hz, 1H), 2.36-2.26 (m, 1H), 2.24-2.12 (m, 1H), 1.85-1.70 (m, 1H), 1.65-1.45 (m, 2H), 1.32-0.74 (m, 6H) ppm. MS: M/e 299 (M+1)$^+$ Example 126a and 126b: (S)-cyclohexyl(6-cyclopropylimidazo[1,5-a]pyridin-5-yl)methanol and (R)-cyclohexyl(6-cyclopropylimidazo[1,5-a]pyridin-5-yl)methanol A126a

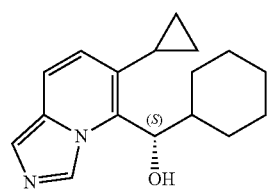

Fast isomer in chiral IC HPLC
Eluting reagent: ACN (0.1% DEA)

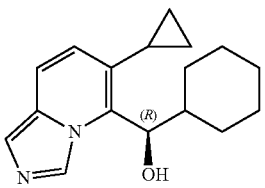

A126b

Slow isomer in chiral IC HPLC
Eluting reagent: ACN (0.1% DEA)

Each enantiomer of racemic A126a and A126b was separated using preparative HPLC on a Chiralpak IC with ACN (0.1% DEA) as an eluent. The enantiomeric excesses were determined by using HPLC on a Chiralpak IC with ACN (0.1% DEA) as an eluent at a flow rate of 1.0 mL/min. The first one enantiomer eluted at the retention time of 4.76 min, and the other enantiomer eluted at the retention time of 7.33 min. The spectral properties of the title compounds were identical with those of Example A126. The absolute configurations of A126a and A126b are tentatively assigned as (S) and (R) respectively based on assumption that the binding model of the more potent isomer A126a is the same as that of A101a with IDO1 enzyme.

Example A127: 2-cyclohexyl-1-(6-(trifluoromethyl)imidazo[1,5-a]pyridine-5-yl)ethan-1-ol

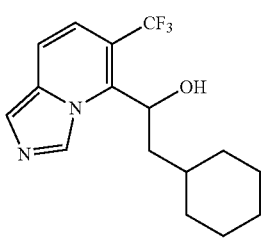 [SMILES: OC(CC1CCCCC1)c1c(C(F)(F)F)ccc2cncn12]

Example A127 was prepared according to the procedures described for Example A126 under appropriate conditions that could be recognized by one skilled in the art. $^1$H NMR (400 MHz, DMSO-$d_6$) δ 9.03 (d, J=4.8 Hz, 1H), 7.72 (d, J=9.2 Hz, 1H), 7.64 (d, J=4.0 Hz, 1H), 7.02 (dd, J=10.0, 2.8 Hz, 1H), 6.35 (br. s, 1H), 5.38 (d, J=10.0 Hz, 1H), 2.25-2.14 (m, 1H), 1.95-1.80 (m, 1H), 1.75-1.55 (m, 5H), 1.40-0.78 (m, 6H) ppm. MS: M/e 313 (M+1)$^+$ Example A127a and A127b: (S)-2-cyclohexyl-1-(6-(trifluoromethyl)imidazo[1,5-a]pyridin-5-yl)ethan-1-ol and (R)-2-cyclohexyl-1-(6-(trifluoromethyl)imidazo[1,5-a]pyridin-5-yl)ethan-1-ol

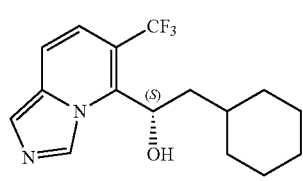

A127a

Fast isomer in chiral OD HPLC
Eluting reagent: CO$_2$/MeOH = 85/15 (/V/V)

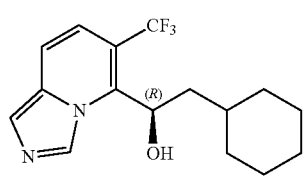

A127b

Slow isomer in chiral OD HPLC
Eluting reagent: CO$_2$/MeOH = 85/15 (/V/V)

Each enantiomer of racemic A127a and A127b was separated using preparative HPLC on a Chiralpak OD with CO$_2$/MeOH=85/15 (/V/V) as an eluent. The enantiomeric excesses were determined by using HPLC on a Chiralpak OD with CO$_2$/MeOH=85/15 (/V/V) as an eluent at a flow rate of 2.0 mL/min. The first one enantiomer eluted at the retention time of 4.86 min, and the other enantiomer eluted at the retention time of 5.53 min. The spectral properties of the title compounds were identical with those of compound A127. The absolute configurations of A127a and A127b are tentatively assigned as (S) and (R) respectively based on assumption that the binding model of the more potent isomer A127a is the same as that of A101a with IDO1 enzyme.

Example A128: 1-(6-chloroimidazo[1,5-a]pyridin-5-yl)-3-cyclohexylpropan-1-ol

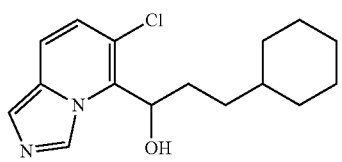 [SMILES: OC(CCC1CCCCC1)c1c(Cl)ccc2cncn12]

Example A128 was prepared according to the similar procedures described for Example A116 using 6-chloroimidazo[1,5-a]pyridine-5-carbaldehyde (the intermediate of Step 8 in the synthesis of Example A116) as the starting material under appropriate conditions that could be recognized by one skilled in the art.

$^1$H NMR (400 MHz, DMSO-$d_6$): $δ_H$ 8.69 (s, 1H), 7.47-7.57 (m, 2H), 6.78-6.80 (m, 1H), 6.05-6.06 (m, 1H), 5.35-5.40 (m, 1H), 1.83-1.86 (m, 2H), 1.58-1.59 (m, 5H), 1.03-1.18 (m, 7H), 0.77-0.83 (m, 2H). MS (ESI) m/e [M+1]$^+$293.

Example A129: cyclohexyl(6-cyclopropylimidazo[1,5-a]pyridin-5-yl)methanol

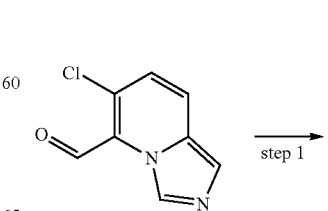

step 1

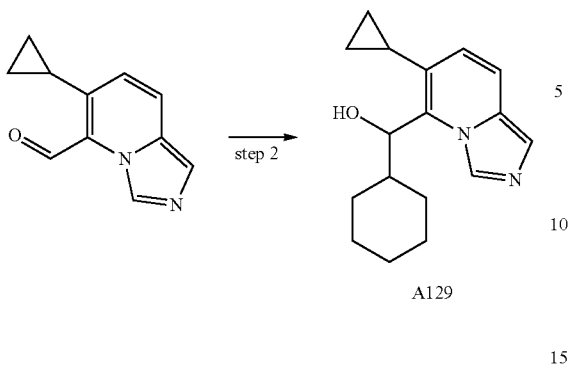

Step 1: 6-cyclopropylimidazo[1,5-a]pyridine-5-carbaldehyde

To a stirred solution of 6-chloroimidazo[1,5-a]pyridine-5-carbaldehyde (50 mg, 0.29 mmol), tricyclohexylphosphane (24.5 mg, 0.087 mmol), Pd(OAc)$_2$ (6.5 mg, 0.029 mmol) and cyclopropylboronic acid (74.7 mg, 0.87 mmol) in toluene/H$_2$O (5 mL)/(2 mL) was stirred at 100° C. under N$_2$ for 4 hours. The reaction mixture was concentrated to give the residue, which was treated with EtOAc/H$_2$O (10 mL/5 mL). The organic layer was separated, washed with brine, dried over Na$_2$SO$_4$, concentrated and purified by column chromatography (petroleum ether/EtOAc=4:1~1:1) to give target compound (40 mg, 74.1%) as a yellow solid. MS: M/e 187 (M+1)$^+$.

Step 2: cyclohexyl(6-cyclopropylimidazo[1,5-a]pyridin-5-yl)methanol

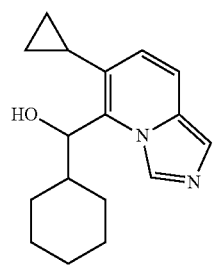 [SMILES: OC(c1c(C2CC2)ccc2cncn12)C1CCCCC1]

To a stirred solution of the product of step 1 (40 mg, 0.215 mmol) in THF (5 mL) was added cyclohexylmagnesium bromide in THF (2 M, 0.2 mL) at room temperature. After stirred for half an hour, the reaction mixture was quenched with H$_2$O (10 mL) and extracted with EtOAc (10 mL×3). The combined organic layers were washed with brine, dried over Na$_2$SO$_4$, and concentrated and purified by prep-HPLC to give the target compound (15 mg) as a TFA salt. $^1$H NMR (400 MHz, DMSO-d$_6$) δ 9.56 (s, 1H), 8.02 (s, 1H), 7.68 (d, J=9.6 Hz, 1H), 6.81 (d, J=9.6 Hz, 1H), 6.12 (s, 1H), 5.27 (d, J=9.6 Hz, 1H), 2.26 (d, J=11.2 Hz, 1H), 2.18-2.00 (m, 2H), 1.78 (m, 1H), 1.61 (m, 2H), 1.31-0.94 (m, 8H), 0.89-0.66 (m, 2H) ppm. MS: M/e 271 (M+1)$^+$.

Example A129a and A129b: (S)-cyclohexyl(6-cyclopropylimidazo[1,5-a]pyridin-5-yl)methanol and (R)-cyclohexyl(6-cyclopropylimidazo[1,5-a]pyridin-5-yl)methanol

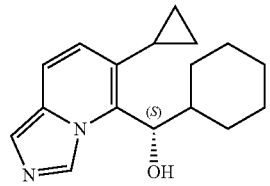

A129a

Fast isomer in chiral IC HPLC
Eluting reagent: ACN/MeOH/DEA = 90/10/0.1 (V/V/V)

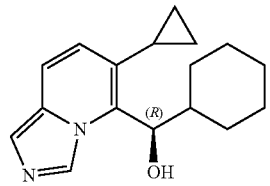

A129b

Slow isomer in chiral IC HPLC
Eluting reagent: ACN/MeOH/DEA = 90/10/0.1 (V/V/V)

Each enantiomer of racemic A129a and A129b was separated using preparative HPLC on a Chiralpak IC with ACN/MeOH/DEA=90/10/0.1 (V/V/V) as an eluent. The enantiomeric excesses were determined by using HPLC on a Chiralpak IC with ACN/MeOH/DEA=90/10/0.1 (V/V/V) as an eluent at a flow rate of 1.0 mL/min. The first one enantiomer eluted at the retention time of 3.02 min, and the other enantiomer eluted at the retention time of 4.33 min. The spectral properties of the title compounds were identical with those of Example A129. The absolute configurations of A129a and A129b are tentatively assigned as (S) and (R) respectively based on assumption that the binding model of the more potent isomer A129a is the same as that of A101a with IDO1 enzyme.

Example A130: cyclohexyl(6-phenylimidazo[1,5-a]pyridin-5-yl)methanol

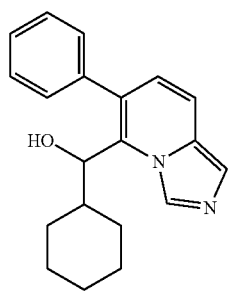 [SMILES: OC(c1c(-c2ccccc2)ccc2cncn12)C1CCCCC1]

$^1$H NMR (400 MHz, DMSO-d$_6$) δ 9.48 (s, 1H), 8.03 (s, 1H), 7.78 (d, J=9.2 Hz, 1H), 7.59-7.41 (m, 5H), 7.00 (d, J=9.2 Hz, 1H), 6.18 (s, 1H), 4.68 (d, J=10.0 Hz, 1H), 2.09 (m, 2H), 1.78-1.57 (m, 2H), 1.42 (m, 2H), 1.27-1.10 (m, 1H), 0.94 (m, 2H), 0.71 (m, 1H), 0.41 (m, 1H) ppm. MS: M/e 307 (M+1)$^+$.

Example 131: cyclohexyl(6-methoxyimidazo[1,5-a]pyridin-5-yl)methanol

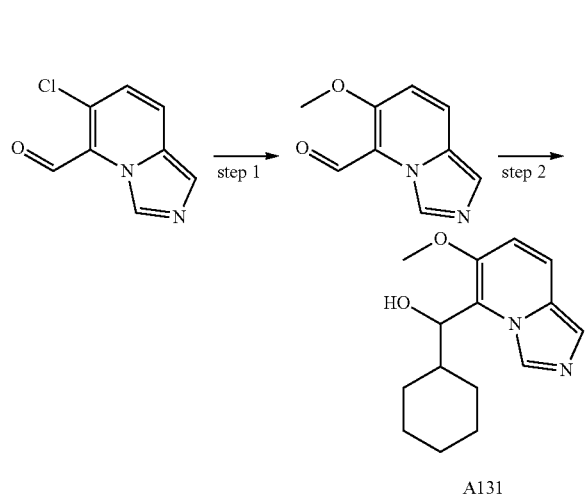

A131

Step 1: 6-methoxyimidazo[1,5-a]pyridine-5-carbaldehyde

To a stirred solution of 6-chloroimidazo[1,5-a]pyridine-5-carbaldehyde (50 mg, 0.29 mmol) in MeOH (5 mL) was added MeONa (5.4 M, 0.5 mL). After for 4 hours at 70° C., the reaction was quenched with aq. HCl (2.0M, 5 mL). Most of MeOH was removed to give the residue, which was extracted with EtOAc (10 mL×3). The combined organic layers were washed with brine, dried over Na$_2$SO$_4$, concentrated to give target compound (50 mg, 100%), which was directly used to the next step. MS: M/e 177 (M+1)$^+$.

Step 2: cyclohexyl(6-methoxyimidazo[1,5-a]pyridin-5-yl)methanol

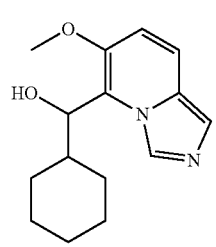 [SMILES: COc1ccc2cncn2c1C(O)C1CCCCC1]

To a stirred solution of the product of step 1 (50 mg, 0.29 mmol) in THF (5 mL) was added cyclohexylmagnesium bromide in THF (2 M, 0.3 mL) at room temperature. After stirred for half an hour, the reaction mixture was quenched with H$_2$O (10 mL) and extracted with EtOAc (10 mL×3). The combined organic layers were washed with brine, dried over Na$_2$SO$_4$, and concentrated and purified by prep-HPLC to give the target compound (12 mg) as a TFA salt. $^1$H NMR (400 MHz, DMSO-d$_6$) δ 9.35 (s, 1H), 7.98 (s, 1H), 7.80 (d, J=10.0 Hz, 1H), 7.36 (d, J=10.0 Hz, 1H), 5.90 (s, 1H), 5.05 (d, J=9.6 Hz, 1H), 3.88 (s, 3H), 2.18 (d, J=12.4 Hz, 1H), 2.00 (m, 1H), 1.75 (m, 1H), 1.57 (m, 2H), 1.22-0.86 (m, 6H) ppm. MS: M/e 261 (M+1)$^+$.

Examples A132 to A142 were prepared according to the procedures described for A126 under appropriate conditions that could be recognized by one skilled in the art.

Example A132: cyclopropyl(6-(trifluoromethyl)imidazo[1,5-a]pyridin-5-yl)methanol

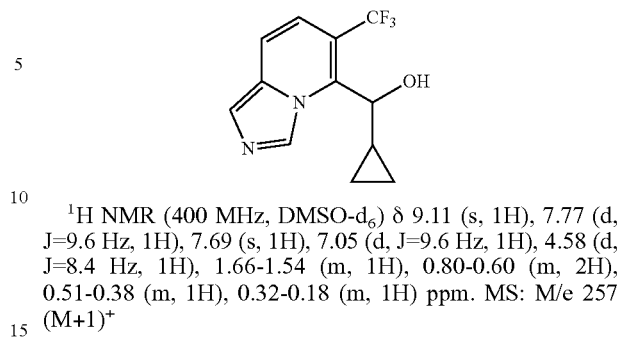

$^1$H NMR (400 MHz, DMSO-d$_6$) δ 9.11 (s, 1H), 7.77 (d, J=9.6 Hz, 1H), 7.69 (s, 1H), 7.05 (d, J=9.6 Hz, 1H), 4.58 (d, J=8.4 Hz, 1H), 1.66-1.54 (m, 1H), 0.80-0.60 (m, 2H), 0.51-0.38 (m, 1H), 0.32-0.18 (m, 1H) ppm. MS: M/e 257 (M+1)$^+$ Example A133: cyclopentyl(6-(trifluoromethyl)imidazo[1,5-a]pyridin-5-yl)methanol

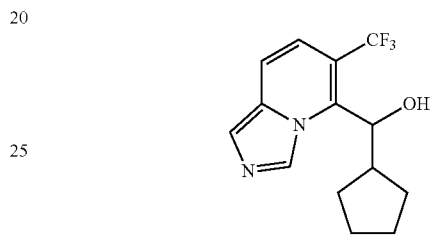

$^1$H NMR (400 MHz, DMSO-d$_6$) δ 8.99 (s, 1H), 7.74 (d, J=10.0 Hz, 1H), 7.63 (s, 1H), 7.02 (dd, J=10.0, 1.6 Hz, 1H), 6.42 (br. s, 1H), 4.94 (d, J=10.0 Hz, 1H), 2.80-2.69 (m, 1H), 2.08-1.98 (m, 1H), 1.70-1.35 (m, 5H), 1.12-0.94 (m, 2H) ppm. MS: M/e 285 (M+1)$^+$.

Example A134: cyclopropyl(6-iodoimidazo[1,5-a]pyridin-5-yl)methanol

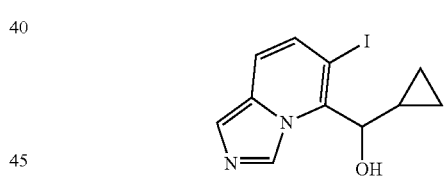

$^1$H NMR (400 MHz, DMSO-d$_6$) δ 9.22 (s, 1H), 7.78 (s, 1H), 7.42 (d, J=7.6 Hz, 1H), 7.25 (d, J=7.6 Hz, 1H), 4.76 (d, J=10.0 Hz, 1H), 1.57-1.60 (m, 1H), 0.41-0.67 (m, 4H) ppm.

Example A135: cyclohexyl(6-isopropylimidazo[1,5-a]pyridin-5-yl)methanol

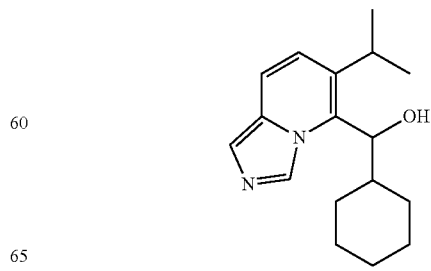

¹H NMR (400 MHz, DMSO-d₆) δ 9.09 (s, 1H), 7.66 (s, 1H), 7.58 (d, J=7.6 Hz, 1H), 7.04 (d, J=7.6 Hz, 1H), 5.91 (s, 1H), 4.99 (d, J=6.0 Hz, 1H), 2.22-2.23 (m, 1H), 2.02-2.04 (m, 1H), 1.58-1.75 (m, 3H), 1.01-1.19 (m, 13H) ppm. MS: M/e 273 (M+1)⁺.

Example A136: cyclohexyl(6-(prop-1en-2-yl)imidazo[1,5-a]pyridin-5-yl)methanol

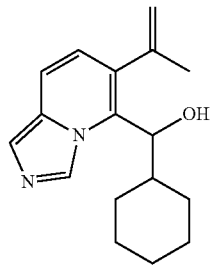 [SMILES: C=C(C)c1ccc2cncn2c1C(O)C1CCCCC1]

¹H NMR (400 MHz, DMSO-d₆) δ 9.31 (s, 1H), 7.88 (s, 1H), 7.67 (d, J=9.2 Hz, 1H), 6.90 (d, J=9.2 Hz, 1H), 6.03 (s, 1H), 5.35 (s, 1H), 5.05 (s, 1H), 4.82 (d, J=9.6 Hz, 1H), 2.22-2.23 (m, 1H), 2.05 (s, 3H), 1.58-1.75 (m, 3H), 0.78-1.19 (m, 7H) ppm. MS: M/e 271 (M+1)⁺.

Example A137: cyclopropyl(6-cyclopropylimidazo[1,5-a]pyridin-5-yl)methanol

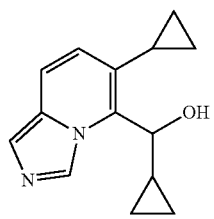 [SMILES: OC(c1c(C2CC2)ccc2cncn12)C1CC1]

¹H NMR (400 MHz, DMSO-d₆) δ 9.49 (s, 1H), 7.91 (s, 1H), 7.64 (d, J=9.6 Hz, 1H), 6.76 (d, J=9.6 Hz, 1H), 6.07 (s, 1H), 4.95 (d, J=8.4 Hz, 1H), 2.08 (m, 1H), 1.69-1.49 (m, 1H), 0.98 (m, 2H), 0.80 (m, 1H), 0.68 (m, 3H), 0.39 (m, 2H) ppm. MS: M/e 229 (M+1)⁺.

Example A138: cyclopentyl(6-cyclopropylimidazo[1,5-a]pyridin-5-yl)methanol

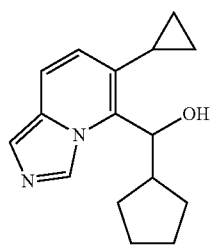 [SMILES: OC(c1c(C2CC2)ccc2cncn12)C1CCCC1]

¹H NMR (400 MHz, DMSO-d₆) δ 9.52 (s, 1H), 7.95 (s, 1H), 7.65 (d, J=9.6 Hz, 1H), 6.78 (d, J=9.6 Hz, 1H), 6.08 (s, 1H), 5.32 (d, J=10.4 Hz, 1H), 2.67 (m, 1H), 2.14 (m, 1H), 1.99 (m, 1H), 1.78-1.52 (m, 4H), 1.44 (m, 1H), 1.19 (m, 2H), 1.10-0.94 (m, 2H), 0.85 (m, 1H), 0.73 (m, 1H) ppm. MS: M/e 257 (M+1)⁺.

Example A139: 2-cyclohexyl-1-(6-cyclopropylimidazo[1,5-a]pyridin-5-yl)ethan-1-ol

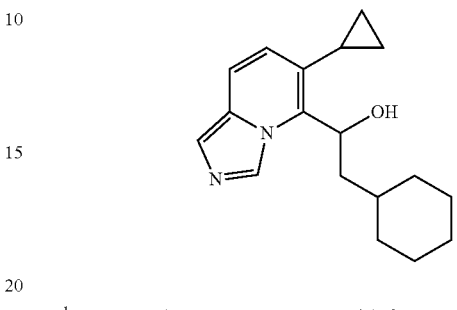

¹H NMR (400 MHz, DMSO-d₆) δ 9.37 (s, 1H), 7.86 (s, 1H), 7.61 (d, J=9.6 Hz, 1H), 6.80 (d, J=9.6 Hz, 1H), 5.98 (s, 1H), 5.82-5.66 (m, 1H), 2.06-1.94 (m, 2H), 1.78 (m, 2H), 1.65 (m, 3H), 1.56-1.47 (m, 2H), 1.25 (m, 8H), 0.81 (m, 1H), 0.69 (m, 1H) ppm. MS: M/e 285 (M+1)⁺.

Example A139a and A139b: (S)-cyclohexyl(6-cyclopropylimidazo[1,5-a]pyridin-5-yl)methanol and (R)-cyclohexyl(6-cyclopropylimidazo[1,5-a]pyridin-5-yl)methanol A139a

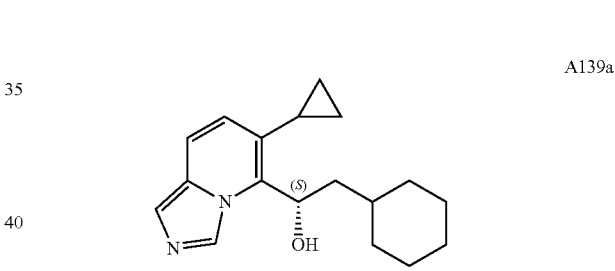

Fast isomer in chiral AD HPLC
Eluting reagent: CO₂/MeOH 0.1% DEA = 80/20 (/V/V)

A139b

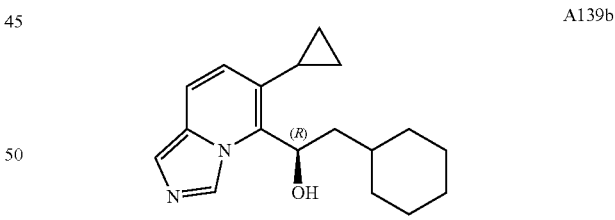

Slow isomer in chiral AD HPLC
Eluting reagent: CO₂/MeOH 0.1% DEA = 80/20 (/V/V)

Each enantiomer of racemic A139a and A139b was separated using preparative HPLC on a Chiralpak AD-H with ACN/MeOH/DEA=90/10/0.1 (V/V/V) as an eluent. The enantiomeric excesses were determined by using HPLC on a Chiralpak IC with ACN/MeOH/DEA=90/10/0.1 (V/V/V) as an eluent at a flow rate of 1.0 mL/min. The first one enantiomer eluted at the retention time of 3.02 min, and the other enantiomer eluted at the retention time of 4.33 min. The spectral properties of the title compounds were identical with those of compound A139. The absolute configurations of A139a and A139b are tentatively assigned as (S) and (R)

respectively based on assumption that the binding model of the more potent isomer A139a is the same as that of A101a with IDO1 enzyme.

Example A140: cyclohexyl(6-(3,5-dimethylisoxazol-4-yl)imidazo[1,5-a] pyridin-5-yl)methanol

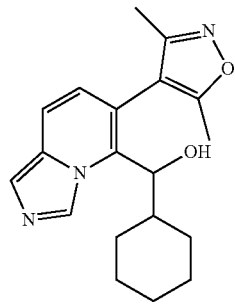 [SMILES: Cc1noc(C)c1-c1ccc2cncn2c1C(O)C1CCCCC1]

¹H NMR (400 MHz, DMSO-d₆) δ 9.24 (d, J=14.4 Hz, 1H), 7.84 (s, 1H), 7.73 (d, J=9.2 Hz, 1H), 6.82 (dd, J=20.8, 9.2 Hz, 1H), 6.24 (s, 1H), 4.38 (dd, J=52.0, 9.6 Hz, 1H), 2.39-2.23 (d, J=36 Hz, 3H), 2.12 (d, J=14.4 Hz, 3H), 2.00 (m, 1H), 1.69 (m, 1H), 1.48 (m, 2H), 1.24-0.77 (m, 6H), 0.50 (m, 1H) ppm. MS: M/e 326 (M+1)⁺.

Example A141: 2-((6-cyclopropylimidazo[1,5-a]pyridin-5-yl)(hydroxy)methyl)cyclohexan-1-ol

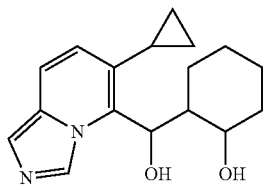 [SMILES: OC1CCCCC1C(O)c1c(C2CC2)ccc2cncn12]

¹H NMR (DMSO-d₆) δ 8.64 (s, 1H), 7.42 (d, 1H, J=9.6 Hz), 7.32 (s, 1H) 6.44 (d, 1H, J=9.6 Hz), 6.35 (s, 1H), 5.65 (d, 1H, J=8.0 Hz), 5.52 (d, 1H, J=3.2 Hz), 3.70-3.74 (m, 1H), 2.17-2.20 (m, 1H), 1.99-2.07 (m, 1H), 1.88-1.91 (m, 1H), 1.59-1.62 (m, 1H), 1.42-1.45 (m, 1H), 1.17-1.33 (m, 2H), 0.88-1.04 (m, 5H), 0.73-0.77 (m, 1H), 0.61-0.65 (m, 1H).

Example A142: 4-((6-cyclopropylimidazo[1,5-a]pyridin-5-yl)(hydroxy)methyl)cyclohexan-1-ol

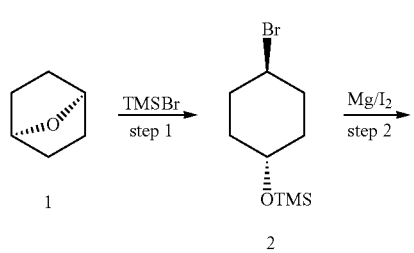

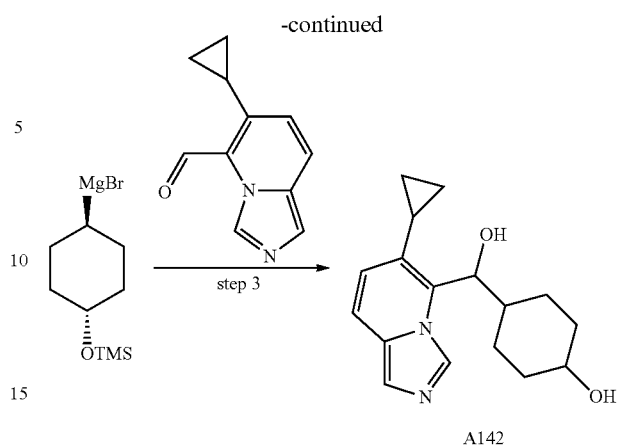

Step 1: ((4-bromocyclohexyl)oxy)trimethylsilane

To a solution of 7-oxabicyclo[2.2.1]heptane (32.8 g, 334 mmol) in dry DCM (500 mL) was added dropwise of TMSBr (54 g, 1.2 eq) at RT. After dropping completely, the resulting mixture was stirred overnight at room temperature. Evaporated the solvent and the residue was distilled to give desired product 50 g in 60% yield.

Steps 2 and 3: 4-((6-cyclopropylimidazo[1,5-a]pyridin-5-yl)(hydroxy)methyl)cyclohexan-1-ol To a suspension of Mg (1.0 g) in dry THF (20 mL) was added ((4-bromocyclohexyl)oxy) trimethylsilane (1.0 g) and catalytic amount of I₂, and the mixture was heated at 50° C. for 0.5 hours. Then ((4-bromocyclohexyl)oxy) trimethylsilane (6.0 g) was added to the mixture, and reacted for 0.5 h till the Grignard Reagent was formed, cooled to room temperature and dropped wise to a solution of 6-cyclopropylimidazo[1,5-a]pyridine-5-carbaldehyde (1.0 g) in dry THF (10 mL) at 0° C. and the mixture was stirred for 0.5 h before saturate aqueous of NH₄C₁ was added, extracted with EA (20 mL*3), dried over Na₂SO₄, filtered and the filtrate was evaporated and purified by CC (D:M=10:1) to give desired product 1.0 g in 70% yield. ¹H NMR (DMSO-d₆) 8.57 (s, 1H), 7.39 (d, 1H, J=9.6 Hz), 7.29 (s, 1H), 6.46 (d, 1H, J=9.6 Hz), 5.73 (d, 1H, J=4.0 Hz), 5.26 (dd, 1H, J=9.6, 3.6 Hz), 4.26 (d, 1H, J=3.2 Hz), 3.74 (s, 1H), 2.08-2.13 (m, 1H), 1.91-1.95 (m, 2H), 1.62-1.71 (m, 5H), 1.18-1.24 (m, 1H), 0.89-0.98 (m, 2H), 0.73-0.81 (m, 2H), 0.62-0.67 (m, 1H).

Example A142a, A142b, A142c and A142d: (1R,4s)-4-((S)-(6-cyclopropylimidazo[1,5-a]pyridin-5-yl)(hydroxy)methyl)cyclohexan-1-ol, (1S,4r)-4-((S)-(6-cyclopropylimidazo[1,5-a]pyridin-5-yl)(hydroxy)methyl)cyclohexan-1-ol, (1R,4s)-4-((R)-(6-cyclopropylimidazo[1,5-a]pyridin-5-yl)(hydroxy)methyl)cyclohexan-1-ol and (1S,4r)-4-((R)-(6-cyclopropylimidazo[1,5-a]pyridin-5-yl)(hydroxy)methyl)cyclohexan-1-ol

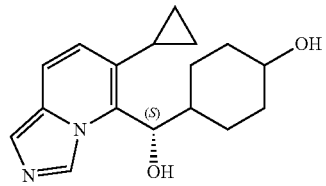

First isomer in chiral AD HPLC
Eluting reagent: CO₂/IPA = 70/30 (/V/V)

A142b

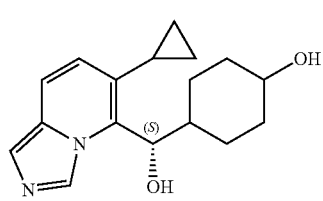

Second isomer in chiral AD HPLC
Eluting reagent: CO₂/IPA = 70/30 (/V/V)

A142c

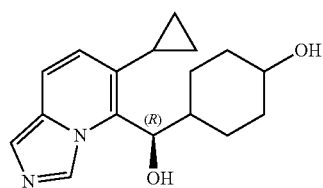

Third isomer in chiral AD HPLC
Eluting reagent: CO₂/IPA = 70/30 (/V/V)

A142d

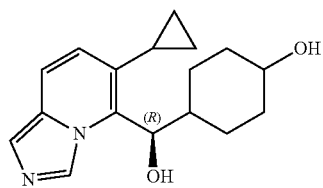

Forth isomer in chiral AD HPLC
Eluting reagent: CO₂/IPA = 70/30 (/V/V)

Each enantiomer was separated using preparative HPLC on a Chiralcel AD-H with 30% propan-2-ol/Carbon dioxide as an eluent. The enantiomeric excesses were determined by using HPLC on a Chiralcel AD-H with 30% propan-2-ol/Carbon dioxide as an eluent at a flow rate of 2.0 mL/min. The first isomer eluted at the retention time of 9.137 min, $^1$H NMR (DMSO-$d_6$) 8.57 (s, 1H), 7.39 (d, 1H, J=9.6 Hz), 7.29 (s, 1H), 6.46 (d, 1H, J=9.6 Hz), 5.73 (d, 1H, J=4.0 Hz), 5.26 (dd, 1H, J=9.6, 3.6 Hz), 4.26 (d, 1H, J=3.2 Hz), 3.74 (s, 1H), 2.09-2.13 (m, 1H), 1.91-1.95 (m, 2H), 1.62-1.71 (m, 5H), 1.18-1.24 (m, 2H), 0.89-0.98 (m, 2H), 0.73-0.81 (m, 2H), 0.63-0.67 (m, 1H); second isomer eluted at the retention time of 12.750 min, $^1$H NMR (DMSO-$d_6$) 8.57 (s, 1H), 7.39 (d, 1H, J=9.6 Hz), 7.29 (s, 1H), 6.45 (d, 1H, J=9.6 Hz), 5.74 (d, 1H, J=4.0 Hz), 5.17 (dd, 1H, J=9.6, 3.6 Hz), 4.45 (d, 1H, J=3.2 Hz), 2.25-2.27 (m, 1H), 1.89-2.03 (m, 3H), 1.66-1.69 (m, 1H), 0.89-0.98 (m, 2H), 0.73-0.81 (m, 7H), 0.63-0.73 (m, 3H); third isomer eluted at the retention time of 15.375 min, $^1$H NMR (DMSO-$d_6$) 8.57 (s, 1H), 7.38 (d, 1H, J=9.6 Hz), 7.29 (s, 1H), 6.45 (d, 1H, J=9.6 Hz), 5.72 (d, 1H, J=4.0 Hz), 5.27 (dd, 1H, J=9.6, 4.0 Hz), 4.26 (d, 1H, J=4.0 Hz), 3.74 (s, 1H), 2.10-2.13 (m, 1H), 1.91-1.95 (m, 2H), 1.21-1.70 (m, 7H), 0.91-0.98 (m, 2H), 0.74-0.81 (m, 2H), 0.63-0.65 (m, 1H); and the forth enantiomer eluted at the retention time of 17.955 min, $^1$H NMR (DMSO-$d_6$) 8.57 (s, 1H), 7.38 (d, 1H, J=9.6 Hz), 7.30 (s, 1H), 6.45 (d, 1H, J=9.6 Hz), 5.75 (d, 1H, J=4.0 Hz), 5.17 (dd, 1H, J=9.6, 4.0 Hz), 4.46 (d, 1H, J=4.0 Hz), 2.25-2.27 (m, 1H), 1.89-2.03 (m, 3H), 1.6-1.70 (m, 1H), 0.89-1.23 (m, 2H), 0.74-0.81 (m, 5H), 0.63-0.75 (m, 2H). The absolute configurations of A142a, A142b, A142c and A142d are tentatively assigned as (S), (S), (R) and (R) respectively based on assumption that the binding model of the more potent isomer A142a and A142b are the same as that of A101a with IDO1 enzyme, but the relative configuration in cyclohexane is uncertain.

Example A143: cyclohexyl(6,7-dichloroimidazo[1,5-a]pyridin-5-yl)methanol

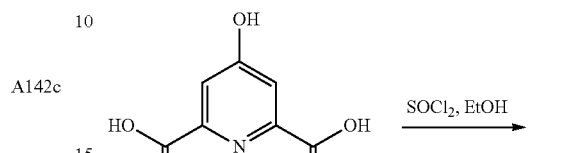

1

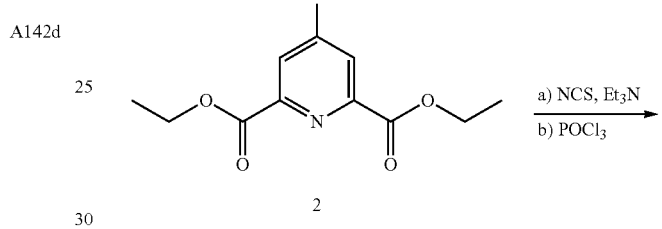

2

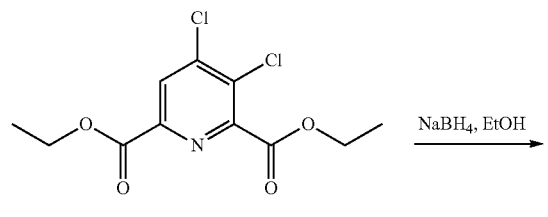

3

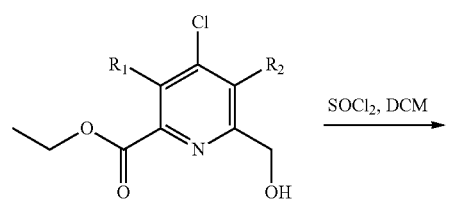

4a: R₁ = Cl, R₂ = H;
4b: R₁ = H, R₂ = Cl;

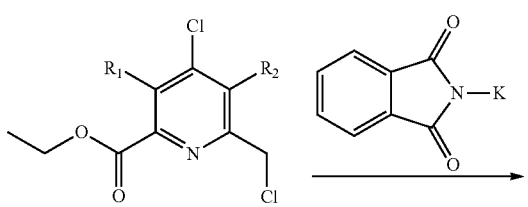

5a: R₁ = Cl, R₂ = H;
5b: R₁ = H, R₂ = Cl;

-continued

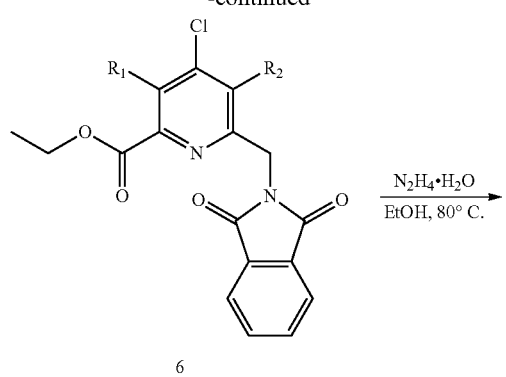

6
6a: R₁ = Cl, R₂ = H;
6b: R₁ = H, R₂ = Cl;

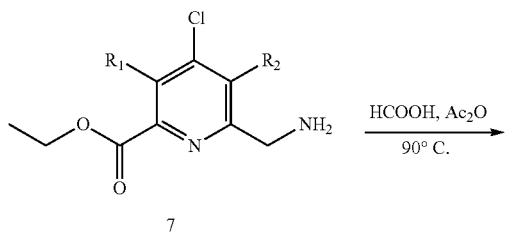

7
7a: R₁ = Cl, R₂ = H;
7b: R₁ = H, R₂ = Cl;

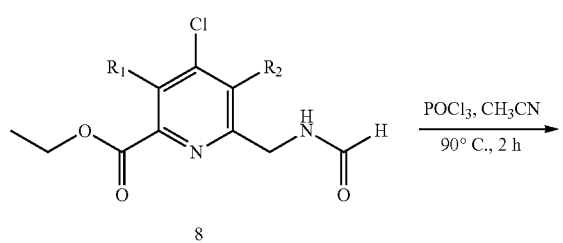

8
8a: R₁ = Cl, R₂ = H;
8b: R₁ = H, R₂ = Cl;

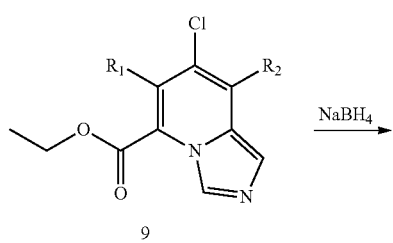

9
9a: R₁ = Cl, R₂ = H;
9b: R₁ = H, R₂ = Cl;

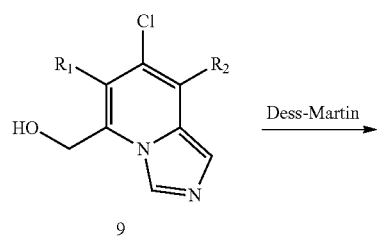

9
10a: R₁ = Cl, R₂ = H;
10b: R₁ = H, R₂ = Cl;

-continued

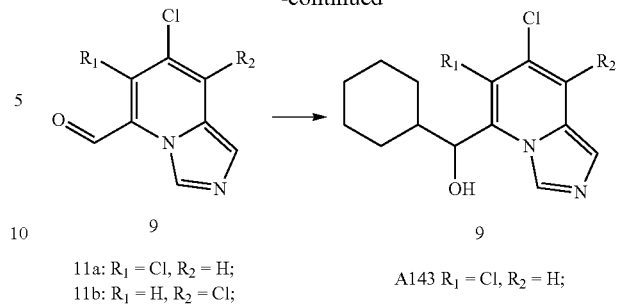

9
11a: R₁ = Cl, R₂ = H;
11b: R₁ = H, R₂ = Cl;

9
A143 R₁ = Cl, R₂ = H;

Step 1: diethyl 4-hydroxypyridine-2,6-dicarboxylate

To a solution of 4-hydroxypyridine-2,6-dicarboxylic acid (183 g, 1.0 mol) in EtOH (1500 ml) was added thionyl chloride (200 ml, 2.0 mol) at room temperature and the mixture was heated at 90'C for 3 h. The mixture was cooled to room temperature, concentrated to dryness. The crude was added water 1 L and stirred at room temperature and neutralized with sodium carbonate, after filtered and washed with water (200 ml*3) to give white solid (201 g, yield: 83.92%). ¹H NMR (CD₃OD-d₄) δ 7.45 (s, 1H), 4.40 (dd, 4H, J=7.2 Hz), 1.40 (t, 3H, J=6.8 Hz).

Step 2: diethyl 3,4-dichloropyridine-2,6-dicarboxylate

To a solution of diethyl 4-hydroxypyridine-2,6-dicarboxylate (140 g, 0.585 mol) in DCM (1400 ml) was added triethylamine (47 ml, 0.703 mol) and N-Chlorosuccinimide (N-chloropyrrolidine-2,5-dione) (86.3 g, 0.644 mol). And the mixture reaction was stirred at room temperature for 1 h, concentrated to dryness. The crude was dissolved in EA 500 mL and extracted with 6N HCl (500 ml*3), combined the organic layer, dried over sodium sulfate, filtered and concentrated to dryness. The crude was dissolved in acetonitrile 800 ml, phosphorus oxychloride (80 ml) was added, and the mixture was stirred at 75° C. for 1 h, after concentrated to dryness. The crude product was purified by column chromatography on silica gel (400 g) using PE:EA=20:1 as eluting to give a white solid (30.0 g in 17.56% yield). ¹H NMR (DMSO-d₆) δ 8.40 (s, 1H), 4.42 (m, 4H), 1.35 (m, 6H).

Step 3: ethyl 3,4-dichloro-6-(hydroxymethyl)picolinate and ethyl 4,5-dichloro-6-(hydroxymethyl) picolinate

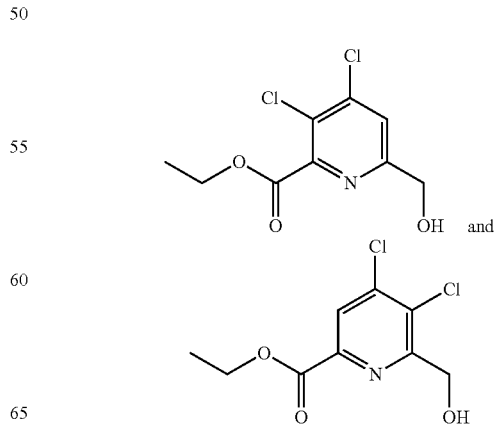

To a solution of diethyl 3,4-dichloropyridine-2,6-dicarboxylate (30 g, 103.09 mmol) in ethyl alcohol (1000 ml) was added sodium borohydride (1.96 g, 51.55 mmol), and the mixture was stirred at 50° C. for 2 h, cooled to room temperature, quenched with water 5 ml and concentrated to dryness. The crude was added water 500 ml, extracted with EA (500 ml*3), combined the organic layer, dried over sodium sulfate, filtered and concentrated to dryness. The crude was purified by column chromatography on silica gel (50 g) PE:EA=1:1, get pale yellow oil (mixture, 9.00 g in 35.06% in yield). ESI-MS m/z 250.0 ([M+H]$^+$).

Step 4: ethyl 3,4-dichloro-6-(chloromethyl)picolinate and ethyl 4,5-dichloro-6-(chloromethyl)picolinate

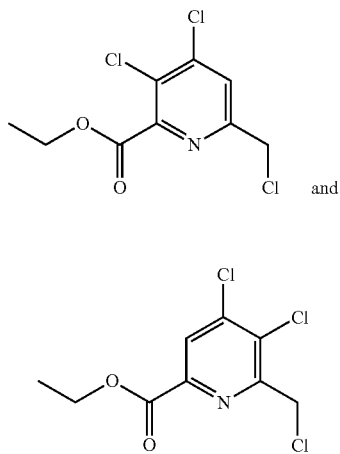

To a solution of ethyl 3,4-dichloro-6-(hydroxymethyl) picolinate and ethyl 4,5-dichloro-6-(hydroxymethyl)picolinate (9.00 g, 36.14 mmol) in dichloromethane (100 ml) was added thionyl chloride (6.6 ml, 90.36 mmol) by dropwise, and the mixture was stirred at 45° C. for 2 h, cooled to room temperature, quenched with water 2 ml and concentrated to dryness. The crude was added saturated sodium bicarbonate solution 50 ml, extracted with EA (50 ml*3), combined the organic layer, dried over sodium sulfate, filtered and concentrated to dryness. This crude product (11.19 g) was used for the next step without further purification.

Step 5: ethyl 3,4-dichloro-6-((1,3-dioxoisoindolin-2-yl)methyl)picolinate and ethyl 4,5-dichloro-6-((1,3-dioxoisoindolin-2-yl)methyl)picolinate

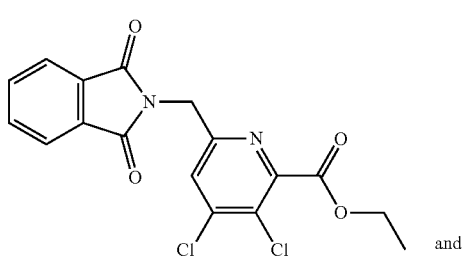

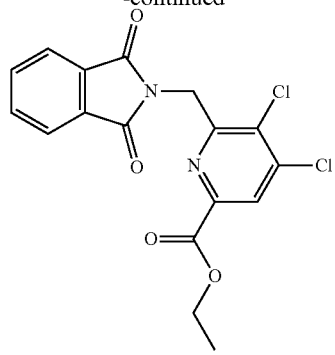

Ethyl 3,4-dichloro-6-(chloromethyl)picolinate and ethyl 4,5-dichloro-6-(chloromethyl) picolinate (11.19 g, 41.95 mmol) were dissolved in anhydrous DMF (100 ml), and Potassium phthalimide (9.26 g, 50.10 mmol) was slowly added at room temperature and the mixture was stirred overnight. Then the reaction mixture was added water 100 ml, extracted with EA (150 ml*3), combined the organic layer, dried over sodium sulfate, filtered and concentrated to dryness. The crude was recrystallized with PE:EA=10:1 (50 ml) to give a pale yellow solid (mixture, 9.50 g in 59.91% yield). One isomer: $^1$H NMR (DMSO-d$_6$) δ 8.11 (s, 1H), 7.86-7.97 (m, 4H), 5.11 (s, 2H), 4.08 (dd, 3H, J=7.2 Hz), 0.93 (t, 2H, J=7.2 Hz). The other isomer: $^1$H NMR (DMSO-d$_6$) 8.08 (s, 1H), 7.86-7.97 (m, 4H), 4.92 (s, 2H), 4.34 (dd, 3H, J=7.2 Hz), 1.19 (t, 2H, J=7.2 Hz).

Steps 6 and 7: 6-(aminomethyl)-3,4-dichloropicolinate and ethyl 6-(aminomethyl)-4,5-dichloro-picolinate

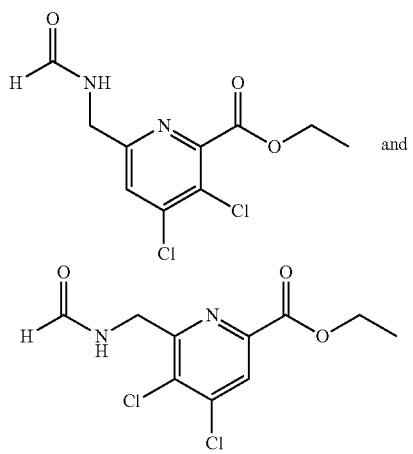

To a solution of ethyl 3,4-dichloro-6-((1,3-dioxoisoindolin-2-yl)methyl)picolinate and ethyl 4,5-dichloro-6-((1,3-dioxoisoindolin-2-yl)methyl)picolinate (9.50 g, 25.13 mmol) in EtOH (100 ml) was added Hydrazine hydrate (1.25 ml, 98%) at room temperature, and the mixture was heated to 80° C. for 2 h. Then cooled to room temperature, HCOOH (5 ml) was added, filtered and washed with EtOH, and the filtrate was evaporated to give crude product as oil. This crude product was dissolved in HCOOH (40 ml) and acetic anhydride (8 ml), and the mixture was stirred at 90° C. for 2 h, then cooled to room temperature, concentrated to dryness. The crude was added saturated sodium bicarbonate (100 ml), extracted with EA (80 ml*3), combined the organic layer, washed with saturated Nalco (200 ml*2), dried over sodium sulfate, filtered and concentrated under vacuum to give yellow oil (mixture, 6.84 g). ESI-MS m/z 277.0 ([M+H]$^+$).

Step 7: ethyl 6,7-dichloroimidazo[1,5-a]pyridine-5-carboxylate and ethyl 7,8-dichloroimidazo [1,5-a]pyridine-5-carboxylate

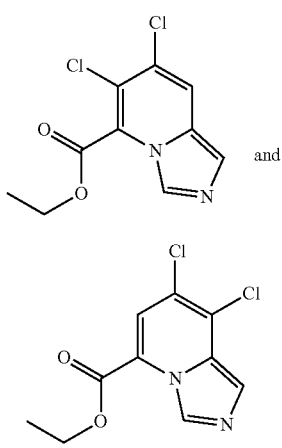

To a solution of 6-(aminomethyl)-3,4-dichloropicolinate and ethyl 6-(aminomethyl)-4,5-dichloropicolinate (6.84 g, 24.78 mmol) in acetonitrile (50 ml) was added POCl$_3$ (4.54 ml, 49.56 mmol) at room temperature and the mixture was heated at 80° C. for 2 h. Then cooled to room temperature and concentrated under vacuum to give crude product, which was dissolved HCl (400 ml, 1N), extracted with EA (200 ml*3), isolated the aqueous layer, adjusted pH=7-8 with sodium carbonate, extracted with EA (400 ml*3), combined the organic layers, evaporated the solvent to give crude product, which was purified by column chromatography on silica gel (50 g) using PE:EA=1:1 as eluting to get one pale yellow solid (2.8 g, ethyl 6,7-dichloroimidazo[1,5-a]pyridine-5-carboxylate): $^1$H NMR (DMSO-d$_6$) δ 9.15 (d, 1H, J=6.4 Hz), 7.75 (d, 1H, J=0.8 Hz), 7.66 (s, 1H), 4.44 (q, 2H, J=7.2 Hz), 1.39 (t, 3H, J=7.2 Hz). And the other one isomer (ethyl 7,8-dichloroimidazo[1,5-a]pyridine-5-carboxylate): $^1$H NMR (DMSO-d$_6$) δ 8.44 (s, 1H), 7.72 (s, 1H), 7.52 (s, 1H), 4.59 (m, 2H, J=7.2 Hz), 1.49 (m, 3H, J=7.2 Hz).

Step 8: (6,7-dichloroimidazo[1,5-a]pyridin-5-yl)methanol

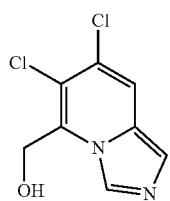 [SMILES: OCc1c(Cl)c(Cl)cc2cncn12]

To a solution of ethyl 6,7-dichloroimidazo[1,5-a]pyridine-5-carboxylate (2.80 g, 10.85 mmol) in EtOH (100 ml) was added NaBH$_4$ (1.23 g, 32.56 mmol) at room temperature, and the mixture was stirred at room temperature for 2 h then quenched with H$_2$O (5 ml). After concentrated to dryness, added water 100 ml to the residue, filtered and concentrated to dryness get a white solid (1.85 g, 78.62% in yield). $^1$H NMR (DMSO-d$_6$) δ 8.49 (s, 1H), 8.02 (s, 1H), 7.49 (s, 1H), 5.84 (t, 1H, J=5.6 Hz), 5.03 (d, 2H, J=5.6 Hz).

Step 9: 6,7-dichloroimidazo[1,5-a]pyridine-5-carbaldehyde

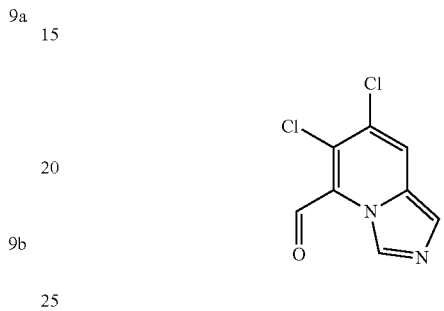

To a solution of (6,7-dichloroimidazo[1,5-a]pyridin-5-yl)methanol (1.85 g, 8.53 mmol) in DCM (15 ml) was added Dess-Martin (5.42 g, 12.79 mmol) reagent at room temperature, and the mixture was stirred for overnight before water (40 ml) was added, and extracted with DCM (100 ml*3), combined the organic layer, dried over sodium sulfate, filtered and concentrated to dryness. The crude was purified by column chromatography on silica gel (50 g) using PE:EA=1:1 as eluting to give a pale yellow solid (1.01 g in 55.07% yield). $^1$H NMR (DMSO-d$_6$) δ 10.62 (s, 1H), 9.64 (s, 1H), 7.99 (s, 1H), 7.70 (s, 1H).

Step 10: cyclohexyl(6,7-dichloroimidazo[1,5-a]pyridin-5-yl)methanol

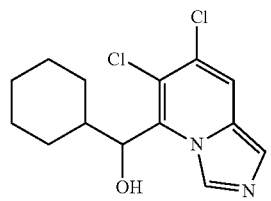 [SMILES: OC(c1c(Cl)c(Cl)cc2cncn12)C1CCCCC1]

To a solution of 6,7-dichloroimidazo[1,5-a]pyridine-5-carbaldehyde (500 mg, 2.32 mmol) in dry THF (10 ml) was added dropwise of cyclohexylmagnesium chloride (5.35 ml, 1.3 mmol/ml) at 0° C. under N$_2$. And the mixture was stirred at room temperature for 1 h. Water (30 ml) was added to the mixture and extracted with EA (30 ml*3), combined the organic layers and dried over sodium sulfate, filtered, and concentrated to dryness, the crude product was purified by pre-TLC (PE:EA=1:1 as eluent) to give product as solid (52 mg in 7.23% yield). $^1$H NMR (DMSO-d$_6$) δ 8.82 (s, 1H), 7.55 (s, 1H), 7.41 (s, 1H), 5.40 (d, 1H, J=9.6 Hz), 3.06 (s, 1H), 1.67-2.27 (m, 5H), 1.07-1.33 (m, 6H).

Examples A143a and A143b: (S)-cyclohexyl(6,7-dichloroimidazo[1,5-a]pyridin-5-yl)methanol and (R)-cyclohexyl(6,7-dichloroimidazo[1,5-a]pyridin-5-yl)methanol

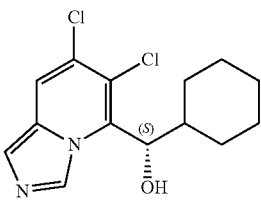

A143a

Fast isomer in chiral OZ HPLC
Eluting reagent: Hexane/IPA = 80/20 (V/V)

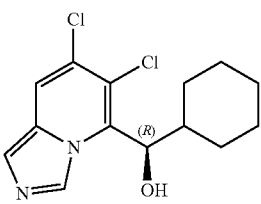

A143b

Slow isomer in chiral OZ HPLC
Eluting reagent: Hexane/IPA = 80/20 (V/V)

Each enantiomer of racemic A143a and A143b was separated using preparative HPLC on a Chiralpak OZ-H with Hexane/IPA=80/20 (V/V) as an eluent. The enantiomeric excesses were determined by using HPLC on a Chiralpak OZ-H with Hexane/IPA=80/20 (V/V) as an eluent at a flow rate of 1.0 mL/min. The first one enantiomer eluted at the retention time of 5.98 min, and the other enantiomer eluted at the retention time of 7.68 min. The spectral properties of the title compounds were identical with those of Example A143. The absolute configurations of A143a and A143b are tentatively assigned as (S) and (R) respectively based on assumption that the binding model of the more potent isomer A143a is the same as that of A101a with IDO1 enzyme.

Examples A144 to A146 were synthesized from the corresponding aldehyde and Grignard reagent by following the procedures similar to those in Example A143.

Example A144: 2-cyclohexyl-1-(6,7-dichloroimidazo[1,5-a]pyridin-5-yl)ethan-1-ol

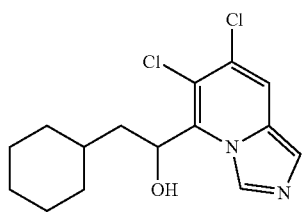 [SMILES: OC(CC1CCCCC1)c1c(Cl)c(Cl)cc2cncn12]

$^1$H NMR (DMSO-d$_6$) δ 8.87 (s, 1H), 7.57 (s, 1H), 7.53 (s, 1H), 5.83 (dd, 1H, J=4.0 Hz), 1.59-2.14 (m, 7H), 0.97-1.35 (m, 6H).

Examples A144a and A144b: (R)-2-cyclohexyl-1-(6,7-dichloroimidazo[1,5-a]pyridin-5-yl)ethan-1-ol and (S)-2-cyclohexyl-1-(6,7-dichloroimidazo[1,5-a]pyridin-5-yl)ethan-1-ol

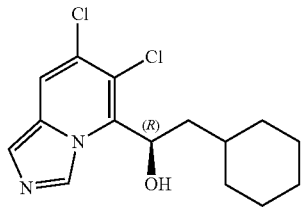

A144a

Fast isomer in chiral AS HPLC
Eluting reagent: Hexane/EtOH = 90/10 (V/V)

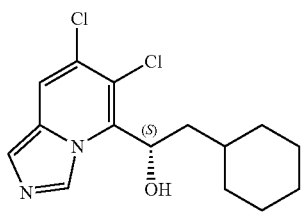

A144b

Slow isomer in chiral AS HPLC
Eluting reagent: Hexane/EtOH = 90/10 (V/V)

Each enantiomer of racemic A144a and A144b was separated using preparative HPLC on a Chiralpak AS-H with Hexane/EtOH=90/10 (V/V) as an eluent. The enantiomeric excesses were determined by using HPLC on a Chiralpak AS-H with Hexane/EtOH=90/10 (V/V) as an eluent at a flow rate of 1.0 mL/min. The first one enantiomer eluted at the retention time of 4.45 min, and the other enantiomer eluted at the retention time of 7.21 min. The spectral properties of the title compounds were identical with those of Example A144. The absolute configurations of A144a and A144b are tentatively assigned as (R) and (S) respectively based on assumption that the binding model of the more potent isomer A144b is the same as that of A101a with IDO1 enzyme.

Example A145: Imidazo[1,5-a]pyridin-5-yl(phenyl)methanol

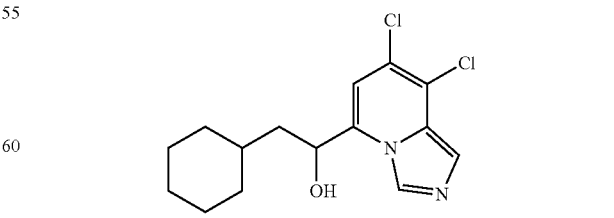

$^1$H NMR (DMSO-d$_6$) δ 8.45 (s, 1H), 7.52 (s, 1H), 6.70 (s, 1H), 5.02 (dd, 2H, J=3.2 Hz), 1.59-1.91 (m, 8H), 0.96-1.30 (m, 6H).

Example A146: cyclohexyl(7,8-dichloroimidazo[1,5-a]pyridin-5-yl)methanol
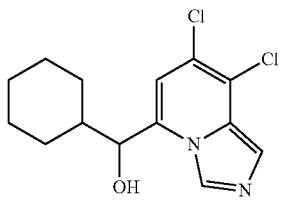 [SMILES: OC(c1cc(Cl)c(Cl)c2cncn12)C1CCCCC1]
$^1$H NMR (DMSO-d$_6$) δ 8.94 (s, 1H), 7.62 (s, 1H), 6.70 (s, 1H), 4.68 (d, 2H, J=7.6 Hz), 1.70-2.05 (m, 5H), 1.10-1.40 (m, 6H).
Example A147: 1-(7-bromo-8-chloroimidazo[1,5-a]pyridin-5-yl)-2-cyclohexylethan-1-ol
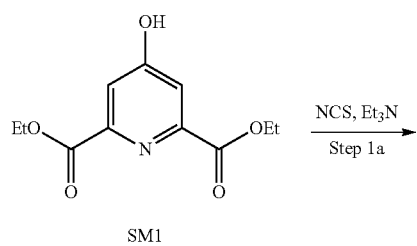
SM1
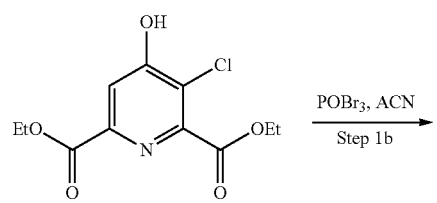
1
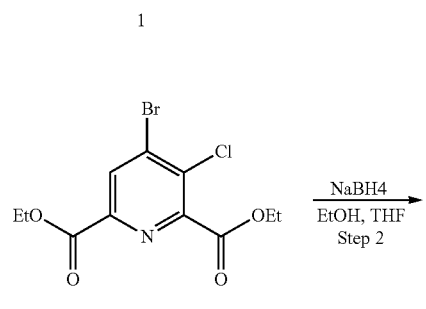
2
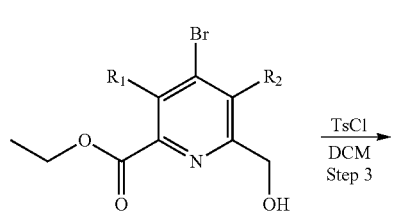
3a: R$_1$ = H, R$_2$ = Cl;
3b: R$_1$ = Cl, R$_2$ = H;
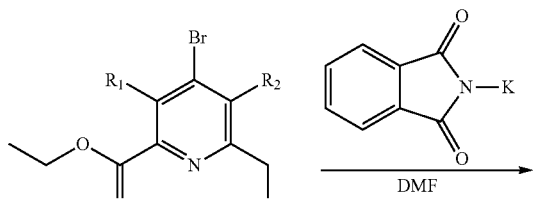
4a: R$_1$ = H, R$_2$ = Cl;
4b: R$_1$ = Cl, R$_2$ = H;
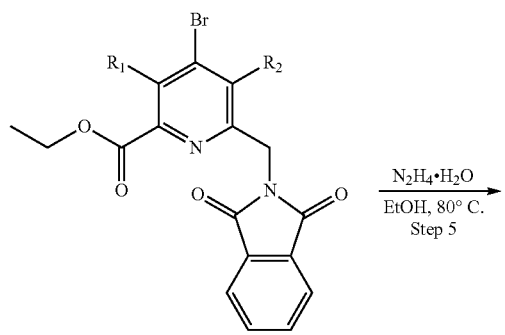
5a: R$_1$ = H, R$_2$ = Cl;
5b: R$_1$ = Cl, R$_2$ = H;
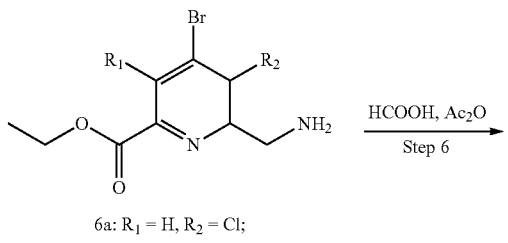
6a: R$_1$ = H, R$_2$ = Cl;
6b: R$_1$ = Cl, R$_2$ = H;
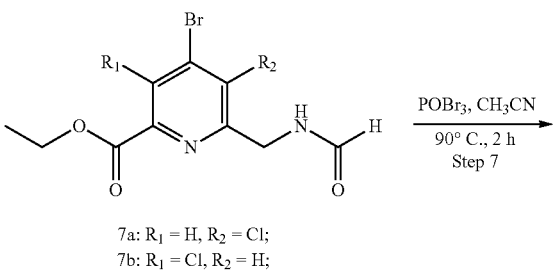
7a: R$_1$ = H, R$_2$ = Cl;
7b: R$_1$ = Cl, R$_2$ = H;
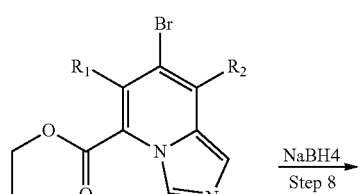
8a: R$_1$ = H, R$_2$ = Cl;
8b: R$_1$ = Cl, R$_2$ = H;

155

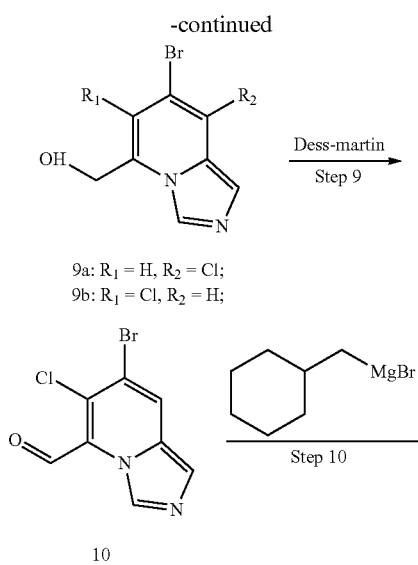

9a: R₁ = H, R₂ = Cl;
9b: R₁ = Cl, R₂ = H;

10

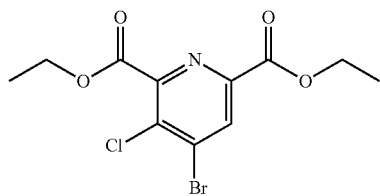 [SMILES: CCOC(=O)c1cc(Br)c(Cl)c(C(=O)OCC)n1]

A147

Step 1: diethyl
4-bromo-3-chloropyridine-2,6-dicarboxylate

To a solution of diethyl 4-hydroxypyridine-2,6-dicarboxylate (200 g, 0.837 mol) in DCM (1400 ml) was shirred at room temperature, and added triethylamine (101 g, 1 mol) N-Chlorosuccinimide (N-chloropyrrolidine-2,5-dione) (65.13 g, 0.488 mol) batch-wise. And the mixture reaction was stirred at room temperature for 1 h, concentrated to dryness. The crude was added EA 500 L and extracted with 6N HCl (500 ml*3), combined the organic layer, dried over sodium sulfate, filtered and concentrated to dryness. The crude was dissolved in acetonitrile 800 ml, and added POBr₃ (219 g, 0.7664 mol) and the mixture was stirred at 75° C. for 1 h, after concentrated to dryness. The crude was purified by column chromatography on silica gel PE:EA=20:1 get a white solid (50.0 g in 32% yield). ¹H NMR (DMSO-d₆) δ 8.50 (s, 1H), 4.40-4.42 (m, 4H), 1.28-1.34 (m, 6H).

156

Step 2: ethyl 4-bromo-3-chloro-6-(hydroxymethyl) picolinate and ethyl 4-bromo-5-chloro-6-(hydroxymethyl)picolinate

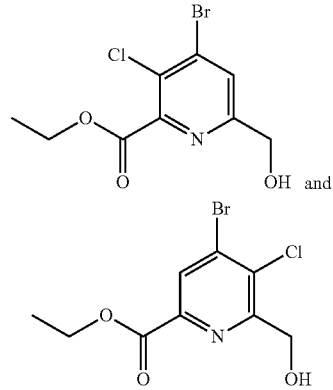

To a solution of compound 2 (21 g, 62.7 mmol) in ethyl alcohol (200 ml) was added sodium NaBH₄ (1.54 g, 40.47 mmol), and the mixture was stirred at 50° C. for 2 h, cooled to room temperature, quenched with water 5 ml and concentrated to dryness. The crude was added water 500 ml, extracted with EA (100 ml*3), combined the organic layer, dried over sodium sulfate, filtered and concentrated to dryness. The crude was purified by column chromatography on silica gel (50 g) PE:EA=1:1, get pale yellow oil (7 g, 38%). One isomer: ¹H NMR (400 MHz, DMSO) δ 9.21 (dd, J=11.6, 6.7 Hz, 1H), 7.93-7.75 (m, 1H), 7.73-7.58 (m, 1H), 4.76-4.32 (m, 3H), 1.57-1.32 (m, 4H). the other isomer: ¹H NMR (400 MHz, DMSO) δ 8.71-8.47 (m, 1H), 8.45-8.32 (m, OH), 8.32-8.18 (m, 1H), 7.58 (dd, J=8.8, 1.6 Hz, 1H), 4.68-4.41 (m, 3H), 1.50-1.28 (m, 4H).

Step 3: ethyl 4-bromo-3-chloro-6-((tosyloxy)methyl)picolinate and ethyl 4-bromo-5-chloro-6-((tosyloxy)methyl)picolinate

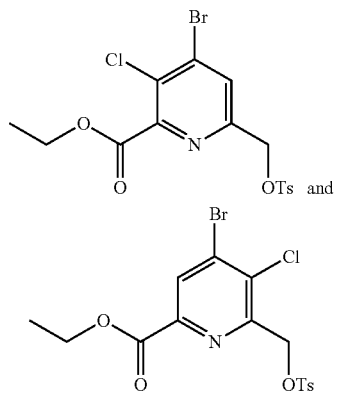

To a solution of compound 3a and 3b (14 g, 48 mmol), Et₃N (9.7 g, 96 mol) and DMAP (0.58, 4.8 mol) in dichloromethane (150 ml) was added TosCl (11 g, 57.6 mmol) was stirred at RT for 2 h, LCMS showed the reaction was completed. The crude was added aqueous NHCl₄ and extracted with EA (100 ml*3), combined the organic layer, dried over sodium sulfate, filtered and concentrated to dryness. This crude product (23 g, >99.9%) was used for next step without further purification.

Step 4: ethyl 4-bromo-3-chloro-6-((1,3-dioxoisoindolin-2-yl)methyl)picolinate and ethyl 4-bromo-5-chloro-6-((1,3-dioxoisoindolin-2-yl)methyl)picolinate

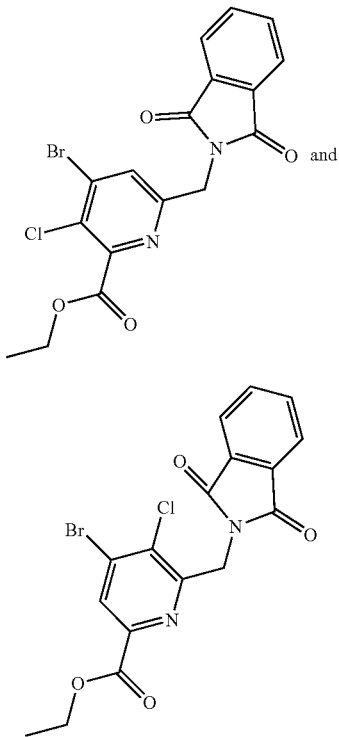

A mixture of compound 4a and 4b (23 g, 51.54 mmol) and potassium 1,3-dioxoisoindoli-2-ide (9.54 g, 51.54 mmol) in anhydrous DMF (200 ml) was stirred at room temperature for 2 h. Then the reaction mixture was added water 100 ml, extracted with EA (150 ml*3), combined the organic layer, dried over sodium sulfate, filtered and concentrated to dryness. The crude was recrystallized with PE:EA=10:1, 50 ml, get a pale yellow oil (two compounds 17 g in 78.3% yield)

Steps 5 and 6: ethyl 4-bromo-3-chloro-6-(formamidomethyl)picolinate and ethyl 4-bromo-5-chloro-6-(formamidomethyl)picolinate

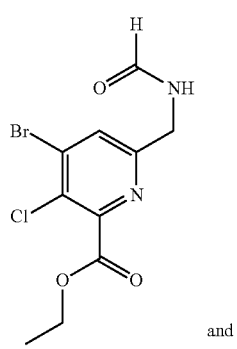

and

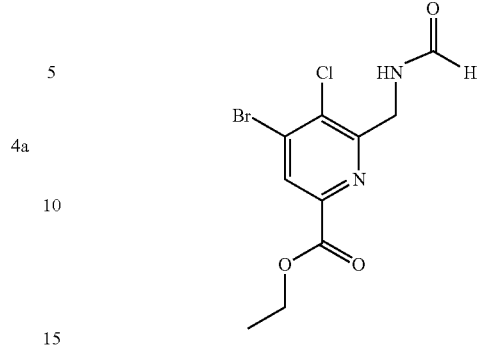

To a solution of compounds 5a and 5b (17 g, 40.28 mmol) in EtOH (100 ml) was added Hydrazine hydrate (2 g, 98%) at room temperature and the mixture was heated at 80° C. for 2 h. Then cooled to room temperature, added HCOOH (10 ml) filtered and washed with to remove white precipitate and the filtrate was evaporated to give crude product as oil. This crude product was added HCOOH 100 ml and acetic oxide 8 ml and the mixture was stirred at 90° C. for 2 h, after cooled to room temperature, concentrated to dryness. The crude was added saturated sodium bicarbonate 100 ml, extracted with EA (80 ml*3), combined the organic layer washed with saturated salt (200 ml*2) dried over sodium sulfate, filtered and concentrated to dryness, get yellow oil (11.5 g, not pure, 91.3%).

Step 7: ethyl 7-bromo-6-chloroimidazo[1,5-a]pyridine-5-carboxylate and ethyl 7-bromo-8-chloroimidazo[1,5-a]pyridine-5-carboxylate

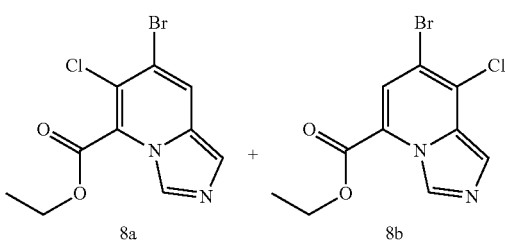 [SMILES: CCOC(=O)c1c(Cl)c(Br)cc2cncn12 ; CCOC(=O)c1cc(Br)c(Cl)c2cncn12]

To a solution of compound 7a and 7b (11.5 g, 36 mmol) in toluene (150 ml) was added POBr$_3$ (15.4 g, 54 mmol) at room temperature and the mixture was heated at 80° C. for 2 h. Then cooled to room temperature and evaporated the solvent before HCl (400 ml, 1N) was added to the residue, extracted with EA (200 ml*3), isolated the aqueous layer, adjusted pH=7-8 with sodium carbonate before extracted with EA (200 ml*3), combined the organic layers, evaporated the solvent to give crud. The crude was purified by column chromatography on silica gel PE:EA=1:1 to give compound 8a (3.6 g), 9 $^1$H NMR (400 MHz, DMSO) δ 8.57 (s, 1H), 8.39 (d, J=0.4 Hz, 1H), 7.59 (s, 1H), 4.56 (q, J=7.1 Hz, 2H), 1.40 (t, J=7.1 Hz, 4H).

Step 8: (7-bromo-6-chloroimidazo[1,5-a]pyridin-5-yl)methanol

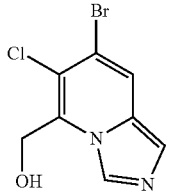

To a solution of compound 9 (3.6 g, 12 mmol) in EtOH (10 ml) was added batch wise of NaBH$_4$ (0.67 g, 18 mmol) at room temperature and the mixture was stirred at room temperature for 2 h then quenched with H$_2$O (1 ml). After concentrated to dryness, added water 10 ml to the residue, filtered and concentrated to dryness get yellow solid (3.1 g, 99.3% in yield).

Step 9: 7-bromo-6-chloroimidazo[1,5-a]pyridine-5-carbaldehyde

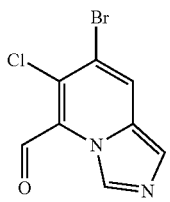 [SMILES: O=Cc1c(Cl)c(Br)cc2cncn12]

To a solution of compound 10 (3.1 g, 11.9 mmol) in DCM (30 ml) was added portion of Dess-Martin (7.58 g, 17.88 mmol) at room temperature and the mixture was stirred for 5 h before water 20 ml was added and extracted with DCM (20 ml*3), combined the organic layer, dried over sodium sulfate, filtered and concentrated to dryness. The crude was purified by column chromatography on silica gel PE:EA=1:1 to give compound 11 (1.8 g, 58%), as yellow solid. 1H NMR (400 MHz, DMSO) δ 10.53-10.38 (m, 1H), 9.41 (d, J=26.4 Hz, 1H), 8.65 (d, J=18.0 Hz, 1H), 7.83-7.67 (m, 2H).

Step 10: 1-(7-bromo-6-chloroimidazo[1,5-a]pyridin-5-yl)-2-cyclohexylethan-1-ol

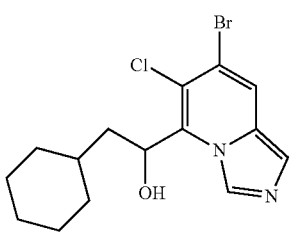 [SMILES: OC(CC1CCCCC1)c1c(Cl)c(Br)cc2cncn12]

To a solution of compound 11 (1 g, 3.78 mmol) in dry THF (20 ml) was added dropwise of cyclohexylmagnesium chloride (5 ml, 1.3 mmol/ml, 1.50 mmol) at 0° C. under N$_2$ air balloon was protected. And the mixture was stirred warmed to room temperature slowly for 1 h. Water (10 ml) was added to the mixture and extracted with EA (10 ml*3), combined the organic layers and dried over sodium sulfate, filtered, and concentrated to dryness, the crude product was purified by pre-TLC (PE:EA=1:2 as eluent) to give 5 mg in 4% yield. $^1$H NMR (400 MHz, cdcl$_3$) δ 8.81 (s, 1H), 7.71 (s, 1H), 7.38 (s, 1H), 7.29 (d, J=26.9 Hz, 2H), 5.81 (dd, J=9.6, 3.9 Hz, 1H), 4.53-4.40 (m, 1H), 1.70-1.53 (m, 1H), 1.31-1.17 (m, 8H), 0.93-0.78 (m, 2H).

Examples A148 to A150 were synthesized from corresponding aldehyde and Grignard reagent by following the procedures similar to those in Example A147.

Example A148: (7-bromo-6-chloroimidazo[1,5-a]pyridin-5-yl)(cyclohexyl)methanol

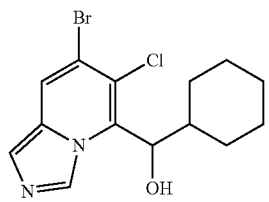

$^1$H NMR (400 MHz, DMSO-d$_6$) δ 8.70 (s, 1H), 8.13 (s, 1H), 7.45 (s, 1H), 6.19 (d, J=4.4 Hz, 1H), 5.17 (dd, J=9.6, 4.4 Hz, 1H), 2.07-2.19 (m, 2H), 1.61-1.72 (m, 3H), 1.04-1.25 (m, 6H).

Example A149: (7-bromo-6-chloroimidazo[1,5-a]pyridin-5-yl)(cyclopentyl)methanol

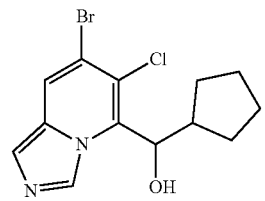 [SMILES: OC(c1c(Cl)c(Br)cc2cncn12)C1CCCC1]

$^1$H NMR (400 MHz, DMSO-d$_6$) δ 8.74 (s, 1H), 8.14 (s, 1H), 7.46 (s, 1H), 6.21 (d, J=4.0 Hz, 1H), 5.22 (dd, J=9.6, 4.0 Hz, 1H), 1.93-1.95 (m, 1H), 1.45-1.58 (m, 5H), 1.20-1.23 (m, 3H).

Example A150: (7-bromo-6-chloroimidazo[1,5-a]pyridin-5-yl)(cyclooropyl)methanol

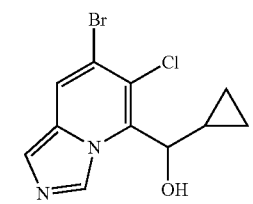 [SMILES: OC(c1c(Cl)c(Br)cc2cncn12)C1CC1]

$^1$H NMR (400 MHz, DMSO-d$_6$) δ 8.82 (s, 1H), 8.14 (s, 1H), 7.47 (s, 1H), 6.25 (d, J=4.0 Hz, 1H), 4.87 (dd, J=8.8, 4.0 Hz, 1H), 1.51-1.59 (m, 1H), 0.51-0.68 (m, 2H), 0.39-0.43 (m, 2H).

Example A151: (6-chloro-7-fluoroimidazo[1,5-a]pyridin-5-yl)(cyclohexyl)methanol

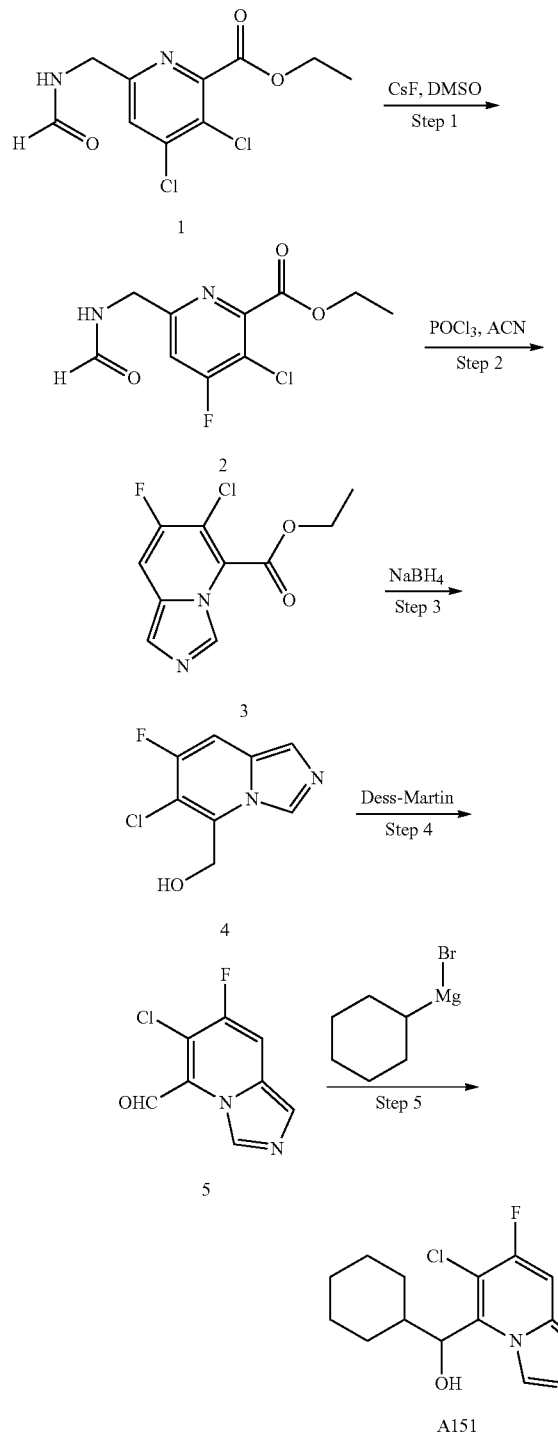

Step 1: Ethyl 3-chloro-4-fluoro-6-(formamidomethyl)picolinate

A mixture of ethyl 3,4-dichloro-6-(formamidomethyl)picolinate (4.3 g, 15.5 mmol, 1.0 eq) and CsF (6.1 g, 40.1 mmol, 2.6 eq) in DMSO (100 mL) was heated to 120° C. for overnight, after cooled down, the mixture was poured into water, extracted with EA, the organic layer was washed with brine, dried over $Na_2SO_4$, concentrated and purified by silica-gel to give crude product (2.5 g). ESI-MS m/z 261 ([M+H]$^+$).

Step 2: Ethyl 6-chloro-7-fluoroimidazo[1,5-a]pyridine-5-carboxylate

A solution of ethyl 3-chloro-4-fluoro-6-(formamidomethyl)picolinate (2.5 g, <9.6 mmol) and $POCl_3$ (1 mL) in ACN (100 mL) was heated to 70° C. for 2 h, after cooled down, the mixture was concentrated, sat. $NaHCO_3$. aq was added, extracted with EA, the EA layer was washed with brine, dried over $Na_2SO_4$, concentrated and purified by silica-gel to give product (1.6 g). ESI-MS m/z 243 ([M+H]$^+$).

Step 3: (6-Chloro-7-fluoroimidazo[1,5-a]pyridin-5-yl)methanol

A mixture of ethyl 6-chloro-7-fluoroimidazo[1,5-a]pyridine-5-carboxylate (1.6 g, 6.6 mmol, 1.0 eq) and $NaBH_4$ (500 mg, 13.2 mmol, 2.0 eq) in EtOH (50 mL) was heated to 80° C. for 2 hours, after cooled down, 100 mL water was added, the mixture was concentrated to remove EtOH, the yellow solid was collected and dried in air to give product (780 mg). ESI-MS m/z 201 ([M+H]$^+$).

Step 4: 6-chloro-7-fluoroimidazo[1,5-a]pyridine-5-carbaldehyde

To a solution of compound 1 (0.3 g, 1.5 mmol) in DCM (20 mL) was added Dess-Martin (1.23 g, 3.0 mmol) at room temperature and the mixture was stirred at rt for 12 hours. Then water (80 mL) was added, extracted with DCM (75 mL×2), dried with $Na_2SO_4$, the filtered to remove $Na_2SO_4$, evaporated the solvent, the residue was purified by silica gel (PE:EA=1:5 then to =1:1) to give product as a yellow solid (0.21 g, 70%). LC-MS (M+H)$^+$=199.1

Step 5: (6-chloro-7-fluoroimidazo[1,5-a]pyridin-5-yl)(cyclohexyl)methanol

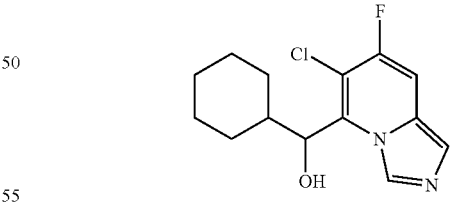

To a solution of compound 2 (0.1 g, 0.51 mmol) in THF (10 mL) was added cyclohexylmagnesium bromide (0.6 mL, 0.77 mmol) at 0° C. and the mixture was stirred at 0° C. for 2 hours. Then water (20 mL) was added, extracted with DCM (20 mL×2), dried with $Na_2SO_4$, the filtered to remove $Na_2SO_4$, evaporated the solvent, the residue was purified pre-HPLC to give product as a white solid (25 mg, 21%). $^1$H NMR (400 MHz, DMSO-d$_6$) δ 8.70 (s, 1H), 7.63 (d, J=8.8 Hz, 1H), 7.44 (s, 1H), 6.02 (s, 1H), 5.07-5.10 (d, J=9.2 Hz, 1H), 2.18-2.22 (m, 1H), 2.07-2.10 (m, 1H), 1.74-1.77 (m, 1H), 1.58-1.60 (m, 1H), 1.02-1.26 (m, 7H).

Example A152: 1-(6-chloro-7-fluoroimidazo[1,5-a]pyridin-5-yl)-2-cyclohexylethan-1-ol
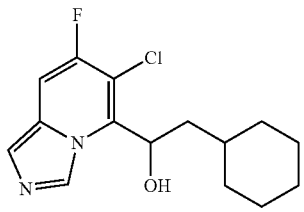
Example A152 was synthesized from the corresponding aldehyde and Grignard reagent by following the procedures similar to those in Example A151. $^1$H NMR (400 MHz, DMSO-$d_6$) δ 8.75 (s, 1H), 7.61-7.63 (d, J=8.8 Hz, 1H), 7.44 (s, 1H), 6.19 (s, 1H), 5.50-5.53 (d, J=8.8 Hz, 1H), 0.83-2.0 (m, 13H). LC-MS (M+H)$^+$=297.1.
Example A153: (8-chloro-7-methoxyimidazo[1,5-a]pyridin-5-yl)(cyclohexyl)methanol
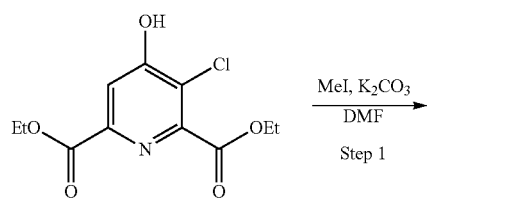
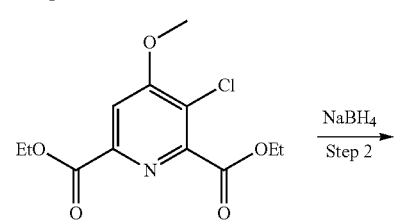
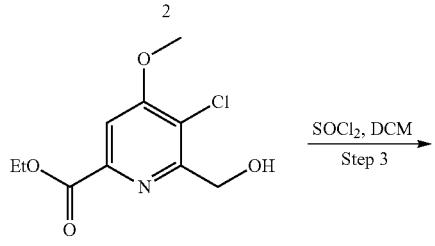
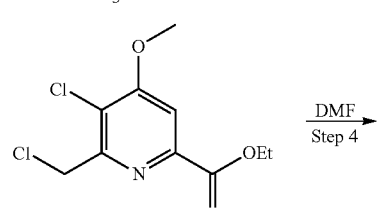
-continued
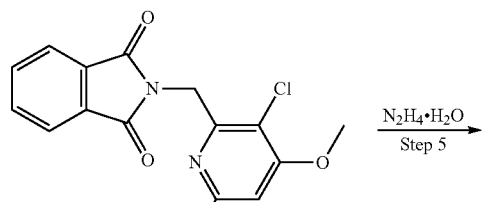
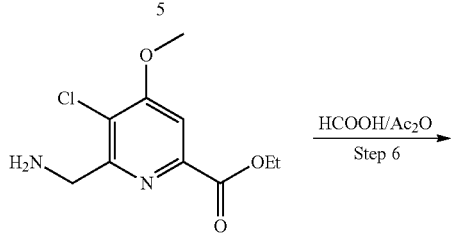
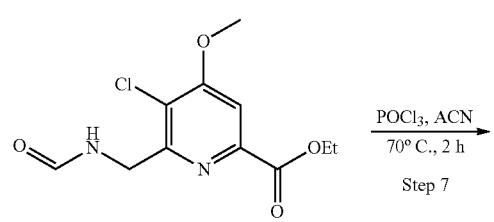
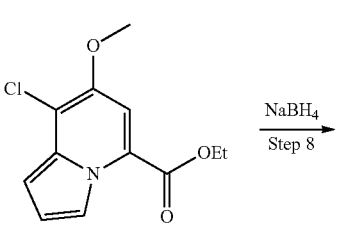
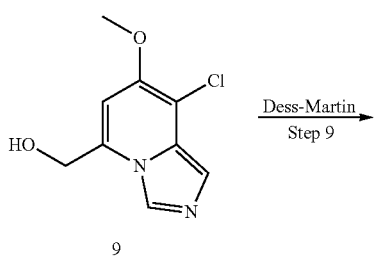
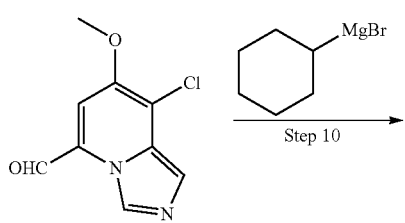

-continued

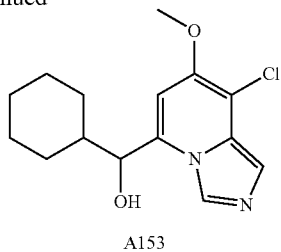

A153

Step 1: Diethyl 3-chloro-4-methoxypyridine-2,6-dicarboxylate

A mixture of diethyl 3-chloro-4-hydroxypyridine-2,6-dicarboxylate (11 g, 40 mmol, 1.0 eq), MeI (10 g, 70 mmol, 1.75 eq) and $K_2CO_3$ (11 g, 80 mmol, 2.0 eq) in DMF (100 mL) was stirred for overnight at room temperature, the reaction mixture was poured into water, extracted with EA, the organic layer was washed with water and brine, dried over $Na_2SO_4$, concentrated and purified by silica-gel to give 6.6 g (57% yield). $^1$H NMR (DMSO-$d_6$) δ 7.83 (s, 1H), 4.35-4.44 (m, 4H), 4.09 (s, 3H), 1.31-1.36 (m, 6H). ESI-MS m/z 288 ([M+H]$^+$).

Step 2: Ethyl 5-chloro-6-(hydroxymethyl)-4-methoxypicolinate

At 50° C., to a solution of diethyl 3-chloro-4-methoxypyridine-2,6-dicarboxylate (6.6 g, 23 mmol, 1.0 eq) in EtOH (100 mL) was added NaBH$_4$ (400 mg, 10.5 mmol, 0.46 eq) slowly, then heated to 80° C. for 1 h, after cooled down, the mixture was concentrated, water was added, extracted with EA, the organic layer was washed with brine, dried over $Na_2SO_4$, concentrated and purified by silica-gel to give 750 mg white solid (13% yield). $^1$H NMR (DMSO-$d_6$) δ 7.69 (s, 1H), 4.64 (s, 2H), 4.37 (q, J=7.2 Hz, 2H), 4.04 (s, 3H), 1.34 (t, J=7.2 Hz, 3H).

Step 3: Ethyl 5-chloro-6-(chloromethyl)-4-methoxypicolinate

A solution of ethyl 5-chloro-6-(hydroxymethyl)-4-methoxypicolinate (750 mg, 3.05 mmol, 1.0 eq) and SOCl$_2$ (0.3 mL) in DCM (10 mL) was stirred for 1 h at room temperature, concentrated under vacuum, EA was added, washed with NaHCO$_3$. aq and brine, dried over $Na_2SO_4$, concentrated to give crude product (700 mg), which was used to the next step without further purification.

Step 4: Ethyl 5-chloro-6-((1,3-dioxoisoindolin-2-yl)methyl)-4-methoxypicolinate A mixture of ethyl 5-chloro-6-(chloromethyl)-4-methoxypicolinate (700 mg, 2.65 mmol, 1.0 eq) and potassium 1,3-dioxoisoindolin-2-ide (740 mg, 4.0 mmol, 1.3 eq) in DMF (15 mL) was stirred for overnight. The mixture was poured into ice, the white solid was collected and dried in air to give 960 mg (84% yield of 2 steps). $^1$H NMR (DMSO-$d_6$) δ 7.88-7.96 (m, 4H), 7.64 (s, 1H), 5.01 (s, 1H), 4.03-4.09 (m, 5H), 0.87-0.91 (t, J=7.2 Hz, 3H). ESI-MS m/z 375 ([M+H]$^+$).

Step 5: Ethyl 6-(aminomethyl)-5-chloro-4-methoxypicolinate

A solution of ethyl 5-chloro-6-((1,3-dioxoisoindolin-2-yl)methyl)-4-methoxypicolinate (960 mg, 2.56 mmol, 1.0 eq) and $N_2H_4 \cdot H_2O$ (128 mg, 2.56 mmol, 1.0 eq) in EtOH (30 mL) was heated to 90° C. for 2 hours, after cooled down, the mixture was filtered, 5 mL HCOOH was added to the filtrate, concentrated to give crude product (1.3 g), which was used to the next step without further purification.

Step 6: Ethyl 5-chloro-6-(formamidomethyl)-4-methoxypicolinate

A solution of ethyl 6-(aminomethyl)-5-chloro-4-methoxypicolinate (1.3 g, 5.3 mmol, 1.0 eq) in HCOOH (30 mL) and Ac$_2$O (10 mL) was heated to 50° C. for 2 hours, concentrated, EA was added, washed with sat.NaHCO$_3$. aq, water and brine, dried over $Na_2SO_4$, concentrated to give crude product (605 mg), which was used to the next step without further purification.

Step 7: Ethyl 8-chloro-7-methoxyimidazo[1,5-a]pyridine-5-carboxylate

To a solution of ethyl 5-chloro-6-(formamidomethyl)-4-methoxypicolinate (600 mg, 2.2 mmol, 1.0 eq) in ACN was added POCl$_3$ (0.3 mL), the reaction mixture was heated to 70° C. for 2 hours, after cooled down, the mixture was concentrated, sat.NaHCO$_3$. aq was added, extracted with EA, the EA layer was washed with brine, dried over $Na_2SO_4$, concentrated and purified by silica-gel to give product as a yellow solid (350 mg, 54% yield of 3 steps). $^1$H NMR (DMSO-$d_6$) δ 9.02 (d, J=0.8 Hz, 1H), 7.64 (s, 1H), 7.48 (d, J=0.8 Hz, 1H), 4.43-4.49 (q, J=7.2 Hz, 2H), 3.99 (s, 3H), 1.38-1.42 (t, J=7.2 Hz, 3H). ESI-MS m/z 255 ([M+H]$^+$).

Step 8: (8-chloro-7-methoxyimidazo[1,5-a]pyridin-5-yl)methanol

To a solution of compound Ethyl 8-chloro-7-methoxyimidazo[1,5-a]pyridine-5-carboxylate (0.5 g, 1.98 mmol) in EtOH (30 mL) was added LiBH$_4$ (0.15 g, 6.25 mmol) and stirred at rt for 4 hours. Then water (100 mL) was added, extracted with DCM (50 mL*2), dried with $Na_2SO_4$, the filtered to remove $Na_2SO_4$, evaporated the solvent to give a crude product as a white solid (1.9 g) which was used for next step without further purification. LC-MS (M+H)$^+$ =213.1

Step 9: 8-chloro-7-methoxyimidazo[1,5-a]pyridine-5-carbaldehyde

To a solution of compound (8-chloro-7-methoxyimidazo[1,5-a]pyridin-5-yl)methanol (0.31 g, 1.46 mmol) in DCM (20 mL) was added Dess-Martin (1.24 g, 2.92 mmol) at room temperature and the mixture was stirred at rt for 12 hours. Then water (40 mL) was added, extracted with DCM (30 mL×2), dried with $Na_2SO_4$, the filtered to remove $Na_2SO_4$, evaporated the solvent, the residue was purified by silica gel (PE:EA=1:5 then to =1:1) to give product as a yellow solid (0.11 g, 35.6%). LC-MS (M+H)$^+$=211.1

Step 10: (8-chloro-7-methoxyimidazo[1,5-a]pyridin-5-yl)(cyclohexyl)methanol

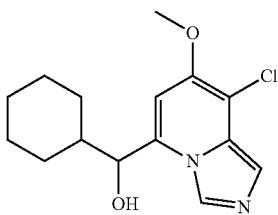 [SMILES: COc1cc(C(O)C2CCCCC2)n2cncc2c1Cl]

To a solution of compound 8-chloro-7-methoxyimidazo[1,5-a]pyridine-5-carbaldehyde (0.05 g, 0.24 mmol) in THF (10 mL) was added cyclohexylmagnesium bromide (0.3 mL, 0.36 mmol) at 0° C. and the mixture was stirred at 0° C. for 2 hours. Then water (20 mL) was added, extracted with DCM (20 mL×2), dried with Na$_2$SO$_4$, the filtered to remove Na$_2$SO$_4$, evaporated the solvent, the residue was purified pre-HPLC to give product as a white solid (6.5 mg, 10.3%). $^1$H NMR (400 MHz, DMSO) δ 9.44 (s, 1H), 7.78 (s, 1H), 7.16 (s, 1H), 3.96 (s, 3H), 1.97-1.99 (m, 1H), 1.82-1.89 (m, 1H), 1.71-1.74 (m, 1H), 1.58-1.60 (m, 3H), 1.03-1.29 (m, 5H). LC-MS (M+H)$^+$=295.1

Example A154: cyclohexyl(6,7,8-trichloroimidazo[1,5-a]pyridin-5-yl)methanol

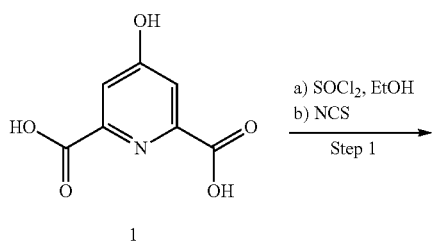

1

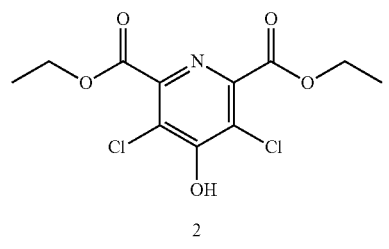

2

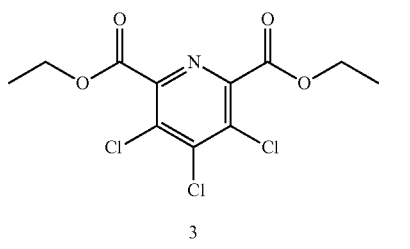

3

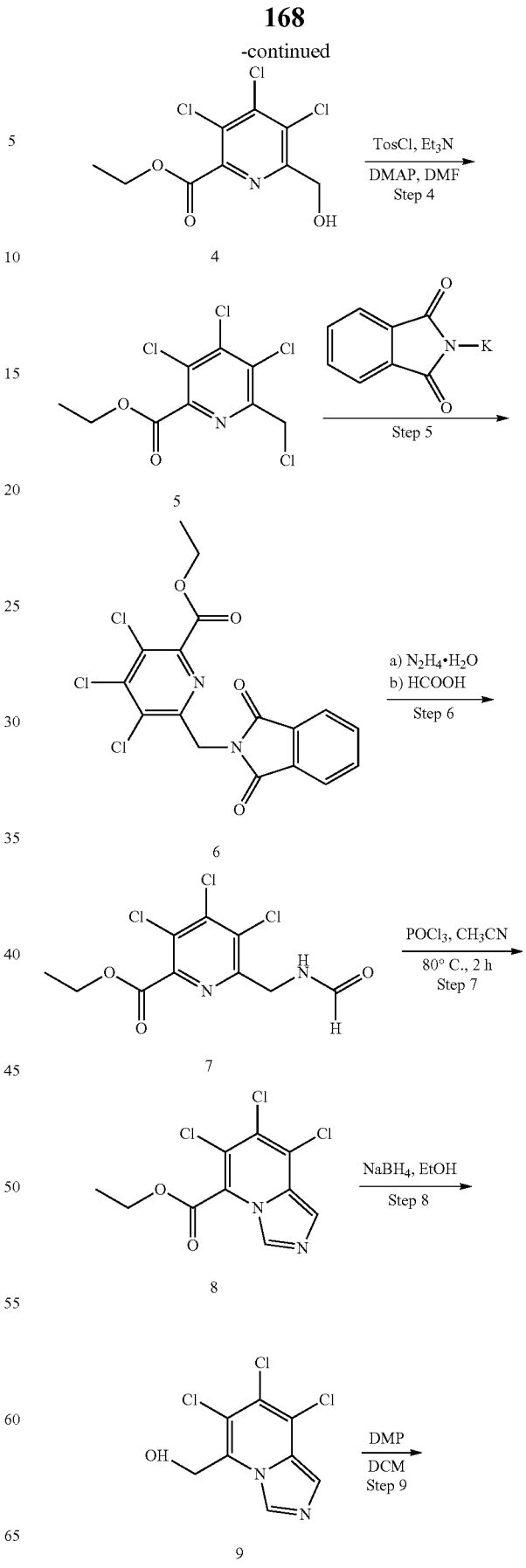

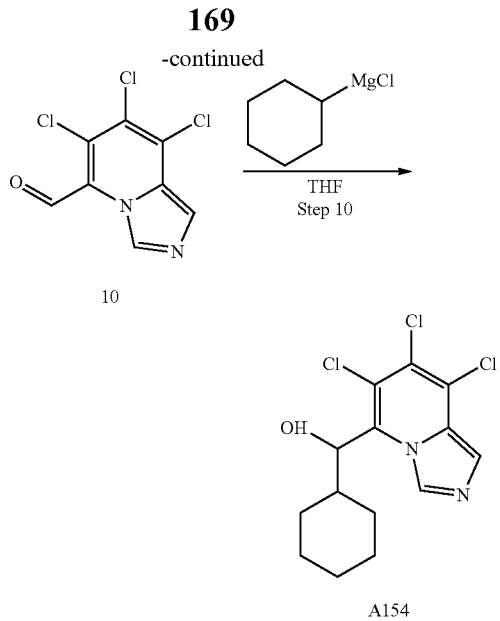

Step 1: Diethyl 4-hydroxypyridine-2,6-dicarboxylate

To a solution of 4-hydroxypyridine-2,6-dicarboxylic acid (183 g, 1.0 mol) in EtOH (1500 ml) was added thionyl chloride (200 ml, 2.0 mol) at room temperature and the mixture was heated at 90° C. for 3 h. The mixture was cooled to room temperature, concentrated to dryness. The crude was added water 1 L and stirred at room temperature and neutralized with sodium carbonate, after filtered and washed with water (200 ml*3) to give a white solid (201 g in 83.92% yield). $^1$H NMR (CD$_3$OD-d$_4$) δ 7.45 (s, 1H), 4.40 (d, J=7.2 Hz, 4H), 1.40 (t, J=7.2 Hz, 6H).

Step 2: Diethyl 3,4,5-trichloropyridine-2,6-dicarboxylate

To a solution of diethyl 4-hydroxypyridine-2,6-dicarboxylate (24 g, 100 mmol) and N-Chlorosuccinimide (N-chloropyrrolidine-2, 5-dione (33 g, 250 mmol) was dissolved in acetonitrile. And the mixture reaction was stirred at 70° C. for overnight. The mixture was added water 100 ml, extracted with EA (200 ml*3), and combined the organic layer, washed with saturated salt water 500 ml, dried over sodium sulfate, filtered and concentrated to dryness. The crude (14.1 g) was dissolved in acetonitrile 200 ml, added phosphorus oxychloride 25 ml, and the mixture was stirred at 70° C. for 2 h. After concentrated to dryness the crude was added EA 500 ml, extracted with saturated salt water (500 ml*3), dried over the organic layer with sodium carbonate, filtered and concentrated to dryness. The crude was purified by column chromatography on silica gel (200 g) PE as eluent, get a clear yellow oil (28 g, 63.62%). $^1$H NMR (DMSO-d$_6$) δ 4.42 (m, 4H), 1.34 (m, 6H).

Step 3: Ethyl 3,4,5-trichloro-6-(hydroxymethyl)picolinate

To a solution of diethyl 3,4,5-trichloropyridine-2,6-dicarboxylate (28 g, 85.89 mmol) in ethyl alcohol (200 ml) was added sodium borohydride (1.66 g, 42.95 mmol), and the mixture was stirred at 70° C. for 2 h, cooled to room temperature, quenched with water 5 ml and concentrated to dryness. The crude was added water 200 ml, extracted with EA (200 ml*3), combined the organic layer, dried over sodium sulfate, filtered and concentrated to dryness. The crude was purified by column chromatography on silica gel (80 g) PE:EA=2:1, get the pale yellow oil (3.31 g, 13.57% in yield). $^1$H NMR (DMSO-d$_6$) δ 4.67 (s, 2H), 4.42 (q, J=8.8 Hz, 4H), 1.34 (t, J=8.8 Hz, 3H).

Step 4: Ethyl 3,4,5-trichloro-6-(chloromethyl)picolinate

To a solution of ethyl 3,4,5-trichloro-6-(hydroxymethyl)picolinate (3.31 g, 11.65 mmol) in DMF (40 ml) was added paratoluensulfonyl chloride (2.66 g, 14.00 mmol), triethylamine (2.35 g, 23.30 mmol) and dimethylaminopyridine (141 mg, 1.16 mmol). And the mixture was stirred at room temperature for overnight. After adding water (80 ml) and some pale yellow solid was separated out, filtered, washed with water 5 ml and concentrated to dryness get a pale yellow solid (2.50 g, 71.05% in yield). $^1$H NMR (DMSO-d$_6$) δ 4.92 (s, 2H), 4.43 (q, J=8.0 Hz, 2H), 1.34 (t, J=8.0 Hz, 3H).

Step 5: Ethyl 3,4,5-trichloro-6-((1,3-dioxoisoindolin-2-yl)methyl)picolinate To a solution of Ethyl 3,4,5-trichloro-6-(chloromethyl)picolinate (11.19 g, 8.28 mmol) in anhydrous DMF (20 ml) was slowly added Potassium phthalimide (5.21 g, 28.16 mmol) at room temperature and the mixture was stirred for overnight. Then the reaction mixture was added water 30 ml, filtered and washed with water 10 ml get a yellow solid (3.97 g, 116.37% in yield). $^1$H NMR (DMSO-d$_6$) δ 7.96-7.89 (m, 4H), 5.07 (s, 2H), 4.16 (q, J=7.2 Hz, 2H), 0.95 (t, J=7.2 Hz, 3H).

Step 6: ethyl 3,4,5-trichloro-6-(formamidomethyl)picolinate

To a solution of ethyl 3,4,5-trichloro-6-((1,3-dioxoisoindolin-2-yl)methyl)picolinate (3.93 g, 8.28 mmol) in EtOH (20 ml) was added Hydrazine hydrate (0.5 ml, 9.94 ml) at room temperature and the mixture was heated at 80° C. for 2 h. Then cooled to room temperature, added HCOOH (5 ml) filtered and washed with to remove white precipitate and the filtrate was evaporated to give crude product as oil (2.41 g). This crude product was added HCOOH 25 ml and acetic oxide 5 ml and the mixture was stirred at 50° C. for 3 h, after cooled to room temperature, concentrated to dryness. The crude was used next step without further purification (2.30 g, 89.31%). ESI-MS m/z 312.8 ([M+H]$^+$).

Step 7: Ethyl 6,7,8-trichloroimidazo[1,5-a]pyridine-5-carboxylate

To a solution of ethyl 3,4,5-trichloro-6-(formamidomethyl)picolinate (2.30 g, 7.39 mmol) in acetonitrile (20 ml) was added POCl$_3$ (4.0 ml) at room temperature and the mixture was heated at 80° C. for 2 h. Then cooled to room temperature and evaporated the solvent before HCl (400 ml, 1N) was added to the residue, extracted with EA (200 ml*3), isolated the aqueous layer, adjusted pH=7-8 with sodium carbonate before extracted with EA (400 ml*3), combined the organic layers, evaporated the solvent to give the crude. The crude was purified by column chromatography on silica gel (50 g) PE:EA=1:1, get a pale yellow solid (1.03 g, 47.73%). ¹H NMR (DMSO-d₆) δ 8.69 (s, 1H), 7.72 (s, 1H), 7.66 (s, 1H), 4.54 (q, J=7.2 Hz, 2H), 1.39 (t, J=7.2 Hz, 3H).

Step 8: (6,7,8-trichloroimidazo[1,5-a]pyridin-5-yl)methanol

To a solution of ethyl 6,7,8-trichloroimidazo[1,5-a]pyridine-5-carboxylate (1.03 g, 3.53 mmol) in EtOH/THF=2/1, (14 ml) was added batch wise of NaBH₄ (268 mg, 7.05 mmol) at room temperature and the mixture was stirred at 40° C. for 1 h then quenched with water (1 ml). After concentrated to dryness, added water 10 ml to the residue, filtered and concentrated to dryness get a pale yellow solid (0.70 g, 78.69% in yield). ESI-MS m/z 250.8 ([M+H]⁺).

Step 9: 6,7,8-trichloroimidazo[1,5-a]pyridine-5-carbaldehyde

To a solution of (6,7,8-trichloroimidazo[1,5-a]pyridin-5-yl)methanol (0.70 g, 2.78 mmol) in DCM (20 ml) was added portion of Dess-Martin (2.35 g, 5.56 mmol) at room temperature and the mixture was stirred for overnight concentrated to dryness. The crude was purified by column chromatography on silica gel (50 g) PE:EA=1:1, get a pale yellow solid 593 mg, 87.55% in yield. ¹H NMR (DMSO-d₆) δ 10.42 (s, 1H), 9.49 (s, 1H), 7.89 (s, 1H).

Step 10: cyclohexyl(6,7,8-trichloroimidazo[1,5-a]pyridin-5-yl)methanol

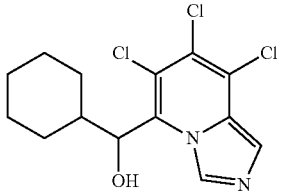

To a solution of 6,7,8-trichloroimidazo[1,5-a]pyridine-5-carbaldehyde (100 mg, 0.4 mmol) in dry THF (10 ml) was added dropwisely of cyclohexylmagnesium chloride (1.54 ml, 1.3 mmol/ml, 2.0 mmol) at 0° C. And the mixture was stirred warmed to room temperature slowly for 1 h. Water (10 ml) was added to the mixture and extracted with EA (10 ml*3), combined the organic layers and dried over sodium sulfate, filtered, and concentrated to dryness, the crude product was purified by HPLC to give product (27.50 mg) in 15.38% yield. ¹H NMR (DMSO-d₆) δ 8.84 (s, 1H), 7.63 (s, 1H), 6.29 (s, 1H), 5.13 (d, J=7.6 Hz, 1H), 1.07-2.08 (m, 11H).

Example A155: (6-chloro-7-(trifluoromethyl)imidazo[1,5-a]pyridin-5-Yl)(cyclohexyl)methanol

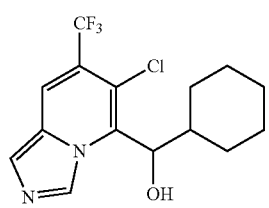 [SMILES: OC(c1c(Cl)c(C(F)(F)F)cc2cncn12)C1CCCCC1]

Example A155 was synthesized from corresponding aldehyde and Grignard reagent by following the procedures similar to those in Example A151. ¹H NMR (DMSO-d₆) δ 8.85 (s, 1H), 8.30 (s, 1H), 7.79 (s, 1H), 5.90 (d, 1H, J=4.0 Hz), 4.80 (m, 1H), 2.10-2.21 (m, 2H), 1.72-1.77 (m, 1H) and 1.03-1.26 (m, 6H). MS (ESI) m/e [M+1]⁺333.

Example A156: (7-chloro-6-fluoroimidazo[1,5-a]pyridin-5-yl)(cyclohexyl)methanol

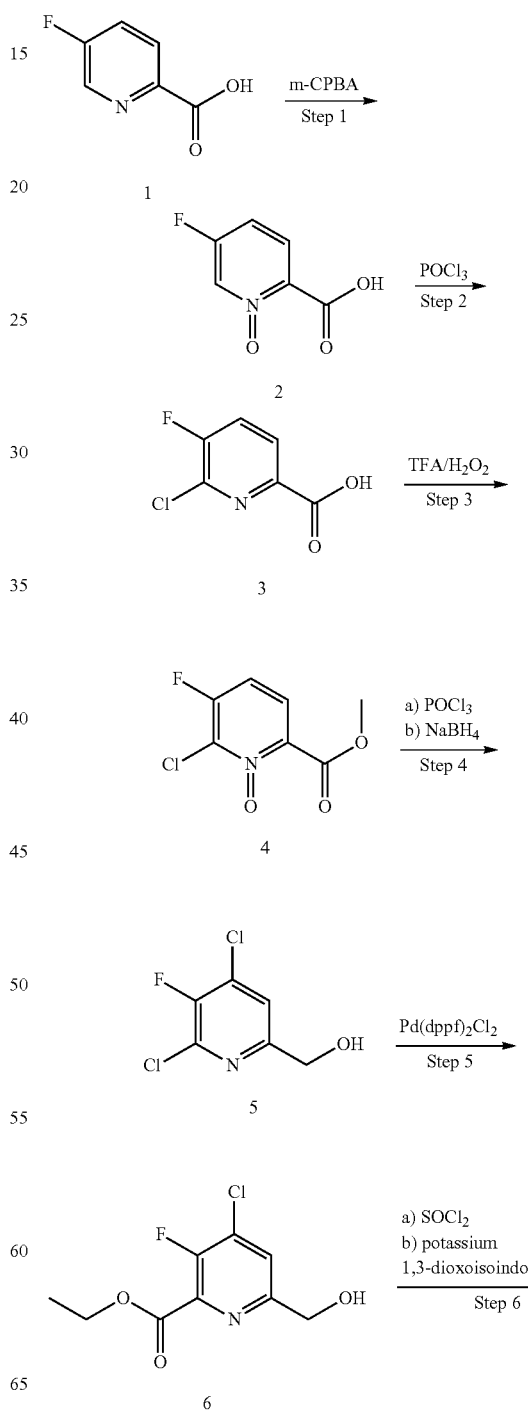

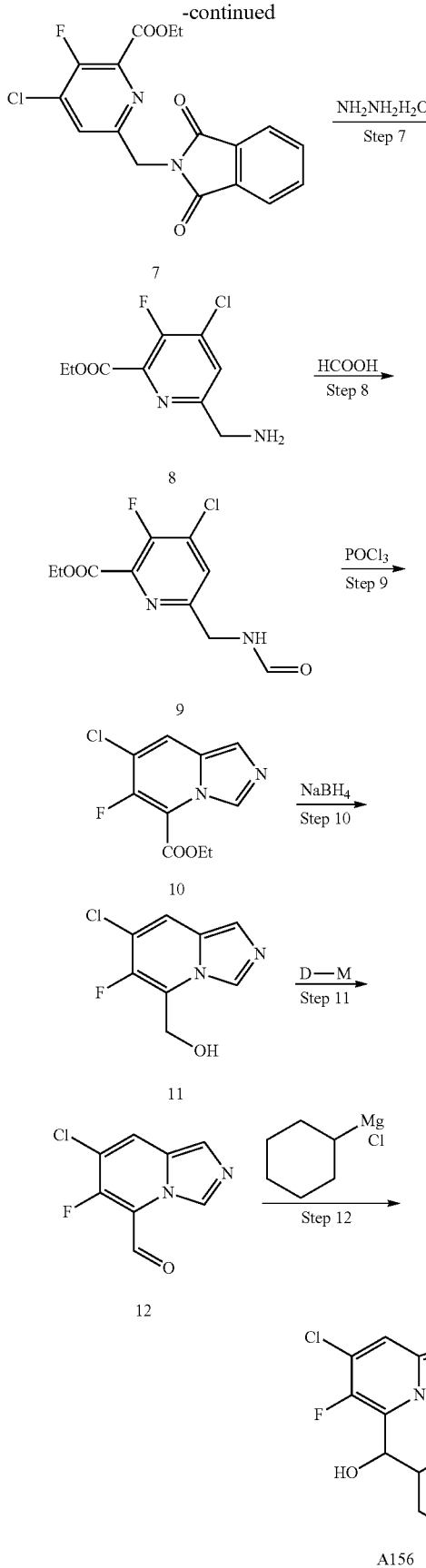

Step 1: 2-carboxy-5-fluoropyridine 1-oxide

To a solution of 5-fluoropicolinic acid (42.3 g, 0.3 mol) in DCM (500 mL) was added 3-chloroperbenzoic acid (77.85 g, 0.45 mol) at RT, The reaction mixture was stirred at RT for overnight. The solvent was removed by reduce pressure. The residue was purified by chromatograph on silica gel (petroleum ether/EA=100:1-5:1) to give a white solid as 2-carboxy-5-fluoropyridine 1-oxide (w=38.0 g, Yield=81%). MS (ESI) m/e [M+1]$^+$158.

Step 2: 6-chloro-5-fluoropicolinic acid 2-carboxy-5-fluoropyridine 1-oxide (37.5 g, 238.8 mmol) was slowly added to POCl$_3$ (300 mL) at RT, the mixture was heated to 60° C. for 6 hours, the solvent was removed by reduce pressure. The residue was quenched with ice/H$_2$O and EA (500 g/1000 mL), the organic layer was washed with brine (500 mL*2), dried over dried over Na$_2$SO$_4$ and concentrated to give crude 6-chloro-5-fluoropicolinic acid (w=30 g, 71%). MS (ESI) m/e [M+1]$^+$176.

Step 3: 2-chloro-3-fluoro-6-(methoxycarbonyl)pyridine 1-oxide

To a solution of 6-chloro-5-fluoropicolinic acid (25.0 g, 141.3 mmol) in TFA (200 mL) was added H$_2$O$_2$ (35 mL, 30% in water) at 80° C. The mixture was stirred at 80° C. for 4 hour. The solvent was removed. The residue was crude 6-carboxy-2-chloro-3-fluoropyridine 1-oxide. The crude 6-carboxy-2-chloro-3-fluoropyridine 1-oxide was suspended on MeOH (500 mL), then SOCl$_2$ (33.5 g, 282 mmol) was added at 0° C. for 5 hours. The solvent was removed by reduce pressure. The residue was quenched with brine (200 mL*2) and EA (500 mL), the organic layer was dried over dried over Na$_2$SO$_4$ and concentrated to give crude 2-chloro-3-fluoro-6-(methoxycarbonyl)pyridine 1-oxide (w=24 g, 83%). MS (ESI) m/e [M+1]$^+$206.

Step 4: (4,6-dichloro-5-fluoropyridin-2-yl)methanol 2-chloro-3-fluoro-6-(methoxycarbonyl)pyridine 1-oxide (24.0 g, 117 mmol) was slowly added to POCl$_3$ (150 mL) at RT, the mixture was heated to 60° C. for 6 hours, the solvent was removed by reduce pressure. The residue was quenched with brine and EA (500 g/500 mL), the organic layer was dried over dried over Na$_2$SO$_4$ and concentrated to give crude (4,6-dichloro-5-fluoropyridin-2-yl)methanol. The (4,6-dichloro-5-fluoropyridin-2-yl) methanol was suspended on MeOH (150 mL), then NaBH$_4$ (13.3 g, 351 mmol) was slowly added for 2 hours. The residue was quenched with H$_2$O (500 mL) and EA (500 mL), the organic layer was dried over dried over Na$_2$SO$_4$ and concentrated The residue was purified by chromatograph on silica gel (petroleum ether/EA=100:1-5:1) to give a white solid as (4,6-dichloro-5-fluoropyridin-2-yl)methanol (w=13.0 g Yield=56%). MS (ESI) m/e [M+1]$^+$197.

Step 5: ethyl 4-chloro-3-fluoro-6-(hydroxymethyl)picolinate (4,6-dichloro-5-fluoropyridin-2-yl)methanol (12.0 g, 61 mmol), Et$_3$N (18.5 g, 183 mmol) and Pd(dppf)$_2$Cl$_2$ (2.23 g, 3.05 mmol) were suspended on EtOH (150 mL), the mixture was heated to 80° C. for 6 hours at CO atmosphere for 60 Psi, the solvent was removed by reduce pressure. The residue was purified by chromatograph on silica gel (petroleum ether/EA=100:1-1:1) to give a yellow solid as ethyl 4-chloro-3-fluoro-6-(hydroxymethyl)picolinate (w=8.0 g Yield=56%). MS (ESI) m/e [M+1]$^+$234. $^1$H NMR (DMSO-d$_6$) δ 7.88 (d, 1H, J=5.2 Hz), 5.73 (s, 1H), 4.57 (s, 2H), 4.35-4.41 (m, 2H), 1.30-1.35 (m, 3H).

Step 6: ethyl 4-chloro-6-((1,3-dioxoisoindolin-2-yl)methyl)-3-fluoropicolinate

To a solution of ethyl 4-chloro-3-fluoro-6-(hydroxymethyl)picolinate (7.5 g, 32 mmol) in DCM (200 mL) was added SOCl$_2$ (10 mL) at RT, The mixture was stirred at RT for overnight. The solvent was removed to give crude ethyl 4-chloro-6-(chloromethyl)-3-fluoropicolinate. The crude ethyl 4-chloro-6-(chloromethyl)-3-fluoropicolinate and potassium 1,3-dioxoisoindolin-2-ide (8.88 g, 48 mmol) were suspended on DMF (100 mL), the mixture was stirred at RT for overnight. The mixture was quenched with H$_2$O (500 mL) and EA (500 mL), the organic layer was dried over dried over Na$_2$SO$_4$ and concentrated. The residue was purified by chromatograph on silica gel (petroleum ether/EA=100:1-1:2) to give a white solid as ethyl 4-chloro-6-((1,3-dioxoisoindolin-2-yl)methyl)-3-fluoropicolinate (w=6.3 g Yield=54%). MS (ESI) m/e [M+1]$^+$363. $^1$H NMR (DMSO-d$_6$) δ 8.1 (d, 1H, J=4.8 Hz), 7.86-7.94 (m, 4H), 4.93 (s, 2H), 4.25-4.30 (m, 2H), 1.15-1.18 (m, 3H).

Step 7: ethyl 6-(aminomethyl)-4-chloro-3-fluoropicolinate

To a solution of ethyl 4-chloro-6-((1,3-dioxoisoindolin-2-yl)methyl)-3-fluoropicolinate (2.1 g, 5.7 mmol) in EtOH (50 mL) was added Hydrazine hydrate (570 mg, 11.4 mmol) at 80° C. for 0.5 hour. The mixture was stirred at 80° C. for 4 hours, quenched with 10 mL HCOOH at RT, then the solvent was removed about 80% EtOH, the precipitate was filtered, the filter liquor was concentrated to give crude ethyl 6-(aminomethyl)-4-chloro-3-fluoropicolinate (w=1.28 g). MS (ESI) m/e [M+1]$^+$233.

Step 8: ethyl 4-chloro-3-fluoro-6-(formamidomethyl)picolinate

Ethyl 6-(aminomethyl)-4-chloro-3-fluoropicolinate (1.28 g, 5.4 mmol) was suspended on HCOOH/CH$_3$CN (12 mL/4 mL), then the mixture was heated to 60° C. for 4 hours, the solvent was removed by reduce pressure. The mixture was quenched with H$_2$O (150 mL) and EA (150 mL), the organic layer was washed with brine (150 mL), dried over dried over Na$_2$SO$_4$ and concentrated to give ethyl 4-chloro-3-fluoro-6-(formamidomethyl)picolinate (w=800 mg). MS (ESI) m/e [M+1]$^+$261

Step 9: ethyl 7-chloro-6-fluoroimidazo[1,5-a]pyridine-5-carboxylate

To a solution of ethyl 4-chloro-3-fluoro-6-(formamidomethyl)picolinate (800 mg, 3.07 mmol) in CH$_3$CN (50 mL) was added POCl$_3$ (939 mg, 6.14 mmol) at RT. the mixture was stirred at 80° C. for 2 hours, the solvent was removed by reduce pressure. The mixture was quenched with H$_2$O (100 mL) and EA (100 mL), the organic layer was dried over dried over Na$_2$SO$_4$ and concentrated to give the ethyl 7-chloro-6-fluoroimidazo[1,5-a]pyridine-5-carboxylate (w=650 mg).

Step 10: (7-chloro-6-fluoroimidazo[1,5-a]pyridin-5-yl)methanol

To a solution of ethyl 7-chloro-6-fluoroimidazo[1,5-a]pyridine-5-carboxylate (650 mg, 2.67 mmol) in EtOH/THF (8 mL/4 mL) was added NaBH$_4$ (203 mg, 5.34 mmol), the mixture was stirred at rt for 4 hours, The mixture was quenched with H$_2$O (100 mL) and EA (100 mL), the organic layer was washed with brine (50 mL), dried over dried over Na$_2$SO$_4$ and concentrated to give the yellow solid as crude (7-chloro-6-fluoroimidazo[1,5-a]pyridin-5-yl)methanol (w=400 mg). MS (ESI) m/e [M+1]$^+$201.

Step 11: 7-chloro-6-fluoroimidazo[1,5-a]pyridine-5-carbaldehyde (7-chloro-6-fluoroimidazo[1,5-a]pyridin-5-yl)methanol (400 mg, 2 mmol) and Dess-Martin periodinane (1.27 g, 3 mmol) were suspended on DCM (50 mL), the mixture was stirred at rt for 4 hours, then the solvent was removed. The residue was purified by chromatograph on silica gel (petroleum ether/EA=100:1-1:2) to give a yellow solid as 7-chloro-6-fluoroimidazo[1,5-a]pyridine-5-carbaldehyde (w=240 mg). MS (ESI) m/e [M+1]$^+$199.

Step 12: (7-chloro-6-fluoroimidazo[1,5-a]pyridin-5-yl)(cyclohexyl)methanol

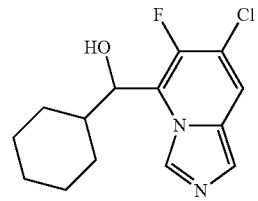 [SMILES: OC(c1c(F)c(Cl)cc2cncn12)C1CCCCC1]

To a solution of 7-chloro-6-fluoroimidazo[1,5-a]pyridine-5-carbaldehyde (60 mg, 0.3 mmol) in THF (20 mL) was added dropwise cyclohexylmagnesium bromide (3 mmol) at 0° C. for 10 minutes. The mixture was quenched with aqueous NH$_4$Cl (50 mL) and EA (50 mL), washed with brine (50 mL), dried over Na$_2$SO$_4$ and concentrated. The residue was purified by Pre-TLC to give yellow solid (W=20 mg). $^1$H NMR (DMSO-d$_6$) δ 8.61 (s, 1H), 7.94 (d, J=6.8 Hz, 1H), 7.47 (s, 1H), 6.05 (d, J=4.4 Hz, 1H), 4.87-4.89 (m, 1H), 1.98-2.20 (m, 3H), 1.57-1.59 (m, 2H), 0.97-1.19 (m, 6H). MS (ESI) m/e [M+1]$^+$283.

Examples A157 to A158 were prepared according to the procedures described for A126 under appropriate conditions that could be recognized by one skilled in the art.

Examples A157: cyclohexyl(6-(cyclopent-1-en-1-yl)imidazo[1,5-a]pyridin-5-yl)methanol

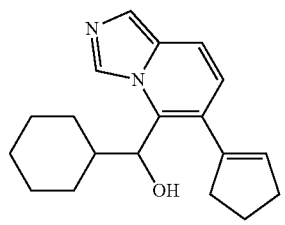 [SMILES: OC(c1c(C2=CCCC2)ccc2cncn12)C1CCCCC1]

¹H NMR (DMSO-d₆). δ 8.58 (s, 1H), 7.34-7.44 (m, 2H), 6.58-6.61 (m, 1H), 5.73-5.77 (m, 2H), 4.77-4.81 (m, 1H), 2.67-2.71 (m, 1H), 1.93-24 (m, 4H), 1.48-1.57 (m, 4H), 0.76-1.17 (m, 7H) MS (ESI) m/e [M+1]⁺297.0.

Examples A158: cyclohexyl(6-cyclopentylimidazo[1,5-a]pyridin-5-yl)methanol

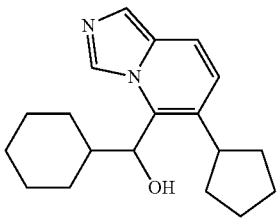 [SMILES: OC(c1c(C2CCCC2)ccc2cncn12)C1CCCCC1]

¹H NMR (DMSO-d₆). δ 8.58 (s, 1H), 8.13 (s, 1H), 7.27-7.47 (m, 2H), 6.73-6.75 (m, 1H), 5.70-5.71 (m, 2H), 4.95 (m, 1H), 1.56-1.77 (m, 10H), 0.97-1.10 (m, 8H). MS (ESI) m/e [M+1]⁺299.0.

Example A159: 3-((6-cyclopropylimidazo[1,5-a]pyridin-5-yl)(hydroxy)methyl)benzoic acid

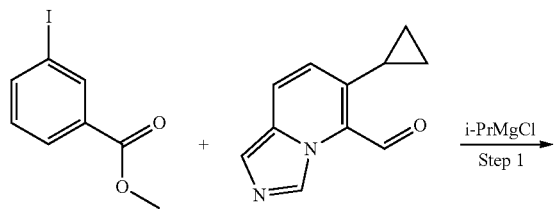

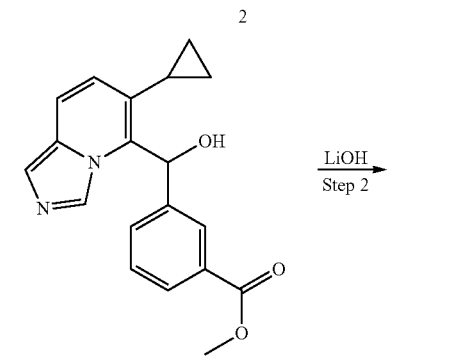

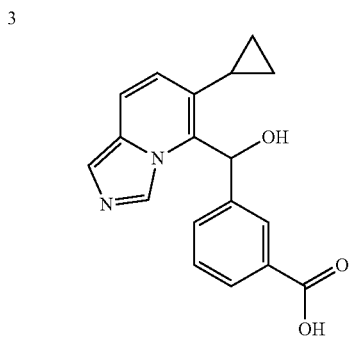

A159

Step 1: Methyl 3-((6-cyclopropylimidazo[1,5-a]pyridin-5-yl)(hydroxy)methyl)benzoate A solution of methyl 3-iodobenzoate (1.15 g, 4.4 mmol, 1.0 eq) in dry THF (20 mL) was cooled −30° C. and i-PrMgCl (1.3M in THF, 3.7 mL, 4.8 mmol, 1.1 eq) was added dropwise, keeping the inside temperature between −20° C.~−30° C., stirred for 30 min, a solution of 6-cyclopropylimidazo[1,5-a]pyridine-5-carbaldehyde in dry THF (20 mL) was added dropwise, the reaction mixture was stirred for 30 min at −20° C.~−30° C. and was allowed to warmed to room temperature, quenched by MeOH (10 mL), poured into water, extracted with EA, the organic layer was washed with water and brine, dried over Na₂SO₄, concentrated, purified by silica-gel to give 220 mg, yield 63%. TH NMR (DMSO-d₆) δ 8.08-8.10 (m, 1H), 7.60-7.64 (m, 1H), 7.45-7.51 (m, 2H), 7.28 (s, 1H), 6.86-6.87 (d, 1H, J=4.4 Hz), 6.74-6.75 (d, 1H, J=4.0 Hz), 6.61-6.63 (d, 1H, J=9.2 Hz), 3.84 (s, 3H), 2.21-2.29 (m, 1H), 0.97-1.03 (m, 2H), 0.86-0.93 (m, 1H), 0.73-0.78 (m, 1H).

Step 2: N-cyclopropyl-3-((6-cyclopropylimidazo[1,5-a]pyridin-5-yl)(hydroxy)methyl)-benzamide

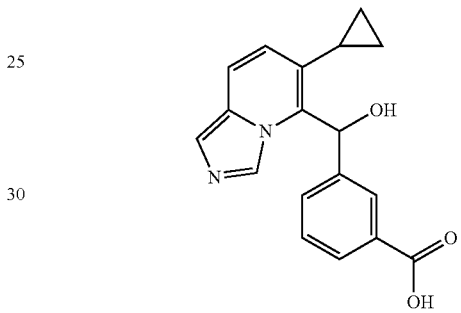

A mixture of methyl 3-((6-cyclopropylimidazo[1,5-a]pyridin-5-yl)(hydroxy)-methyl)benzoate and LiOH.H₂O in MeOH/THF/H₂O was stirred for overnight at room temperature, concentrated, the residue's pH value was adjusted to 6 with 1N HCl. aq, the white solid was collected and dried in air to give 130 mg, yield 62%. ¹H NMR (DMSO-d₆) δ 8.57 (s, 1H), 8.05 (s, 1H), 7.84-7.86 (d, 1H, J=7.6 Hz), 7.59-7.63 (m, 3H), 7.45-7.50 (t, 1H, J=7.6 Hz), 6.90 (s, 2H), 6.78-6.81 (d, 1H, J=9.6 Hz), 2.26-2.36 (m, 1H), 1.00-1.09 (m, 2H), 0.90-0.96 (m, 1H), 0.77-0.85 (m, 1H).

Example A160: N-cyclopropyl-3-((6-cyclopropylimidazo[1,5-a]pyridin-5-yl)(hydroxy)methyl)benzamide

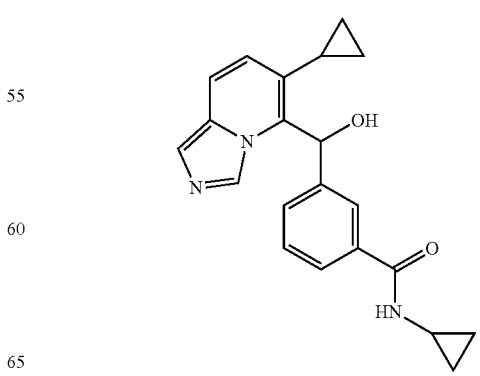

A mixture of 3-((6-cyclopropylimidazo[1,5-a]pyridin-5-yl)(hydroxy)methyl)-benzoic acid, cyclopropanamine, HATU and Et₃N in DMF was stirred for 2 hours at room temperature, the reaction mixture was poured into water, extracted with EA, the organic layer was washed with water and brine, dried over Na₂SO₄, concentrated and purified by Silica-gel to give Example A160 (40 mg) as white solid, yield 59%. ¹H NMR (DMSO-d₆) 8.51 (d, 1H, J=3.6 Hz), 8.15 (s, 1H), 7.98 (s, 1H), 7.71 (d, 1H, J=7.6 Hz), 7.35-7.50 (m, 3H), 7.28 (s, 1H), 6.83 (d, 1H, J=3.6 Hz), 6.60-6.65 (m, 2H), 2.76-2.85 (m, 1H), 2.20-2.28 (m, 1H), 0.98-1.02 (m, 2H), 0.73-0.93 (m, 3H), 0.65-0.70 (m, 2H), 0.53-0.58 (m, 2H).

Example A161: 3-((6-cyclopropylimidazo[1,5-a]pyridin-5-yl)(hydroxy)methyl)bicyclo[2.2.1]heptan-2-one

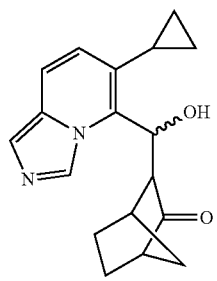 [SMILES: O=C1C2CCC(C2)C1C(O)c1c(C2CC2)ccc2cncn12]

To a solution of (1S,4R)-bicyclo[2.2.1]heptan-2-one (440 mg 4 mmol) in THF was added LDA (1.0M in THF) at −70° C. under N₂ atmosphere. The mixture was stirred at this temperature for 0.5 hour. Then 6-cyclopropylimidazo[1,5-a]pyridine-5-carbaldehyde (362 mg 2 mmol) in THF was dropwisely to the mixture. The mixture was stirred at this temperature for 0.5 hour. The reaction mixture was quenched with EA (50 mL) and saturated NH₄Cl solution (50 mL), the organic layer was washed with brine (50 mL*2), dried over Na₂SO₄ and concentrated. The residue was purified by Pre-TLC to give 3-((6-cyclopropylimidazo[1,5-a]pyridin-5-yl)(hydroxy)methyl)bicyclo[2.2.1]heptan-2-one as yellow solid. ¹HNMR (DMSO-d₆) δ_H 7.30-7.32 (m, 2H), 6.22-6.24 (m, 1H), 5.73-5.76 (m, 1H), 5.53 (s, 1H), 5.13-5.17 (m, 1H), 2.96-2.98 (m, 1H), 2.51-2.53 (m, 1H), 2.04-2.09 (m, 2H), 1.41-1.52 (m, 3H), 0.85-0.86 (m, 3H), 0.58-0.84 (m, 2H), 0.38-0.41 (m, 1H). MS (ESI) m/e [M+1]⁺ 297.0.

Example A162: (Bicyclo[2.2.1]heptan-2-yl)(6-cyclopropylimidazo[1,5-a]pyridin-5-yl)methanol

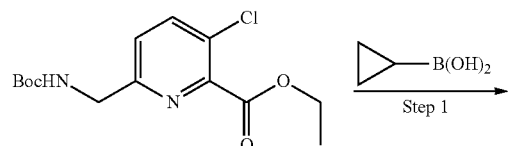

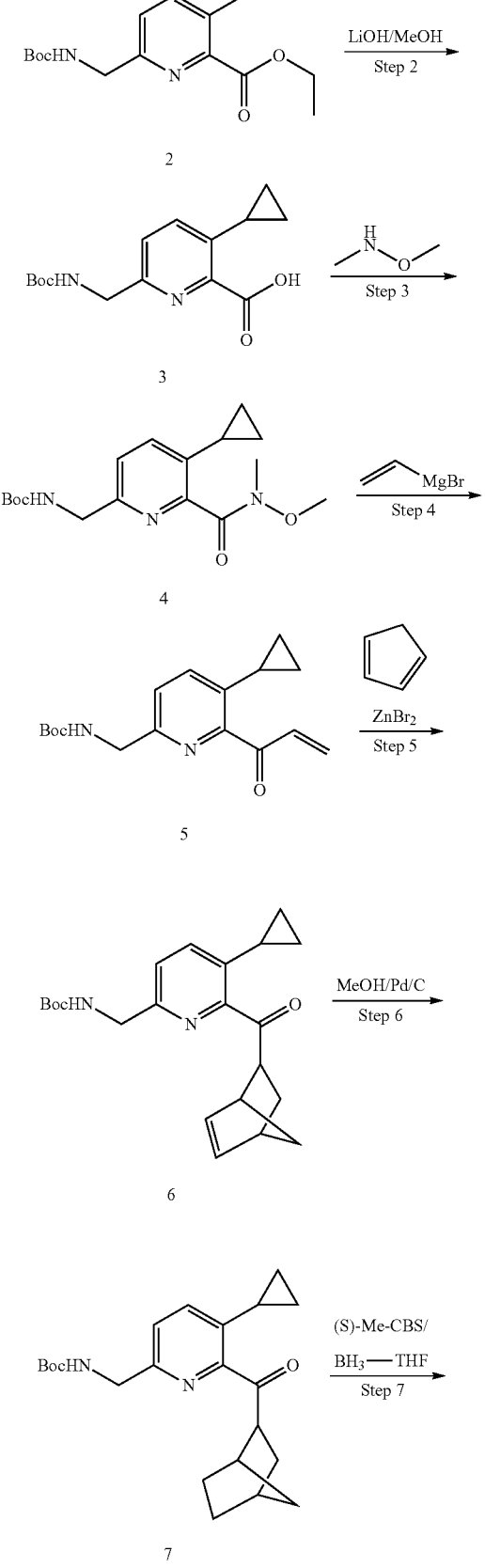

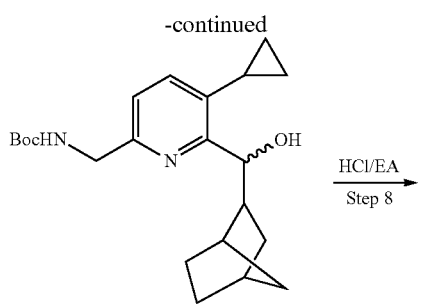

8

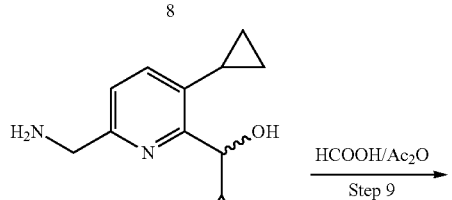

9

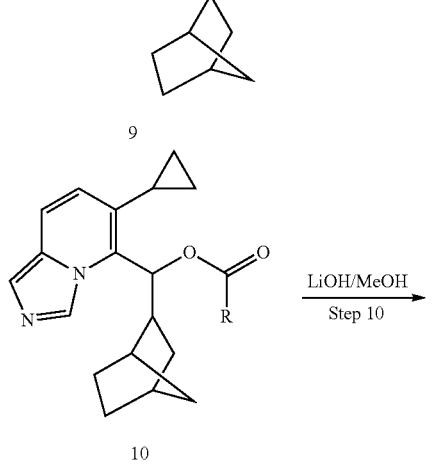

10

R = H and CH₃

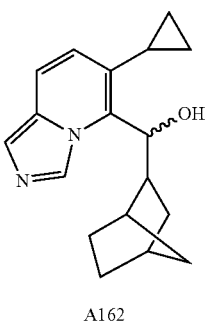

A162

Step 1: ethyl 6-(((tert-butoxycarbonyl)amino)methyl)-3-cyclopropylpicolinate Ethyl 6-(((tert-butoxycarbonyl)amino)methyl)-3-chloropicolinate (37.8 g, 120 mmol), Pd(dppf)Cl₂ (13.16 g, 18 mmol), cyclopropylboronic acid (12.38 g, 144 mmol) and Cs₂CO₃ (46.8 g, 144 mmol) were suspended on toluene (750 mL). The resulting mixture was stirred at 90° C. for 4 hours under N₂ atmosphere. After cooling to rt, the residue was added EA (200 mL) and filtered through celite and concentrated to give ethyl 6-(((tert-butoxycarbonyl)amino)methyl)-3-cyclopropylpicolinate (26.0 g) as a yellow solid. ¹H NMR (DMSO-d1). $\delta_H$ 7.45-7.47 (m, 2H), 7.28-7.31 (m, 1H), 4.34-4.38 (m, 2H), 4.17-4.19 (m, 2H), 2.09-2.14 (m, 1H), 1.23-1.40 (m, 12H), 0.95 (m, 2H), 0.67-0.70 (m, 2H).

Step 2: 6-(((tert-butoxycarbonyl)amino)methyl)-3-cyclopropylpicolinic acid

Ethyl 6-(((tert-butoxycarbonyl)amino)methyl)-3-cyclopropylpicolinate (28.0 g, 87.5 mmol) and LiOH (7.0 g, 1750 mmol) were suspended on MeOH/H₂O (200 mL/20 mL), the resulting mixture was stirred at RT for overnight. The solvent was removed by reduce pressure, and acidified with 1N HCl to PH=6-7, extracted with EA (500 mL), washed with brine (200 mL), dried over Na₂SO₄ and concentrated to give crude 6-(((tert-butoxycarbonyl)amino) methyl)-3-cyclopropylpicolinic acid (25.0 g) as yellow oil. MS (ESI) m/e [M+1]⁺293.0.

Step 3: Tert-butyl 1 ((5-cyclopropyl-6-(methoxy(methyl)carbamoyl)pyridin-2-yl)methyl)carbamate 6-(((tert-butoxycarbonyl)amino) methyl)-3-cyclopropylpicolinic acid (25.0 g, 87 mmol), HATU (33.0 g, 87 mmol), Et₃N (26.0 g, 262 mmol) and N,O-dimethylhydroxylamine hydrochloride (9.8 g, 100 mmol) were suspended in DCM (350 mL). The resulting mixture was stirred at RT for 4 hours under N₂ atmosphere. The mixture was added DCM (200 mL), washed with brine (200 mL*2), dried over Na₂SO₄ and concentrated. The residue was purified by chromatography to give tert-butyl ((5-cyclopropyl-6-(methoxy-(methyl) carbamoyl)pyridin-2-yl)methyl)carbamate (27 g) as yellow oil. ¹H NMR (DMSO-d₆). $\delta_H$ 7.35-7.43 (m, 2H), 7.18-7.21 (m, 1H), 4.21-4.22 (m, 2H), 3.53 (s, 3H), 3.29 (s, 1H), 1.79 (m, 1H), 1.19 (s, 9H), 0.93 (m, 2H), and 0.67-0.70 (m, 2H).

Step 4: Tert-butyl ((6-acryloyl-5-cyclopropylpyridin-2-yl)methyl)carbamate

To a solution of tert-butyl ((5-cyclopropyl-6-(methoxy(methyl)carbamoyl) pyridin-2-yl)methyl)carbamate (26.0 g, 77 mmol) in dry THF (500 mL) was added by dropwisely vinylmagnesium bromide (194 mL, 1.0M in THF) at 0° C. under N₂ atmosphere. The resulting mixture was stirred at 0° C. for 1 hour under N₂ atmosphere. The reaction mixture was quenched with 0.5N HCl (50 mL) and extracted with EA (200 mL*2), washed with brine (200 mL*2), dried over Na₂SO₄ and concentrated. The residue was purified by chromatography to give tert-butyl ((6-acryloyl-5-cyclopropylpyridin-2-yl)methyl)carbamate (15.2 g) as yellow solid. ¹H NMR (DMSO-d₆) $\delta_H$ 7.44-7.49 (m, 2H), 7.27-7.34 (m, 2H), 6.23-6.27 (m, 1H), 6.03-6.06 (m, 1H), 4.21-4.22 (m, 1H), 2.39-2.43 (m, 1H), 1.40 (s, 9H), 0.94-0.98 (m, 2H), and 0.68-0.71 (m, 2H).

Step 5: Tert-butyl ((6-(bicyclo[2.2.1]hept-5-ene-2-carbonyl)-5-cyclopropylpyridin-2-yl)methyl)carbamate To a solution of ZnBr₂ (2.0 g) in DCM was added cyclopenta-1,3-diene (3 mL) at −78° C. under N₂ atmosphere, The resulting mixture was stirred at −78° C. for 0.5 hours under N₂ atmosphere, then tert-butyl ((6-acryloyl-5-cyclopropylpyridin-2-yl)methyl)carbamate (2.1 g, 7 mmol) in DCM was added by dropwisely at −78° C. under N₂ atmosphere, the mixture was stirred at −78° C. for another 0.5 hour under N₂ atmosphere. Then the reaction mixture was quenched with saturated NaHCO₃ solution (150 mL)

and DCM (200 mL), washed with brine (200 mL), dried over Na₂SO₄ and concentrated. The residue was purified by chromatography to give tert-butyl ((6-(bicyclo[2.2.1]hept-5-ene-2-carbonyl)-5-cyclopropylpyridin-2-yl)methyl)carbamate (2.2 g) as oil. ¹HNMR (DMSO-d₆) δ_H 7.26-7.46 (m, 3H), 6.15-6.18 (m, 1H), 5.75-5.78 (m, 1H), 4.13-4.24 (m, 3H), 3.10 (s, 1H), 2.91 (s, 1H), 2.18-2.21 (m, 1H), 1.81-1.85 (m, 1H), 1.15-1.30 (m, 12H), 0.91-0.96 (m, 2H), and 0.61-0.66 (m. 2H). MS (ESI) m/e [M+1]⁺369.0.

Step 6: Tert-butyl ((6-(bicyclo[2.2.1]heptane-2-carbonyl)-5-cyclopropylpyridin-2-yl)methyl)carbamate A reaction mixture of tert-butyl ((6-(bicyclo[2,2,1]hept-5-ene-2-carbonyl)-5-cyclopropylpyridin-2-yl)methyl)carbamate (9.2 g, 25 mmol) and Pd/Carbon (920 mg) in MeOH (100 mL) was stirred at ambient temperature under H₂ (4 atm) for 2 hours. The resulted solution was filtered through celite and concentrated to give tert-butyl ((6-(bicyclo[2.2.1] heptane-2-carbonyl)-5-cyclopropylpyridin-2-yl)methyl)carbamate (W=9.2 g) as yellow oil.

Step 7: tert-butyl ((6-((bicyclo[2.2.1]heptan-2-yl) (hydroxy)methyl)-5-cyclopropylpyridin-2-yl)methyl) carbamate To a solution of tert-butyl ((6-(bicyclo[2.2.1]heptane-2-carbonyl)-5-cyclopropylpyridin-2-yl)methyl)carbamate (9.2 g, 25 mmol) in dry THF (100 mL) was added (S)-3,3-Diphenyl-1-methylpyrrolidino[1,2-c]-1,3,2-oxazaborole (5 mL, 1.0M in toluene) and borane-dimethyl sulfide complex (25 mL, 2.0M in THF) by portion at RT. The resulting mixture was stirred at this temperature for 5 hours and then quenched with 6N HCl (5 mL) for 2 hours, extracted with EA (200 mL*2), washed with brine (200 mL*2), dried over Na₂SO₄ and concentrated. The residue was purified by chromatography to give tert-butyl ((6-((bicyclo[2.2.1]heptan-2-yl)(hydroxy)methyl)-5-cyclopropylpyridin-2-yl) methyl) carbamate (4.2 g, 45%) as an oil. ¹H NMR (DMSO-d₆) δ_H 7.26-7.35 (m, 2H), 6.99-7.01 (m, 1H), 4.80-4.86 (m, 2H), 4.14-4.16 (m, 2H), 2.51-2.53 (m, 1H), 2.43 (m, 1H), 2.21-2.25 (m, 1H), 2.07 (m, 1H), 1.77-1.82 (m, 1H), 1.05-1.50 (m, 14H), 0.90-0.97 (m, 2H), 0.70-0.73 (m, 2H), and 0.38-0.43 (m, 2H).

Step 8: (6-(aminomethyl)-3-cyclopropylpyridin-2-yl)((1R,4S)-bicyclo[2.2.1 heptan-2-yl)methanol hydrochloride tert-butyl((6-((bicyclo[2.2.1]heptan-2-yl)(hydroxy) methyl)-5-cyclopropyl-pyridin-2-yl)methyl)carbamate (1.2 g, 3.2 mmol) was suspended on HCl (gas)/EA (20 mL, 4.0M in EA), The resulting mixture was stirred at this temperature for 5 hours. The solvent was removed by reduce pressure to give (6-(aminomethyl)-3-cyclopropylpyridin-2-yl)((1R,4S)-bicyclo[2.2.1]heptan-2-yl)methanol hydrochloride (0.96 g, 97%) as a white solid. MS (ESI) m/e [M+1]⁺273.0.

Step 9: (bicyclo[2.2.1]heptan-2-yl)(6-cyclopropylimidazo 1,5-a]pyridin-5-yl)methanol

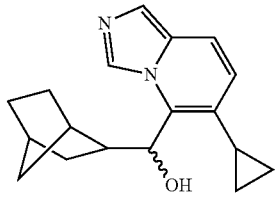 [SMILES: OC(c1c(C2CC2)ccc2cncn12)C1CC2CCC1C2]

HCOOH/Ac₂O (6 mL/20 mL) was heated to 55° C. for 2 hours. Then (6-(aminomethyl)-3-cyclopropylpyridin-2-yl) (bicyclo[2.2.1]heptan-2-yl)methanol hydrochloride (0.95 g, 3.0 mmol) was added into HCOOH/Ac₂O solution. The resulting mixture was stirred at 55° C. for overnight. The solvent was removed by reduce pressure, the residue was quenched with saturated NaHCO₃ solution (100 mL) and EA (150 mL), washed with brine (200 mL*2) dried over Na₂SO₄ and concentrated. The residue was dissolved in MeOH (15 mL), then LiOH.H₂O (0.95 g, 24 mmol) was added, the mixture was stirred at RT for 1 hour. The residue was quenched with saturated NaHCO₃ solution (50 mL) and EA (50 mL), washed with brine (20 mL*2), dried over Na₂SO₄ and concentrated. The residue was purified by MTBE/petroleum ether recrystal to give ((bicyclo[2.2.1] heptan-2-yl)(6-cyclopropylimidazo[1,5-a]pyridin-5-yl) methanol as yellow solid. MS (ESI) m/e [M+1]⁺283.0.

Examples A162a and A162b: (1S)-(bicyclo[2.2.1] heptan-2-yl)(6-cyclopropylimidazo[1,5-a]pyridin-5-yl)methanol and (1R)-(bicyclo[2.2.1]heptan-2-yl)(6-cyclopropylimidazo[1,5-a]pyridin-5-yl)methanol A162a

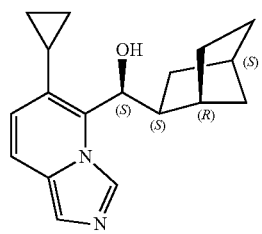

Fast isomer in chiral AC HPLC
Eluting reagent: Hexane/EtOH = 90/10(V/V)

A162b

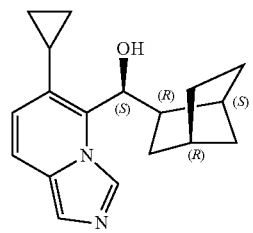

Slow isomer in chiral AC HPLC
Eluting reagent: Hexane/EtOH = 90/10(V/V)

Bicyclo[2.2.1]heptan-2-yl)(6-cyclopropylimidazo[1,5-a] pyridin-5-yl)methanol (1.9 g, 6.7 mmol) was dissolved in CH₃CN (90 ml) at 85° C., then L-(−)-Dibenzoyl-L-tartaric acid (2.78 g, 7.38 mmol) in 10 mL CH₃CN was added at 85° C. The mixture was slowly cooled to RT and stirred at RT for overnight. The white solid was obtained by filtered. The white solid was dissolved in EA (100 mL), washed with saturated NaHCO₃ solution (100 mL), the organic layer was washed with brine (50 mL*2), dried over Na₂SO₄ and concentrated. The residue was recrystallized with EA/Petroleum ether to give bicyclo[2.2.1]heptan-2-yl)(6-cyclopropylimidazo[1,5-a]pyridin-5-yl)methanol (590 mg) as white solid. $^1$H NMR (DMSO-d₆) $\delta_H$ 8.62 (s, 1H), 7.38 (d, 1H, J=9.6 Hz), 7.30 (s, 1H), 6.48 (d, 1H, J=9.6 Hz), 5.63 (d, 1H, J=3.2 Hz), 5.41-5.45 (m, 1H), 2.67-2.74 (m, 1H), 2.51-2.53 (m, 1H), 1.99-2.08 (m, 2H), 1.80-1.82 (m, 1H), 1.45-1.50 (m, 2H), 1.32 (m, 2H), 1.09-1.16 (m, 2H), 0.95-0.99 (m, 1H), 0.85-0.86 (m, 1H), 0.61-0.64 (m, 2H). MS (ESI) m/e [M+1]⁺283.0. The mother liquid was treated with (+)-Dibenzoyl-D-tartaric acid using the same procedure as Example A162a to give A162b as white solid. $^1$H NMR (DMSO-d₆). $\delta_H$ 8.61 (s, 1H), 7.38 (d, 1H, J=9.6 Hz), 7.30 (s, 1H), 6.48 (d, 1H, J=9.6 Hz), 5.63 (d, 1H, J=3.2 Hz), 5.43 (dd, 1H, J=11.2, 3.2 Hz), 2.68-2.74 (m, 1H), 2.51-2.53 (m, 1H), 1.99-2.08 (m, 2H), 1.80-1.82 (m, 1H), 1.45-1.50 (m, 2H), 1.32 (m, 2H), 1.09-1.16 (m, 2H), 0.95-0.99 (m, 1H), 0.85-0.86 (m, 1H), 0.61-0.65 (m, 2H). MS (ESI) m/e [M+1]⁺ 283.0. The absolute configuration of A162a is tentatively assigned as (S) based on assumption that the binding model of the more potent isomer A162a is the same as that of A101a with IDO1 enzyme.

Examples A163 and A164 were prepared according to the procedures described for A129 under appropriate conditions that could be recognized by one skilled in the art.

Example A163: 2-(Adamantan-1-yl)-1-(6-cyclopropylimidazo[1,5-a]pyridin-5-yl)ethan-1-ol

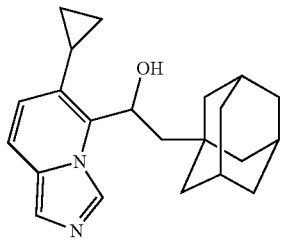 [SMILES: OC(CC12CC3CC(CC(C3)C1)C2)c1c(C2CC2)ccc2cncn12]

$^1$H NMR (DMSO-d₆) δ 8.65 (s, 1H), 7.38 (d, J=9.2 Hz, 1H), 7.32 (s, 1H), 6.51 (d, J=9.2 Hz, 1H), 5.83-5.77 (m, 1H), 5.55 (d, J=3.6 Hz, 1H), 2.08-1.88 (m, 4H), 1.70-1.33 (m, 14H), 1.00-0.90 (m, 2H), 0.88-0.75 (m, 1H), 0.65-0.57 (m, 1H). MS (ESI) m/e [M+1]⁺337.2.

Example A164: 3-((6-Cyclopropylimidazo[1,5-a]pyridin-5-yl)(hydroxy)methyl)cyclohexan-1-ol

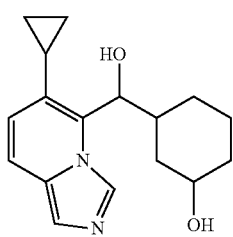

Fast isomer on normal HPLC
Two isomers

A164a

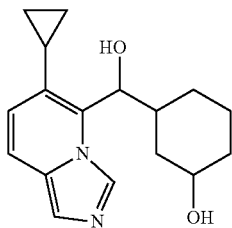

Second isomer on normal HPLC
Four isomers

A164b

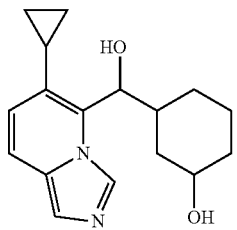

Third isomer on normal HPLC
Two isomers

A164c

The desired product was prepared by following the procedures similar to those in Example A126. After separation by Pre-HPLC, gave A164a (35 mg, included two racemic isomers) as off-white solid. $^1$H NMR (DMSO-d₆) $\delta_H$ 8.59 (s, 1H), 7.41 (d, J=9.4 Hz, 1H), 7.32 (s, 1H), 6.59 (d, J=9.4 Hz, 1H), 5.79 (d, J=3.6 Hz, 1H), 5.23 (dd, J=3.6, 9.6 Hz, 1H), 4.42 (br s, 1H), 3.20-3.08 (m, 1H), 2.24-2.10 (m, 2H), 2.04-1.92 (m, 1H), 1.90-1.70 (m, 2H), 1.30-1.12 (m, 3H), 1.06-0.82 (m, 4H), 0.77-0.62 (m, 2H). MS (ESI) m/e [M+1]⁺ 287.2. A164b (135 mg, included four isomers) as a yellow solid. $^1$H NMR (DMSO-d₆) δ 8.57 (s, 1H), 7.39 (d, J=9.2 Hz, 1H), 7.30 (s, 1H), 6.45 (d, J=9.2 Hz, 1H), 5.79 (d, J=4.0 Hz, 0.65H), 5.70 (d, J=3.6 Hz, 0.35H), 5.25-5.17 (m, 1H), 4.63-4.53 (m, 0.65H), 4.20-4.14 (m, 0.35H), 3.80-3.73 (m, 0.35), 2.48-2.38 (m, 1H), 2.20-2.10 (m, 1H), 2.04-1.90 (m, 1H), 1.80-1.70 (m, 1H), 1.65-1.42 (m, 2H), 1.20-0.80 (m, 6H), 0.79-0.69 (m, 1H), 0.68-0.58 (m, 1H). MS (ESI) m/e [M+1]⁺287.2. A164c (40 mg, included two racemic isomers) as a pale yellow solid. $^1$H NMR (DMSO-d₆) δ 8.57 (s, 1H), 7.39 (d, J=9.6 Hz, 1H), 7.30 (s, 1H), 6.45 (d, J=9.6 Hz, 1H), 5.70 (d, J=2.6 Hz, 1H), 5.20 (dd, J=2.6, 9.2 Hz, 1H), 4.35 (br s, 1H), 3.97 (br s, 1H), 2.24-2.14 (m, 1H), 2.24-1.92 (m, 1H), 1.85-1.20 (m, 6H), 1.10-0.85 (m, 4H), 0.80-0.70 (m, 1H), 0.68-0.58 (m, 1H). MS (ESI) m/e [M+1]⁺287.2.

Example A165: 5-((6-cyclopropylimidazo[1,5-a]pyridin-5-yl)(hydroxy)methyl)bicyclo[2.2.1]heptan-2-ol

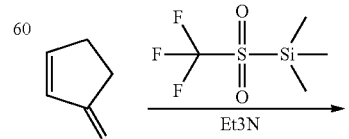

Step 1

-continued

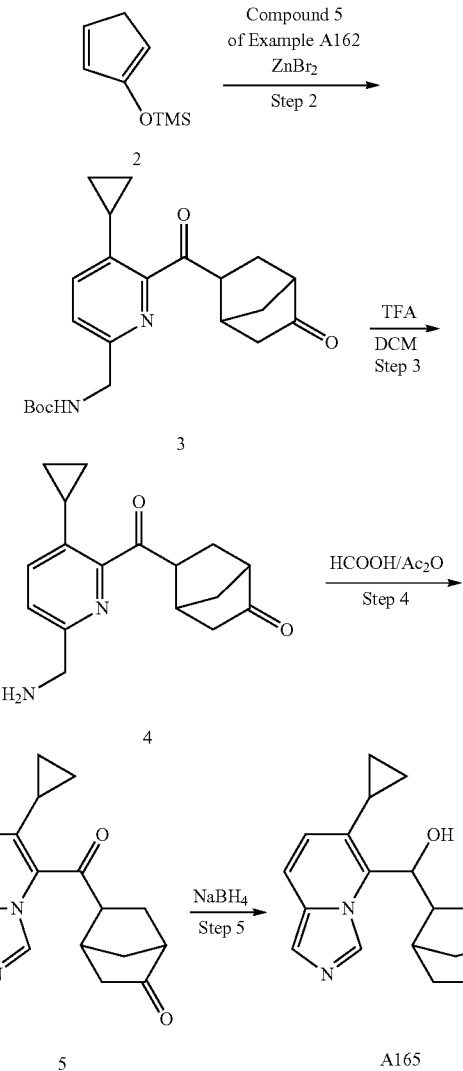

mL) and DCM (200 mL), and washed with brine (20 mL), dried over Na$_2$SO$_4$ and concentrated. The residue was purified by chromatography to give product (80 mg) as yellow oil. MS (ESI) m/e [M+1]$^+$384.7.

Step 3: 5-(6-(aminomethyl)-3-cyclopropylpicolinoyl)bicyclo[2.2.1]heptan-2-one

A mixture of tert-butyl ((5-cyclopropyl-6-(5-oxobicyclo[2.2.1]heptane-2-carbonyl) pyridin-2-yl)methyl)carbamate (80 mg, 0.2 mmol) in DCM (10 ml) was added TFA (1 ml) dropwisely, the mixture was stirred at RT for 2 hour. LCMS showed the reaction was completed. Then solvent was removed under vacuum to give the crude product (60 mg, 99%, yellow oil) which was used for the next step without further purification.

Step 4: 5-(6-cyclopropylimidazo[1,5-a]pyridine-5-carbonyl)bicyclo[2,2,1]heptan-2-one HCOOH/Ac$_2$O (6 mL/20 mL) was heated to 55° C. for 2 hours, and then 5-(6-(aminomethyl)-3-cyclopropylpicolinoyl)bicyclo[2.2.1]heptan-2-one (60 mg, 0.2 mmol) was added to the mixture, the mixture was stirred at 55° C. for overnight. Solvent was removed by reduce pressure, the residue was quenched with saturated NaHCO$_3$ solution (100 mL) and EA (20 mL), washed with brine (20 mL*2), dried over Na$_2$SO$_4$, filtered and concentrated to give crude product. The crude was purified by silica gel chromatography (PE:EA=20:1-1:1) to give product (40 mg, 68%) as a yellow solid. MS (ESI) m/e [M+1]$^+$294.7.

Step 5: 5-((6-cyclopropylimidazo[1,5-a]pyridin-5-yl)(hydroxy)methyl)bicycle[2.2.1]heptan-2-ol

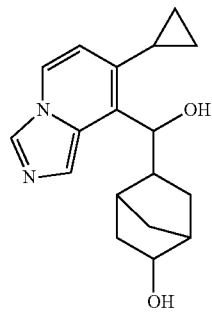 [SMILES: OC1CC2CC1CC2C(O)c1c(C2CC2)ccn2cncc12]

To a solution of 5-(6-cyclopropylimidazo[1,5-a]pyridine-5-carbonyl)bicyclo[2.2.1]heptan-2-one (20 mg, 0.068 mmol) in MeOH (10 ml) was added NaBH$_4$ (5.2 mg, 0.136 mmol) dropwisely, and stirred at RT for 2 hour. LCMS showed the reaction was completed. The solvent was removed under vacuum and the crude product was purified by Pre-HPLC to give product (15 mg, 75%) as a white solid. $^1$H NMR (DMSO-d$_6$) δ 9.70 (s, 1H), 8.07 (s, 1H), 7.71 (d, J=9.6 Hz, 1H), 6.86 (d, J=9.6 Hz, 1H), 5.23 (d, J=10.4 Hz, 1H), 4.01 (d, J=10.4 Hz, 1H), 2.51 (m, 3H), 2.31 (dd, J=13.8, 9.6 Hz, 1H), 2.10 (d, J=16.3 Hz, 2H), 2.03-1.86 (m, 1H), 1.50 (d, J=5.8 Hz, 2H), 1.28 (d, J=9.8 Hz, 1H), 1.05 (d, J=8.4 Hz, 2H), 0.95-0.82 (m, 2H), 0.72 (d, J=5.0 Hz, 1H). [M+1]$^+$ 298.7.

Step 1: (cyclopenta-1,4-dien-1-yloxy)trimethylsilane

To a solution of cyclopent-2-en-1-one (2 g, 24.4 mmol) and Et$_3$N (3.7 g, 36.6 mmol) at 0° C. was added triethylsilyl trifluoromethanesulfonate (5.42 g, 24.4 mmol). After 15 min, the reaction mixture was acidified with trifluoromethanesulfonate via syringe, and concentrated under reduced pressure. The residue was used to the next step without further purification.

Step 2: tert-butyl ((5-cyclopropyl-6-(5-oxobicyclo[2.2.1]heptane-2-carbonyl)pyridin-2-yl)methyl)carbamate To a solution of ZnBr$_2$ (1.3 g) in DCM was added (cyclopenta-1,4-dien-1-yloxy) trimethylsilane (1.3 g, 4.3 mmol) at -78° C. under N$_2$ atmosphere, The resulting mixture was stirred at -78° C. for 0.5 hours under N$_2$ atmosphere. Tert-butyl ((6-acryloyl-5-cyclopropylpyridin-2-yl)methyl)carbamate (0.99 g, 6.45 mmol) in DCM was added by dropwisely at -78° C. under N$_2$ atmosphere, the mixture was stirred at -78° C. for 0.5 hours. The reaction mixture was quenched with saturated NaHCO$_3$ solution (150

Example B: Synthesis of 8-Substituted imidazo[1,5-a]pyridines

Example B001: Cyclohexyl(imidazo[1,5-a]pyridin-8-yl)methanol

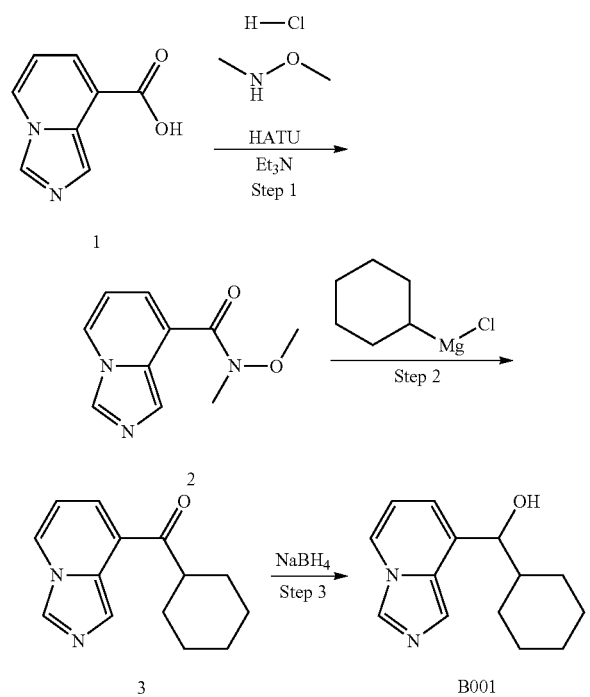

Step 1: N-methoxy-N-methylimidazo[1,5-a]pyridine-8-carboxamide

To a solution of imidazo[1,5-a]pyridine-8-carboxylic acid (50 mg, 0.31 mmol) in DMF (5 mL) was added TEA (94 mg, 0.37 mmol), N,O-dimethylhydroxylamine hydrochloride (36 mg, 0.37 mmol) and HATU (140 mg, 0.37 mmol), the reaction was stirred at ambient temperature for about 2 hours. Concentrated under reduced pressure to remove solvent, to the residue was added water (5 mL). The mixture was extracted with $CH_2Cl_2$ (3*10 mL), the combined organic phases were washed with sat. NaCl (5 mL), dried over anhydrous $Na_2SO_4$, filtered, concentrated and purified by column chromatography on silica gel to give the product about 100 mg (>95%, crude) as a pale yellow oil. MS (ESI) m/e $[M+1]^+$ 206.1.

Step 2: Cyclohexyl(imidazo[1,5-a]pyridin-8-yl)methanone

To a solution of N-methoxy-N-methylimidazo[1,5-a]pyridine-8-carboxamide (100 mg, 0.30 mmol) in THF (10 mL) was added cyclohexylmagnesium chloride (2 M, 0.45 mL, 0.9 mmol), the reaction was stirred at ambient temperature for about 2 hours. Added sat. $NH_4Cl$ (5 mL) to quench the reaction. Then extracted with EA (3*10 mL), the combined organic phases were washed with sat. NaCl (5 mL), dried over anhydrous $Na_2SO_4$, filtered and concentrated to yield the crude product (about 100 mg) as a yellow solid. MS (ESI) m/e $[M+1]^+$ 229.1.

Step 3: Cyclohexyl(imidazo[1,5-a]pyridin-8-yl)methanol

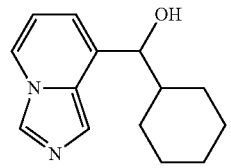 [SMILES: OC(c1cccn2cncc12)C1CCCCC1]

To a solution of cyclohexyl(imidazo[1,5-a]pyridin-8-yl)methanone (100 mg, 0.30 mmol) in EtOH (5 mL) was added $NaBH_4$ (23 mg, 0.60 mmol), the reaction was stirred at ambient temperature for about 3 hours. Added sat. $NH_4Cl$ (3 mL) to the reaction, then concentrated under reduced pressure to remove the organic solvent, extracted with $CH_2Cl_2$ (3*10 mL), the combined organic phases were washed with sat. NaCl (5 mL), dried over anhydrous $Na_2SO_4$, filtered and concentrated, the crude product was purified by Pre-TLC (DCM:MeOH=15:1) to give the product (5.0 mg, 7.2%) as a pale yellow solid. $^1H$ NMR (DMSO-$d_6$) δ 8.34 (s, 1H), 8.21 (d, J=6.8 Hz, 1H), 7.39 (s, 1H), 6.68 (d, J=6.8 Hz, 1H), 6.62 (dd, J=6.8, 6.8 Hz, 1H), 5.24 (d, J=4.4 Hz, 1H), 4.47 (dd, J=4.4, 6.0 Hz, 1H), 1.82-1.52 (m, 5H), 1.40-1.00 (m, 6H). MS (ESI) m/e $[M+1]^+$ 231.1.

Example B002: Cyclopentyl(imidazo[1,5-a]pyridin-8-yl)methanol

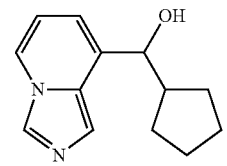 [SMILES: OC(c1cccn2cncc12)C1CCCC1]

The desired product was prepared from N-methoxy-N-methylimidazo[1,5-a]pyridine-8-carboxamide and cyclopentylmagnesium bromide using the similar procedure (step 2 to step 3) for Example B001 under appropriate conditions recognized by one of ordinary skill in the art. $^1H$ NMR (DMSO-$d_6$) δ 8.40 (s, 1H), 8.23 (d, J=6.8 Hz, 1H), 7.44 (s, 1H), 6.73 (d, J=6.4 Hz, 1H), 6.63 (dd, J=6.4, 6.8 Hz, 1H), 5.33 (d, J=3.6 Hz, 1H), 4.51 (dd, J=3.6, 4.8 Hz, 1H), 2.37-2.28 (m, 1H), 1.65-1.20 (m, 8H). MS (ESI) m/e $[M+1]^+$ 217.1.

Example B003: Imidazo[1,5-a]pyridin-8-yl(phenyl)methanone

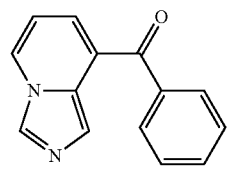 [SMILES: O=C(c1ccccc1)c1cccn2cncc12]

The desired product was prepared from N-methoxy-N-methylimidazo[1,5-a]pyridine-8-carboxamide and phenylmagnesium bromide using the similar procedure (step 2) for Example B001 under appropriate conditions recognized by one of ordinary skill in the art. ¹H NMR (DMSO-d₆) δ 8.67-8.63 (m, 1H), 8.54 (d, J=0.8 Hz, 1H), 8.78-8.74 (m, 2H), 7.72-7.66 (m, 2H), 7.61-7.55 (m, 2H), 7.23 (dd, J=0.8, 6.8 Hz, 1H), 6.82 (dd, J=6.8, 6.8 Hz, 1H). MS (ESI) m/e [M+1]⁺223.1.

Example B004: Imidazo[1,5-a]pyridin-8-yl(phenyl)methanol

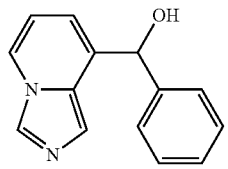 [SMILES: OC(c1ccccc1)c1cccn2cncc12]

The desired product was prepared from Example B003 using the similar procedure (step 3) for Example B001 under appropriate conditions recognized by one of ordinary skill in the art. ¹H NMR (DMSO-d₆) δ 8.43 (s, 1H), 8.23 (d, J=6.8 Hz, 1H), 7.47 (d, J=7.6 Hz, 2H), 7.32-7.27 (m, 3H), 7.24-7.18 (m, 1H), 6.93 (d, J=6.8 Hz, 1H), 6.68 (dd, J=6.8, 6.8 Hz, 1H), 6.05 (d, J=4.2 Hz, 1H), 5.85 (d, J=4.2 Hz, 1H). MS (ESI) m/e [M+1]⁺225.1.

Example B005: Cycloheptyl(imidazo[1,5-a]pyridin-8-yl)methanol

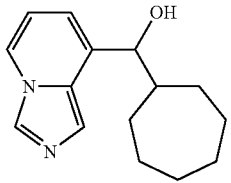 [SMILES: OC(c1cccn2cncc12)C1CCCCCC1]

The desired product was prepared from N-methoxy-N-methylimidazo[1,5-a]pyridine-8-carboxamide and cycloheptylmagnesium bromide using the similar procedure (steps 2 to 3) for Example B001 under appropriate conditions recognized by one of ordinary skill in the art. Got the product (20 mg, 15%) as an off-white solid. ¹H NMR (DMSO-d₆) δ 8.37 (s, 1H), 8.22 (d, J=7.2 Hz, 1H), 7.38 (s, 1H), 6.72 (d, J=6.4 Hz, 1H), 6.63 (dd, J=6.4, 7.2 Hz, 1H), 5.28 (d, J=4.0 Hz, 1H), 4.53 (dd, J=4.0, 5.2 Hz, 1H), 2.00-1.20 (m, 13H). MS (ESI) m/e [M+1]⁺245.2.

Example B006: 2-Cyclohexyl-1-(imidazo[1,5-a]pyridin-8-yl)ethan-1-ol

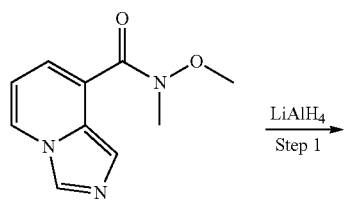

Compound 2 of Example B001

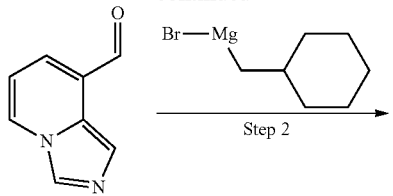

Step 1: Imidazo[1,5-a]pyridine-8-carbaldehyde

To a solution of N-methoxy-N-methylimidazo[1,5-a]pyridine-8-carboxamide (4.2 g, 20.5 mmol) in 60 mL of dry THF was added LiAlH₄ (3.9 g, 102.5 mmol) portionwise at RT. The mixture was stirred at RT for 0.5 h. 50 mL of saturated NH₄Cl aqueous solution and 150 mL of saturated brine were added. Then 300 mL of ethyl acetate was added. Organic layer was separated from aqueous layer. Washed with saturated brines (200 mL*2), dried over sodium sulfate. Purified by chromatography column on silica gel (elution with DCM/MeOH) to afford 0.9 g (30%) of imidazo[1,5-a]pyridine-8-carbaldehyde as a yellow solid. MS (ESI) m/e [M+1]+147.1.

Step 2: 2-Cyclohexyl-1-(imidazo[1,5-a]pyridin-8-yl)ethan-1-ol

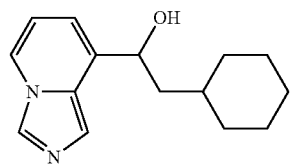

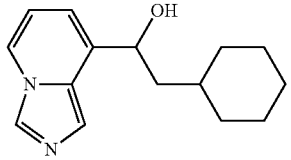 [SMILES: OC(CC1CCCCC1)c1cccn2cncc12]

To a solution of imidazo[1,5-a]pyridine-8-carbaldehyde (50 mg, 0.34 mmol) in THF (5 mL) was added (cyclohexylmethyl)magnesium chloride (2.0 mL, 0.5 M, 1.0 mmol), the reaction was stirred at ambient temperature for about 1 hour. Added sat. NH₄C (5 mL) to quench the reaction, then extracted with EA (3*10 mL), the combined organic phases were washed with sat. NaCl (5 mL), dried over anhydrous Na₂SO₄, filtered, concentrated, the crude product was purified by Pre-TLC (DCM:MeOH=15:1), got the product (45 mg, 53.6%) as a white solid. ¹H NMR (DMSO-d₆) δ 8.42 (s, 1H), 8.24 (d, J=7.0 Hz, 1H), 7.34 (s, 1H), 6.77 (d, J=6.8 Hz, 1H), 6.66 (dd, J=6.8, 7.0 Hz, 1H), 5.31 (d, J=4.4 Hz, 1H), 4.84-4.80 (m, 1H), 1.99-0.79 (m, 13H). MS (ESI) m/e [M+1]⁺245.2.

Example B007: 2-cyclopropyl-1-(imidazo[1,5-a]pyridin-8-yl)ethan-1-ol

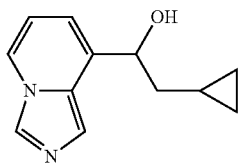 [SMILES: OC(CC1CC1)c1cccn2cncc12]

The desired product was prepared from imidazo[1,5-a]pyridine-8-carbaldehyde and (cyclopropylmethyl)magnesium bromide using the similar procedure (step 2) for Example B006 under appropriate conditions recognized by one of ordinary skill in the art. Got the product (50 mg, 60.2%) as a brown oil. $^1$H NMR (DMSO-$d_6$) δ 8.40 (s, 1H), 8.24 (d, J=6.8 Hz, 1H), 7.39 (s, 1H), 6.76 (d, J=6.6 Hz, 1H), 6.65 (dd, J=6.6, 6.8 Hz, 1H), 5.89-5.78 (m, 1H), 5.41 (d, J=4.4 Hz, 1H), 5.03-4.92 (m, 2H), 4.79-4.74 (m, 1H), 2.15-2.07 (m, 2H), 1.88-1.70 (m, 2H). MS (ESI) m/e [M+1]$^+$ 203.1.

Example B008: 3-cyclohexyl-1-(imidazo[1,5-a]pyridin-8-yl)propan-1-ol

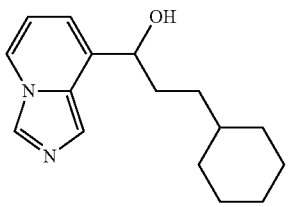 [SMILES: OC(CCC1CCCCC1)c1cccn2cncc12]

The desired product was prepared from imidazo[1,5-a]pyridine-8-carbaldehyde and (2-cyclohexylethyl)magnesium bromide using the similar procedure (step 2) for Example B006 under appropriate conditions recognized by one of ordinary skill in the art. Got the product (45 mg, 42.4%) as a white solid. $^1$H NMR (DMSO-$d_6$) δ 8.42 (s, 1H), 8.24 (d, J=6.8 Hz, 1H), 7.34 (s, 1H), 6.75 (d, J=6.6 Hz, 1H), 6.66 (dd, J=6.6, 6.8 Hz, 1H), 5.33 (d, J=4.0 Hz, 1H), 4.72-4.68 (m, 1H), 1.77-1.53 (m, 8H), 1.38-1.00 (m, 7H). MS (ESI) m/e [M+1]$^+$ 259.2.

Example B009: 1-cyclohexyl-2-(imidazo[1,5-a]pyridin-8-yl)propan-2-ol

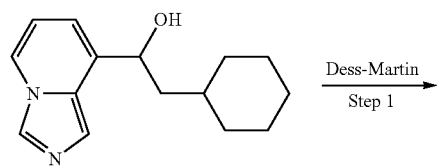

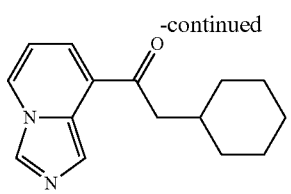

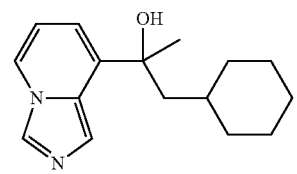 [SMILES: CC(O)(CC1CCCCC1)c1cccn2cncc12]

Step 1: 2-Cyclohexyl-1-(imidazo[1,5-a]pyridin-8-yl)ethan-1-one

To a solution of 2-cyclohexyl-1-(imidazo[1,5-a]pyridin-8-yl)ethan-1-ol (40 mg, 0.16 mmol) in CH$_2$Cl$_2$ (5 mL) was added Dess-Martin (204 mg, 0.48 mmol), the reaction was stirred at ambient temperature for about 3 hours. Added sat. NH$_4$Cl (5 mL) to the reaction, then extracted with CH$_2$Cl$_2$ (3*10 mL), the combined organic phases were washed with sat. NaCl (5 mL), dried over anhydrous Na$_2$SO$_4$, filtered and concentrated, the crude product was purified by Pre-TLC (DCM:MeOH=15:1), got the product (30 mg, 75.6%) as a yellow solid. MS (ESI) m/e [M+1]$^+$243.2.

Step 2: 1-Cyclohexyl-2-(imidazo[1,5-a]pyridin-8-yl)propan-2-ol

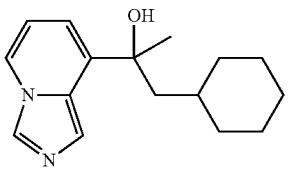

To a solution of 2-cyclohexyl-1-(imidazo[1,5-a]pyridin-8-yl)ethan-1-one (30 mg, 0.12 mmol) in THF (5 mL) was added methylmagnesium bromide (0.5 mL, 2.0 M, 1.0 mmol), the reaction was stirred at ambient temperature for about 1 hour. Added sat. NH$_4$Cl (5 mL) to the reaction, then extracted with EA (3*10 mL), the combined organic phases were washed with sat. NaCl (5 mL), dried over anhydrous Na$_2$SO$_4$, filtered, concentrated, the crude product was purified by Pre-TLC (DCM:MeOH=15:1), got the product (15 mg, 46.9%) as a brown oil. $^1$H NMR (DMSO-$d_6$) δ 8.33 (s, 1H), 8.20 (d, J=6.8 Hz, 1H), 7.43 (s, 1H), 6.81 (d, J=6.8 Hz, 1H), 6.63 (dd, J=6.8, 6.8 Hz, 1H), 5.03 (s, 1H), 1.73-1.63 (m, 2H), 1.53 (s, 3H), 1.52-0.80 (m, 11H). MS (ESI) m/e [M+1]$^+$259.2.

Example B010: 1-Cyclohexyl-3-(imidazo[1,5-a]pyridin-8-yl)propan-1-ol

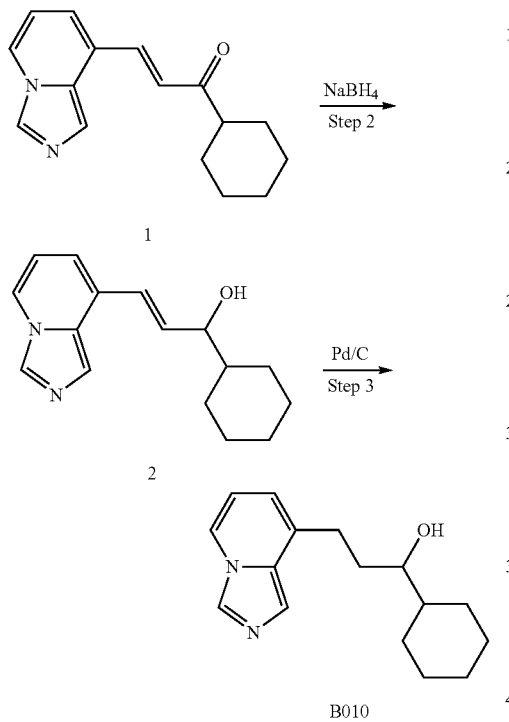

Step 1: (E)-1-Cyclohexyl-3-(imidazo[1,5-a]pyridin-8-yl)prop-2-en-1-one

To a solution of imidazo[1,5-a]pyridine-8-carbaldehyde (60 mg, 0.41 mmol) in $H_2O$ (10 mL) was added 1-cyclohexylethan-1-one (52 mg, 0.41 mmol) and $NaHCO_3$ (18 mg, 0.21 mmol), the reaction was warmed to reflux and stirred at for about 40 hours. Extracted with $CH_2Cl_2$ (3*10 mL), the combined organic phases were washed with sat. NaCl (5 mL), dried over anhydrous $Na_2SO_4$, filtered, concentrated, the crude product was purified by Pre-TLC (DCM:MeOH=15:1), got the product (10 mg, 9.6%) as a pale yellow solid. MS (ESI) m/e $[M+1]^+255.1$.

Step 2: (E)-1-Cyclohexyl-3-(imidazo[1,5-a]pyridin-8-yl)prop-2-en-1-ol

To a solution of (E)-1-cyclohexyl-3-(imidazo[1,5-a]pyridin-8-yl)prop-2-en-1-one (10 mg, 0.039 mmol) in EtOH (5 mL) was added $NaBH_4$ (4.5 mg, 0.12 mmol), the reaction was stirred at ambient temperature for about 3 hours. Added sat. $NH_4Cl$ (3 mL) to the reaction, then concentrated under reduced pressure to remove solvent, extracted with $CH_2Cl_2$ (3*10 mL), the combined organic phases were washed with sat. NaCl (5 mL), dried over anhydrous $Na_2SO_4$, filtered, concentrated, the crude product was purified by Pre-TLC (DCM:MeOH=15: 1), got the product (5.0 mg, 49.6%) as a pale yellow solid. $^1$H NMR ($CDCl_3$-d) δ 8.59 (s, 1H), 7.97 (d, J=6.8 Hz, 1H), 7.75 (s, 1H), 6.90 (d, J=6.8 Hz, 1H), 6.76 (dd, J=6.8, 6.8 Hz, 1H), 6.70 (d, J=16.0 Hz, 1H), 6.48 (dd, J=6.2, 16.0 Hz, 1H), 4.14 (dd, J=5.8, 6.2 Hz, 1H), 2.20-1.00 (m, 11H). MS (ESI) m/e $[M+1]^+257.2$.

Step 3: 1-Cyclohexyl-3-(imidazo[1,5-a]pyridin-8-yl)propan-1-ol

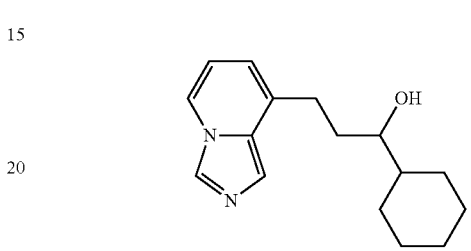

To a solution of (E)-1-cyclohexyl-3-(imidazo[1,5-a]pyridin-8-yl)prop-2-en-1-ol (3.0 mg, 0.012 mmol) in EtOH (5 mL) was added Pd/C (3 mg), the reaction was exchanged with $H_2$ for 3 times, then stirred at ambient temperature under $H_2$ atmosphere for about 3 hours. Filtered, washed with EtOH (5 mL), the filtrate was concentrated and purified by Pre-TLC (DCM:MeOH=15: 1), got the product (1.0 mg, 33.1%) as off-white solid. $^1$H NMR ($CDCl_3$-d) δ 8.42 (s, 1H), 7.92 (d, J=4.8 Hz, 1H), 7.56 (s, 1H), 6.65-6.61 (m, 2H), 5.39-5.30 (m, 2H), 2.00-1.00 (m, 15H). MS (ESI) m/e $[M+1]^+259.2$.

Example B011: Cyclohexyl (6-methylimidazo[1,5-a]pyridin-8-yl)methanol

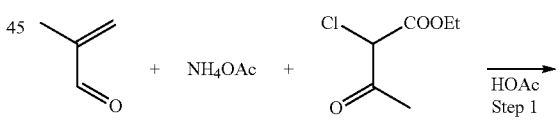

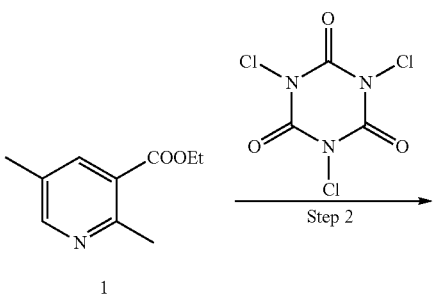

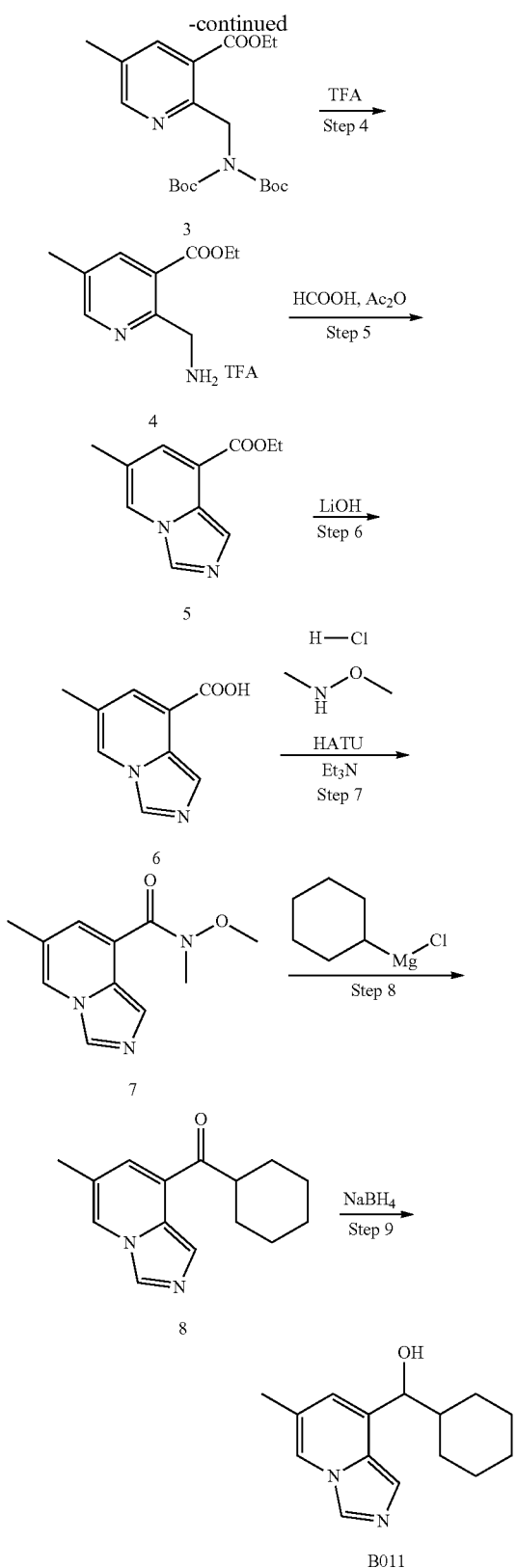

Step 1: Ethyl 2,5-dimethylnicotinate

A mixture of ethyl 2-chloro-3-oxobutanoate (10.0 g, 61.0 mmol), methacrylaldehyde (5.12 g, 73.2 mmol) and NH₄OAc (11.74 g, 152.5 mmol) in AcOH (150 mL) was heated to reflux for 1.0 hr, then the mixture was stirred for 16 hr at RT. The mixture was filtered and the filtrate was concentrated to give a residue. The residue was distributed in DCM (200 mL) and H₂O (200 mL). The organic layer was washed with aqueous NaHCO₃ (200 mL) solution, brine (200 mL), dried over Na₂SO₄, concentrated to give ethyl 2,5-dimethylnicotinate (6.2 g, 56.8%) as a yellow solid. MS (ESI, m/e) [M+1]⁺179.9.

Step 2: Ethyl 2-(chloromethyl)-5-methylnicotinate

A mixture of ethyl 2,5-dimethylnicotinate (6.0 g, 33.52 mmol), 1,3,5-trichloro-1,3,5-triazinane-2,4,6-trione (11.3 g, 50.3 mmol) in DCM (200 mL) was stirred for 16 hr at RT. The mixture was poured into aqueous NaHCO₃ solution (100 mL), the organic layer was dried over Na₂SO₄, concentrated and purified by column chromatograph on silica gel using 20% EA in PE as an eluent to afford ethyl 2-(chloromethyl)-5-methylnicotinate (4.5 g, 63.0%) as yellow oil. MS (ESI, m/e) [M+1]⁺214.0.

Step 3: Ethyl 2-((bis(tert-butoxycarbonyl)amino) methyl)-5-methylnicotinate

To a solution of di-tert-butyl iminodicarbonate (6.87 g, 31.6 mmol) in DMF (40 mL) was added t-BuOK (3.54 g, 31.6 mmol). After 2 hr, a solution of ethyl 2-(chloromethyl)-5-methylnicotinate (4.5 g, 21.1 mmol) in DMF (10 ml) was added to the mixture, then stirred at 50° C. for 16 hr. The mixture was poured into H₂O (200 mL) and extracted with EA (100 mL*3). The combined organic layers were dried over Na₂SO₄, concentrated and purified by chromatography column on silica gel using 10% of EA in PE as a eluent to give ethyl 2-((bis(tert-butoxycarbonyl)amino)methyl)-5-methylnicotinate (6.5 g, 78.3%) as a yellow solid. MS (ESI, m/e) [M+1]⁺394.9.

Step 4: Ethyl 2-(aminomethyl)-5-methylnicotinate TFA salt

A solution of ethyl 2-((bis(tert-butoxycarbonyl)amino) methyl)-5-methy nicotinate (6.5 g, 16.50 mmol) in DCM/TFA (50 mL/5 mL) was stirred for 16 h at RT, The mixture was concentrated to give ethyl 2-(aminomethyl)-5-methylnicotinate (2.6 g, 81.3%) as a yellow solid. MS (ESI, m/e) [M+1]⁺ 194.9.

Step 5: Ethyl 6-methylimidazo[1,5-a]pyridine-8-carboxylate

A mixture of Ac₂O (2.0 mL) and HCOOH (4 mL) was heated to 60° C. for 3.0 hr. Then the mixture was cooled to RT and ethyl 2-(aminomethyl)-5-methylnicotinate (2.0 g, 10.3 mmol) was added to the mixture. The mixture solution was stirred for 16 hr at RT, but no reaction by LCMS, so the mixture was heated to reflux for 16 h. The mixture was concentrated to give a residue and purified by chromatography column on silica gel using 10% of MeOH in DCM as a eluent to give ethyl 6-methylimidazo[1,5-a] pyridine-8-carboxylate (1.0 g, 47.7%) as a yellow solid. MS (ESI, m/e) [M+1]⁺ 204.9.

Step 6: 6-Methylimidazo[1,5-a]pyridine-8-carboxylic acid

A mixture of ethyl 6-methylimidazo[1,5-a]pyridine-8-carboxylate (800 mg, 3.92 mmol), LiOH (330 mg, 7.84 mmol) in THF (15 mL) and H₂O (2.0 mL) was stirred for 16 hr at RT. The mixture was adjusted PH about 1-2 and concentrated to give 6-methylimidazo[1,5-a]pyridine-8-carboxylic acid (1.2 g, crude). MS (ESI, m/e) [M+1]⁺176.9.

Step 7: N-methoxy-N,6-dimethylimidazo[1,5-a]pyridine-8-carboxamide

A mixture of 6-methylimidazo[1,5-a]pyridine-8-carboxylic acid (1.2 g, 6.8 mmol), O,N-dimethylhydroxylamine HCl salt (6.6 mg, 6.8 mmol), HATU (2.58 g, 6.80 mmol), Et₃N (1.38 g, 13.6 mmol) in DMF (10 mL) was stirred for 16 hr at RT. The mixture was poured into H₂O (50 mL) and extracted with EA (50 mL*3). The combined organic layers were dried over Na₂SO₄, concentrated and purified by chromatography column on silica gel using 5% of MeOH in DCM as a eluent to give N-methoxy-N,6-dimethylimidazo[1,5-a]pyridine-8-carboxamide (320 mg, 20%) as a yellow solid. MS (ESI, m/e) [M+1]⁺219.9.

Step 8: Cyclohexyl (6-methylimidazo[1,5-a]pyridin-8-yl)methanone

To a solution of N-methoxy-N,6-dimethylimidazo[1,5-a]pyridine-8-carboxamide (100 mg, 0.46 mmol) in THF (5 mL) was added cyclohexylmagnesium chloride (2.0 M in Et₂O, 0.35 mL) at RT. After 5 min, the reaction was quenched with aqueous NH₄Cl (5 mL) and extracted with EA (5 mL*3). The combined organic layers were dried over Na₂SO₄, concentrated to give cyclohexyl (6-methylimidazo[1,5-a]pyridin-8-yl)methanone (60 mg, 54.0%) as a yellow solid. MS (ESI, m/e) [M+1]⁺242.9.

Step 9: Cyclohexyl (6-methylimidazo[1,5-a]pyridin-8-yl)methanol

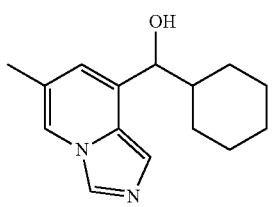 [SMILES: Cc1cc(C(O)C2CCCCC2)c2cncn2c1]

To a solution of cyclohexyl (6-methylimidazo[1,5-a]pyridin-8-yl)methanone (60 mg, 0.25 mmol) in MeOH (5 mL) was added NaBH₄ (38 mg, 1.0 mmol) at RT. After 5 min, the reaction was quenched with H₂O (5 mL), extracted with EA (5 mL*3). The combined organic layers were dried over Na₂SO₄, concentrated and purified by Prep-TLC (MeOH/DCM=1/10) to give cyclohexyl (6-methylimidazo[1,5-a]pyridin-8-yl)methanol (5.0 mg, 8.2%) as a yellow solid. 1H NMR (400 MHz, DMSO-d₆) δ 9.28 (s, 1H), 8.22 (s, 1H), 8.01 (s, 1H), 6.91 (s, 1H), 5.50 (br s, 1H), 4.51 (d, J=6.4 Hz, 1H), 2.27 (s, 3H), 1.8-1.08 (m, 13H). MS (ESI, m/e) [M+1]⁺244.9.

Example B012: 2-Cyclohexyl-1-(6-methylimidazo[1,5-a]pyridin-8-yl)ethanol

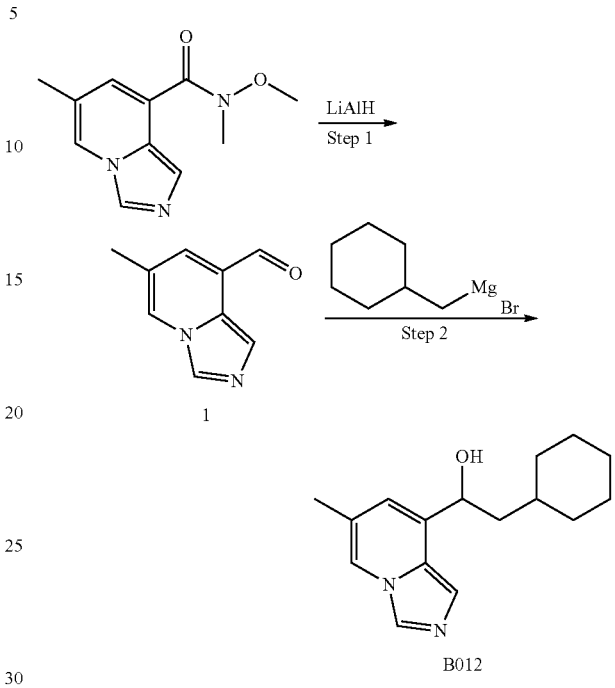

Step 1: 6-Methylimidazo[1,5-a]pyridine-8-carbaldehyde

To a solution of N-methoxy-N,6-dimethylimidazo[1,5-a]pyridine-8-carboxamide (200 mg, 0.91 mmol) in THF (5 mL) was added LiAlH₄ (64 mg, 1.82 mmol) at RT. After 5 min, the reaction was quenched with H₂O (5 mL), extracted with EA (10 mL*3). The combined organic layers were washed with brine (10 mL*3), dried over Na₂SO₄, concentrated to give 6-methylimidazo[1,5-a]pyridine-8-carbaldehyde (40 mg, 27.4%) as a yellow solid. MS (ESI, m/e) [M+1]⁺160.9.

Step 2: 2-Cyclohexyl-1-(6-methylimidazo[1,5-a]pyridin-8-yl)ethanol

To a solution of 6-methylimidazo[1,5-a]pyridine-8-carbaldehyde (40 mg, 0.25 mmol) in THF (10 ml) was added (cyclohexylmethyl)magnesium bromide (1.0 M in THF, 0.5 mL) at RT. After 5 min, the reaction was quenched with aqueous NH₄Cl (5 mL), extracted with EA (10 mL*3). The combined organic layers were dried over Na₂SO₄, concentrated and purified by Prep-TLC (MeOH/DCM=1/10) to give 2-cyclohexyl-1-(6-methylimidazo[1,5-a]pyridin-8-yl)

ethanol (25 mg, 38.5%) as a yellow solid. 1H NMR (400 MHz, DMSO-d$_6$) δ 8.26 (s, 1H), 8.01 (s, 1H), 7.26 (s, 1H), 6.63 (s, 1H), 5.30 (d, J=4.6 Hz, 1H), 4.81 (m, 1H), 2.20 (s, 3H), 1.89-0.95 (m, 13H). MS (ESI, m/e) [M+1]$^+$258.9.

Example B013: 1-(6-Chloroimidazo[1,5-a]pyridin-8-yl)-2-cyclohexylethan-1-ol

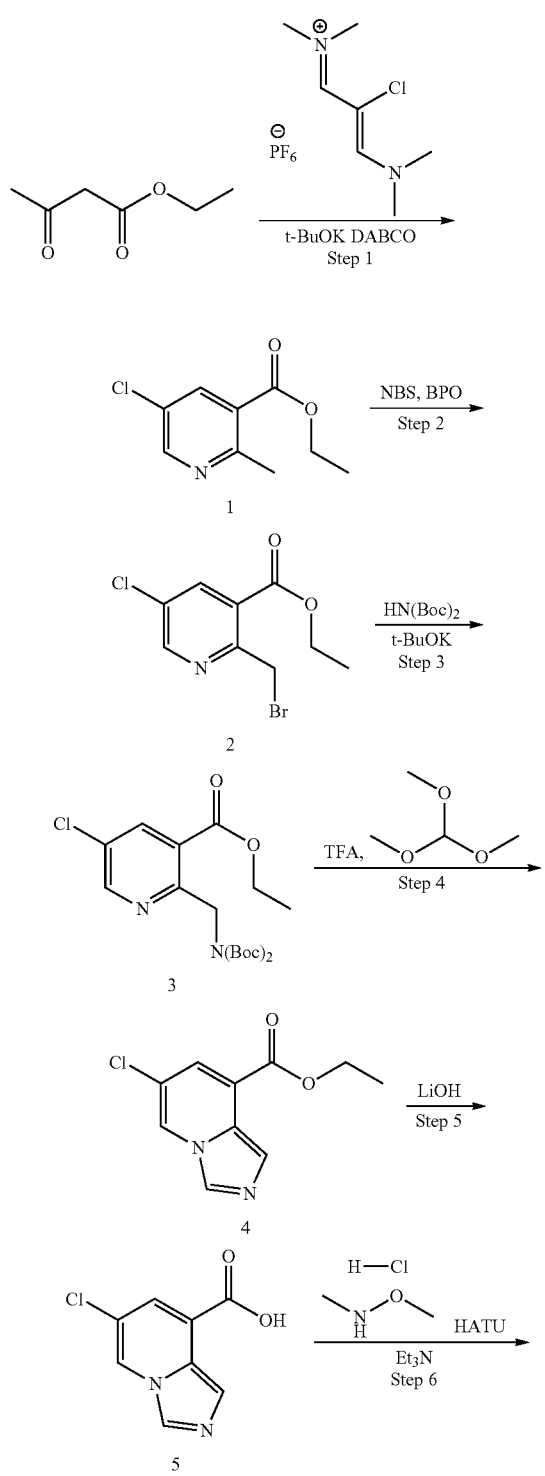

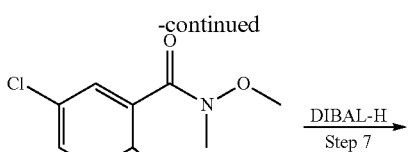

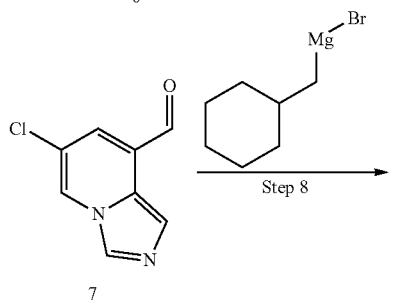

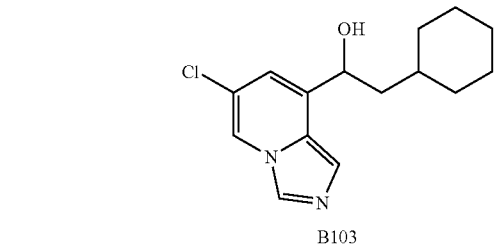

Step 1: Ethyl 5-chloro-2-methylnicotinate

Ethyl 3-oxobutanoate (6.5 g, 50 mmol) and t-BuOK (5.85 g, 52.5 mmol) in THF (100 mL) was stirred at 0~5° C. for 1 h. Then DABCO (5.85 g, 52.5 mmol) and 2-choloro-1,3-bis(dimentylamino)trimethinium hexafluorophosphate (16.2 g, 53 mmol) were added and stirred at RT for 3 h, NH$_4$OAc (10.8 g, 140 mmol) was added and stirred at RT for 16 h. Then the mixture was concentrated and the residue was purified by chromatography column on silica (EA/PE=1/5) to give the product (7.85 g, 78.9%) as a white solid. MS (ESI, m/e) [M+1]$^+$200.0, 202.0.

Step 2: Ethyl 2-(bromomethyl)-5-chloronicotinate

A mixture of ethyl 5-chloro-2-methylnicotinate (4.6 g, 23 mmol), NBS (4.52 g, 25 mmol) and BPO (556 mg, 2.3 mmol) in CCl$_4$ (100 mL) was stirred at 65° C. for 24 h. Then the mixture was cooled to RT, and pour into water (200 mL), extracted with DCM (100 mL*3). The combined organic layers were dried over Na$_2$SO$_4$, filtered and concentrated to give the product (6.4 g, 99.2%) as yellow oil. MS (ESI, m/e) [M+1]$^+$277.9, 279.9.

Step 3: Ethyl 2-((bis(tert-butoxycarbonyl)amino)methyl)-5-chloronicotinate t-BuOK (5.13 g, 45.8 mmol) and Di-tert-butyl iminodicarboxylate (7.4 g, 34.4 mmol) in THF (100 mL) was stirred at RT for 1 h. Then ethyl 2-(bromomethyl)-5-chloronicotinate (6.4 g, 22.9 mmol) was added and heated to 65° C. for 16 h. The mixture was added to brine (200 mL), extracted with EA (200 mL*2). The combined organic layers were dried over Na$_2$SO$_4$, filtered and concentrated to give a crude product, which was used in the next step without further purification (9.47 g, 100%). MS (ESI, m/e) [M+1]$^+$415.1, 417.1.

Step 4: Ethyl 6-chloroimidazo[1,5-a]pyridine-8-carboxylate

A solution of ethyl 2-((bis(tert-butoxycarbonyl)amino)methyl)-5-chloronicotinate (9.0 g, 21.7 mmol) in a mixture of TFA (5 mL) and trimethoxymethane (100 mL) was stirred at 100° C. for 5 h. Then the resultant solution was concentrated and the residue was purified by chromatography silica-gel (eluting with EA/PE=1/5 gradient to MeOH/DCM=1/10) to give a product as yellow solid (2.82 g, 57.7%). MS (ESI, m/e) [M+1]$^+$225.1, 227.1.

Step 5: 6-Chloroimidazo[1,5-a]pyridine-8-carboxylic acid

To a solution of ethyl 6-chloroimidazo[1,5-a]pyridine-8-carboxylate (2.82 g, 12.5 mmol) in THF (20 mL) and water (20 mL) was added LiOH (1.05 g, 25 mmol). The mixture was stirred at RT for 16 h. Then the THF was removed under vacuum, the residue was adjusted to pH=5, concentrated. The residue was used in the next step without further purification (2.4 g, 100%). MS (ESI, m/e) [M+1]$^+$ 197.1, 199.0.

Step 6: 6-Chloro-N-methoxy-N-methylimidazo[1,5-a]pyridine-8-carboxamide

A mixture of 6-chloroimidazo[1,5-a]pyridine-8-carboxylic acid (2.4 g, 12.5 mmol), N,O-dimethylhydroxylamine hydrochloride (1.46 g, 15 mmol), HATU (5.7 g, 25 mmol) and TEA (2.5 g, 25 mmol) in DMF (30 mL) was stirred at RT for 16 h. Then the mixture was quenched with water (150 mL), extracted with EA (70 mL*3). The combined organic layers were dried over Na$_2$SO$_4$, filtered and concentrated to give the desired compound as oil (2.4 g, 81.6%). MS (ESI, m/e) [M+1]$^+$240.1, 242.0.

Step 7: 6-Chloroimidazo[1,5-a]pyridine-8-carbaldehyde

A solution of 6-chloro-N-methoxy-N-methylimidazo[1,5-a]pyridine-8-carboxamide (367 mg, 1.6 mmol) in THF (20 mL) was cooled to −78° C. DIBAL-H (1.2 M, 1.5 mL, 1.8 mmol) was added and stirred at −78° C. for 1 h. Then the mixture was quenched with MeOH (2 mL) and concentrated. The residue was dissolved in EA (100 mL), washed with brine (50 mL*2), dried over Na$_2$SO$_4$, filtered and concentrated to give a crude product as yellow solid (115 mg, 40.5%). MS (ESI, m/e) [M+1]$^+$181.1, 183.0.

Step 8: 1-(6-Chloroimidazo[1,5-a]pyridin-8-yl)-2-cyclohexylethan-1-ol

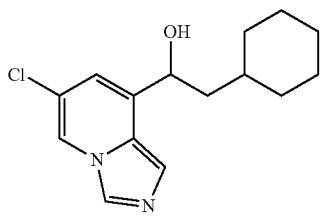 [SMILES: OC(CC1CCCCC1)c1cc(Cl)cn2cncc12]

(Cyclohexylmethyl)magnesium bromide (1 M, 1.5 mL) was added to a solution of 6-chloroimidazo[1,5-a]pyridine-8-carbaldehyde (115 mg, 0.64 mmol) in THF (10 mL) at 0° C. and stirred for 1 h. Then the reaction was quenched with saturated NH$_4$Cl, extracted with EA (10 mL*3). The combined organic layers were dried over Na$_2$SO$_4$, filtered and concentrated to give a crude product, which was purified by pre-HPLC to give the product as a yellow solid (7 mg, 3.9%). $^1$H NMR (400 MHz, CD$_3$OD) δ 9.15 (s, 1H), 8.43 (s, 1H), 7.90 (s, 1H), 7.06 (s, 1H), 4.90 (dd, J=9.6, 3.2 Hz, 1H), 1.84 (d, J=12.4 Hz, 1H), 1.71-1.42 (m, 6H), 1.27-1.06 (m, 4H), 0.99-0.84 (m, 2H). MS (ESI, m/e) [M+1]$^+$279.1, 281.1.

Example B014: (6-Chloroimidazo[1,5-a]pyridin-8-yl)(cyclohexyl)methanol

Example B014 was synthesized by following the procedures similar to those in Example B012 under appropriate conditions recognized by one of ordinary skill in the art.

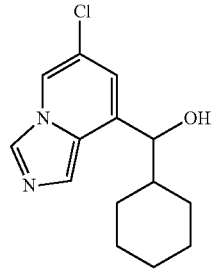 [SMILES: OC(c1cc(Cl)cn2cncc12)C1CCCCC1]

$^1$H NMR (400 MHz, CD$_3$OD) δ 9.09 (s, 1H), 8.45 (s, 1H), 7.96 (s, 1H), 7.00 (s, 1H), 4.52 (d, J=6.6 Hz, 1H), 1.85-1.77 (m, 1H), 1.74-1.51 (m, 4H), 1.40-1.31 (m, 1H), 1.17-0.99 (m, 5H). MS (ESI, m/e) [M+1]$^+$265.1, 267.1.

Example B101: 2-cyclohexyl-1-(7-methylimidazo[1,5-a]pyridin-8-yl)ethan-1-ol

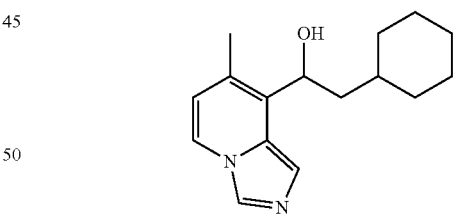

Example B101 was synthesized by following the procedures similar to those in Example B006 under appropriate conditions recognized by one of ordinary skill in the art. $^1$H NMR (400 MHz, DMSO-d$_6$) δ 8.23 (s, 1H), 8.11 (d, J=7.1 Hz, 1H), 7.41 (s, 1H), 6.42 (d, J=7.1 Hz, 1H), 5.24-5.18 (m, 1H), 5.08-5.01 (m, 1H), 2.20 (s, 3H), 1.83-1.71 (m, 2H), 1.67-1.59 (m, 4H), 1.48-1.42 (m, 1H), 1.36-1.32 (m, 1H), 1.23-1.11 (m, 3H), 0.97-0.86 (m, 2H). MS (ESI, m/e) [M+1]+259.1.

Examples B102 to B105 were synthesized by following the procedures similar to those in Example B012 under appropriate conditions recognized by one of ordinary skill in the art.

Example B102: cyclohexyl(7-methylimidazo[1,5-a]pyridin-8-yl)methanol

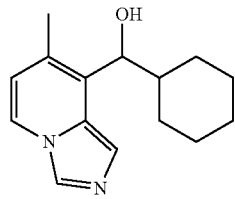

$^1$H NMR (400 MHz, DMSO-$d_6$) δ 8.21 (s, 1H), 8.11 (d, J=7.2 Hz, 1H), 7.37 (s, 1H), 6.42 (d, J=7.2 Hz, 1H), 5.18 (d, J=3.6 Hz, 1H), 4.62 (dd, J=8.4, 3.6 Hz, 1H), 2.22 (s, 3H), 2.16-2.13 (m, 1H), 1.85-1.80 (m, 1H), 1.74-1.71 (m, 1H), 1.59-1.54 (m, 2H), 1.19-0.92 (m, 6H). MS (ESI, m/e) [M+1]$^+$245.1.

Examples B102a and B102b: (S)-cyclohexyl(7-methylimidazo[1,5-a]pyridin-8-yl)methanol and (R)-cyclohexyl(7-methylimidazo[1,5-a]pyridin-8-yl)methanol

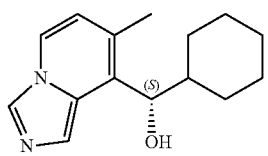

B102a

Fast isomer in chiral AS HPLC
Eluting reagent: CO$_2$/MeOH 0.1% DEA = 80/20(/V/V)

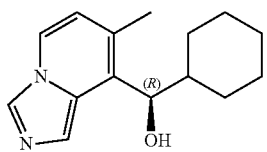

B102b

Slow isomer in chiral AS HPLC
Eluting reagent: CO$_2$/MeOH 0.1% DEA = 80/20(/V/V)

Each enantiomer of racemic B102a and B102b was separated using preparative HPLC on a Chiralpak AS with Eluting reagent (CO$_2$/MeOH 0.1% DEA=80/20 (/V/V)) as an eluent. The enantiomeric excesses were determined by using HPLC on a Chiralpak AS with CO$_2$/MeOH 0.1% DEA=80/20 (/V/V) as an eluent at a flow rate of 2.0 mL/min. The first one enantiomer eluted at the retention time of 6.73 min, $^1$H NMR (DMSO-$d_6$) δ 8.21 (s, 1H), 8.11 (d, J=6.8 Hz, 1H), 7.36 (s, 1H), 6.41 (d, J=6.8 Hz, 1H), 5.18 (d, J=3.2 Hz, 1H), 4.60 (dd, J=8.4, 3.2 Hz, 1H), 2.20 (s, 3H), 2.13-2.16 (m, 1H), 1.54-1.91 (m, 4H), 0.91-1.19 (m, 6H). MS (ESI) m/e [M+1]$^+$245; and the other enantiomer eluted at the retention time of 9.31 min, $^1$H NMR (DMSO-$d_6$) δ 8.21 (s, 1H), 8.11 (d, J=6.8 Hz, 1H), 7.36 (s, 1H), 6.41 (d, J=6.8 Hz, 1H), 5.18 (d, J=3.2 Hz, 1H), 4.60 (dd, J=8.4, 3.2 Hz, 1H), 2.20 (s, 3H), 2.13-2.16 (m, 1H), 1.54-1.91 (m, 4H), 0.91-1.19 (m, 6H). MS (ESI) m/e [M+1]$^+$245. The absolute configurations of B102a and B102b are tentatively assigned as (S) and (R) respectively based on assumption that the binding model of the more potent isomer B102a is the same as that of A101a with IDO1 enzyme.

Example B103: cyclohexyl(7-iodoimidazo[1,5-a]pyridin-8-yl)methanol

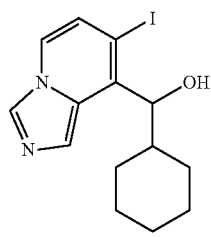

$^1$H NMR (400 MHz, CD$_3$OD-$d_4$) δ 9.36 (s, 1H), 8.09 (d, J=7.2 Hz, 2H), 7.40 (d, J=7.6 Hz, 1H), 4.82 (d, J=7.2, 1H), 1.64-1.99 (m, 5H), 1.16-1.37 (m, 5H). MS (ESI, m/e) [M+1]$^+$357.1.

Example B104: (7-chloroimidazo[1,5-a]pyridin-8-yl)(cyclohexyl)methanol

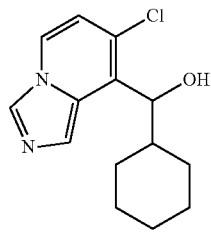 [SMILES: OC(c1c(I)ccn2cncc12)C1CCCCC1]

$^1$H NMR (400 MHz, DMSO-$d_6$) δ 8.34 (s, 1H), 8.25 (d, J=7.2 Hz, 1H), 7.54 (s, 1H), 6.62 (d, J=7.2 Hz, 1H), 5.53 (d, J=3.6 Hz, 1H), 4.62 (dd, J=8.4, 3.6 Hz, 1H), 2.06-2.09 (m, 1H), 1.57-1.87 (m, 4H), 1.03-1.23 (m, 6H). MS (ESI, m/e) [M+1]$^+$265.1.

Example B105: 1-(7-chloroimidazo[1,5-a]pyridin-8-yl)-2-cyclohexylethan-1-ol

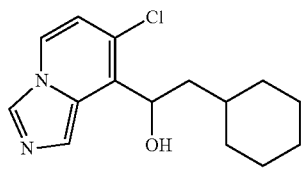 [SMILES: OC(CC1CCCCC1)c1c(Cl)ccn2cncc12]

$^1$H NMR (400 MHz, DMSO-$d_6$) δ 8.36 (s, 1H), 8.25 (d, J=7.2 Hz, 1H), 7.59 (s, 1H), 6.62 (d, J=7.2 Hz, 1H), 5.55 (d, J=4.0 Hz, 1H), 5.18 (dd, J=7.2, 4.0 Hz, 1H), 1.40-1.82 (m, 9H), 0.87-1.23 (m, 4H). MS (ESI) m/e [M+1]$^+$279.1.

Example B106: Cyclohexyl (7-isopropylimidazo[1,5-a]pyridin-8-yl)methanol

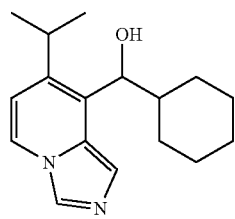 [SMILES: CC(C)c1ccn2cncc2c1C(O)C1CCCCC1]

Step 1: Cyclohexyl (7-(prop-1-en-2-yl)imidazo[1,5-a]pyridin-8-yl)methanol

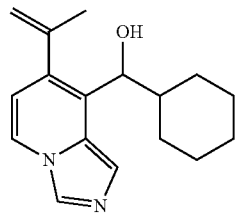 [SMILES: C=C(C)c1ccn2cncc2c1C(O)C1CCCCC1]

The desired product was prepared from 7-(prop-1-en-2-yl)imidazo[1,5-a]pyridine-8-carbaldehyde using the similar procedure for Example A136 under appropriate conditions recognized by one of ordinary skill in the art. Got the product (150 mg crude) as pale yellow oil. MS (ESI) m/e [M+1]$^+$271.0.

Step 2: Cyclohexyl (7-isopropylimidazo[1,5-a]pyridin-8-yl)methanol

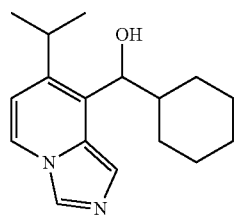 [SMILES: CC(C)c1ccn2cncc2c1C(O)C1CCCCC1]

To a solution of cyclohexyl (7-(prop-1-en-2-yl)imidazo[1,5-a]pyridin-8-yl)methanol (100 mg, 0.37 mmol) in MeOH (20 mL) was added wet Pd/C (50 mg, 50% m/m). The mixture was exchanged with H$_2$ for three times, stirred under H$_2$ atmosphere for about 16 hours. Filtered and washed with MeOH (20 mL), the filtrate was concentrated under reduced pressure to get the crude product about 150 mg, which was purified by column chromatography on silica gel (200-300 mesh, DCM/MeOH=50/1), got the product about 40 mg which was further purified by pre-TLC (DCM/MeOH=15/1) to give the product as a pale yellow solid (15 mg, 14.9%). $^1$H NMR (CD$_3$OD-d$_4$) 8.18 (s, 1H), 8.01 (d, J=7.6 Hz, 1H), 7.44 (s, 1H), 6.61 (d, J=7.6 Hz, 1H), 4.73 (d, J=9.2 Hz, 1H), 3.37-3.27 (m, 1H), 2.20-0.80 (m, 17H). MS (ESI) m/e [M+1]$^+$273.0.

Examples B106a and B106b: (S)-cyclohexyl(7-isopropylimidazo[1,5-a]pyridin-8-yl)methanol and (R)-cyclohexyl(7-isopropylimidazo[1,5-a]pyridin-8-yl)methanol

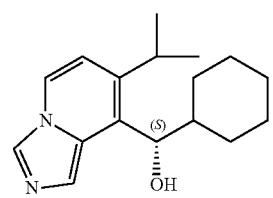

B106a

Fast isomer in chiral AS HPLC
Eluting reagent: CO$_2$/MeOH(0.1% DEA) = 80/20(/V/V)

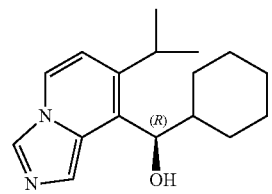

B106b

Slow isomer in chiral AS HPLC
Eluting reagent: CO$_2$/MeOH(0.1% DEA) = 80/20(/V/V)

Each enantiomer of racemic B106a and B106b was separated using preparative HPLC on a CHIRALCEL AS-H column with Eluting reagent: CO$_2$/MeOH 0.1% DEA= 80/20 (/V/V) as an eluent. The enantiomeric excesses were determined by using HPLC on a CHIRALCEL AS-H column with CO$_2$/MeOH 0.1% DEA=80/20 (/V/V) as an eluent at a flow rate of 2.0 mL/min. The first one enantiomer eluted at the retention time of 6.45 min; and the other enantiomer eluted at the retention time of 10.76 min. The absolute configurations of B106a and B106b are tentatively assigned as (S) and (R) respectively based on assumption that the binding model of the more potent isomer B106a is the same as that of A101a with IDO1 enzyme.

Example B107: Cyclohexyl (7-cyclopropylimidazo[1,5-a]pyridin-8-yl)methanol

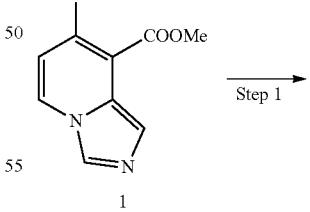

1

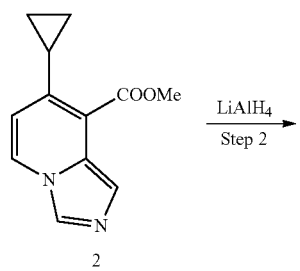

2

-continued

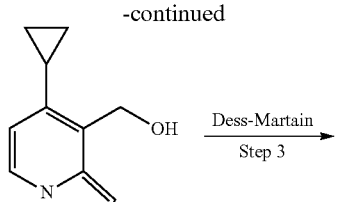

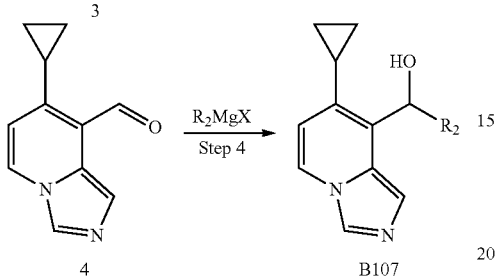

Step 1: Methyl 7-cyclopropylimidazo[1,5-a]pyridine-8-carboxylate

To a solution of methyl 7-chloroimidazo[1,5-a]pyridine-8-carboxylate (7.0 g, 33.3 mmol) in 1,4-dioxane (250 mL) was added cyclopropylboronic acid (5.72 g, 66.6 mmol), $Pd(PPh_3)_2Cl_2$ (2.34 g, 3.33 mol) and $K_3PO_4$ (17.65 g, 83.3 mmol). The mixture was exchanged with $N_2$ for three times, and then warmed to 100° C. for about 16 hours. Cooled to ambient temperature, concentrated under reduced pressure to remove solvent, the residue was portioned with $CH_2Cl_2$ (200 mL) and water (100 mL), the aqueous was extracted with $CH_2Cl_2$ (3*100 mL), the combined organic phases were washed with sat. NaCl (20 mL), dried over anhydrous $Na_2SO_4$, filtered and concentrated under reduced pressure to give the crude product about 9.0 g, which was purified by column chromatography on silica gel (200~300 mesh, DCM/MeOH=50/1), got the product (5.1 g, 71.5%) as a pale yellow solid. $^1$H NMR (DMSO-$d_6$) δ 8.38 (d, J=7.4 Hz, 1H), 8.34 (s, 1H), 7.35 (s, 1H), 6.21 (d, J=7.4 Hz, 1H), 3.93 (s, 3H), 2.69-2.60 (m, 1H), 1.07-0.98 (m, 2H), 0.86-0.79 (m, 2H). MS (ESI) m/e $[M+1]^+$217.0.

Step 2: (7-Cyclopropylimidazo[1,5-a]pyridin-8-yl)methanol

To a solution of methyl 7-cyclopropylimidazo[1,5-a]pyridine-8-carboxylate (1.1 g, 5.09 mmol) in THF (40 mL) was added $LiAlH_4$ (580 mg, 15.28 mmol) at −40° C., then slowly warmed to 0° C. stirred for about 30 min. Cooled to −40° C., added $Na_2SO_4.10\ H_2O$, warmed to ambient temperature, filtered and concentrated to give the crude product (850 mg) as a pale yellow solid, which was not purified and directly used in the next step. MS (ESI) m/e $[M+1]^+$189.0.

Step 3: 7-Cyclopropylimidazo[1,5-a]pyridine-8-carbaldehyde

To a solution of (7-cyclopropylimidazo[1,5-a]pyridin-8-yl)methanol (850 mg, 4.52 mmol) in $CH_2Cl_2$ (40 mL) was added Dess-Martin (2.30 g, 5.43 mmol) at ambient temperature, the reaction was stirred for about 30 min. Added sat. $Na_2S_2O_3$ (10 mL), the aqueous was extracted $CH_2Cl_2$ (3*100 mL), the combined organic phases were washed sat. NaCl (10 mL), dried over anhydrous $Na_2SO_4$, filtered and concentrated under reduced pressure to give the crude product (1.0 g), which was purified by column chromatography on silica gel (200~300 mesh, DCM/MeOH=50/1), got the product (500 mg, 59.4%) as a yellow solid. MS (ESI) m/e $[M+1]^+$187.0.

Step 4: Cyclohexyl(7-cyclopropylimidazo[1,5-a]pyridin-8-yl)methanol

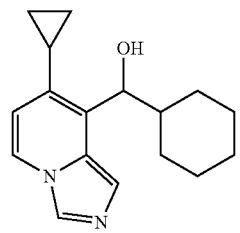 [SMILES: OC(c1c(C2CC2)ccn2cncc12)C1CCCCC1]

To a solution of 7-cyclopropylimidazo[1,5-a]pyridine-8-carbaldehyde (500 mg, 2.69 mmol) in THF (40 mL) was added cyclohexylmagnesium chloride (6.2 mL, 1.3 M, 8.07 mmol), the reaction was stirred at 0° C. for about 30 min. Added sat. $NH_4Cl$ (10 mL) to the reaction, the aqueous was extracted with EA (3*100 mL), the combined organic phases were washed with sat. NaCl (10 mL), dried over anhydrous $Na_2SO_4$, filtered and concentrated under reduced pressure to give the crude product (about 600 mg), which was purified by column chromatography on silica gel (100~200 mesh, DCM/MeOH=50/1), got the product (300 mg, 41.1%) as a pale yellow solid. $^1$H NMR (DMSO-$d_6$) δ 8.19 (s, 1H), 8.10 (d, J=7.2 Hz, 1H), 7.38 (s, 1H), 6.14 (d, J=7.2 Hz, 1H), 5.24 (d, J=3.6 Hz, 1H), 4.91 (dd, J=3.6, 8.4 Hz, 1H), 2.23-2.08 (m, 2H), 1.98-1.85 (m, 1H), 1.77-1.68 (m, 1H), 1.62-1.51 (m, 2H), 1.25-0.85 (m, 8H), 0.75-0.60 (m, 2H). MS (ESI) m/e $[M+1]^+$271.0.

Example B107a and B107b: (S)-cyclohexyl(7-cyclopropylimidazo[1,5-a]pyridin-8-yl)methanol and (R)-cyclohexyl(7-cyclopropylimidazo[1,5-a]pyridin-8-1 methanol

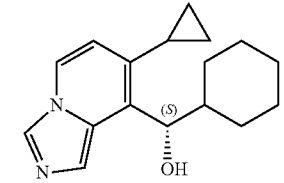

Fast isomer in chiral AY HPLC
Eluting reagent: $CO_2$/EtOH 0.1% DEA = 75/25(/V/V)

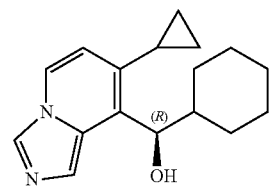

Slow isomer in chiral AY HPLC
Eluting reagent: $CO_2$/EtOH 0.1% DEA = 75/25(/V/V)

Each enantiomer of racemic B107a and B107b was separated using preparative HPLC on a Chiralpak AY with Eluting reagent: CO₂/EtOH 0.1% DEA=75/25 (/V/V) as an eluent. The enantiomeric excesses were determined by using HPLC on a Chiralpak AY with CO₂/EtOH 0.1% DEA=75/25 (/V/V) as an eluent at a flow rate of 2.0 mL/min. The first one enantiomer eluted at the retention time of 5.01 min; and the other enantiomer eluted at the retention time of 7.35 min. The absolute configurations of B107a and B107b are tentatively assigned as (S) and (R) respectively based on assumption that the binding model of the more potent isomer B107a is the same as that of A101a with IDO1 enzyme.

Examples B108 to B114 were synthesized by following the procedures similar to those in Example B107 under appropriate conditions recognized by one of ordinary skill in the art.

Example B108: 2-Cyclohexyl-1-(7-isopropylimidazo[1,5-a]pyridin-8-yl)ethan-1-ol

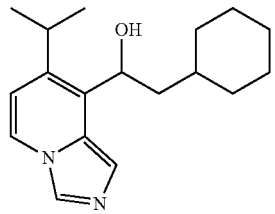 [SMILES: CC(C)c1ccn2cncc2c1C(O)CC1CCCCC1]

$^1$H NMR (CD₃OD-d₄) δ 9.25 (s, 1H), 8.26 (d, J=7.6 Hz, 1H), 7.99 (s, 1H), 7.06 (d, J=7.6 Hz, 1H), 5.30 (dd, J=4.4, 9.6 Hz, 1H), 3.30-3.20 (m, 1H), 1.90-0.70 (m, 19H). MS (ESI) m/e [M+1]⁺287.0.

Example B109: 2-Cyclohexyl-1-(7-isopropylimidazo[1,5-a]pyridin-8-yl)ethan-1-ol

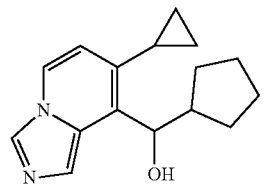 [SMILES: OC(c1c(C2CC2)ccn2cncc12)C1CCCC1]

$^1$H NMR (DMSO-d₆) δ 8.19 (s, 1H), 8.09 (d, J=7.6 Hz, 1H), 7.41 (s, 1H), 6.13 (d, J=7.6 Hz, 1H), 5.29 (d, J=3.6 Hz, 1H), 4.97 (dd, J=3.6, 9.2 Hz, 1H), 2.50-2.51 (m, 1H), 1.90-0.64 (m, 13H).

Example B110: 2-cyclohexyl-1-(7-cyclopropylimidazo[1,5-a]pyridin-8-yl)ethan-1-ol

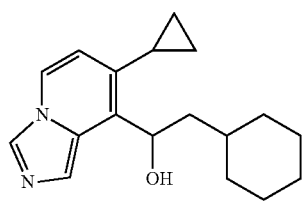 [SMILES: OC(CC1CCCCC1)c1c(C2CC2)ccn2cncc12]

$^1$H NMR (DMSO-d₆) δ 8.21 (s, 1H), 8.09 (d, J=7.2 Hz, 1H), 7.43 (s, 1H), 6.18 (d, J=7.2 Hz, 1H), 5.24-5.40 (m, 1H), 5.25 (d, J=3.6 Hz, 1H), 1.98-2.09 (m, 1H), 1.85-0.64 (m, 17H).

Examples B110a and B110b: (S)-cyclohexyl(7-cyclopropylimidazo[1,5-a]pyridin-8-yl)methanol and (R)-cyclohexyl(7-cyclopropylimidazo[1,5-a]pyridin-8-yl)methanol

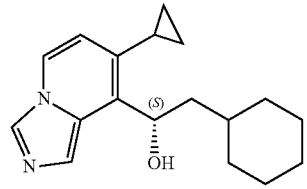

B110a

Fast isomer in chiral AS HPLC
Eluting reagent: CO₂/MeOH = 80/20(/V/V)

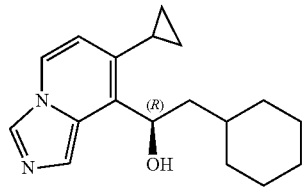

B110b

Slow isomer in chiral AS HPLC
Eluting reagent: CO₂/MeOH = 80/20(/V/V)

Each enantiomer of racemic B110a and B110b was separated using preparative HPLC on a CHIRALCEL AS-H column with Eluting reagent: CO₂/MeOH=80/20 (/V/V) as an eluent. The enantiomeric excesses were determined by using HPLC on a CHIRALCEL AS-H column with CO₂/MeOH=80/20 (/V/V) as an eluent at a flow rate of 2.0 mL/min. The first one enantiomer eluted at the retention time of 5.04 min; and the other enantiomer eluted at the retention time of 8.87 min. The absolute configurations of B110a and B110b are tentatively assigned as (S) and (R) respectively based on assumption that the binding model of the more potent isomer B110a is the same as that of A101a with IDO1 enzyme.

Example B111: Cyclohexyl(7-(trifluoromethyl)imidazo[1,5-a]pyridin-8-yl)methanol

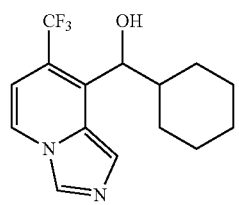 [SMILES: OC(c1c(C(F)(F)F)ccn2cncc12)C1CCCCC1]

$^1$H NMR (400 MHz, DMSO-d₆) δ 8.51 (s, 1H), 8.38 (d, J=7.4 Hz, 1H), 7.85 (s, 1H), 6.80 (d, J=7.4 Hz, 1H), 5.77-5.75 (m, 1H), 4.66 (d, J=8.6 Hz, 1H), 2.25-2.22 (m, 1H), 1.97-1.94 (m, 1H), 1.75-1.72 (m, 1H), 1.61-1.55 (m, 2H), 1.28-0.84 (m, 6H). MS (ESI, m/e) [M+1]⁺298.9.

Example B112: (7-Cyclopropylimidazo[1,5-a]pyridin-8-yl)(tetrahydro-2H-pyran-4-yl)methanol

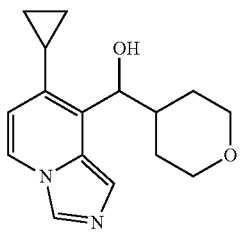 [SMILES: OC(c1c(C2CC2)ccn2cncc12)C1CCOCC1]

¹H NMR (DMSO-d₆) δ 8.21 (s, 1H), 8.12 (d, J=7.2 Hz, 1H), 7.42 (s, 1H), 6.15 (d, J=7.2 Hz, 1H), 5.38 (d, J=3.6 Hz, 1H), 4.96 (dd, J=8.7, 3.6 Hz, 1H), 3.93-3.87 (dd, J=11.2, 3.0 Hz, 1H), 3.73 (dd, J=11.2, 3.0 Hz, 1H), 3.29-3.24 (m, 1H), 3.12-3.06 (m, 1H), 2.23-2.08 (m, 2H), 2.01-1.96 (m, 1H), 1.44-1.24 (m, 2H), 0.97-0.88 (m, 3H), 0.73-0.63 (m, 2H). MS (ESI, m/e) [M+1]⁺273.1.

Example B113: (7-(tert-Butyl)imidazo[1,5-a]pyridin-8-yl)(cyclohexyl)methanol

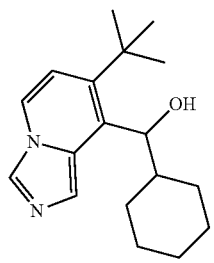 [SMILES: CC(C)(C)c1ccn2cncc2c1C(O)C1CCCCC1]

¹H NMR (DMSO-d₆) δ 8.20 (s, 1H), 8.11 (d, J=7.2 Hz, 1H), 7.48 (s, 1H), 6.68 (d, J=7.2 Hz, 1H), 5.19 (d, J=4.0 Hz, 1H), 5.02 (dd, J=8.8, 4.0 Hz, 1H), 2.34 (br d, J=10.8 Hz, 1H), 2.12 (m, 1H), 1.76 (m, 1H), 1.64-1.53 (m, 1H), 1.49 (m, 1H), 1.38 (s, 9H), 1.31-1.14 (m, 2H), 1.14-0.72 (m, 4H). MS (ESI) m/e [M+1]⁺287.2.

Example B114: (7-Cyclobutylimidazo[1,5-a]pyridin-8-yl)(cyclohexyl)methanol

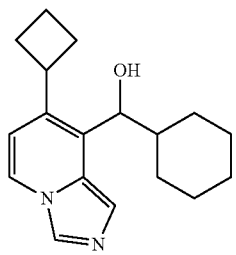 [SMILES: OC(c1c(C2CCC2)ccn2cncc12)C1CCCCC1]

¹H NMR (CD₃OD) δ 9.30 (s, 1H), 8.36 (d, J=7.5 Hz, 1H), 8.01 (s, 1H), 7.33 (d, J=7.5 Hz, 1H), 4.01-3.84 (m, 1H), 2.37-0.99 (m, 18H). MS (ESI) m/e [M+1]⁺ 285.2.

Example B115: 1-(7-Cyclopropylimidazo[1,5-a]pyridin-8-yl)prop-2-en-1-ol

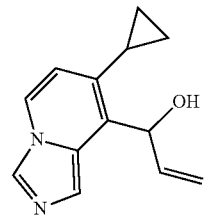 [SMILES: C=CC(O)c1c(C2CC2)ccn2cncc12]

To a solution of 7-cyclopropylimidazo[1,5-a]pyridine-8-carbaldehyde (500 mg, 2.74 mmol) in THF (20 mL) was added vinylmagnesium bromide (1.0 M in THF, 4.12 mL, 4.12 mmol) at −78° C. The reaction mixture was stirred at −78° C. for 45 min and then quenched with sat. aq. NH₄Cl (10 mL). The mixture was diluted with DCM (50 mL) and the organic phase was separated and washed with brine (20 mL), dried over Na₂SO₄ and purified on silica gel chromatography (DCM/MeOH=30:1) to provide 1-(7-cyclopropylimidazo[1,5-a]pyridin-8-yl)prop-2-en-1-ol (301 mg, 51%) as a yellow solid. ¹H NMR (CDCl₃) δ 7.93 (s, 1H), 7.71 (d, J=7.2 Hz, 1H), 7.51 (s, 1H), 6.27-6.14 (m, 2H), 5.96 (m, 1H), 5.43 (d, J=11.2 Hz, 1H), 5.20 (d, J=10.4 Hz, 1H), 2.12-1.98 (m, 1H), 1.01-0.91 (m, 2H), 0.74-0.62 (m, 2H). MS (ESI) m/e 215.1.

Example B116: (7-Chloroimidazo[1,5-a]pyridin-8-yl)(cyclohex-3-en-1-yl)methanol

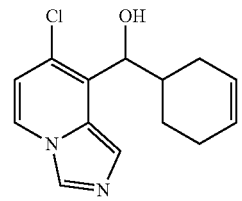 [SMILES: OC(c1c(Cl)ccn2cncc12)C1CC=CCC1]

Example B116 was synthesized by following the procedures similar to those in Example B115 under appropriate conditions recognized by one of ordinary skill in the art. ¹H NMR (DMSO-d₆) δ 8.36 (s, 1H), 8.27 (d, J=7.2 Hz, 1H), 7.56 (s, 1H), 6.64 (d, J=7.2 Hz, 1H), 5.67 (dd, J=17.9, 4.0 Hz, 1H), 5.65 (dd, J=17.9, 4.0 Hz, 1H), 5.58-53 (m, 1H), 4.92-4.87 (m, 1H), 2.32-1.24 (m, 7H). MS (ESI, m/e) [M+1]⁺263.1, 265.1.

Example B117: (Adamantan-2-yl)(7-cyclopropylimidazo[1,5-a]pyridin-8-yl)methanol

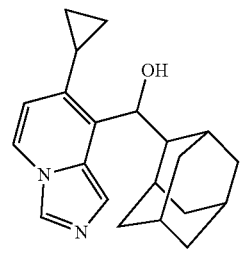

¹H NMR (DMSO-d₆) δ 8.23 (s, 1H), 8.10 (d, J=6.6 Hz, 1H), 7.38 (s, 1H), 6.14 (d, J=6.6 Hz, 1H), 5.51 (br s, 1H), 5.14 (br s, 1H), 2.45-2.30 (m, 2H), 2.15-1.15 (m, 15H), 1.00-0.80 (m, 2H), 0.65-0.50 (m, 1H). MS (ESI) m/e [M+1]⁺ 323.2.

Example B118: 2-(Adamantan-1-yl)-1-(7-cyclopropylimidazo[1,5-a]pyridin-8-yl)ethan-1-ol

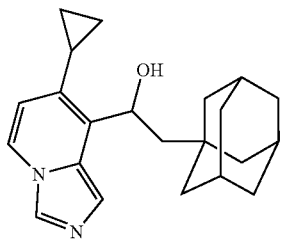 [SMILES: OC(CC12CC3CC(CC(C3)C1)C2)c1c(C2CC2)ccn2cncc12]

¹H NMR (DMSO-d₆) δ 8.31 (s, 1H), 8.11 (d, J=7.6 Hz, 1H), 7.47 (s, 1H), 6.22 (d, J 7.6 Hz, 1H), 5.50 (d, J=8.8 Hz, 1H), 5.15-5.05 (m, 1H), 2.13-2.03 (m, 1H), 1.96-1.82 (m, 3H), 1.71-1.55 (m 12H), 1.34-1.20 (m, 2H), 0.97-0.90 (m 2H), 0.75-0.62 (m, 2H). MS (ESI) m/e [M+1]⁺337.2.

Example B119: 4-((7-Cyclopropylimidazo[1,5-a]pyridin-8-yl)(hydroxy)methyl)cyclohexan-1-ol

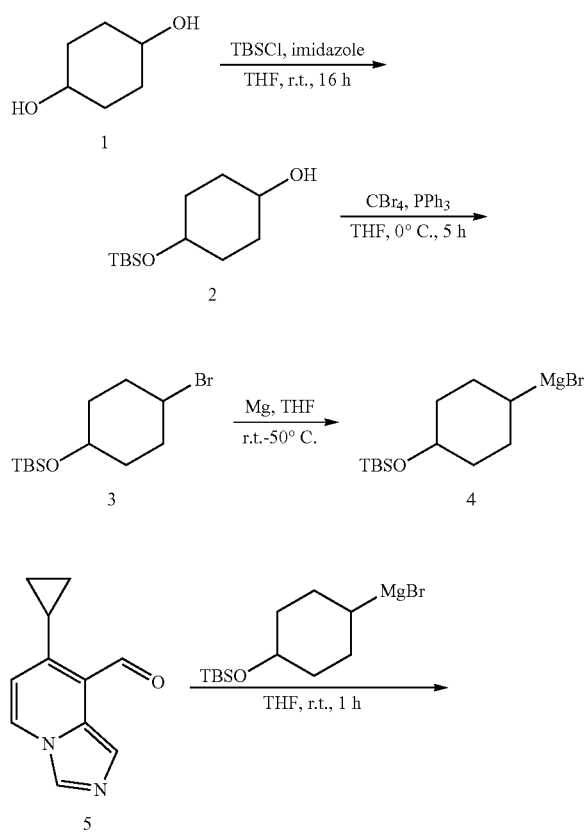

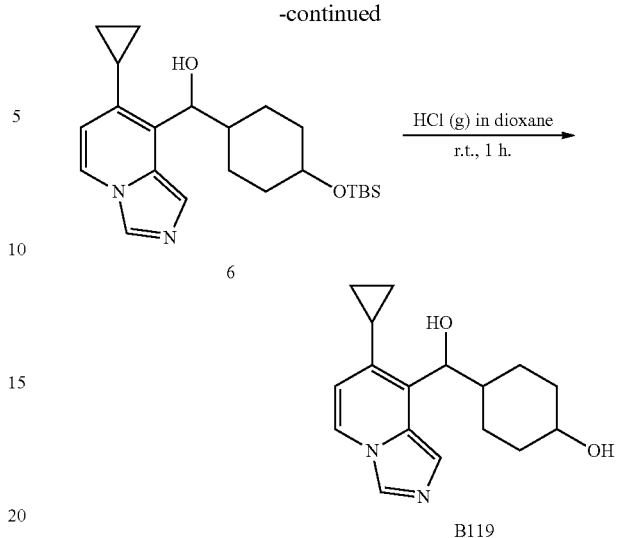

Step 1:
4-((tert-Butyldimethylsilyl)oxy)cyclohexan-1-ol

To a solution of cyclohexane-1,4-diol (100 g, 862 mol) in THF (1000 mL) was added imidazole (58.6 g, 862 mmol) and TBSCl (130 g, 862 mmol), the reaction was stirred at ambient temperature for about 16 hours. The solid was filtered, washed with THF (100 mL), the filtrate was concentrated under reduced pressure. The crude product (about 60 g) was purified by column of Al₂O₃ to give the product as colorless oil (172 g, 86.7%). MS (ESI) m/e [M+1]+231.0.

Step 2:
((4-Bromocyclohexyl)oxy)(tert-butyl)dimethylsilane

To a solution of 4-((tert-butyldimethylsilyl)oxy)cyclohexan-1-ol (80 g, 348 mmol) in THF (800 mL) was added CBr₄ (138 g, 417 mmol) and PPh₃ (108 g, 417 mmol) at 0° C., the reaction was stirred at 0° C. for about 6 hours. Water (200 mL) was added to the reaction, the aqueous was extracted with EA (3*200 mL), the combined organic phases were washed with sat. NaCl (10 mL), dried over anhydrous Na₂SO₄, filtered and concentrated, the crude product was extracted with PE (3*500 mL), the combined organic phases were purified by column chromatography on silica gel (200-300 mesh, PE) to give the product as colorless oil (73.0 g, 71.6%).

Step 3: (4-((tert-Butyldimethylsilyl)oxy)cyclohexyl) magnesium bromide

To a solution of ((4-bromocyclohexyl)oxy)(tert-butyl)dimethylsilane (2.5 g, 8.53 mmol) in THF (5.0 mL) was added Mg (1.03 g, 43.0 mmol) and I2 (10 mg) at ambient temperature under N₂ atmosphere, the reaction warmed until reaction generated, a solution of ((4-bromocyclohexyl)oxy)(tert-butyl)dimethylsilane (8.0 g, 27.3 mmol) in THF (35 mL) was added dropwise to the reaction. The reaction was warmed to 50° C. stirred for about 3 hours after addition, cooled to ambient temperature and used directly to next step.

Step 4: (4-((tert-Butyldimethylsilyl)oxy)cyclohexyl)(7-cyclopropylimidazo[1,5-a]pyri din-8-yl)methanol To a solution of (4-((tert-butyldimethylsilyl)oxy)cyclohexyl)magnesium bromide (40 mL, 35.8 mmol in THF) was added a solution of 7-cyclopropylimidazo[1,5-a]pyridin-8-carbaldehyde (1.2 g, 6.45 mmol) in THF (30 mL) at ambient temperature, the reaction was stirred ambient temperature for about 1 hour. sat. NH₄Cl (10 mL) was added to the reaction, the aqueous was extracted with EA (15 mL*3), the combined organic phases were washed with sat. NaCl (10 mL), dried over anhydrous Na₂SO₄, filtered and concentrated. The crude product was purified by column chromatography on silica gel (200-300 mesh, eluent: DCM: MeOH=50:1), to give the product as a white solid (1.5 g, 58.1%). MS (ESI) m/e [M+1]⁺401.2.

Step 5: 4-((7-Cyclopropylimidazo[1,5-a]pyridin-8-yl)(hydroxy)methyl)cyclohexan-1-ol (4-((tert-Butyldimethylsilyl)oxy)cyclohexyl)(7-cyclopropylimidazo[1,5-a]pyridin-8-yl)methanol (2.5 g, 6.25 mmol) was added to HCl (gas in dioxane, 30 mL), the reaction was stirred at ambient temperature for about 1 hour. Concentrated under reduced pressure to remove solvent to give the crude product about 2.0 g. MS (ESI) m/e [M+1]⁺287.1.

Step 6: (trans)-4-((7-Cyclopropylimidazo[1,5-a]pyridin-8-yl)(hydroxy)methyl)cyclohexan-1-ol and (cis-4-((7-Cyclopropylimidazo[1,5-a]pyridin-8-1)(hydroxy)meth 1 yl)cyclohexan-1-ol

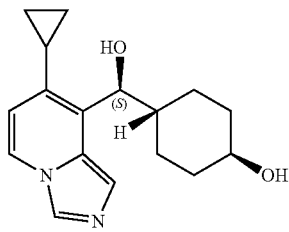

B119a

Fast trans isomer in chiral OJ HPLC
Eluting reagent: EtOH (100%)

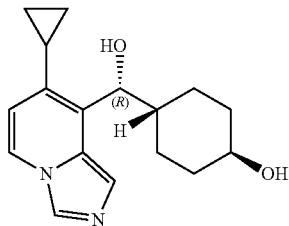

B119b

Slow trans isomer in chiral OJ HPLC
Eluting reagent: EtOH (100%)

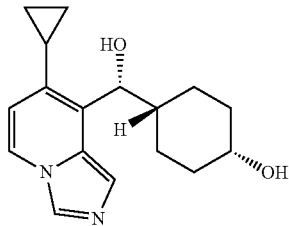

B119c

Fast cis isomer in chiral ADHPLC
Eluting reagent: EtOH/DEA = 100/0.1 (V/V)

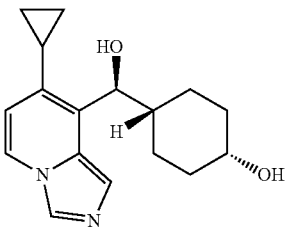

B119d

Slow cis isomer in chiral AD HPLC
Eluting reagent: EtOH/DEA = 100/0.1 (V/V)

4-((7-Cyclopropylimidazo[1,5-a]pyridin-8-yl)(hydroxy)methyl)cyclohexan-1-ol (2.0 g, 6.25 mmol) was separated by pre-HPLC, to give a trans isomers 750 mg as a white solid. ¹H NMR (DMSO-d₆) δ 8.20 (s, 1H), 8.10 (d, J=7.2 Hz, 1H), 7.38 (s, 1H), 6.14 (d, J=7.2 Hz, 1H), 5.27 (d, J=3.2 Hz, 1H), 4.88 (dd, J=3.2, 8.8 Hz, 1H), 4.43 (d, J=4.0 Hz, 1H), 3.34-3.24 (m, 1H), 2.20-2.08 (m, 2H), 1.90-1.78 (m, 2H), 1.75-1.65 (m, 1H), 1.20-0.85 (m, 7H), 0.72-0.62 (m, 2H). MS (ESI) m/e [M+1]⁺287.1. 300 mg cis isomers as a white solid. ¹H NMR (DMSO-d₆) δ 8.20 (s, 1H), 8.10 (d, J=7.2 Hz, 1H), 7.38 (s, 1H), 6.14 (d, J=7.6 Hz, 1H), 5.24 (d, J=3.6 Hz, 1H), 4.97 (dd, J=3.6, 9.0 Hz, 1H), 4.22 (d, J=2.8 Hz, 1H), 2.20-2.08 (m, 1H), 2.00-1.90 (m, 1H), 1.88-1.80 (m, 1H), 1.70-1.45 (m, 3H), 1.45-1.29 (m, 2H), 1.25-1.15 (m, 2H), 0.96-0.85 (m, 3H), 0.75-0.62 (m, 2H). MS (ESI) m/e [M+1]⁺ 287.1.

Trans isomer was then separated using preparative HPLC on a CHIRALCEL OJ-H column with Eluting reagent: EtOH (100%) as an eluent. The enantiomeric excesses were determined by using HPLC on a CHIRALCEL OJ-H column with EtOH (100%) as an eluent at a flow rate of 1.0 mL/min. The first one enantiomer (B119a) eluted at the retention time of 7.02 min; and the other enantiomer (B119b) eluted at the retention time of 9.45 min. Cis isomer was then separated using preparative HPLC on a CHIRALCEL AD-H column with Eluting reagent: EtOH/DEA=100/0.1 (V/V) as an eluent. The enantiomeric excesses were determined by using HPLC on a CHIRALCEL AD-H column with EtOH/DEA=100/0.1 (V/V) as an eluent at a flow rate of 0.4 mL/min. The first one enantiomer (B119c) eluted at the retention time of 5.27 min; and the other enantiomer (B119d) eluted at the retention time of 6.85 min. The absolute configurations of B119a, B119b, B119c and B119d are tentatively assigned as (S), (R), (R) and (S) respectively based on assumption that the binding model of the more potent isomer B119a and B119d are the same as that of A101a with IDO1 enzyme.

Example B120: (4-((tert-Butyldimethylsilyl)oxy)cyclohexyl)(7-isopropylimidazo[1,5-a] pyridin-8-yl)methanol

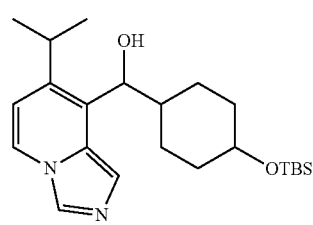 [SMILES: CC(C)c1ccn2cncc2c1C(O)C1CCC(O[Si](C)(C)C(C)(C)C)CC1]

The desired product as a white solid was prepared by following the procedures similar to those in Example B119. $^1$H NMR (DMSO-$d_6$) δ 8.24 (s, 1H), 8.18 (d, J=7.4 Hz, 1H), 7.40 (s, 1H), 6.62 (d, J=7.4 Hz, 1H), 5.35-5.25 (m, 1H), 4.73-4.63 (m, 1H), 3.60-3.45 (m, 1H), 2.20-2.12 (m, 1H), 1.90-1.40 (m, 4H), 1.30-1.10 (m, 11H), 0.90-0.78 (m, 9H), 0.06-0.04 (m, 6H). MS (ESI) m/e [M+1]$^+$403.3.

Example B121 (trans)-4-(Hydroxy(7-isopropylimidazo[1,5-a]pyridin-8-yl)methyl) cyclohexan-1-ol (Examples B121a and B121b) and (cis)-4-(hydroxy (7-isopropylimidazo[1,5-a]pyridin-8-ylmethyl)cyclohexan-1-ol (Two Isomers: Examples B121c and B121d)

B121a
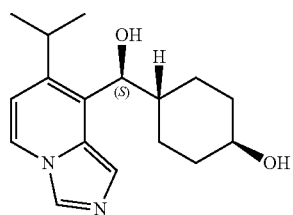

Fat trans isomer in chiral OJ HPLC
Eluting reagent: $CO_2$/MeOH = 80/20 (/V/V)

B121b
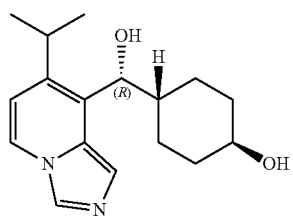

Slow trans isomer in chiral OJ HPLC
Eluting reagent: $CO_2$/MeOH = 80/20 (/V/V)

B121c
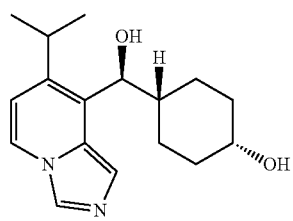

Fast cis isomer in chiral ADHPLC
Eluting reagent: $CO_2$/MeOH 0.1% DEA = 75/25 (V/V)

B121d
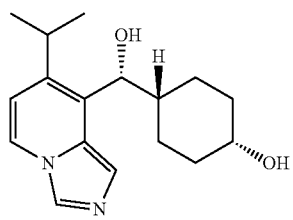

Slow cis isomer in chiral AD HPLC
Eluting reagent: $CO_2$/MeOH 0.1% DEA = 75/25 (V/V)

The desired product was prepared by following the procedures similar to those in Example B119. Trans as white a solid. $^1$H NMR (DMSO-$d_6$) δ 8.21 (s, 1H), 8.17 (d, J=7.2 Hz, 1H), 7.38 (s, 1H), 6.60 (d, J=7.4 Hz, 1H), 5.30 (br s, 1H), 4.65 (d, J=7.2 Hz, 1H), 4.45 (br s, 1H), 3.50-3.30 (m, 1H), 2.21-2.14 (m, 1H), 1.90-1.84 (m, 1H), 1.78-1.55 (m, 2H), 1.17-0.85 (m, 12H). MS (ESI) m/e [M+1]$^+$289.2. Cis also as a white solid. $^1$H NMR (DMSO-$d_6$) δ 8.20 (s, 1H), 8.17 (d, J=7.2 Hz, 1H), 7.37 (s, 1H), 6.61 (d, J=7.2 Hz, 1H), 5.23 (d, J=3.2 Hz, 1H), 4.73 (dd, J=3.2, 8.8 Hz, 1H), 4.22 (d, J=3.6 Hz, 1H), 1.92-1.82 (m, 2H), 1.72-1.66 (m, 1H), 1.60-1.33 (m, 3H), 1.30-1.10 (m, 9H), 0.88-0.78 (m, 1H). MS (ESI) m/e [M+1]$^+$289.2. Trans isomer was then separated using preparative HPLC on a CHIRALCEL AD-H column with Eluting reagent: $CO_2$/MeOH=80/20 (/V/V) as an eluent. The enantiomeric excesses were determined by using HPLC on a CHIRALCEL AD-H column with $CO_2$/MeOH=80/20 (/V/V) as an eluent at a flow rate of 2.0 mL/min. The first one enantiomer (B121a) eluted at the retention time of 6.68 min; and the other enantiomer (B121b) eluted at the retention time of 7.60 min. Cis isomer was then separated using preparative HPLC on a CHIRALCEL AS-H column with Eluting reagent: $CO_2$/MeOH 0.1% DEA=75/25 (V/V) as an eluent. The enantiomeric excesses were determined by using HPLC on a CHIRALCEL AS-H column with $CO_2$/MeOH 0.1% DEA=75/25 (V/V) as an eluent at a flow rate of 2.0 mL/min. The first one enantiomer (B121c) eluted at the retention time of 6.93 min; and the other enantiomer (B121d) eluted at the retention time of 11.18 min. The absolute configurations of B121a, B121b, B121c and B121d are tentatively assigned as (S), (R), (S) and (R) respectively based on assumption that the binding model of the more potent isomer B121a and B121c are the same as that of A101a with IDO1 enzyme.

Example B122: bicyclo[2.2.1]heptan-2-yl(7-cyclopropylimidazo[1,5-a]pyridin-8-yl)methanol

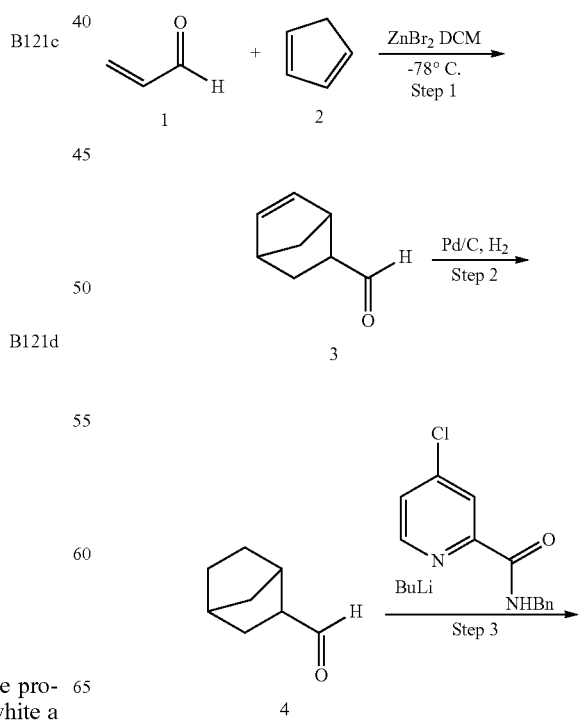

221
-continued

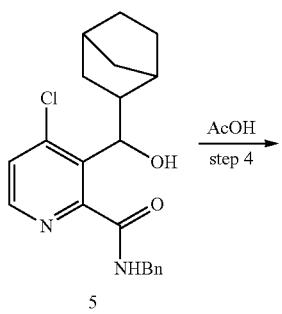
5

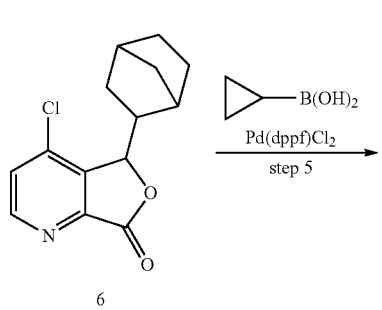
6

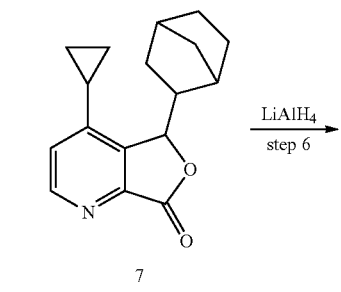
7

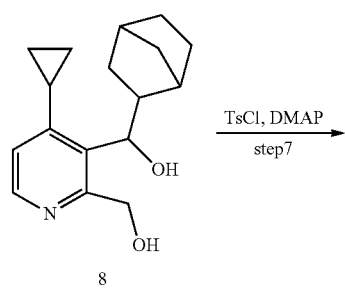
8

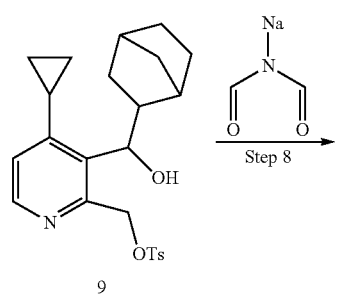
9

222
-continued

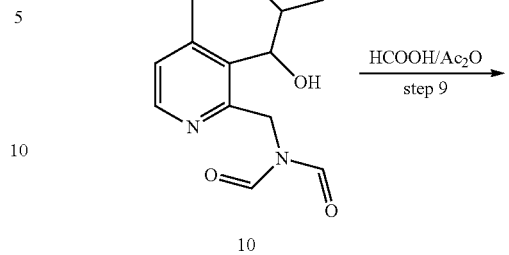
10

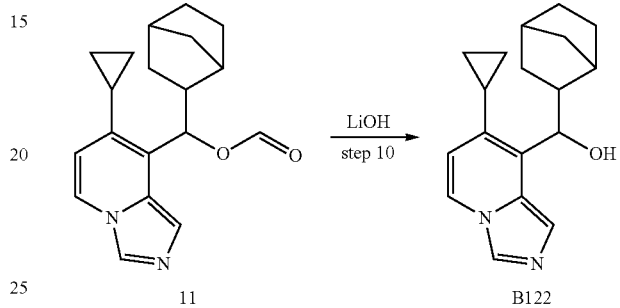
11                                    B122

Step 1: Bicyclo[2.2.1]hept-5-ene-2-carbaldehyde

To a suspension of ZnBr₂ (83 g, 0.37 mol) in dry DCM (1.5 L) was added acrylaldehyde (208 g, 3.7 mol) at −70° C. and followed by addition of cyclopenta-1,3-diene (320 g, 3.7 mol) slowly at −70° C. And the mixture was stirred for 0.5 h when addition was completely. Filtered to remove the solid, the filtrate was evaporated to give the crude product. $^1$H NMR (DMSO-d$_6$) 9.42 (m, 1H), 6.21-6.23 (m, 1H), 5.99-6.01 (m, 1H), 3.26 (s, 1H), 2.99 (s, 1H), 2.91-2.95 (m, 1H), 1.89-1.95 (m, 1H), 1.42-1.50 (m, 2H), 1.31-1.33 (m, 1H).

Step 2: Bicyclo[2.2.1]heptane-2-carbaldehyde

To a suspension of (1S,2S,4S)-bicyclo[2.2.1]hept-5-ene-2-carbaldehyde (300 g, 2.5 mol) in a mixture of MeOH (1.1 L) and EA (1.1 L) was added Pd/C (25 g) at room temperature and the mixture was stirred overnight under H₂ (0.4 MPa). Filtered to remove Pd/C and the filtrate was evaporated to give crude product. $^1$H NMR (DMSO-d$_6$) 9.78 (s, 1H), 2.71-2.75 (m, 2H), 2.33 (m, 1H), 1.34-1.70 (m, 11H).

Step 3: N-benzyl-3-((-bicyclo[2.2.1]heptan-2-yl)(hydroxy)methyl)-4-chloropicolinamide To a solution of ''Bu-Li (0.3 L, 2.4 M) in dry THF (1.1 L) was added a solution of N-benzyl-4-chloropicolinamide (70 g, 0.28 mol) in dry THF (0.4 L) slowly at −70° C. Followed by addition of bicyclo[2.2.1]heptane-2-carbaldehyde (174 g, 1.4 mol) slowly at −70° C. and the mixture was stirred for 2 hours before EA (0.3 L) and water (0.3 L) was added, isolated the organic layer, evaporated the solvent and the residue was poured in to PE (3.0 L) with vigorous stirring, filtered to give crude product. The crude product was first recrystallization by EtOH and then recrystallization by EA to give 38 g as a white solid. $^1$H NMR (DMSO-d$_6$) 8.41-8.43

(dd, 1H, J=5.2 Hz), 8.29 (s, 1H), 8.24-8.25 (dd, 1H, J=2.0 Hz), 7.42-7.11 (m, 1H), 7.28-7.36 (m, 5H), 4.67 (d, 2H, J=6.0 Hz).

Step 4: 5-(bicyclo[2.2.1]heptan-2-yl)-4-chlorofuro [3,4-b]pyridin-7 (5H)-one

A mixture of N-benzyl-3-((bicyclo[2.2.1]heptan-2-yl)(hydroxy)methyl)-4-chloropicolinamide (38 g, 0.1 mol) in AcOH (0.5 L) was heated at 50° C. for overnight. Evaporated the solvent before EA (0.5 L) was added and washed with saturated aqueous of NaHCO$_3$, isolated the organic layer and evaporated the solvent to give 27 g as a white solid. $^1$H NMR (DMSO-d$_6$) 8.88 (d, 1H, J=5.2 Hz), 7.98 (d, 1H, J=5.2 Hz), 5.90 (d, 1H, J=8.0 Hz), 2.49-2.50 (m, 1H), 2.34 (s, 1H), 2.19 (s, 1H), 1.89-1.95 (m, 1H), 1.54-1.58 (m, 2H), 1.26-1.42 (m, 5H).

Step 5: 5-((bicyclo[2.2.1]heptan-2-yl)-4-cyclopropylfuro[3,4-b]pyridin-7 (5H)-one To a solution of 5-(bicyclo[2.2.1]heptan-2-yl)-4-chlorofuro[3,4-b]pyridin-7 (5H)-one (27 g, 102 mmol) in 1,4-dioxane (0.6 L) was added cyclopropylboronic acid (17.5 g, 204 mmol), Pd(dppf)Cl$_2$ (7.5 g, 10.2 mmol) and K$_2$CO$_3$ (56 g, 408 mmol) and the mixture was heated at 90° C. for 3 hours. Cooled to room temperature and filtered to remove the solid, the filtrate was evaporated before EA (1.0 L) was added, and filtered by silicone pad, the filtrate was evaporated to give 24 g crude as a brown solid. $^1$H NMR (DMSO-d$_6$) 8.65 (s, 1H), 7.22 (d, 1H, J=5.2 Hz), 5.96 (d, 1H, J=6.8 Hz), 2.45-2.48 (m, 2H), 2.26-2.28 (m, 1H), 2.02-2.13 (m, 2H), 1.80-1.88 (m, 1H), 1.45-1.52 (m, 2H), 1.07-1.34 (m, 8H), 0.78-0.84 (m, 1H).

Step 6: (bicyclo[2.2.1]heptan-2-yl)(4-cyclopropyl-2-(hydroxymethyl)pyridin-3-yl)methanol To a suspension of LAH (5.1 g, 135 mmol) in dry THF (0.5 L) was added drop wise a solution of 5-(bicyclo[2.2.1] heptan-2-yl)-4-cyclopropylfuro[3,4-b]pyridin-7 (5H)-one (12 g, 45 mmol) in dry THF (120 mL) at 0° C. and the mixture was stirred for 2 h when the addition was completely. Then water (5.1 mL) was added slowly, followed by addition of NaOH (10.2 mL, 10%) and water (15.3 mL) and the mixture was stirred for 1 h before filtered and the filtrate was evaporated to give 12 g as a crude product.

Step 7: (bicyclo[2.2.1]heptan-2-yl)(2-(chloromethyl)-4-cyclopropylpyridin-3-yl)methanol To a solution of (bicyclo[2.2.1]heptan-2-yl)(4-cyclopropyl-2-(hydroxymethyl)pyridin-3-yl)methanol (32 g, 117 mmol) in dry DCM (1.4 L) was added Et$_3$N (36.5 g, 351 mmol), TsCl (44.8 g, 234 mmol) and 4-DMAP (1.5 g, 11.7 mmol) at room temperature and the mixture was stirred for overnight. Washed the mixture with water and purified by column chromatography (DCM:MeOH=95:5) to give 27 g as a brown solid.

Step 8: N-((3-((bicyclo[2.2.1]heptan-2-yl)(hydroxy) methyl)-4-cyclopropylpyridin-2-yl)methyl)-N-formylformamide To a solution of (bicyclo[2.2.1]heptan-2-yl)(2-(chloromethyl)-4-cyclopropylpyridin-3-yl)methanol (27 g, 93 mmol) in dry DMF (0.5 L) was added sodium diformamide (17.7 g, 186 mmol) at room temperature and the mixture was heated at 80° C. for 2 hours. Evaporated the solvent before EA (0.5 L) was added and washed with brine, isolated the organic layer and evaporated to give crude product as a brown solid.

Step 9: (bicyclo[2.2.1]heptan-2-yl)(7-cyclopropylimidazo[1,5-a]pyridin-8-yl)methyl formate To a solution of crude N-((3-((bicyclo[2.2.1]heptan-2-yl) (hydroxy)methyl)-4-cyclopropylpyridin-2-yl)methyl)-N-formylformamide (93 mmol) in Ac$_2$O (0.4 L) was added HCOOH (0.2 L) at room temperature and the mixture was heated at 60° C. for 3 hours. Evaporated the solvent before EA (0.6 L) was added and washed with saturated aqueous of NaHCO$_3$, isolated the organic layer, evaporated the solvent and purified by column chromatography (PE:EA=1:1 to EA) to give 15 g as a light brown solid.

Step 10: (bicyclo[2.2.1]heptan-2-yl)(7-cyclopropylimidazo[1,5-a]pyridin-8-yl)methanol

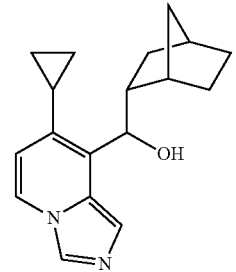 [SMILES: OC(c1c(C2CC2)ccn2cncc12)C1CC2CCC1C2]

To a solution of (bicyclo[2.2.1]heptan-2-yl)(7-cyclopropylimidazo[1,5-a]pyridin-8-yl)methyl formate (15 g, 48 mmol) in a mixture of THF (0.4 L) and water (0.1 L) was added LiOH H$_2$O (4.0 g, 96 mmol) at room temperature and the mixture was stirred for 1 hour. EA (0.2 L) was added and isolated the organic layer, evaporated the solvent and washed with EA/PE=1:1 to give 13 g as a white solid. $^1$H NMR (DMSO-d$_6$) δ 8.24-8.21 (m, 1H), 8.13-8.08 (m, 1H), 7.44-7.38 (m, 1H), 6.20-6.13 (m, 1H), 5.35-5.15 (m, 1H), 5.10-4.80 (m, 1H), 2.70-2.50 (m, 1H), 2.30-2.00 (m, 3H), 1.72-0.60 (m, 12H). MS (ESI) m/e [M+1]$^+$283.2.

Example B122a: (S)-((1R,2S,4S)-bicyclo[2.2.1] heptan-2-yl)(7-cyclopropylimidazo[1,5-a]pyridin-8-yl)methanol

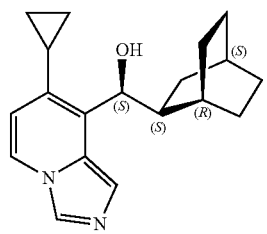

Second isomer in chiral AC HPLC
Eluting reagent: Hexane/EtOH = 90/10 (/V/V)

To a suspension of (bicyclo[2.2.1]heptan-2-yl)(7-cyclopropylimidazo [1,5-a] pyridin-8-yl)methanol (0.9 g, 3.2 mmol) in CH₃CN (100 mL) was added drop wise a solution of L-DBTA (1.26 g, 1.1 eq) in CH₃CN (36 mL) at 60° C. until the mixture was completely dissolved. Then cooled to room temperature slowly and filtered to give 0.7 g as a white solid. Followed by recrystallization with CH₃CN (70 mL) to give 490 mg as a white solid. Next the solid was dispersed in DCM (50 mL), saturated aqueous of K₂CO₃ (5 mL) was added with vigorous stirring. Isolated the organic layer and evaporated the solvent to give 230 mg as a white solid. $^1$H NMR (DMSO-d₆) 8.20 (s, 1H), 8.09 (d, 1H, J=7.2 Hz), 7.40 (s, 1H), 6.14 (d, 1H, J=7.2 Hz), 5.13-5.19 (m, 2H), 2.59 (s, 1H), 2.06-2.17 (m, 2H), 1.81-1.85 (m, 1H), 1.38-1.54 (m, 2H), 0.58-1.29 (m, 10H).

Figure 2:
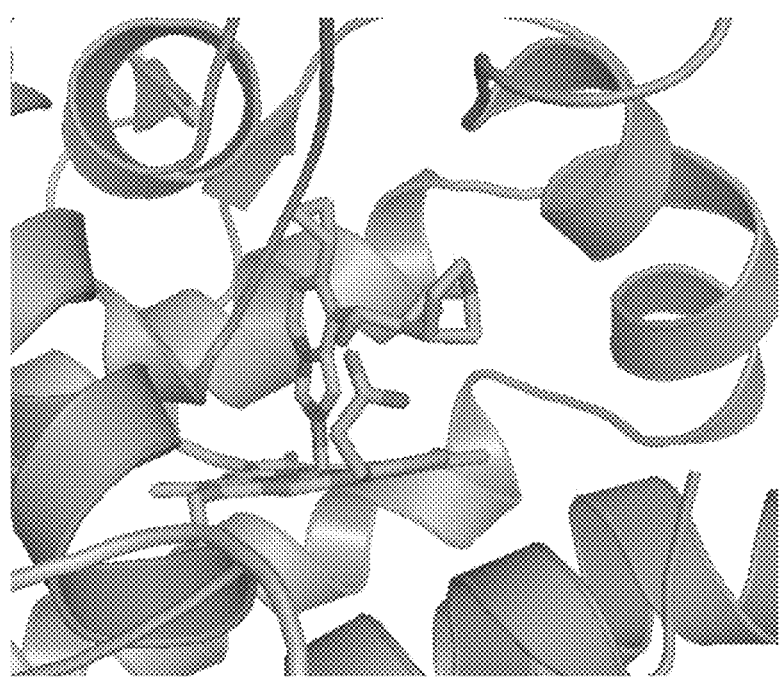
FIG. 2 shows B122a/IDO1 cocrystal structure (Resolution=2.60 Å).

The absolute stereochemistry of the more potent compound of Example B122a in enzymatic and cellular assays is assigned as (S), (S)-configuration on the chiral α-carbon atom based on its cocrystal structure with IDO1 enzyme (FIG. 2).

Example B122b: (1S)-Bicyclo[2.2.1]heptan-2-yl(7-cyclopropylimidazo[1,5-a]pyridin-8-yl)methanol (exo enantiomer)

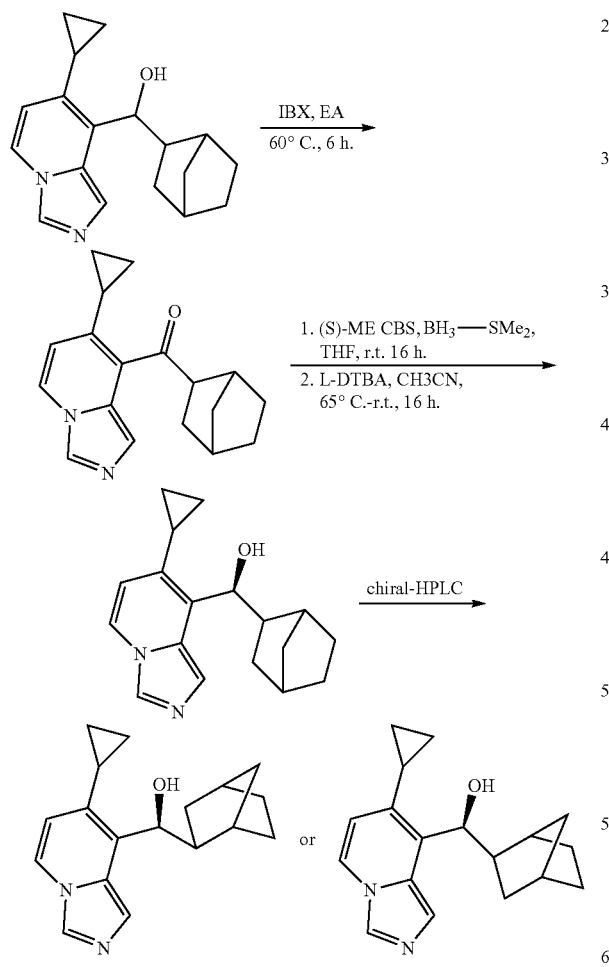

Step 1: Bicyclo[2.2.1]heptan-2-yl(7-cyclopropylimidazo[1,5-a]pyridin-8-yl)methanone To a solution of bicyclo[2.2.1]heptan-2-yl(7-cyclopropylimidazo[1,5-a]pyridine-8-yl)methanol (2.0 g, 7.09 mol) in EA (150 mL) was added IBX (6.0 g, 21.3 mmol), the reaction was warmed to 60° C. and stirred for about 6 hrs. Cooled to ambient temperature, filtered and the solid was washed with EA (20 mL), the filtrate was concentrated, the crude product was purified by column chromatography on silica gel (200-300 mesh, eluent: DCM:MeOH=100:1), got the product as yellow oil (1.8 g, 90.6%). MS (ESI) m/e [M+1]⁺281.1.

Step 2: (1S)-Bicyclo[2.2.1]heptan-2-yl(7-cyclopropylimidazo[1,5-a]pyridin-8-yl)methanol To a solution of bicyclo[2.2.1]heptan-2-yl(7-cyclopropylimidazo[1,5-a]pyridin-8-yl) methanone (1.8 g, 6.43 mol) in THF (100 mL) was added (S)-ME CBS (CAS: 112022-81-8, 1 M, 1.65 mL, 0.064 mmol). After stirring for about 15 min, borane-methyl sulfide complex (2.0 M, 6.5 mL, 13.0 mmol) was added dropwise to the reaction, the reaction was stirred at ambient temperature for about 16 hrs. Con. HCl (5.0 mL) was added to the reaction, the solid was filtered, washed with THF (10 mL), dissolved into CH₂Cl₂ (20 mL), sat. Na₂CO₃ was added to the solution to adjust the pH value to 8-9, the aqueous solution was extracted with CH₂Cl₂ (20 mL*3). The combined organic phases were washed sat. NaCl (10 mL), dried over anhydrous Na₂SO₄, filtered and concentrated to give the product as a pale brown solid (1.3 g, 71.7%).

The solid (1.3 g, 4.61 mmol) was added to CH₃CN (65 mL), warmed to 56° C. stirred until all solid dissolved. L-DBTA (1.65 g, 4.61 mmol) was added to the solution, the reaction was slowly cooled to ambient temperature stirred for about 16 h. The solid was filtered, washed with CH₃CN (15 mL), the solid was added to CH₂Cl₂ (20 mL), sat. Na₂CO₃ was added to the solution to adjust the pH value to 8-9, the aqueous was extracted with CH₂Cl₂ (3*10 mL), the combined organic phases were washed with sat. NaCl (10 mL), dried over anhydrous Na₂SO₄, filtered and concentrated to give the product as a pale yellow solid (900 mg, 69.2%).

Step 3: (1S)-Bicyclo[2.2.1]heptan-2-yl(7-cyclopropylimidazo[1,5-a]pyridin-8-yl)methanol (exo enantiomer)

The pale yellow solid (100 mg) was separated using preparative HPLC on a CHIRALCEL IC-H column with Eluting reagent: CO₂/IPA=50/50 (/V/V) as an eluent to collect the first peak. The enantiomeric excesses were determined by using HPLC on a CHIRALCEL AC-H column with Hexane/EtOH 0.1% DEA=70/30 (/V/V) as an eluent at a flow rate of 1.0 mL/min. The enantiomer (20 mg, 20%) eluted at the retention time of 4.59 min. $^1$H NMR (DMSO-d₆) δ 8.30 (s, 1H), 8.12 (d, J=7.4 Hz, 1H), 7.46 (s, 1H), 6.19 (d, J=7.4 Hz, 1H), 5.34 (br s, 1H), 4.85 (d, J=8.8 Hz, 1H), 2.57-2.52 (m, 1H), 2.22-2.07 (m, 3H), 1.59-1.37 (m, 3H), 1.27-0.60 (m, 9H). MS (ESI) m/e [M+1]⁺ 283.2.

Example B123: Bicyclo[2.2.2]oct-5-en-2-yl(7-cyclopropylimidazo[1,5-a]pyridin-8-yl)methanol

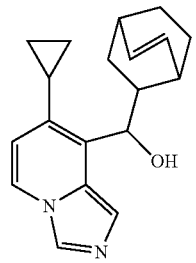 [SMILES: OC(c1c(C2CC2)ccn2cncc12)C1CC2C=CC1CC2]

The desired product was prepared by following the procedures similar to those in Example B122. ¹H NMR (400 MHz, CDCl₃) δ 9.12 (s, 1H), 8.00 (s, 1H), 7.97 (s, 1H), 6.51-6.27 (m, 4H), 4.98 (d, J=9.7 Hz, 1H), 3.04-3.02 (m, 1H), 2.49-2.30 (m, 2H), 2.03-1.98 (m, 1H), 1.58-1.55 (m, 1H), 1.41-1.36 (m, 2H), 1.29-1.23 (m, 2H), 1.11-1.08 (m, 2H), 0.77-0.74 (m, 3H).

Example B124: Bicyclo[2.2.2]octan-2-yl(7-cyclopropylimidazo[1,5-a]pyridin-8-yl)methanol

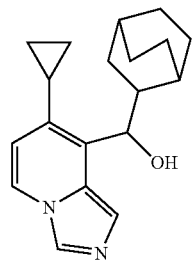 [SMILES: OC(c1c(C2CC2)ccn2cncc12)C1CC2CCC1CC2]

The desired product was reduced by following the procedure similar to that in Example B122. ¹H NMR (400 MHz, CDCl₃) δ 9.08 (s, 1H), 8.02 (d, J=7.4 Hz, 1H), 7.95 (s, 1H), 6.51 (d, J=7.4 Hz, 1H), 5.44 (d, J=10.3 Hz, 1H), 2.30-0.75 (m, 18H). MS (ESI) m/e [M+1]⁺297.2.

Example B125: N-cyclopropyl-3-((7-cyclopropylimidazo[1,5-a]pyridin-8-yl)(hydroxy)methyl)benzamide

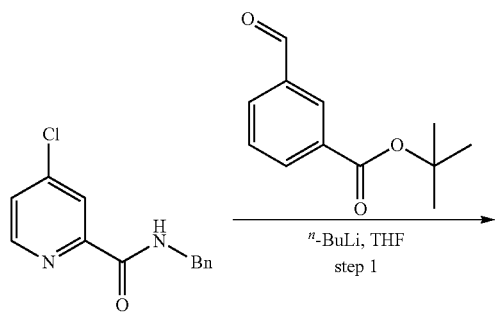

-continued

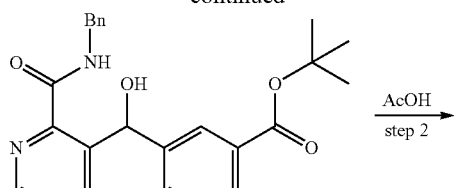

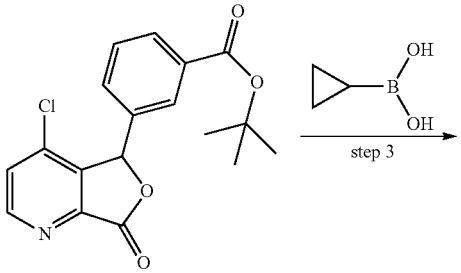

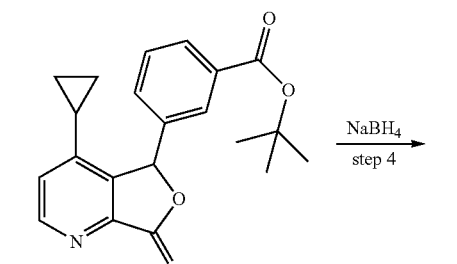

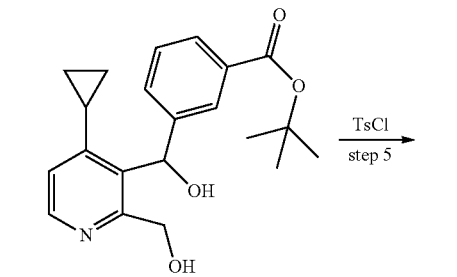

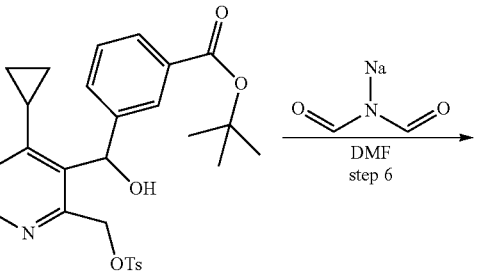

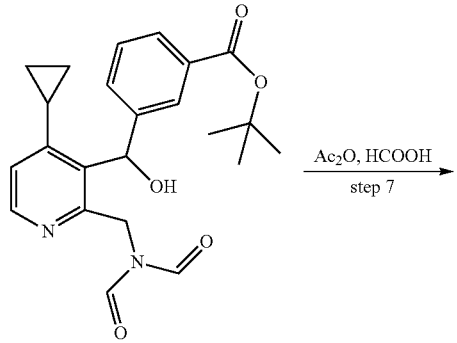

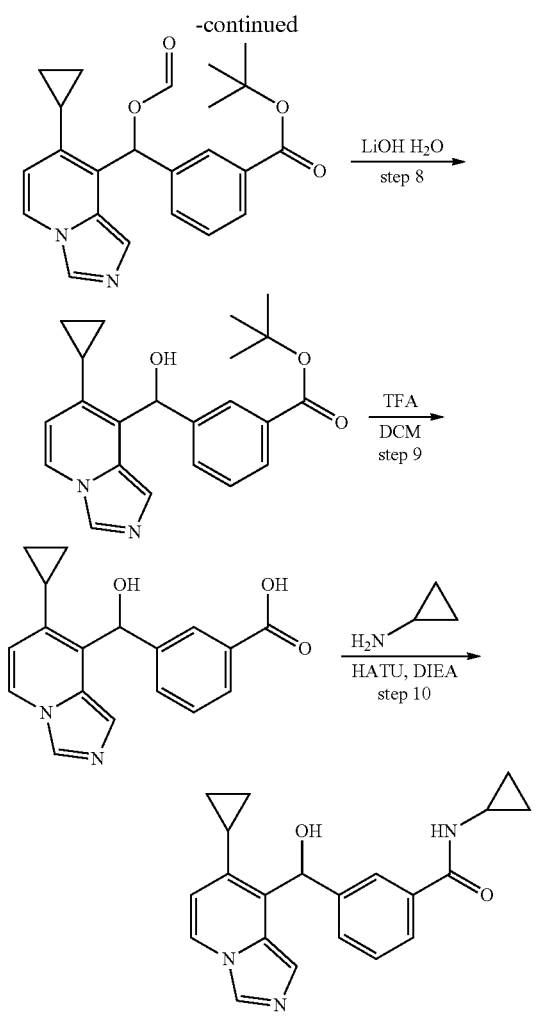

Step 1: tert-butyl 3-((2-(benzylcarbamoyl)-4-chloro-pyridin-3-yl)(hydroxy)methyl)-benzoate To a solution of "Bu-Li (40 mL, 2.4 M) in dry THF (40 mL) was added a solution of N-benzyl-4-chloropicolinamide (12 g, 48 mmol) in dry THF (50 mL) slowly at −70° C. under nitrogen and the mixture was stirred for 30 min before tert-butyl 3-formylbenzoate (20 g, 120 mmol) was added drop wise at −70° C. and the mixture was stirred for 1 h before quenched with water (0.2 L), extracted with EA (40 mL*3), combined and dried over Na₂SO₄, filtered to remove solid and the filtrate was evaporated to give crude product and this crude was use for next step without further purification.

Step 2: tert-butyl 3-(4-chloro-7-oxo-5,7-dihydrofuro[3,4-b]pyridin-5-yl)benzoate A mixture of tert-butyl 3-((2-(benzylcarbamoyl)-4-chloropyridin-3-yl)(hydroxy)methyl) benzoate (crude, 48 mmol) in AcOH (0.2 L) was stirred at room temperature for overnight. Evaporated the solvent before EA (0.4 L) was added, washed with water, saturated aqueous of NaHCO₃ and brine, the organic layer was evaporated to give crude product, further purification by column chromatography (PE:EA=5:1 to PE:EA=1:1) to give 11 g light solid.

Step 3: tert-butyl 3-(4-cyclopropyl-7-oxo-5,7-dihydrofuro[3,4-b]pyridin-5-yl)benzoate To a solution of tert-butyl 3-(4-chloro-7-oxo-5,7-dihydrofuro[3,4-b]pyridin-5-yl)benzoate (3.5 g, 10 mmol) in 1,4-Dioxane (0.1 L) was added cyclopropylboronic acid (1.7 g, 20 mmol), Pd(dppf)Cl₂ (0.8 g, 1.0 mmol) and K₂CO₃ (5.5 g, 40 mmol) and the mixture was heated at 90° C. for 6 hours. Cooled to room temperature and filtered to remove the solid, the filtrate was evaporated before EA (1.0 L) was added, and filtered by silicone pad, the filtrate was evaporated and purified by column chromatography (PE:EA=1:1) to give 3.3 g as a brown solid.

Step 4: tert-butyl 3-((4-cyclopropyl-2-(hydroxymethyl)pyridin-3-yl)(hydroxy)methyl) benzoate To a solution of tert-butyl 3-(4-cyclopropyl-7-oxo-5,7-dihydrofuro[3,4-b]pyridin-5-yl)benzoate (12 g, 34 mmol) in EtOH (0.3 L) was added batch wise of NaBH₄ (2.6 g, 68 mmol) at room temperature and the mixture was heated at 50° C. for 2 hours. Evaporated the solvent and water (0.1 L) was added, extracted with EA (0.2 L*3), combined the organic layer, dried over Na₂SO₄, filtered and the filtrate was evaporated to give crude product and this was used for next step without further purification.

Step 5: tert-butyl 3-((4-cyclopropyl-2-((tosyloxy)methyl)pyridin-3-yl)(hydroxy)methyl) benzoate To a solution of tert-butyl 3-((4-cyclopropyl-2-(hydroxymethyl)pyridin-3-yl)(hydroxy)-methyl)benzoate (crude, 34 mmol) in dry DCM (0.3 L) was added Et₃N (7.0 g, 68 mmol) and TsCl (7.8 g, 41 mmol) at room temperature and the mixture was stirred for 4 hours. Water (0.2 L) was added, isolated the organic layer and dried over Na₂SO₄, filtered and the filtrate was evaporated to give crude product. And this was used for next step without further purification.

Step 6: tert-butyl 3-((4-cyclopropyl-2-((N-formylformamido)methyl)pyridin-3-yl)(hydroxy)methyl) benzoate To a solution of tert-butyl 3-((4-cyclopropyl-2-((tosyloxy)methyl)pyridin-3-yl)(hydroxy)methyl)benzoate (crude, 34 mmol) in dry DMF (0.3 L) was added sodium diformamide (6.4 g, 68 mmol) at room temperature and the mixture was heated at 80° C. for 2 hours. Evaporated the solvent before EA (0.5 L) was added and washed with brine, isolated the organic layer and evaporated to give crude product as a brown solid. And this was used for next step without further purification.

Step 7: tert-butyl 3-((7-cyclopropylimidazo[1,5-a]pyridin-8-yl)(formyloxy)methyl)benzoate To a solution of tert-butyl 3-((4-cyclopropyl-2-((N-formylformamido)methyl)pyridin-3-yl)(hydroxy)methyl)benzoate (crude, 34 mmol) in Ac₂O (0.2 L) was added HCOOH (0.1 L) at room temperature and the mixture was heated at 50° C. for 4 hours. Evaporated the solvent and EA (0.2 L) was added, washed with saturated aqueous of NaHCO₃ and brine, evaporated the solvent to give crude product and this was used for next step without further purification.

Step 8: tert-butyl 3-((7-cyclopropylimidazo[1,5-a]pyridin-8-yl)(hydroxy)methyl)benzoate To a solution of tert-butyl 3-((7-cyclopropylimidazo[1,5-a]pyridin-8-yl)(formyloxy) methyl)benzoate (crude, 34 mmol) in a MeOH (60 mL) was added LiOH H₂O (3.0 g, 68 mmol) at room temperature and the mixture was stirred for 4 hours. Evaporated the solvent, water (0.1 L) was added, extracted with EA (40 mL*3), combined the organic layer, evaporated the solvent and purified by column chromatography (EA/PE=1:1 to EA) to give 2.0 g as a white solid. $^1$H NMR (DMSO-d$_6$) 8.18 (s, 1H), 8.14 (d, 1H, J=7.2 Hz), 8.00 (s, 1H), 7.67-7.72 (m, 2H), 7.40 (t, 1H, J=7.6 Hz), 7.20 (s, 1H), 6.18-6.23 (m, 2H), 2.30-2.31 (m, 1H), 1.50 (s, 9H), 0.90-0.98 (m, 2H), 0.70-0.80 (m, 2H).

Step 9: 3-((7-cyclopropylimidazo[1,5-a]pyridin-8-yl)(hydroxy)methyl)benzoic acid To a solution of tert-butyl 3-((7-cyclopropylimidazo[1,5-a]pyridin-8-yl)(hydroxy)methyl) benzoate (2.0 g, 5.5 mmol) in dry DCM (50 mL) was added TFA (10 mL) at room temperature and the mixture was stirred for overnight. Evaporated the solvent to give crude product, and this was used for next step without further purification.

Step 10: N-cyclopropyl-3-((7-cyclopropylimidazo[1,5-a]pyridin-8-yl)(hydroxy)methyl)benzamide (Example B125)

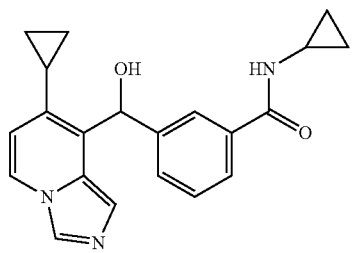 [SMILES: O=C(NC1CC1)c1cccc(C(O)c2c(C3CC3)ccn3cncc23)c1]

To a solution of 3-((7-cyclopropylimidazo[1,5-a]pyridin-8-yl)(hydroxy)methyl) benzoic acid (0.1 g, 0.32 mmol) in dry DMF (10 mL) was added HATU (243 mg, 0.64 mmol), DIEA (165 mg, 1.28 mmol) at room temperature and the mixture was stirred for 0.5 h before cyclopropanamine (37 mg, 0.64 mmol) was added and the mixture was stirred for 6 hours. Water (20 mL) was added and extracted with EA (20 mL*3), combined and washed with brine, evaporated the solvent to give crude product, further purification by Pre-HPLC to give 15 mg in 14% yield. $^1$H NMR (DMSO-d$_6$) 8.43 (d, 1H, J=4.0 Hz), 8.21 (s, 1H), 8.16 (d, 1H, J=6.8 Hz), 7.95 (s, 1H), 7.63 (d, 1H, J=7.6 Hz), 7.53 (d, 1H, J=7.6 Hz), 7.33 (t, 1H, J=7.6 Hz), 7.23 (s, 1H), 6.49 (d, 1H, J=3.2 Hz), 6.25 (d, 1H, J=7.2 Hz), 6.15 (s, 1H), 2.79-2.81 (m, 1H), 2.29-2.32 (m, 1H), 0.92-0.96 (m, 2H), 0.74-0.76 (m, 2H), 0.65-0.69 (m, 2H), 0.55-0.57 (m, 2H).

Example B126: cyclohexyl(7-(cis-2-fluorocyclopropyl)imidazo[1,5-a]pyridin-8-yl)methanol

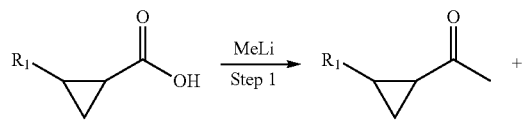

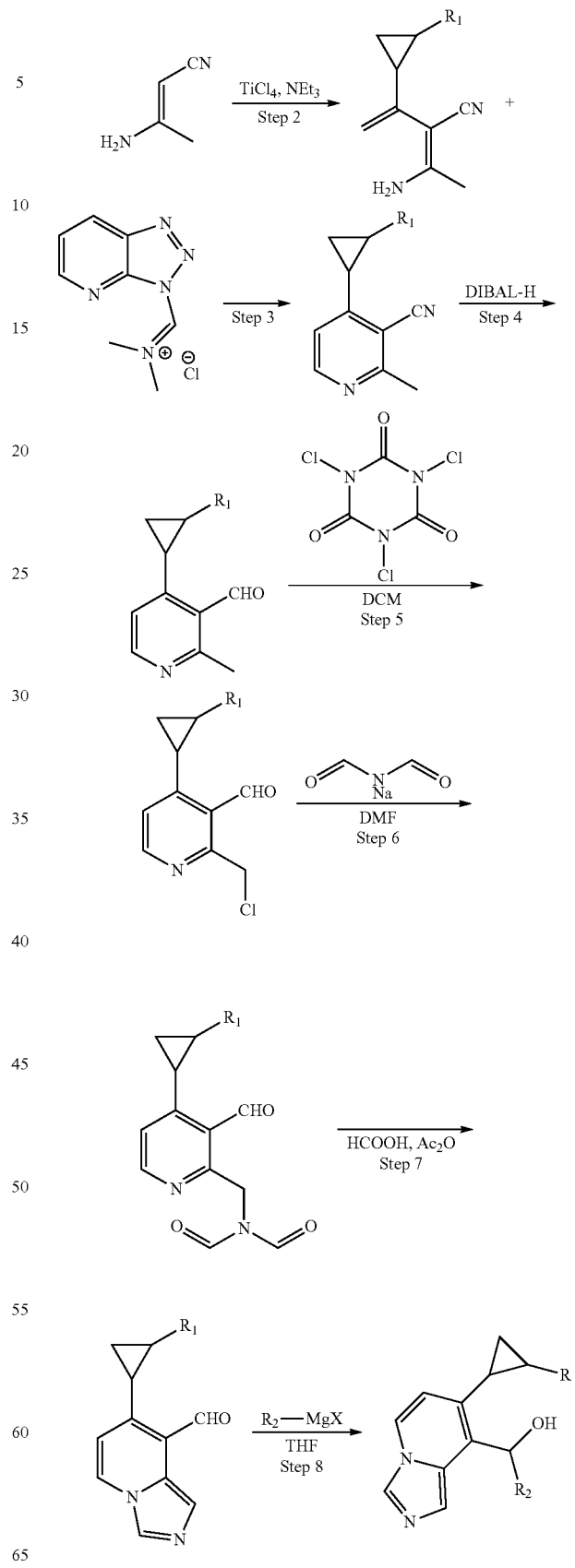

Step 1: (cis-2-Fluorocyclopropyl) ethan-1-one

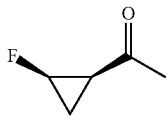

MeLi (1.6 M in Et$_2$O, 44 mL, 70 mmol) was slowly added to a cooled solution of cis-2-fluorocyclopropane-1-carboxylic acid (3.63 g, 35 mmol) in anhydrous Et$_2$O (60 mL) at −78° C. over 1.5 h. The resultant mixture was stirred at −78° C. for 15 min and slowly warmed to 0° C. and stirred for 2 h. The reaction mixture was carefully treated with water (100 mL), extracted with MeOt-Bu (100 mL*2), dried over Na$_2$SO$_4$ and concentrated to give (cis-2-fluorocyclopropyl) ethan-1-one (2.8 g, 77%) as a colorless oil. $^1$H NMR (DMSO-d$_6$) δ 5.01-4.82 (m, 1H), 2.27 (m, 1H), 2.23 (s, 3H), 1.69-1.59 (m, 1H), 1.12-1.06 (m, 1H).

Steps 2 and 3: 4-((cis-2-Fluorocyclopropyl)-2-methylnicotinonitrile

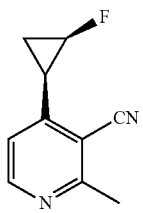

To a solution of β-aminocrotononitrile (3.4 g, 42 mmol) and NEt$_3$ (10.7 mL, 77 mmol) in DCM (50 mL) cooled with an ice bath was added slowly with stirring a solution of TiCl$_4$ (1M in DCM, 21 mL, 21 mmol). Subsequently, (cis-2-fluorocyclopropyl) ethan-1-one (2.8 g, 27.5 mmol) in DCM (20 mL) was added in one portion. 4 h later, the reaction mixture was concentrated and MeOt-Bu (300 mL) was added. The resultant slurry was stirred at room temperature for 1 h, then filtered and washed with MeOt-Bu (200 mL). Evaporation of the solvent afforded the crude product which was used directly for the next step.

To the crude β-enaminonitrile in DCM (200 mL) was added iminium salt (11 g, 52.5 mmol) in one portion. The reaction mixture was stirred at room temperature for 20 h and 2N NaOH (200 mL) was added. After stirred for 15 min later, the organic phase was separated and the water phase was extracted with DCM (100 mL*2). The combined organic phase was washed with brine (200 mL), dried over Na$_2$SO$_4$ and purified on silica gel chromatography (Petroleum ether/Ethyl acetate=10:1) to provide 4-((cis-2-fluorocyclopropyl)-2-methylnicotinonitrile (1.92 g, 40%) as a colorless oil. $^1$H NMR (DMSO-d$_6$) δ 8.58 (d, J=5.2 Hz, 1H), 7.26 (d, J=5.2 Hz, 1H), 5.16 (m, 1H), 2.68 (s, 3H), 2.46-2.34 (m, 1H), 1.69 (dtd, J=23.2, 7.7, 3.0 Hz, 1H), 1.51-1.38 (m, 1H). MS (ESI) m/e [M+1]$^+$177.1.

Step 4: 4-(cis-2-Fluorocyclopropyl)-2-methylnicotinaldehyde

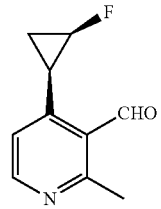

To a stirred solution of 4-((cis-2-fluorocyclopropyl)-2-methylnicotinonitrile (1.76 g, 10 mmol) in DCM (25 mL) was added DIBAL-H (1.0 M in PhMe, 25 mL, 25 mmol) dropwise at −78° C. and stirred at the same temperature for 1 h. The reaction mixture was poured into 2N HCl (100 mL) at 0° C. and then neutralized with NaOH. Then extracted with EA (100 mL*3), washed with brine (100 mL), dried over Na$_2$SO$_4$ and purified on silica gel chromatography (Petroleum ether/Ethyl acetate=10:1) to provide 4-(cis-2-fluorocyclopropyl)-2-methylnicotinaldehyde (1.42 g, 79%) as a light yellow solid. $^1$H NMR (DMSO-d$_6$) δ 10.67 (s, 1H), 8.55 (d, J=5.2 Hz, 1H), 7.33 (d, J=5.2 Hz, 1H), 5.17-4.96 (m, 1H), 2.72 (s, 3H), 2.69 (m, 1H), 1.54-1.47 (m, 1H), 1.40-1.27 (m, 1H). MS (ESI) m/e [M+1]$^+$180.1.

Step 5: 2-(Chloromethyl)-4-(cis-2-fluorocyclopropyl)nicotinaldehyde

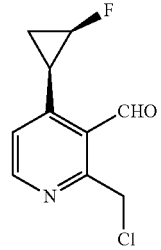 [SMILES: O=Cc1c([C@H]2C[C@H]2F)ccnc1CCl]

To a stirred solution of 4-(cis-2-fluorocyclopropyl)-2-methylnicotinaldehyde (1.42 g, 7.9 mmol) in DCM (40 mL) was added 1,3,5-trichloro-1,3,5-triazinane-2,4,6-trione (2.21 g, 9.5 mmol) at room temperature. After stirring for 20 h, the mixture was filtered and the filtrate was washed with aqueous NaHCO$_3$(50 mL). Dried over Na$_2$SO$_4$ and concentrated to give 2-(chloromethyl)-4-(cis-2-fluorocyclopropyl) nicotinaldehyde (1.7 g, quant.) as a white solid. $^1$H NMR (DMSO-d$_6$) δ 10.69 (s, 1H), 8.66 (d, J=5.2 Hz, 1H), 7.51 (d, J=5.2 Hz, 1H), 5.17-5.00 (m, 3H), 2.73 (m, 1H), 1.60-1.54 (m, 1H), 1.40-1.34 (m, 1H). MS (ESI) m/e [M+1]$^+$214.0.

Steps 6 and 7: 7-(cis-2-Fluorocyclopropyl)imidazo[1,5-a]pyridine-8-carbaldehyde

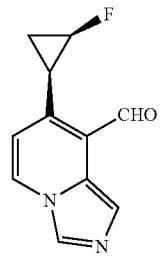 [SMILES: O=Cc1c([C@H]2C[C@H]2F)ccn2cncc12]

Sodium diformamide (1.5 g, 15.8 mmol) was added to a stirred solution of 2-(chloromethyl)-4-(cis-2-fluorocyclopropyl)nicotinaldehyde (1.69 g, 7.9 mmol) in DMF (30 mL). The reaction mixture was stirred at room temperature for 5.5 h. Then the mixture was concentrated and EA/water (100 mL/100 mL) was added. The organic phase was separated and the water phase was extracted with EA (100 mL*3). The combined organic phase was washed with brine (100 mL), dried over Na$_2$SO$_4$ and concentrated to give N-((4-(cis-2-fluorocyclopropyl)-3-formylpyridin-2-yl)methyl) formamide. MS (ESI) m/e [M+1]$^+$223.1; A 1:1 mixture (20 mL) of HCOOH and Ac$_2$O was stirred at 50° C. for 1.5 h. After cooled to room temperature, the mixture was added to N-((4-(cis-2-fluorocyclopropyl)-3-formylpyridin-2-yl)methyl)formamide at the same temperature. 20 h later, the reaction mixture was concentrated and sat. aq. NaHCO$_3$ (50 mL) was carefully added. Then 2N NaOH was added to maintain the pH>12. The water phase was extracted with EA (3*50 mL), dried over Na$_2$SO$_4$ and purified on silica gel chromatography (DCM/MeOH=50:1) to provide 7-(cis-2-fluorocyclopropyl)imidazo[1,5-a]pyridine-8-carbaldehyde (1.32 g, 82%) as a waxy solid. $^1$H NMR (DMSO-d$_6$) δ 10.62 (s, 1H), 8.62 (d, J=7.2 Hz, 1H), 8.43 (s, 1H), 7.84 (s, 1H), 6.79 (d, J=7.2 Hz, 1H), 5.25-4.98 (m, 1H), 2.80-2.73 (m, 1H), 1.55-1.37 (m, 2H). MS (ESI) m/e [M+1]$^+$ 205.1.

Step 8: Cyclohexyl (7-(cis-2-fluorocyclopropyl) imidazo[1,5-a]pyridin-8-yl)methanol

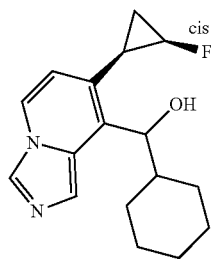

B126a

Fast isomer in normal HPLC
Two isomers

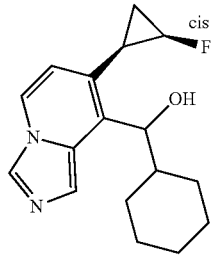

B126b

Slow isomer in normal HPLC
Two isomers

To a solution of 7-(cis-2-fluorocyclopropyl)imidazo[1,5-a]pyridine-8-carbaldehyde (114 mg, 0.56 mmol) in THF (2 mL) was added cyclohexylmagnesium chloride (1.3 M in PhMe/THF, 0.64 mL, 0.84 mmol) at 0° C. The reaction mixture was stirred at 0° C. for 40 min and then quenched with sat. aq. NH$_4$Cl (10 mL). The mixture was diluted with DCM (50 mL) and the organic phase was separated and washed with brine (20 mL), dried over Na$_2$SO$_4$ and purified on silica gel chromatography (DCM/MeOH=100:3) to provide cyclohexyl(7-(cis-2-fluorocyclopropyl)imidazo [1,5-a]pyridin-8-yl)methanol as two diastereoisomers (95 mg, 59%). Major (Example B126a): light yellow solid, $^1$H NMR (CDCl$_3$) δ 8.09 (s, 1H), 7.82 (d, J=7.2 Hz, 1H), 7.67 (s, 1H), 6.51 (d, J=7.2 Hz, 1H), 5.02-4.82 (m, 1H), 4.94 (d, J=9.2 Hz, 1H), 2.37 (br d, J=12.4 Hz, 1H), 2.20-2.06 (m, 2H), 1.83 (br d, J=12.4 Hz, 1H), 1.65-1.58 (m, 2H), 1.28-1.06 (m, 7H), 0.95-0.86 (m, 1H). MS (ESI) m/e [M+1]$^+$289.1; Minor (Example B126b): light yellow solid, $^1$H NMR (CDCl$_3$) δ 8.05 (s, 1H), 7.77 (d, J=7.2 Hz, 1H), 7.63 (s, 1H), 6.46 (d, J=7.2 Hz, 1H), 5.04 (d, J=9.0 Hz, 1H), 4.94-4.74 (m, 1H), 2.30-2.27 (m, 1H), 2.14-2.05 (m, 1H), 1.89-1.60 (m, 3H), 1.38-1.06 (m, 7H), 0.97-0.88 (m, 1H). MS (ESI) m/e [M+1]$^+$ 289.1.

Example B127a and B127b: 2-Cyclohexyl-1-(7-(cis-2-fluorocyclopropyl)imidazo[1,5-a]pyridin-8-yl)ethan-1-ol

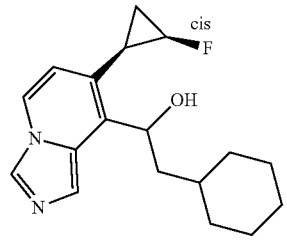

B127a

Fast isomer in normal HPLC
Two isomers

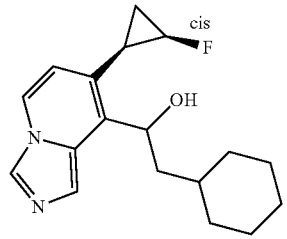

B127b

Slow isomer in normal HPLC
Two isomers

To a solution of 7-(cis-2-fluorocyclopropyl)imidazo[1,5-a]pyridine-8-carbaldehyde (52 mg, 0.25 mmol) in THF (2 mL) was added cyclohexyl methyl magnesium bromide (0.5 M in THF, 0.76 mL, 0.38 mmol) at 0° C. The reaction mixture was stirred at 0° C. for 1.5 h and then quenched with sat. aq. NH$_4$Cl (10 mL). The mixture was diluted with DCM (50 mL) and the organic phase was separated and washed with brine (20 mL), dried over Na$_2$SO$_4$ and purified on prepared TLC (DCM/MeOH=100:5) to provide 2-cyclohexyl-1-(7-(cis-2-fluorocyclopropyl) imidazo[1,5-a] pyridine-8-yl)ethan-1-ol (12 mg, 16%) as two diastereoisomers. Major (Example B127a: light yellow solid, $^1$H NMR (DMSO-d$_6$) δ 8.30 (s, 1H), 8.15 (d, J=7.2 Hz, 1H), 7.51 (s, 1H), 6.51 (d, J=7.2 Hz, 1H), 5.31 (br d, J=3.6 Hz, 1H), 5.27-5.24 (m, 1H), 5.10-4.91 (m, 1H), 2.16-2.08 (m, 1H), 1.94-1.81 (m, 2H), 1.77-1.49 (m, 4H), 1.45-1.03 (m, 7H), 0.96-0.85 (m, 2H). MS (ESI) m/e [M+1]$^+$303.2; Minor (Example B127b: light yellow solid, $^1$H NMR (DMSO-d$_6$) δ 8.29 (s, 1H), 8.14 (d, J=7.2 Hz, 1H), 7.50 (s, 1H), 6.49 (d, J=7.2 Hz, 1H), 5.46-5.33 (m, 1H), 5.26 (d, J=3.2 Hz, 1H), 5.06-4.71 (m, 1H), 2.24-2.10 (m, 1H), 1.93-1.82 (m, 2H), 1.76-1.45 (m, 5H), 1.45-1.05 (m, 6H), 0.96-0.87 (m, 2H). MS (ESI) m/e [M+1]$^+$303.1.

Example B128: Cyclohexyl(7-((trans)-2-fluorocyclopropyl)imidazo[1,5-a]pyridin-8-yl)methanol

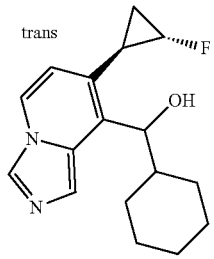 [SMILES: OC(c1c([C@H]2C[C@@H]2F)ccn2cncc12)C1CCCCC1]

This compound including four isomers was prepared by following the similar procedures as Example B126. $^1$H NMR (CDCl$_3$) δ 8.04 (s, 1H), 7.76 (d, J=7.2 Hz, 1H), 7.62 (s, 1H), 6.11 (d, J=7.2 Hz, 0.5H), 6.06 (d, J=7.2 Hz, 0.5H), 5.08 (d, J=8.8 Hz, 0.5H), 5.02 (d, J=7.2 Hz, 0.5H), 4.79-4.71 (m, 0.5H), 4.63-4.55 (m, 0.5H), 3.75-3.62 (m, 0.5H), 3.43-3.35 (m, 0.5H), 2.60-2.42 (m, 1H), 2.35-1.95 (m, 2H), 1.90-0.80 (m, 11H). MS (ESI) m/e [M+1]+289.1.

Example B128a, B128b and B128c: Cyclohexyl(7-((trans)-2-fluorocyclopropyl)imidazo[1,5-a]pyridin-8-yl)methanol

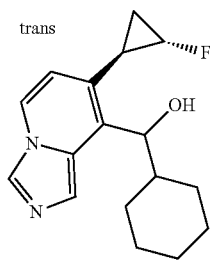

B128a

First trans isomer in chiral AS HPLC
Eluting reagent:
CO$_2$/EtOH 0.1% DEA = 60/40 (/V/V)
Two isomers

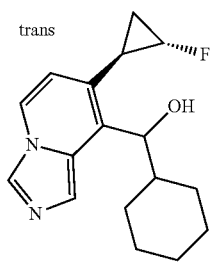

B128b

Second trans isomer in chiral AS HPLC
Eluting reagent:
CO$_2$/EtOH 0.1% DEA = 60/40 (/V/V)
single isomer -continued

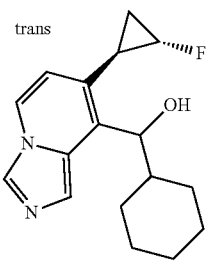

B128c

Third trans isomer in chiral AS HPLC
Eluting reagent:
CO$_2$/EtOH 0.1% DEA = 60/40 (/V/V)
single isomer This compound including four isomers was then separated using preparative HPLC on a CHIRALCEL AS-H column with Eluting reagent: CO$_2$/EtOH 0.1% DEA=60/40 (/V/V) as an eluent. The enantiomeric excesses were determined by using HPLC on a CHIRALCEL AS-H column with CO$_2$/EtOH 0.1% DEA=60/40 (/V/V) as an eluent at a flow rate of 2.0 mL/min. Peak 1 (B128a) including two isomers eluted at the retention time of 4.60 min, (20 mg, two isomers) as an off-white solid. $^1$H NMR (DMSO-d$_6$) δ 8.35 (s, 1H), 8.13 (d, J=7.2 Hz, 1H), 7.43 (s, 1H), 5.38-5.28 (m, 1H), 5.04-4.80 (m, 2H), 2.25-2.13 (m, 1H), 2.04-1.85 (m, 2H), 1.81-1.41 (m, 3H), 1.30-0.80 (m, 8H). MS (ESI) m/e [M+1]$^+$289.1; Peak 2 (B128b) as a single isomer eluted at the retention time of 5.60 min, (6.0 mg, single isomer) as an off-white solid. $^1$H NMR (CDCl$_3$-dl) δ 8.06 (s, 1H), 7.76 (d, J=7.0 Hz, 1H), 7.62 (s, 1H), 6.06 (d, J=7.0 Hz, 1H), 5.08 (d, J=8.8 Hz, 1H), 4.77-4.55 (m, 1H), 3.10-2.90 (m, 1H), 2.62-2.48 (m, 1H), 2.38-1.96 (m, 3H), 1.90-1.45 (m, 4H), 1.40-0.80 (m, 6H). MS (ESI) m/e [M+1]$^+$ 289.1; and Peak 3 (B128c) as a single isomer eluted at the retention time of 7.14 min, (6.0 mg, single isomer) as an off-white solid. $^1$H NMR (CDCl$_3$-d$_1$) δ 8.07 (s, 1H), 7.77 (d, J=7.0 Hz, 1H), 7.63 (s, 1H), 6.11 (d, J=7.0 Hz, 1H), 5.03 (d, J=8.8 Hz, 1H), 4.90-4.57 (m, 1H), 3.10-2.95 (m, 1H), 2.62-2.48 (m, 1H), 2.38-1.96 (m, 3H), 1.90-1.50 (m, 4H), 1.40-0.80 (m, 6H). MS (ESI) m/e [M+1]$^+$ 289.1.

Example B129: Benzyl-3-((7-cyclopropylimidazo[1,5-a]pyridin-8-yl)(hydroxy)methyl) piperidine-1-carboxylate

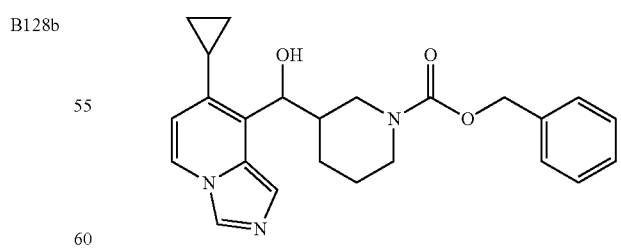

Example B129 was synthesized by following the procedures similar to those in Example B107 under appropriate conditions recognized by one of ordinary skill in the art. $^1$H NMR (DMSO-d$_6$) δ 8.27-8.25 (m, 1H), 8.20-8.10 (m, 1H), 7.42-7.29 (m, 5H), 6.17 (d, J=7.4 Hz, 1H), 5.52-5.49 (m, 1H), 5.08-5.05 (m, 1H), 4.99-4.93 (m, 1H), 4.49-4.47 (m, 0.5H), 3.94-3.91 (m, 1H), 3.60-3.57 (m, 0.5H), 2.88-2.62 (m, 2H), 2.28-1.98 (m, 2H), 1.71-0.68 (m, 8H). MS (ESI, m/e) [M+1]$^+$406.2.

Example B130a and B130b: (7-Cyclopropylimidazo[1,5-a]pyridin-8-yl)(1-(methylsulfonyl)piperidin-3-yl)methanol

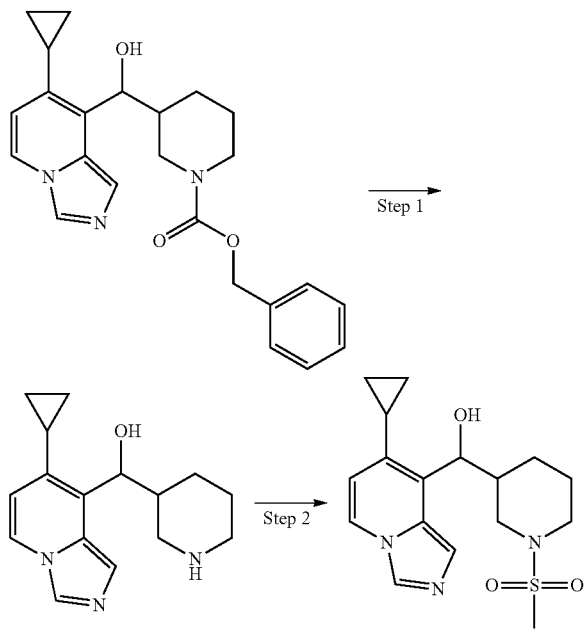

Step 1: (7-cyclopropylimidazo[1,5-a]pyridin-8-yl)(piperidin-3-yl)methanol

A mixture of benzyl 3-((7-cyclopropylimidazo[1,5-a]pyridin-8-yl)(hydroxy)methyl) piperidine-1-carboxylate (1.0 g, 2.47 mmol), Pd/C (50 mg) in EtOH (10 ml) was stirred at RT for 16 hr then the mixture was filtrated and the filtrate was concentrated to give the 500 mg (74.6%) of (7-cyclopropylimidazo[1,5-a]pyridin-8-yl)(piperidin-3-yl)methanol as yellow solid. MS (ESI, m/e) [M+1]$^+$272.2.

Step 2: (7-cyclopropylimidazo[1,5-a]pyridin-8-yl)(1-(methylsulfonyl)piperidin-3-yl)methanol

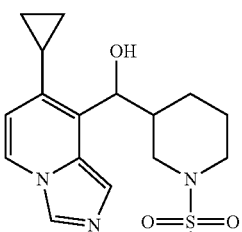

B130a

Fast isomer in normal HPLC
Two isomers

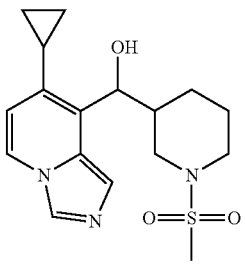

B130b

Slow isomer in normal HPLC
Two isomers

To a solution of (7-cyclopropylimidazo[1,5-a]pyridin-8-yl)(piperidin-1-yl)methanol (100 mg, 0.37 mmol), Et$_3$N (56 mg, 0.56 mmol) in DCM (10 mL) was added methanesulfonyl chloride (42 mg, 0.37 mmol). The mixture was stirred at RT for 30 min, then was quenched with aqueous NH$_4$Cl (10 ml) and extracted with EA (10 mL*3). The organic layer was concentrated to give crude product and purified by Prep-HPLC to afford two diastereoisomers: 2.6 mg (2.0%) as an off-white solid (B130a). $^1$H NMR (CD$_3$OD) δ 8.09 (s, 1H), 7.94 (d, J=7.4 Hz, 1H), 7.42 (s, 1H), 6.18 (d, J=7.4 Hz, 1H), 5.18 (d, J=8.4 Hz, 1H), 3.49-3.36 (m, 1H), 3.19-3.12 (m, 1H), 2.72-2.63 (m, 1H), 2.60 (s, 3H), 2.57-0.60 (m, 11H). MS (ESI) m/e [M+1]$^+$350.2, and 3.5 mg (2.7%) as an off-white solid (B130b). $^1$H NMR (CD$_3$OD) δ 8.09 (s, 1H), 7.95 (d, J=7.4 Hz, 1H), 7.42 (s, 1H), 6.17 (d, J=7.4 Hz, 1H), 5.12 (d, J=9.4 Hz, 1H), 4.10-3.99 (m, 1H), 3.53-3.49 (m, 1H), 2.76 (s, 3H), 2.69-0.60 (m, 12H). MS (ESI) m/e [M+1]$^+$350.2.

Example B131: tert-Butyl (2-(3-((7-cyclopropylimidazo[1,5-a]pyridin-8-yl)(hydroxy) methyl)piperidin-1-yl)-2-oxoethyl) carbamate

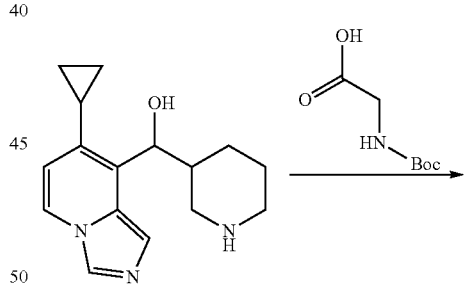

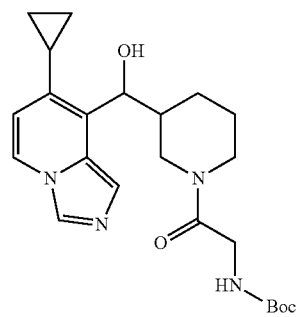

A solution of (7-cyclopropylimidazo[1,5-a]pyridin-8-yl)(piperidin-3-yl)methanol (150 mg, 0.55 mmol), (tert-butoxycarbonyl)glycine (96 mg, 0.55 mmol), HATU (210 mg, 0.55 mmol), Et$_3$N (56 mg, 0.56 mmol) in DMF (5 mL) was stirred at RT for 16 hr, then the mixture was quenched with H₂O (10 ml) and extracted with EA (10 mL*3). The organic layer was concentrated to give crude product and purified by Prep-TLC to afford 120 mg (51.1%) of tert-butyl (2-(3-((7-cyclopropylimidazo[1,5-a]pyridin-8-yl)(hydroxy)methyl) piperidin-1-yl)-2-oxoethyl)carbamate as a yellow solid. ¹H NMR (CDCl₃) δ 8.29-8.16 (m, 1H), 7.82-7.80 (m, 1H), 7.55-7.54 (m, 1H), 6.19-6.16 (m, 1H), 5.56-5.43 (m, 1H), 5.20-5.17 (m, 1H), 4.43-0.72 (m, 25H). MS (ESI, m/e) [M+1]⁺429.2.

Example B132: 2-Amino-1-(3-((7-cyclopropylimi-dazo[1,5-a]pyridin-8-yl)(hydroxy)methyl) piperidin-1-yl)ethan-1-one

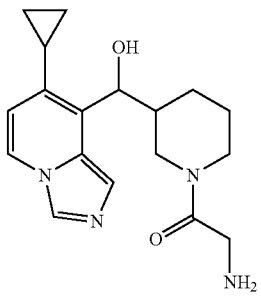 [SMILES: NCC(=O)N1CCCC(C(O)c2c(C3CC3)ccn3cncc23)C1]

A solution of tert-butyl (2-(3-((7-cyclopropylimidazo[1,5-a]pyridin-8-yl)(hydroxy) methyl)piperidin-1-yl)-2-oxo-ethyl)carbamate (100 mg, 0.23 mmol), TFA (1 mL) in DCM (5 mL) was stirred at RT for 2 hr, then the mixture was quenched with aqueous NaHCO₃ and extracted with DCM (10 mL*3). The organic layer was concentrated to give crude product and purified by Prep-TLC to afford 35 mg (46.7%) of tert-butyl (2-(3-((7-cyclopropylimidazo[1,5-a]pyridin-8-yl)(hydroxy)methyl)piperidin-1-yl)-2-oxoethyl)carbamate as a yellow solid. ¹H NMR (DMSO-d₆) δ 8.24-8.22 (m, 1H), 8.15-8.13 (m, 1H), 7.47 (s, 1H), 7.37-7.35 (m, 1H), 7.20 (br s, 2H), 6.18-6.15 (m, 1H), 5.58-4.85 (m, 1H), 4.14-0.73 (m, 16H). MS (ESI, m/e) [M+1]⁺329.2.

Example B133a and B133b: 1-(3-((7-Cyclopropy-limidazo[1,5-a]pyridin-8-yl)(hydroxy)methy)piperi-din-1-yl)ethan-1-one

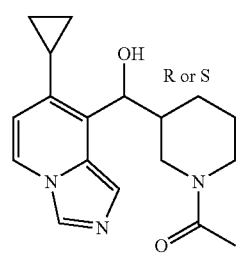

Fast isomer in normal HPLC
Two isomers

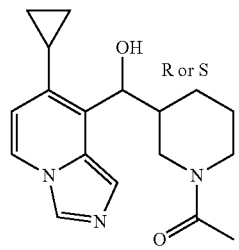

Slow isomer in normal HPLC
Two isomers

The desired compound was synthesized by following the procedures similar to those in Example B107 under appropriate conditions recognized by one of ordinary skill in the art and purified by Prep-HPLC to afford two diastereoisomers. (B133a as a rotomer): ¹H NMR (400 MHz, DMSO-d₆) δ 8.23 (s, 0.4H), 8.22 (s, 0.5H), 8.15 (d, J=7.2 Hz, 0.4H), 8.13 (d, J=7.2 Hz, 0.5H), 7.44 (s, 0.4H), 7.37 (s, 0.5H), 6.17 (d, J=7.2 Hz, 1H), 5.52 (d, J=3.7 Hz, 0.4H), 5.43 (d, J=3.7 Hz, 0.5H), 5.11-5.02 (m, 0.4H), 5.02-4.94 (m, 0.5H), 4.21-0.64 (m, 14H), 1.89 (s, 1.7), 1.59 (s, 1.3H). MS (ESI, m/e) [M+1]⁺314.2; (B133b as a rotomer): ¹H NMR (400 MHz, DMSO-d₆) δ 8.23 (s, 0.5H), 8.22 (s, 0.5H), 8.14 (d, J=7.2 Hz, 0.5H), 8.12 (d, J=7.2 Hz, 0.5H), 7.43 (s, 0.5H), 7.37 (s, 0.5H), 6.17 (d, J=7.2 Hz, 0.5H), 6.15 (d, J=7.2 Hz, 0.5H), 5.54 (d, J=3.0 Hz, 0.5H), 5.46 (d, J=3.0 Hz, 0.5H), 5.08-4.75 (m, 1H), 4.17-3.99 (m, 1H), 3.71-0.64 (m, 14H), 2.05 (s, 1.5H), 1.98 (s, 1.5H). MS (ESI, m/e) [M+1]⁺314.2.

Example B134: (3-((7-Cyclopropylimidazo[1,5-a]pyridin-8-yl)(hydroxy)methyl)piperidin-1-yl)(phe-nyl) methanone

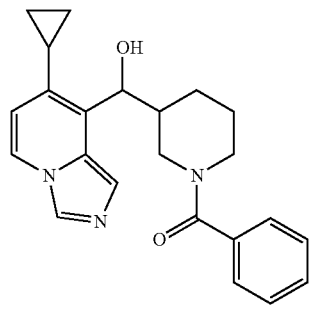 [SMILES: O=C(c1ccccc1)N1CCCC(C(O)c2c(C3CC3)ccn3cncc23)C1]

The desired compound was synthesized by following the procedures similar to those in Example B107 under appropriate conditions recognized by one of ordinary skill in the art. ¹H NMR (DMSO-d₆) δ 8.43-8.39 (m, 1H), 8.15 (s, 1H), 7.40-7.33 (m, 6H), 6.21 (s, 1H), 5.61-3.98 (m, 3H), 2.92-0.70 (m, 14H). MS (ESI, m/e) [M+1]⁺ 376.2.

Example B135a and B135b: 3-((7-Cyclopropylimidazo[1,5-a]pyridin-8-yl)(hydroxy)methyl)piperidine-1-sulfonamide

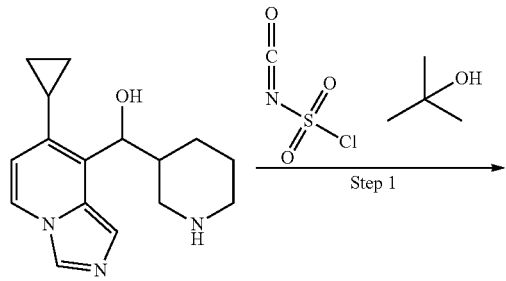

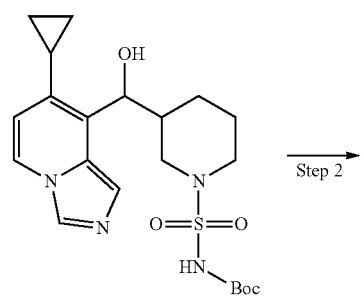

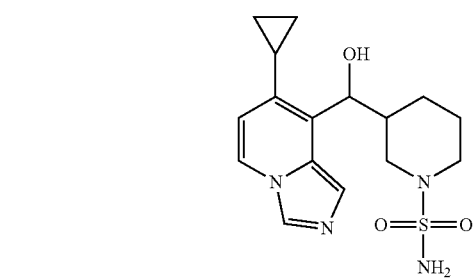

Step 1: tert-butyl ((3-((7-cyclopropylimidazo[1,5-a]pyridin-8-yl)(hydroxy)methyl)piperidin-1-yl)sulfonyl)carbamate A solution of (7-cyclopropylimidazo[1,5-a]pyridin-8-yl)(piperidin-3-yl)methanol (50 mg, 0.19 mmol), sulfurisocyanatidic chloride (26 mg, 0.19 mmol), t-BuOH (14 mg, 0.19 mmol), Et₃N (37 mg, 0.37 mmol) in DCM (5 mL) was stirred at RT for 2 hr, then was quenched with H₂O (5 ml) and extracted with DCM (5 mL*3). The organic layer was concentrated to give crude product and purified by column chromatograph using 5% MeOH in DCM to afford 45 mg (54.2%) of tert-butyl ((3-((7-cyclopropylimidazo[1,5-a]pyridin-8-yl)(hydroxy)methyl)piperidin-1-yl)sulfonyl)carbamate as a yellow solid. MS (ESI) m/e [M+1]⁺450.2.

Step 2: 3-((7-cyclopropylimidazo[1,5-a]pyridin-8-yl)(hydroxy)methyl)piperidine-1-sulfonamide

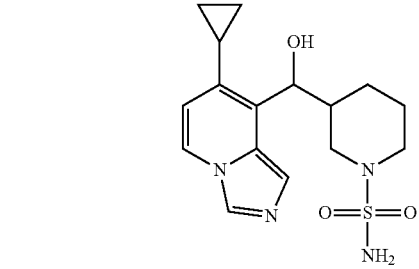

Fast isomer in normal HPLC
Two isomers

B135b

Slow isomer in normal HPLC
Two isomers

A solution of tert-butyl ((3-((7-cyclopropylimidazo[1,5-a]pyridin-8-yl)(hydroxy) methyl)piperidin-1-yl)sulfonyl)carbamate (45 mg, 0.10 mmol), TFA (2 mL) in DCM (10 mL) was stirred at RT for 16 hr then the mixture was quenched with aqueous NaHCO₃ and extracted with DCM (10 mL*3). The organic layer was concentrated to give crude product and purified by Prep-HPLC to afford two diastereoisomers. (5.5 mg, 15.7%, B135a): ¹H NMR (400 MHz, DMSO-d₆) δ 8.22 (s, 1H), 8.13 (d, J=7.2 Hz, 1H), 7.40 (s, 1H), 6.61 (s, 2H), 6.22 (d, J=7.2 Hz, 1H), 5.46 (d, J=3.4 Hz, 1H), 5.11-4.99 (m, 1H), 3.06-2.97 (m, 1H), 2.55-0.63 (m, 13H). MS (ESI, m/e) [M+1]⁺351.1; (9.0 mg, 25.7%, B135b): ¹H NMR (400 MHz, DMSO-d₆) δ 8.23 (s, 1H), 8.13 (d, J=7.2 Hz, 1H), 7.40 (s, 1H), 6.72 (s, 2H), 6.17 (d, J=7.2 Hz, 1H), 5.52 (d, J=2.8 Hz, 1H), 5.07-4.91 (m, 1H), 2.47-2.36 (m, 2H), 2.28-2.09 (m, 2H), 1.70-1.55 (m, 1H), 1.37-0.64 (m, 9H). MS (ESI, m/e) [M+1]⁺351.1.

Example B137: (7-Cyclopropylimidazo[1,5-a]pyridin-8-yl)(1-((2,2-diethoxyethoxy)methyl)cyclohexyl)methanol

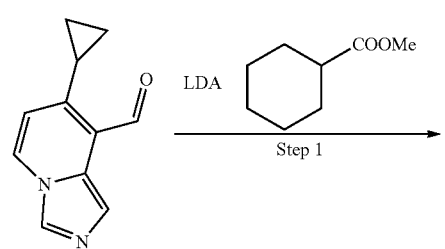

-continued

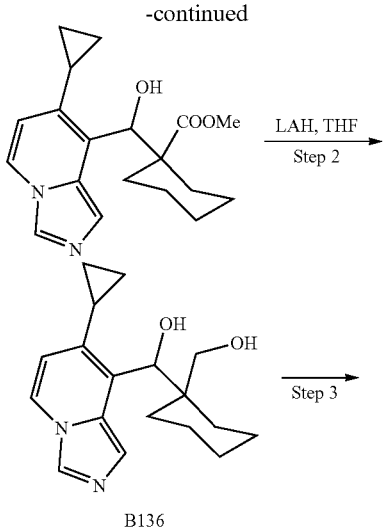

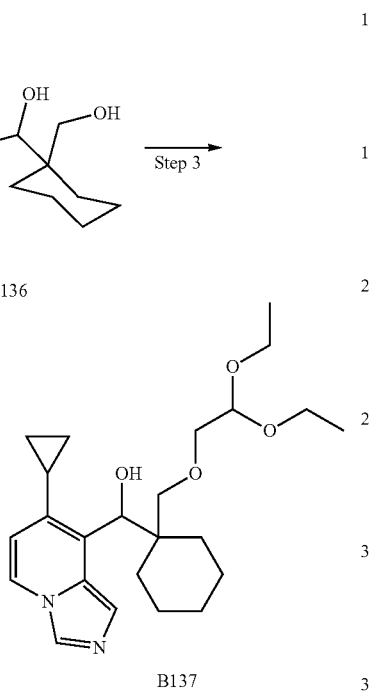

B136

Step 1: Methyl 1-((7-cyclopropylimidazo[1,5-a]pyridin-8-yl)(hydroxy)methyl)cyclohexane-1-carboxylate

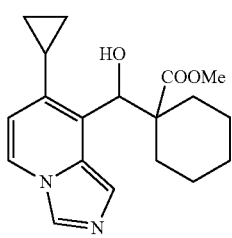 [SMILES: COC(=O)C1(C(O)c2c(C3CC3)ccn3cncc23)CCCCC1]

To a solution of (i-Pr)$_2$NH (518 mg, 5.13 mmol) in THF (20 mL) was added n-BuLi (3.2 mL, 1.6 mol/L) at −30° C. under N$_2$. The mixture was stirred for 30 min. A solution of methyl cyclohexanecarboxylate (767 mg, 5.4 mmol) in THF (5 mL) was added at −70° C. and stirred for 1 h. A solution of 7-cyclopropylimidazo[1,5-a]pyridine-8-carbaldehyde (500 mg, 2.7 mmol) in THF (10 mL) was then added at −70° C. Then slowly warmed up to RT and stirred overnight. The reaction was quenched with water (30 mL) and extracted with DCM (50 mL*2). The combined organic layers were washed with brine (80 mL*3), dried over anhydrous Na$_2$SO$_4$, filtered and concentrated. The residue was purified by pre-HPLC to give the desired product as a light green solid (61 mg, 7%). $^1$H NMR (400 MHz, DMSO-d$_6$) 9.33 (s, 1H), 8.37 (d, J=7.4 Hz, 1H), 7.82 (s, 1H), 6.53 (d, J=7.4 Hz, 1H), 6.13 (br s, 1H), 5.39 (s, 1H), 3.47 (s, 3H), 2.28-0.75 (m, 15H). MS (ESI) m/e [M+1]$^+$329.2.

Step 2: (7-Cyclopropylimidazo[1,5-a]pyridin-8-yl)(1-(hydroxymethyl)cyclohexyl)methanol (Example B136)

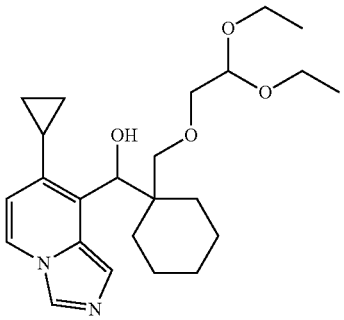 [SMILES: CCOC(COCC1(C(O)c2c(C3CC3)ccn3cncc23)CCCCC1)OCC]

To a mixture of LiAlH$_4$ (13 mg, 0.33 mmol) in THF (5 mL) was added a solution of methyl 1-((7-cyclopropylimidazo[1,5-a]pyridin-8-yl)(hydroxy)methyl)cyclohexane-1-carboxylate (36 mg, mmol) in THF (1 mL) dropwise at 5° C. The mixture was then stirred for 3 h and quenched with 4 N NaOH (5 mL). The resultant mixture was extracted with DCM (15 mL*2). The combined organic layers was washed with brine (20 mL*2), dried over anhydrous Na$_2$SO$_4$, filtered and concentrated. The residue was purified by pre-HPLC to give the desired product as a white solid (61 mg, 7%). $^1$H NMR (400 MHz, DMSO-d$_6$) δ 8.14 (s, 1H), 8.10 (d, J=7.2 Hz, 1H), 7.46 (s, 1H), 6.05 (d, J=7.2 Hz, 1H), 5.47 (d, J=8.8 Hz, 1H), 5.24 (d, J=8.8 Hz, 1H), 4.52-4.49 (m, 1H), 3.85-3.55 (m, 2H), 2.08-0.76 (m, 13H). MS (ESI) m/e [M+1]$^+$301.2.

Step 3: (7-Cyclopropylimidazo[1,5-a]pyridin-8-yl)(1-((2,2-diethoxyethoxy)methyl)cyclohexyl)methanol (Example B137)

To a solution of (7-cyclopropylimidazo[1,5-a]pyridin-8-yl)(1-(hydroxymethyl)cyclohexyl)methanol (300 mL, 1 mmol) in DMF (1 mL), with an ice-water bath, was added 60% NaH (120 mg). It was then stirred at RT for 30 min. 2-Bromo-1,1-diethoxyethane (1.18 g, 6 mmol) was added and heated to 60° C. and stirred overnight. The reaction was cooled to RT and was added water (10 mL). The resultant mixture was extracted with EA (20 mL*2). The combined organic layers were washed with brine (20 mL*2), dried over anhydrous Na$_2$SO$_4$, filtered and concentrated. The residue was purified by pre-HPLC to give the desired product (81 mg, 19%). $^1$H NMR (400 MHz, DMSO-d$_6$) δ

8.19 (s, 1H), 8.10 (d, J=7.3 Hz, 1H), 7.44 (s, 1H), 6.04 (d, J=7.3 Hz, 1H), 5.39 (s, 1H), 5.19 (s, 1H), 4.52 (t, J=5.1 Hz, 1H), 3.62-3.32 (m, 8H), 2.06-1.99 (m, 1H), 1.74-0.73 (m, 20H). MS (ESI) m/e [M+1]$^+$417.3.

Example B138: 3-((7-Cyclopropylimidazo[1,5-a]pyridin-8-yl)(hydroxy)methyl)cyclohexane-1-carboxylic acid Step 1: Dimethyl cyclohexane-1,3-dicarboxylate

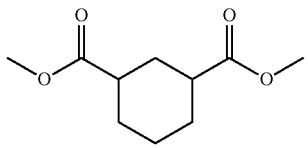

A solution of cyclohexane-1,3-dicarboxylic acid (10.32 g, 60 mmol) in MeOH (130 mL) was added conc. H$_2$SO$_4$ (2.5 mL) and stirred at reflux for 16 hr. The mixture was concentrated and the residue was adjust pH to 7 with saturated aq. NaHCO$_3$, extracted with of EA (200 mL*3), combined the organic layers and dried over Na$_2$SO$_4$, filtered and concentrated to give the desired compound as a colorless oil (12 g, 100%). $^1$H NMR (400 MHz, DMSO-d$_6$) δ 3.61 (s, 6H), 2.69-1.13 (m, 10H). MS (ESI) m/e [M+1]$^+$201.1.

Step 2: 3-(Methoxycarbonyl)cyclohexane-1-carboxylic acid

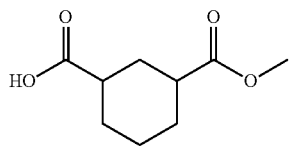

To a solution of dimethyl cyclohexane-1,3-dicarboxylat (2 g, 10 mmol) in MeOH (20 mL) was added a 1N NaOH (10 mL) dropwise over 20 min at 0° C. The resulting mixture was stirred at 0° C. for 30 min and RT for 2 hr. The mixture was concentrated under reduce pressure, and the residue solution was partitioned between EA and water. The aqueous phase was separated, acidified with conc. HCl, saturate with NaCl, and then extracted with EA. The extract was dried over Na$_2$SO$_4$, filtered and concentrated to give the desired compound as colorless oil. $^1$H NMR (400 MHz, DMSO-d$_6$) δ 12.12 (br s, 1H), 3.60 (s, 3H), 2.40-1.15 (m, 10H).

Step 3: Methyl 3-(hydroxymethyl)cyclohexane-1-carboxylate

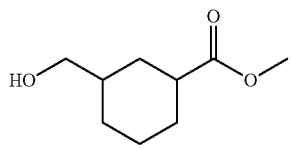

To a solution of 3-(methoxycarbonyl)cyclohexane-1-carboxylic acid (30 g, 160 mmol) in THF (300 mL) was cooled to −78° C. Then BH$_3$.S(CH$_3$)$_2$ (81 mL, 2.0 M) was added dropwise over 2 h. Then the solution was stirred at −78° C. for 2 hr and RT for 16 hrs, and quenched with 2N HCl (20 mL) and water (200 mL), extracted with EA (200 mL*3). Combined organic layers, washed with sat. NaCO$_3$ (200 mL*2), dried over Na$_2$SO$_4$, filtered and concentrated to give the desired compound as colorless oil. MS (ESI) m/e [M+1]$^+$ 173.1.

Step 4: Methyl 3-formylcyclohexane-1-carboxylate

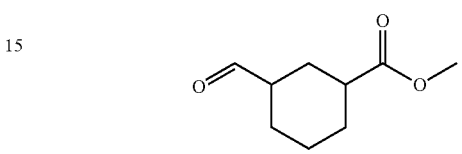

To a solution of methyl 3-(hydroxymethyl)cyclohexane-1-carboxylate (8.7 g, 50.6 mmol) and triethylamine (30.3 g, 300 mmol) in DMSO (100 mL) was added pyridine sulfur trioxide (24.1 g, 150 mmol) and stirred at RT for 16 hrs. Then the solution was pour into water (300 mL) and EA (300 mL), separated. The aqueous phase was extracted with EA (200 mL*2), combined organic layers, dried over Na$_2$SO$_4$, filtered and concentrated, the residue was purified by column chromatography silica-gel (eluting with EA/PE=1/10) to give the desired compound as an oil. MS (ESI) m/e [M+1]$^+$171.1.

Step 5: Methyl 3-((7-cyclopropylimidazo[1,5-a]pyridin-8-yl)(hydroxy)methyl) cyclohexane-1-carboxylate

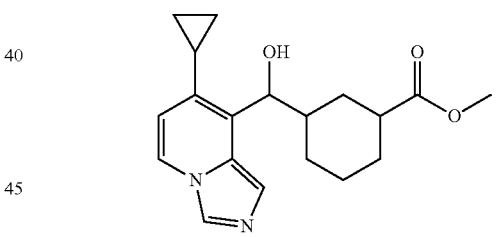

Methyl 3-((7-cyclopropylimidazo[1,5-a]pyridin-8-yl)(hydroxy)methyl)cyclohexane-1-carboxylate was prepared by following the procedures similar to those in Example B122.

Step 6: 3-((7-Cyclopropylimidazo[1,5-a]pyridin-8-yl)(hydroxy)methyl) cyclohexane-1-carboxylic acid

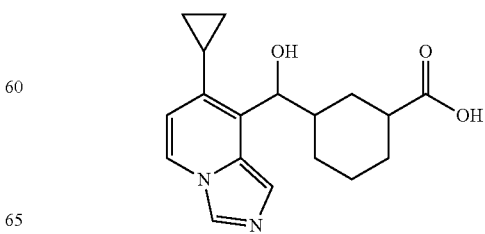

To a solution of methyl 3-((7-cyclopropylimidazo[1,5-a]pyridin-8-yl)(hydroxy) methyl) cyclohexane-1-carboxylate (126 mg, 0.38 mmol) in THF (1 mL) and H₂O (1 mL) was added LiOH (18 mg, 0.76 mmol) and stirred at RT for 16 hrs. Then the THF was removed under vacuum, the residue was extracted with DCM (2 mL*3), combined organic layers, dried over Na₂SO₄, filtered and concentrated, the residue was purified by pre-HPLC to give the desired compound (mixed isomers) as a yellow solid. ¹H NMR (400 MHz, DMSO-d₆) δ 9.30 (s, 1H), 8.34 (d, J=7.4 Hz, 1H), 7.96 (s, 1H), 6.57 (d, J=7.4 Hz, 1H), 5.58-5.55 (m, 1H), 5.01 (d, J=8.1 Hz, 1H), 2.46-2.19 (m, 3H), 1.91-1.65 (m, 3H), 1.24-1.15 (m, 3H), 1.10-1.00 (m, 4H), 0.80-0.77 (m, 2H). MS (ESI) m/e [M+1]⁺315.1.

Examples B139 to B141 were synthesized by following the procedures similar to those in Example B107 under appropriate conditions recognized by one of ordinary skill in the art.

Example B139: bicyclo[3.1.0]hexan-3-yl(7-cyclopropylimidazo[1,5-a]pyridin-8-yl)methanol

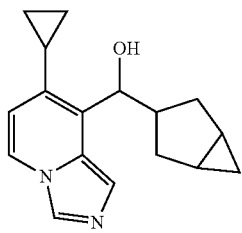 [SMILES: OC(c1c(C2CC2)ccn2cncc12)C1CC2CC2C1]

¹H NMR (CDCl₃-dl₁) δ 9.08 (s, 1H), 7.96 (s, 2H), 6.52-6.40 (m, 1H), 5.33-5.12 (m, 1H), 2.20-1.99 (m, 3H), 1.80-1.76 (m, 1H), 1.64-1.58 (m, 1H), 1.40-0.80 (m, 10H) and 0.31-0.07 (m, 2H). MS (ESI) m/e [M+1]⁺269.

Example B140: bicyclo[4.1.0]heptan-3-yl(7-cyclopropylimidazo[1,5-a]pyridin-8-yl)methanol

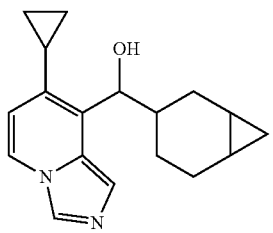 [SMILES: OC(c1c(C2CC2)ccn2cncc12)C1CCC2CC2C1]

¹H NMR (DMSO-d₆) δ 9.22 (s, 1H), 8.31 (d, 1H, J=7.6 Hz), 7.90 (d, 1H, J=7.6 Hz), 6.51-6.55 (m, 1H), 5.57-5.59 (m, 1H), 4.81-4.98 (m, 1H), 1.15-2.37 (m, 7H) and 0.42-0.89 (m, 9H). MS (ESI) m/e [M+1]⁺283.

Example B141: cyclohex-2-en-1-yl(7-cyclopropylimidazo[1,5-a]pyridin-8-yl)methanol

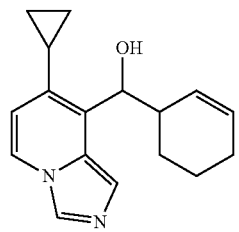 [SMILES: OC(c1c(C2CC2)ccn2cncc12)C1C=CCCC1]

¹H NMR (DMSO-d₆) δ 8.14 (d, 1H, J=7.6 Hz), 7.40 (s, 1H), 6.81-6.85 (m, 1H), 6.36-6.43 (m, 1H), 6.25 (d, 1H, J=7.6 Hz), 4.77-4.79 (m, 1H), 3.87-3.89 (m, 1H), 1.45-2.05 (m, 7H), 0.96-0.97 (m, 2H), 0.79-0.85 (m, 1H) and 0.68-0.70 (m, 2H). MS (ESI) m/e [M+1]⁺269.

Example B142: 5-((7-cyclopropylimidazo[1,5-a]pyridin-8-yl)(hydroxy)methyl)bicyclo[2.2.1]heptan-2-ol

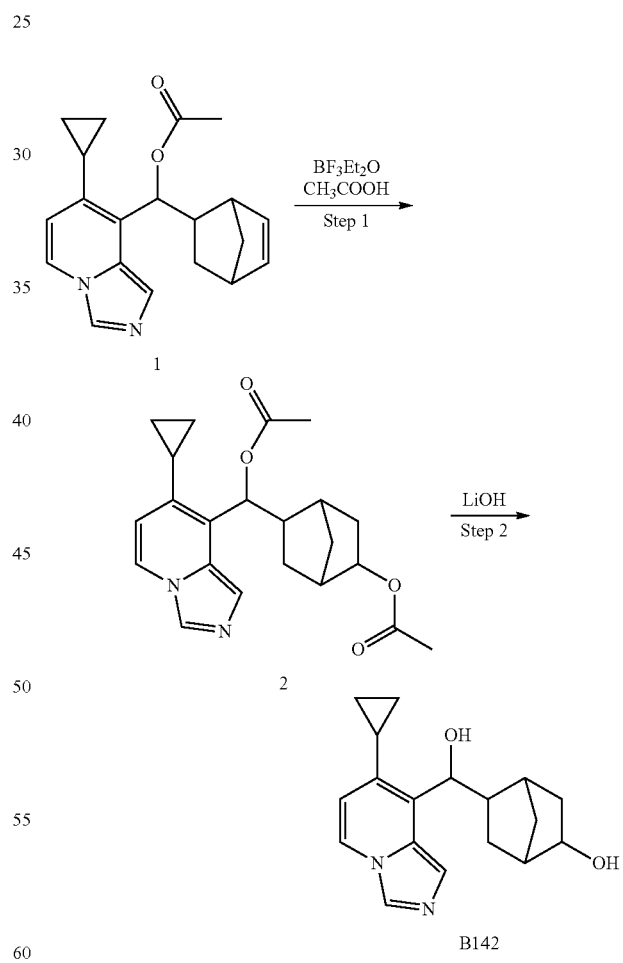

Step 1: 5-(acetoxy(7-cyclopropylimidazo[1,5-a]pyridin-8-yl)methyl)bicyclo[2.2.]heptan-2-yl acetate To a solution of bicyclo[2.2.1]hept-5-en-2-yl(7-cyclopropylimidazo[1,5-a]pyridin-8-yl)methyl acetate (Compound 1 was synthesized as the same procedure as described in the Example B122, 140 mg, 0.43 mmol) in AcOH (10 mL) was slowly added BF$_3$.Et$_2$O (5 drops) at r.t. Then the mixture was stirred for 2 h at 80° C. under N$_2$. The reaction was quenched by the solution of Na$_2$CO$_3$, and extracted with EtOAc (30 ml*3), the organic layer was dried over with Na$_2$SO$_4$, filtered and concentrated to give the crude product, which was further purified by pre-HPLC to give the product 5-(acetoxy(7-cyclopropylimidazo[1,5-a]pyridin-8-yl)methyl) bicyclo[2.2.1]heptan-2-yl acetate (20 mg). MS (ESI) m/e [M+1]$^+$382.7.

Step 2: 5-((7-cyclopropylimidazo[1,5-a]pyridin-8-yl)(hydroxy)methyl)bicyclo[2.2.1]heptan-2-ol

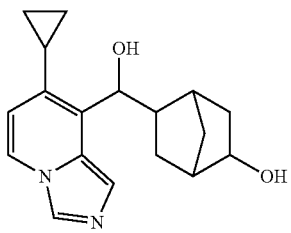 [SMILES: OC1CC2CC1CC2C(O)c1c(C2CC2)ccn2cncc12]

To a solution of 5-(acetoxy(7-cyclopropylimidazo[1,5-a]pyridin-8-yl)methyl) bicyclo[2.2.1]heptan-2-yl acetate (20 mg, 0.052 mmol) in MeOH (10 mL) and H$_2$O (2 ml) was added LiOH (6.24 mg, 0.26 mmol) and stirred for 0.5 h at r.t. under N$_2$. The solvent was removed under vacuum, the residue H$_2$O (20 mL) was added to the mixture, and extracted with EtOAc (25 ml×3), the organic layer was dried over with Na$_2$SO$_4$, filtered and concentrated to give the crude product which was further purified by pre-HPLC to give the product 5-((7-cyclopropylimidazo[1,5-a]pyridin-8-yl)(hydroxy)methyl)bicyclo[2.2.1]heptan-2-ol (5 mg). $^1$H NMR (CD$_3$OD) δ 8.11 (s, 1H), 7.96-7.91 (m, 1H), 7.41-7.35 (m, 1H), 7.26-7.23 (m, 1H), 6.23-6.18 (m, 1H), 3.63-3.52 (m, 2H), 2.50-2.47 (m, 1H), 2.11-2.01 (m, 3H), 1.64-1.21 (m, 4H), 0.95-0.92 (m, 3H), 0.64-0.60 (m, 1H) and 0.45-0.35 (m, 1H). MS (ESI) m/e [M+1]$^+$299.

Example B143: 5-((7-cyclopropylimidazo[1,5-a]pyridin-8-yl)(hydroxy)methyl bicyclo[2.2.1]heptan-2-ol

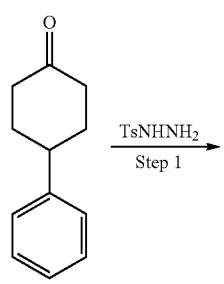

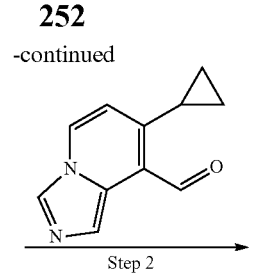

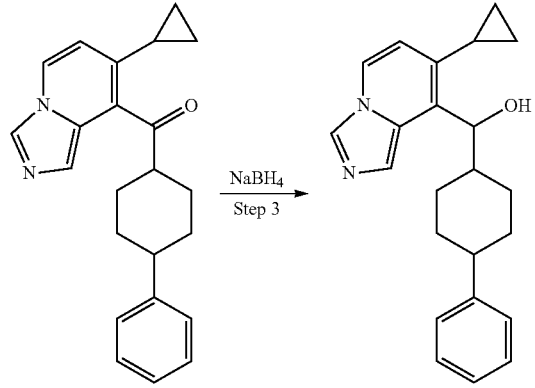

Step 1: Synthesis of 4-methyl-N'-(4-phenylcyclohexylidene)benzenesulfono hydrazide To a solution of 4-phenylcyclohexan-1-one (5.00 g, 28.74 mmol) in methanol (50 mL) was added p-toluenesulfonyl hydrazide (5.34 g, 28.74 mmol). And the mixture was stirred at 70° C. for 3 hours, after cooled to room temperature, water (50 mL) was added and sonicated for 3 minutes, filtered and the filter cake was washed with methanol to give a white solid (4.81 g, yield: 48.94%). $^1$H NMR (DMSO-d$_6$) δ 10.17 (s, 1H), 7.73 (d, J=8.0 Hz, 2H), 7.39 (d, J=8.0 Hz, 2H), 7.15-7.29 (m, 5H), 3.77 (s, 1H), 2.92 (m, 1H), 2.78 (m, 1H), 2.38 (s, 3H), 2.25 (m, 2H), 19.3 (m, 2H), 1.51 (m, 2H).

Step 2: Synthesis of (7-cyclopropylimidazo[1,5-a]pyridin-8-yl)(4-phenyl cyclohexyl)methanone

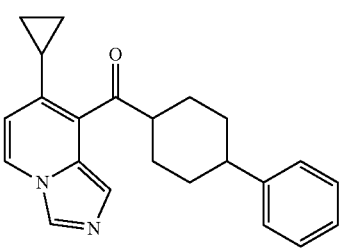

To a solution of 4-methyl-N'-(4-phenylcyclohexylidene)benzenesulfonohydrazide (3.40 g, 10 mmol) and 7-cyclopropylimidazo[1,5-a]pyridine-8-carbaldehyde (1.90 g, 10 mmol) in 1,4-dioxane (200 mL) was added cesium carbonate (4.90 g, 15 mmol). And the mixture was stirred at 110° C. for 8 hours, after cooled to room temperature, concentrated to dryness. The crude product was purified by column chromatography on silica gel (150 g) (PE/EA=1:2 as eluent) to give 1.01 g in 29.07% yield. $^1$H NMR (DMSO-d$_6$) δ 8.29 (m, 2H), 7.20 (m, 6H), 6.24 (m, 1H), 3.18 (m, 1H), 2.64 (m, 1H), 2.36 (m, 1H), 2.01 (m, 1H), 1.79 (m, 4H), 1.53 (m, 2H), 0.91 (m, 2H), 0.78 (m, 2H).

Step 3: Synthesis of (7-cyclopropylimidazo[1,5-a]pyridin-8-yl)(4-phenyl cyclohexyl)methanol

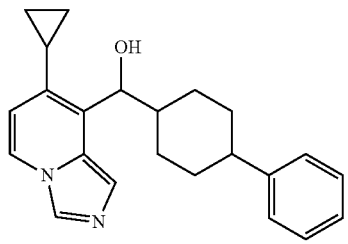 [SMILES: OC(c1c(C2CC2)ccn2cncc12)C1CCC(c2ccccc2)CC1]

To a solution of (7-cyclopropylimidazo[1,5-a]pyridin-8-yl)(4-phenylcyclohexyl) methanone (1.01 g, 2.9 mmol) in ethanol (100 mL) was added sodium borohydride (220 mg, 5.8 mmol). And the mixture was stirred at room temperature for overnight, quenched with water (5 mL), and the mixture was concentrated to dryness. The crude product was purified by column chromatography on silica gel (150 g) (DCM/MeOH=40:1 as eluent) to give 0.88 g in 87.70% yield. $^1$H NMR (DMSO-d$_6$) δ 8.14 (m, 2H), 7.20 (m, 6H), 6.15 (m, 1H), 5.32 (m, 1H), 4.96 (m, 1H), 6.15 (m, 1H), 1.15-2.67 (m, 11H), 0.92 (m, 2H), 0.70 (m, 2H).

Examples B143a and B143b: (S)-(7-cyclopropylimidazo[1,5-a]pyridin-8-yl)(trans or cis-4-phenylcyclohexyl)methanol and (S)-(7-cyclopropylimidazo[1,5-a]pyridin-8-yl)(cis or trans-4-phenylcyclohexyl)methanol

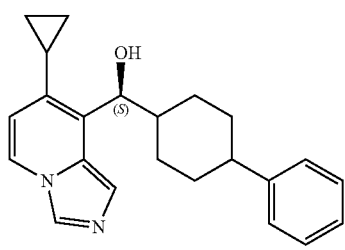

B143a (trans or cis-phenyl)
First isomer in chiral OD HPLC
Eluting reagent: CO$_2$/IPA(0.1% DEA) = 60/40(V/V)

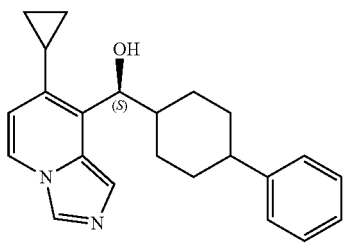

B143b (cis or trans-phenyl)
Third isomer in chiral OD HPLC
Eluting reagent: CO$_2$/IPA(0.1% DEA) = 60/40(V/V)

B143 (4 diastereomeric mixture) was separated into optically pure isomers using preparative HPLC on a Chiralpak OD-H with CO$_2$/EtOH (0.1% DEA)=70/30 (V/V) as an eluent. The enantiomeric excesses were determined by using HPLC on a Chiralpak OD-H with CO$_2$/IPA (0.1% DEA)=60/40 (V/V) as an eluent at a flow rate of 1.0 mL/min. The first enantiomer (the first peak) eluted at the retention time of 7.077 min (B143a), $^1$H NMR (DMSO-d$_6$) δ 8.20 (s, 1H), 8.12 (d, 1H, J=7.2 Hz), 7.43 (s, 1H), 7.11-7.26 (m, 5H), 6.15 (d, 1H, J=7.2 Hz), 5.30 (m, 1H), 4.96 (d, 1H, J=8.4 Hz), 1.15-2.45 (m, 11H), 0.92 (m, 2H), 0.70 (m, 2H); a possible mixture of two isomers (the second peak) co-eluted at the retention time of 9.332 min, but this mixture decomposed when the solution was condensed in vacuum; the third enantiomer (the third peak) eluted at the retention time of 12.13 min (B143b), $^1$H NMR (DMSO-d$_6$) δ 8.20 (m, 1H), 8.12 (m, 1H), 7.55 (s, 1H), 7.16-7.29 (m, 5H), 6.15 (m, 1H), 4.60 (m, 1H), 4.24 (d, 2H, J=5.6 Hz), 1.65-2.81 (m, 11H), 0.94 (m, 2H), 0.77 (m, 2H). The absolute configurations of chiral carbons in B143a and B143b are tentatively assigned as (S) and (S) respectively based on assumption that the binding model of the more potent isomer B143a is the same as that of A101a with IDO1 enzyme.

Example C: Biological Assays

IDO1 Enzymatic Assay

Recombinant IDO1 was overexpressed and purified from *E. coli* cells with an N-terminal His tag. IDO1 enzymatic assay was carried out using a methodology similar to described in the literature (J. Biol. Chem. (1980), 255, 1339-1345.). The reaction mixture contains 50 nM IDO1, 1.3 mM D-tryptophan, 5 mM L-ascorbic acid, 6.25 μM methylene Blue, 0.4 mg/mL catalase and compound (or DMSO) in a buffer containing 50 mM potassium phosphate pH 7.5 and 0.1% BSA. After incubation at 24° C. for 1.5 hours, absorbance of the reaction mixture was continuously read at 321 nm to monitor the formation of N'-formylkynurenine by a FULOstar OMEGA plate reader (BMG LABTECH) for 1 hour. The enzymatic activity was determined by measuring the slope of the linear absorbance increase as a function of time. The IC$_{50}$s are calculated based on remaining enzyme activity in the presence of increasing concentrations of compounds.

TDO Enzymatic Assay

Recombinant TDO was overexpressed and purified from *E. coli* cells with a C-terminal His tag. TDO enzymatic assay was performed using the same methodology as IDO1 enzymatic assay except that 100 nM TDO and 0.5 mM L-tryptophan (Km concentration) were used in the TDO assay.

HeLa Cell-Based IDO1 Kyn (Kynurenine) Production Assay:

The inhibitory activity of IDO1 inhibitors is determined by using a colorimetric reaction to measure Kyn generated from L-Trp (L-Tryptophon) oxidation by cellular IDO1 in HeLa cells after induction of IDO1 by IFN-γ.

Hela cells were obtained from the American Type Tissue Culture Collection and recovered in 10% FBS-containing phenol red-free DMEM medium supplemented with 0.4 mM L-Trp. Cells were plated onto a 96-well plate (100 μl/well) at 8000 cells per well. Human recombinant IFN-γ (8901SC, CST) was added to cells (final concentration 100 ng/mL) to stimulate endogenous IDO1. Compounds at different concentrations diluted in dimethylsulfoxide (DMSO) were added simultaneously with IFN-γ. Cells were kept at 37° C. in a humidified incubator supplied with 5% $CO_2$. After 48 hours of incubation, 100 μl supernatant from each well was removed to a new plate. The protein in the medium was precipitated with the addition of 8 μl 6N trichloroacetic acid. The plate was incubated at 60° C. for 45 min and then centrifugation at 2500 rpm for 10 min to remove sediments. 80 μl supernatants were carefully removed to a new clean plate and added with an equal volume of 2% 4-(Dimethylamino) benzaldehyde (D2004, sigma) dissolved in glacial acetic acid. The absorbance at 480 nm wavelength derived from Kyn was measured using a FULOstar OMEGA plate reader (BMG LABTECH). The $IC_{50}$ for each compound was derived from fitting the dose-response data to the four-parameter logistic model by using Graphpad Prism software.

Protein Purification and Co-Crystallization (A101a)

IDO1 protein was expressed and purified following a protocol similar to described in the literature (Biochimica et Biophysica Acta 1814 (2011) 1947-1954). IDO1 protein was concentrated to 40 mg/ml in a buffer containing 10 mM MES pH6.5, 25 mM NaCl, and 0.5 mM TCEP. Protein solution was incubated with A101a by a molar ratio 1:5 for 1 h at 20° C., and then mixed with a reservoir solution containing 0.1M HEPES pH6.5 and 10% PEG6000. Co-crystals of IDO1 with A101a were obtained by vapor diffusion from sitting drops at 20° C.

X-Ray Data Collection and Structure Determination (A101a)

Nylon loops was used to harvest the IDO1 crystals and then immersed the crystals in mother liquor supplemented with 30% xylitol for 1 min. Synchrotron data were collected on ADSC Q315 CCD detectors at the Shanghai Synchrotron Radiation Facility. Diffraction images were processed with the program HKL2000. The preliminary structure of the IDO1 was solved by molecular replacement using the program PHASER. The IDO1 crystal structure (PDB code 2D0T) was used as the search model. REFMAC5 was used to perform rigid body, TLS, restrained refinement against X-ray data, followed by manually adjustment in COOT program and further refinement in REFMAC5 program.

| Data collection and refinement statistics (A101a). | |
| --- | --- |
| Data collection | |
| Beamline | Shanghai Synchrotron Radiation Facility |
| Space group | P212121 |
| Cell dimensions (Å) | a = 86.062   b = 96.414   c = 130.248 |
| Angles (°) | α = 90.000   β = 90.000   γ = 90.000 |
| Resolution (Å) | 50.00-2.90 |
| Total number of reflections | 24236 |
| Number of unique reflections | 3275 |
| Completeness (%) | 99.5 (100.0) |
| Average redundancy | 7.4 (7.6) |
| $R^a$ merge | 0.167 (0.632) |
| I/sigma (I) | 34.12 (4.59) |
| Wilson B factor (Å) | 62.4 |
| Refinement | |
| Resolution (Å) | 50-2.90 (2.99-2.90) |
| Number of reflections | 22881 |
| rmsd bond lengths (Å) | 0.011 |
| rmsd bond angles (°) | 1.537 |
| $R_{work}^b$ (%) | 22.8 |
| $R_{free}^c$ (%) | 29.0 |
| Average B-factors of protein | 64.910 |
| Ramachandran plot (%) | |
| Allowed | 91.8 |
| Generously allowed | 6.9 |
| Disallowed | 1.4 |

$^a R_{merge} = \Sigma\Sigma_i |I(h)_i - \langle I(h) \rangle| / \Sigma\Sigma_i |I(h)_i|$, where $\langle I(h) \rangle$ is the mean intensity of equivalent
$^b R = \Sigma |Fo - Fc| / \Sigma |Fo|$, where Fo and Fc are the observed and calculated structure factor amplitudes, respectively.
$^c R_{free} = \Sigma |Fo - Fc| / \Sigma |Fo|$, calculated using a test data set, 5% of total data randomly selected from the observed reflections.

Protein Purification and Co-Crystallization (B122a)

IDO1 protein was expressed and purified following a protocol similar to described in the literature (Biochimica et Biophysica Acta 1814 (2011) 1947-1954). IDO1 protein was concentrated to 40 mg/ml in a buffer containing 10 mM MES pH6.5, 25 mM NaCl, and 0.5 mM TCEP. Protein solution was incubated with B122a by a molar ratio 1:4 for 1 h at 20° C., and then mixed with a reservoir solution containing 0.1M HEPES pH7.5 and 10% PEG8000. Co-crystals of IDO1 with B122a were obtained by vapor diffusion from sitting drops at 20° C.

X-Ray Data Collection and Structure Determination (B122a)

Nylon loops was used to harvest the IDO1 crystals and then immersed the crystals in mother liquor supplemented with 20% ethylene glycol for 1 min. Synchrotron data were collected on ADSC Q315 CCD detectors at the Shanghai Synchrotron Radiation Facility. Diffraction images were processed with the program HKL2000. The preliminary structure of the IDO1 was solved by molecular replacement using the program PHASER. The IDO1 crystal structure (PDB code 2D0T) was used as the search model. REFMAC5 was used to perform rigid body, TLS, restrained refinement against X-ray data, followed by manually adjustment in COOT program and further refinement in REFMAC5 program.

| Data collection and refinement statistics (B122a). | |
| --- | --- |
| Data collection | |
| Beamline | Shanghai Synchrotron Radiation Facility |
| Space group | P212121 |
| Cell dimensions (Å) | a = 85.453   b = 91.678   c = 128.087 |
| Angles (°) | α = 90.000   β = 90.000   γ = 90.000 |
| Resolution (Å) | 50.00-2.60 |
| Total number of reflections | 565900 |
| Number of unique reflections | 39381 |
| Completeness (%) | 99.9 (100.0) |
| Average redundancy | 14.4 (14.6) |
| $R^a$ merge | 0.099 (0.547) |
| I/sigma (I) | 52.7 (14.1) |
| Wilson B factor (Å) | 53.2 |

| Data collection and refinement statistics (B122a). | |
|---|---|
| Data collection | |
| Refinement | |
| Resolution (Å) | 50-2.60 (2.67-2.60) |
| Number of reflections | 29916 |
| rmsd bond lengths (Å) | 0.012 |
| rmsd bond angles (Å) | 1.621 |
| $R_{work}^{b}$ (%) | 0.206 |
| $R_{free}^{c}$ (%) | 0.271 |
| Average B-factors of protein | 62 |
| Ramachandran plot (%) | |
| Allowed | 94.71 |
| Generously allowed | 4.07 |
| Disallowed | 1.22 |

[a] $R_{merge} = \Sigma\Sigma_i|I(h)_i - \langle I(h)\rangle|/\Sigma\Sigma_i|I(h)_i|$, where $\langle I(h)\rangle$ is the mean intensity of equivalent
[b] $R = \Sigma|Fo - Fc|/\Sigma|Fo|$, where Fo and Fc are the observed and calculated structure factor amplitudes, respectively.
[c] $R_{free} = \Sigma|Fo - Fc|/\Sigma|Fo|$, calculated using a test data set, 5% of total data randomly selected from the observed reflections.

TABLE 1

Enzymatic activity data IC$_{50}$s (IDO1 and TDO) and cellular activity data EC$_{50}$s (Hela Cell-Based IDO1) of 5-substituted imidazo[1,5-a]pyridines

| | Enzyme IC$_{50}$ (nM) | | Hela Cell-Based |
|---|---|---|---|
| Ex. No. | IDO1 | TDO | IDO1 EC$_{50}$ (nM) |

Table 1a: activity data of 5-substituted imidazo[1,5-a]pyridines having no further ortho and/or meta substitution or having no hydroxyl-substituted chiral α-carbon atom

| Ex. No. | IDO1 | TDO | IDO1 EC$_{50}$ (nM) |
|---|---|---|---|
| A001 | 150 | 260 | >10000 |
| A001a | 41 | 610 | >10000 |
| A001b | 11000 | — | |
| A002 | 150 | — | |
| A003 | 3800 | — | |
| A004 | 360 | — | >10000 |
| A005 | 1500 | — | >10000 |
| A006 | 4600 | — | |
| A007 | 5100 | — | |
| A008 | 2400 | — | >10000 |
| A009 | 110 | 260 | >10000 |
| A010 | 3100 | — | |
| A011 | >100000 | — | |
| A012 | 41000 | — | |
| A013 | >100000 | — | |
| A014 | >100000 | — | |
| A015 | 540 | 260 | >10000 |
| A016 | 23000 | — | >10000 |
| A017 | 62000 | | |
| A018 | 1800 | | |
| A019 | 21000 | | |
| A020 | 8900 | 350 | >10000 |
| A021 | 1800 | — | >10000 |
| A022 | 1200 | 570 | >10000 |
| A023 | 6500 | — | |
| A024 | 3300 | — | |
| A025 | 2500 | — | >10000 |
| A026 | 107 | 73 | |

Table 1b: activity data of 5-substituted imidazo[1,5-a]pyridines having further ortho and/or mesa substitution

| Ex. No. | IDO1 | TDO | IDO1 EC$_{50}$ (nM) |
|---|---|---|---|
| A101 | 29 | 68 | 1358 |
| A101a | 9.6 | 29 | 326 |
| A101b | 890 | 230 | |
| A102 | 67 | 300 | 1764 |
| A102a | 15 | 73 | 346 |
| A102b | 510 | 1200 | >10000 |
| A103 | 22 | 22 | 1514 |
| A104 | 29 | 270 | 2180 |
| A105 | 127 | 1600 | 1693 |
| A106 | 120 | — | 1661 |
| A107 | 26 | 110 | 968 |
| A108 | 36 | 150 | 4438 |
| A109 | 49 | 110 | 1544 |
| A109a | 15 | 97 | 2102 |
| A109b | 1400 | 1200 | >10000 |
| A110 | 66 | 120 | 2088 |
| A111 | 25 | 63 | 962 |
| A112 | 24 | 48 | 1040 |
| A113 | 26 | 1100 | 3222 |
| A114 | 260 | 420 | ND |
| A114a | 890 | 2600 | >10000 |
| A114b | 74 | 170 | 5434 |
| A115 | 180 | 320 | 3157 |
| A116 | 7.5 | 270 | 231 |
| A116a | 11 | 610 | 270 |
| A116b | 4800 | 67000 | >10000 |
| A117 | 28 | 9700 | 143 |
| A117a | 11 | 4100 | 92 |
| A117b | 1600 | 35000 | >10000 |
| A118 | 15 | 5700 | 420 |
| A118a | 14 | 1700 | 346 |
| A118b | 1600 | 53000 | >10000 |
| A119 | 22 | 12000 | 511 |
| A119a | 14 | 14000 | 66 |
| A119b | 1300 | 38000 | 9428 |
| A120 | 37 | 3700 | 1414 |
| A121 | 29 | — | 1575 |
| A122 | 28 | 430 | 268 |
| A123 | 19 | 7900 | 556 |
| A124 | 19 | 8700 | 275 |
| A124a | 9 | 8800 | 92 |
| A124b | 1100 | 95000 | >10000 |
| A125 | 31 | 5600 | 205 |
| A125a | 15 | 4500 | 138 |
| A125b | 12000 | 46000 | >10000 |
| A126 | 65 | 3100 | 291 |
| A126a | 36 | 14000 | 156 |
| A126b | 6800 | 74000 | >10000 |
| A127 | 44 | 3500 | 165 |
| A127a | 17 | 15000 | 169 |
| A127b | 3200 | 25000 | 8008 |
| A128 | 46 | 1100 | 2164 |
| A129 | 30 | 4700 | 69.5 |
| A129a | 14 | 1700 | 38 |
| A129b | 21000 | 37000 | >10000 |
| A130 | 850 | 1700 | 9148 |
| A131 | 28 | 4100 | 939 |
| A132 | 210 | 75000 | ND |
| A133 | 58 | 36000 | 2038 |
| A134 | 59 | 26000 | 8609 |
| A135 | 39 | 2700 | 54 |
| A136 | 30 | 3300 | 1605 |
| A137 | 25 | | 3761 |
| A138 | 25 | 6600 | 418 |
| A139 | 35 | 2400 | 435 |
| A139a | 11 | 1800 | |
| A139b | 4500 | 13000 | |
| A140 | 10000 | 17000 | 7812 |
| A141 | 51 | 3900 | 3149 |
| A142 | 130 | 64000 | 574 |
| A142a | 12 | | 661 |
| A142b | 31 | | 312 |
| A142c | 2000 | | >10000 |
| A142d | 9200 | | >10000 |
| A143 | 15 | 270 | 1115 |
| A143a | 20 | 690 | 274 |
| A143b | 3400 | 14000 | 6097 |
| A144 | 32 | 1500 | 1237 |
| A144a | >100000 | 23000 | >10000 |
| A144b | 14 | 240 | 291 |
| A145 | 110 | 2400 | 3493 |
| A146 | 28 | 210 | 1253 |
| A147 | 420 | | 2787 |

TABLE 1-continued

Enzymatic activity data IC$_{50}$s (IDO1 and TDO) and cellular activity data EC$_{50}$s (Hela Cell-Based IDO1) of 5-substituted imidazo[1,5-a]pyridines

| Ex. No. | Enzyme IC$_{50}$ (nM) IDO1 | TDO | Hela Cell-Based IDO1 EC$_{50}$ (nM) |
|---|---|---|---|
| A148 | 39 | 420 | 1492 |
| A149 | 35 | 160 | 2063 |
| A150 | 130 | 200 | ND |
| A151 | 39 | 600 | 415 |
| A152 | 33 | 7400 | 202 |
| A153 | 500 | 1800 | 6763 |
| A154 | 430 | 8400 | 657 |
| A155 | 1000 | 1600 | |
| A156 | 48 | 190 | 1653 |
| A157 | 200 | | 2684 |
| A158 | 880 | | 933 |
| A159 | 5500 | | >10000 |
| A160 | 81 | | 5607 |
| A161 | 57000 | | >10000 |
| A162 | 32 | | 34 |
| A162a | 11 | | 8.8 |
| A162b | 1600 | | 6038 |
| A163 | 94 | | 102 |
| A164a | 71 | | 598 |
| A164b | 42 | | 226 |
| A164c | 54 | | 570 |
| A165 | 430 | | 1201 |

TABLE 2

Enzymatic activity data IC$_{50}$s (IDO1 and TDO) and cellular activity data EC$_{50}$s (Hela Cell-Based IDO1) of 8-substituted imidazo[1,5-a]pyridines

| Ex. No. | Enzyme IC$_{50}$ (nM) IDO1 | TDO | Hela Cell-Based IDO1 EC$_{50}$ (nM) |
|---|---|---|---|

TABLE 2a: Activity data of 8-substituted imidazo[1,5-a]pyridines having no further ortho substitution or having no hydroxyl-substituted chiral α-carbon atom

| Ex. No. | IDO1 | TDO | IDO1 EC$_{50}$ (nM) |
|---|---|---|---|
| B001 | 1000 | 630 | >10000 |
| B002 | 2000 | 810 | |
| B003 | >100000 | — | |
| B004 | 17000 | 3900 | |
| B005 | 990 | 740 | |
| B006 | 330 | 3300 | >10000 |
| B007 | 6600 | — | >10000 |
| B008 | 620 | 17000 | >10000 |
| B009 | 18000 | — | >10000 |
| B010 | 14000 | — | >10000 |
| B011 | 170 | 190 | >10000 |
| B012 | 130 | 130 | >10000 |
| B013 | 240 | 190 | >10000 |
| B014 | 180 | 100 | >10000 |

TABLE 2b: activity data of 5-substituted imidazo[1,5-a]pyridines having further ortho substitution

| Ex. No. | IDO1 | TDO | IDO1 EC$_{50}$ (nM) |
|---|---|---|---|
| B101 | 14 | 1000 | 439 |
| B102 | 23 | 360 | 1557 |
| B102a | 15 | 150 | 995 |
| B102b | 3100 | 31000 | >10000 |
| B103 | 69 | 8000 | 575 |
| B104 | 38 | 940 | 2930 |
| B105 | 33 | 4900 | 876 |
| B106 | 138 | 1200 | 457 |
| B106a | 23 | | 129 |
| B106b | 1800 | | >10000 |
| B107 | 48 | 850 | 256 |
| B107a | 47 | 1300 | 136 |
| B107b | 21000 | 11000 | >10000 |
| B108 | 59 | 560 | 389 |
| B109 | 35 | 4600 | 940 |
| B110 | 53 | 1000 | 259 |
| B110a | 18 | | 215 |
| B110b | 4.9 | | >10000 |
| B111 | 85 | | 415 |
| B112 | 530 | | 1678 |
| B113 | 1300 | | 9337 |
| B114 | 630 | | 3037 |
| B115 | 120 | | >10000 |
| B116 | 61 | | 4584 |
| B117 | 1100 | | 401 |
| B118 | 280 | | 179 |
| B119a | 280 | | 1357 |
| B119b | 5500 | | >10000 |
| B119c | 7700 | | >10000 |
| B119d | 110 | | 2990 |
| B120 | 790 | | >10000 |
| B121a | 210 | | 719 |
| B121b | 21000 | | >10000 |
| B121c | 110 | | 1675 |
| B121d | 46000 | | >10000 |
| B122 | 53 | | 116 |
| B122a | 58 | | 33 |
| B122b | 78 | | 295 |
| B123 | 260 | | 754 |
| B124 | 440 | | 376 |
| B125 | 170 | | 8502 |
| B126a | 340 | | 942 |
| B126b | 340 | | 676 |
| B127a | 88 | | 595 |
| B127b | 93 | | 1125 |
| B128a | 100 | | 184 |
| B128b | 39000 | | >10000 |
| B128c | 110000 | | >10000 |
| B129 | 310 | | >10000 |
| B130a | 1400 | | >10000 |
| B130b | 1200 | | 909 |
| B131 | 1700 | | >10000 |
| B132 | 13000 | | >10000 |
| B133a | 1900 | | >10000 |
| B133b | 1100 | | 6810 |
| B134 | 2000 | | >10000 |
| B135a | 1100 | | >10000 |
| B135b | 950 | | 1351 |
| B136 | 760 | | 286 |
| B137 | 2200 | | 3288 |
| B138 | 1000 | | >10000 |
| B139 | 85 | | 199 |
| B140 | 71 | | 147 |
| B141 | 45 | | 1696 |
| B142 | 1300 | | 6321 |
| B143 | 100 | | 149 |
| B143a | 56 | | 79 |
| B143b | 300 | | 8662 |

Examples A101 to A165 and Examples B101 to B143 exhibited activity of inhibiting both IDO1 and TDO with IC$_{50}$ values ranging from 0.1 nM to 10 µM as well as activity of inhibiting Hela Cell-Based IDO1 with EC$_{50}$ values ranging less than 10000 nM.

It is to be understood that, if any prior art publication is referred to herein, such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A compound having the structure of Formula (IA):

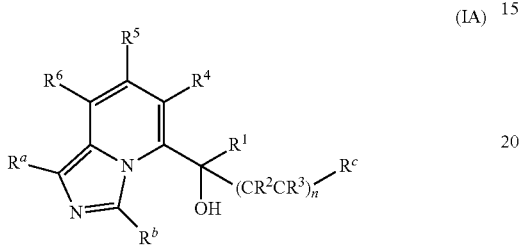

(IA)

or a stereoisomer thereof, or a pharmaceutically acceptable salt thereof,
wherein:
n is 0, 1, 2, 3, or 4;
$R^a$ and $R^b$ are each independently hydrogen, halogen, $C_{1-8}$ alkyl, $C_{1-8}$ haloalkyl, $C_{2-8}$ alkenyl, $C_{2-8}$ alkynyl, $C_{3-8}$ cycloalkyl, heterocyclyl, aryl, or heteroaryl;
$R^1$ is hydrogen, halogen, $C_{1-8}$ alkyl or $C_{1-8}$ haloalkyl;
$R^2$ and $R^3$ are each independently hydrogen, halogen, $OR^7$, $NR^7R^8$, $COR^7$, $SO_2R^7$, $C(=O)OR^7$, $C(=O)NR^7R^8$, $C_{1-8}$ alkyl, $C_{2-8}$ alkenyl, $C_{2-8}$ alkynyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^9$;
$R^4$, $R^5$ and $R^6$ are each independently hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, —CN, —$OR^7$, or —$SR^7$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituent $R^9$,
provided that at least one of $R^4$ and $R^5$ is not hydrogen;
$R^C$ is $C_{3-10}$ cycloalkyl, heterocyclyl or heteroaryl, each optionally substituted with at least one substituent $R^9$;
$R^7$ and $R^8$ are each independently hydrogen, $C_{1-8}$ alkyl, $C_{1-8}$ haloalkyl, $C_{3-8}$ cycloalkyl, heterocyclyl, aryl, or heteroaryl optionally substituted with at least one substituent $R^9$; or $R^7$ and $R^8$ together with the nitrogen atom to which they are attached form a heterocyclyl or heteroaryl ring which optionally comprises a further hetero atom selected from nitrogen, oxygen and sulfur atom, and is optionally substituted with at least one substituent $R^9$;
$R^9$ is hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-NR'R", —CN, —OR', —NR'R", —COR', —$CO_2R'$, —CONR'R", —C(=NR')NR"R'", nitro, —NR'COR", —NR'CONR'R", —NR'CO$_2$R", —SO$_2$R', —SO$_2$aryl, —NR'SO$_2$NR"R'", NR'SO$_2$R", or —NR'SO$_2$aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl; and R', R", and R'" are each independently H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, or heteroaryl, each of which is optionally substituted by one or more halogen, $C_{1-4}$ haloalkyl and $C_{1-4}$ alkyl, or (R' and R"), and/or (R" and R'") together with the atoms to which they are attached, form a ring selected from heterocyclyl optionally substituted by halogen, $C_{1-4}$ haloalkyl and $C_{1-4}$ alkyl and heteroaryl rings optionally substituted by halogen, $C_{1-4}$ haloalkyl and $C_{1-4}$ alkyl.

2. The compound of claim 1 having the structure of Formula (IA):

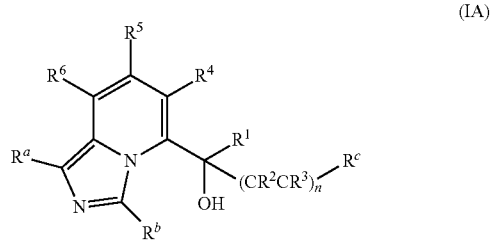

(IA)

or a stereoisomer thereof, or a pharmaceutically acceptable salt thereof,
wherein:
n is 0, 1, 2, 3, or 4;
$R^a$ and $R^b$ are each independently hydrogen, halogen, $C_{1-8}$ alkyl, $C_{1-8}$ haloalkyl, $C_{2-8}$ alkenyl, $C_{2-8}$ alkynyl, $C_{3-8}$ cycloalkyl, heterocyclyl, aryl, or heteroaryl;
$R^1$ is hydrogen, halogen, $C_{1-8}$ alkyl or $C_{1-8}$ haloalkyl;
$R^2$ and $R^3$ are each independently hydrogen, halogen, $C_{1-8}$ alkyl, $C_{2-8}$ alkenyl, $C_{2-8}$ alkynyl, $C_{3-8}$ cycloalkyl, heterocyclyl, aryl, or heteroaryl, wherein said $C_{1-8}$ alkyl, $C_{2-8}$ alkenyl, $C_{2-8}$ alkynyl, $C_{3-8}$ cycloalkyl, heterocyclyl, aryl, and heteroaryl are each independently optionally substituted with at least one substituent $R^9$;
$R^4$, $R^5$ and $R^6$ are each independently hydrogen, halogen, $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, heteroaryl, or —$OR^7$, wherein said $C_{1-8}$ alkyl, $C_{2-8}$ alkenyl, $C_{2-8}$ alkynyl, $C_{3-8}$ cycloalkyl, $C_{1-8}$ haloalkyl, aryl, heterocyclyl, and heteroaryl are each independently optionally substituted with at least one substituted $R^9$,
provided that at least one of $R^4$ and $R^5$ is not hydrogen;
$R^C$ is $C_{3-10}$ cycloalkyl optionally substituted with at least one substituent $R^9$;
$R^7$ is hydrogen, $C_{1-8}$ alkyl, $C_{1-8}$ haloalkyl, $C_{3-8}$ cycloalkyl, heterocyclyl, aryl, or heteroaryl optionally substituted with at least one substituent $R^9$;
$R^9$ is hydrogen, halogen, $C_{1-4}$ haloalkyl, $C_{1-4}$ alkyl, $C_{2-8}$ alkenyl, $C_{3-6}$ cycloalkyl, aryl, heteroaryl, heterocyclyl, alkynyl, oxo, —$C_{1-4}$ alkyl-NR'R", —CN, —OR', —NR'R", —COR', —$CO_2R'$, —CONR'R", nitro, —NR'COR", —NR'CONR'R", —NR'CO₂R", —SO₂R', —SO₂aryl, NR'SO₂R", or —NR'SO₂aryl, wherein said $C_{1-4}$ alkyl, $C_{1-4}$ haloalkyl, $C_{3-6}$ cycloalkyl, aryl, heteroaryl, or heterocyclyl group are each independently optionally substituted by one, two or three substituents selected from halo, hydroxyl, $C_{1-4}$ alkyl and $C_{1-4}$ haloalkyl; and R' and R" are each independently selected from H, $C_{1-4}$ haloalkyl, $C_{1-4}$ alkyl, $C_{2-4}$ alkenyl, $C_{2-4}$ alkynyl, $C_{3-6}$ cycloalkyl, heterocyclyl, aryl, and heteroaryl, each of which is optionally substituted by one or more halogen, $C_{1-4}$ haloalkyl and $C_{1-4}$ alkyl.

3. The compound of claim 1, wherein n is 0, 1 or 2.

4. The compound of claim 1, wherein $R^a$ and $R^b$ are hydrogen.

5. The compound of claim 1, wherein $R^1$ is hydrogen, halogen, $C_{1-6}$ alkyl or $C_{1-6}$ haloalkyl.

6. The compound of claim 1, wherein $R^2$ and $R^3$ are each independently hydrogen, halogen, $C_{1-6}$alkyl, or $C_{1-6}$ haloalkyl.

7. The compound of claim 1, wherein $R^4$ is halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, or —O$C_{1-6}$ alkyl, wherein said aryl or heteroaryl is independently optionally substituted with at least one $R^9$ independently selected from halogen, $C_{1-4}$ haloalkyl, or $C_{1-4}$ alkyl.

8. The compound of claim 7, wherein $R^4$ is halogen, $C_{1-6}$ alkyl, $C_{2-6}$ alkenyl, $C_{2-6}$ alkynyl, $C_{3-6}$ cycloalkyl, $C_{1-6}$ haloalkyl, phenyl optionally substituted with halogen, $C_{1-4}$ alkyl or $C_{1-4}$ haloalkyl, heteroaryl optionally substituted with halogen, $C_{1-4}$ alkyl or $C_{1-4}$ haloalkyl, or —O$C_{1-6}$ alkyl.

9. The compound of claim 7, wherein $R^4$ is F, Cl, Br, I, methyl, isopropyl, propenyl, ethynyl, cyclopropyl, $CF_3$, phenyl, dimethylisoxazolyl or methoxy.

10. The compound of claim 1, wherein $R^4$ is not hydrogen, and $R^5$ is halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, or —O$C_{1-6}$ alkyl, wherein said aryl or heteroaryl is independently optionally substituted with at least one $R^9$ independently selected from halogen, $C_{1-4}$ haloalkyl, or $C_{1-4}$ alkyl.

11. The compound of claim 10, wherein $R^5$ is halogen, $C_{1-6}$alkyl, $C_{2-6}$alkenyl, $C_{2-6}$ alkynyl, $C_{3-6}$ cycloalkyl, $C_{1-6}$ haloalkyl or —O$C_{1-6}$ alkyl.

12. The compound according to claim 7, wherein $R^6$ is halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, or —O$C_{1-6}$ alkyl, wherein said aryl or heteroaryl is independently optionally substituted with at least one $R^9$ independently selected from halogen, $C_{1-4}$ haloalkyl, or $C_{1-4}$ alkyl.

13. The compound according to claim 10, wherein $R^6$ is halogen, $C_{1-6}$ alkyl, $C_{2-6}$ alkenyl, $C_{2-6}$ alkynyl, $C_{3-6}$ cycloalkyl, $C_{1-6}$ haloalkyl, heterocyclyl, aryl, heteroaryl, or —O$C_{1-6}$ alkyl, wherein said aryl or heteroaryl is independently optionally substituted with at least one $R^9$ independently selected from halogen, $C_{1-4}$ haloalkyl, or $C_{1-4}$ alkyl.

14. The compound of claim 1, wherein $R^C$ is $C_{3-8}$ cycloalkyl optionally substituted with at least one substituent $R^9$.

15. The compound of claim 1, wherein $R^C$ is $C_{3-8}$ cycloalkyl optionally substituted with a phenyl.

16. The compound of claim 1, wherein $R^C$ is $C_{3-8}$ cycloalkyl optionally substituted with halogen, $C_{1-4}$ haloalkyl, $C_{1-4}$ alkyl or —NR'COR", wherein said $C_{1-4}$ haloalkyl and $C_{1-4}$ alkyl are optionally substituted with one or more halo or hydroxyl; wherein R' and R" are each independently H, $C_{1-4}$ haloalkyl, $C_{1-4}$ alkyl, $C_{3-6}$ cycloalkyl, heterocyclyl, aryl, or heteroaryl, each of which is optionally substituted by one or more halogen, $C_{1-4}$ haloalkyl or $C_{1-4}$ alkyl.

17. The compound of claim 1, wherein $R^C$ is unsubstituted cyclohexyl.

18. The compound of claim 1, wherein n is zero, and $R^C$ is unsubstituted cyclohexyl or unsubstituted cyclopentyl.

19. The compound of claim 1, wherein n is 1, and $R^C$ is unsubstituted cyclohexyl or unsubstituted cyclopentyl.

20. The compound of claim 1, wherein n is 2, and $R^C$ is unsubstituted cyclohexyl or unsubstituted cyclopentyl.

21. The compound of claim 1, wherein n is zero, and $R^C$ is unsubstituted bicyclo[2.2.1]heptan-2-yl.

22. The compound of claim 1, wherein n is zero, and $R^C$ is 4-phenyl substituted cyclohexyl.

23. The compound of claim 1, wherein the chiral α-carbon atom to which $R^1$ is bonded to is in an S-configuration.

24. A compound selected from the group consisting of:

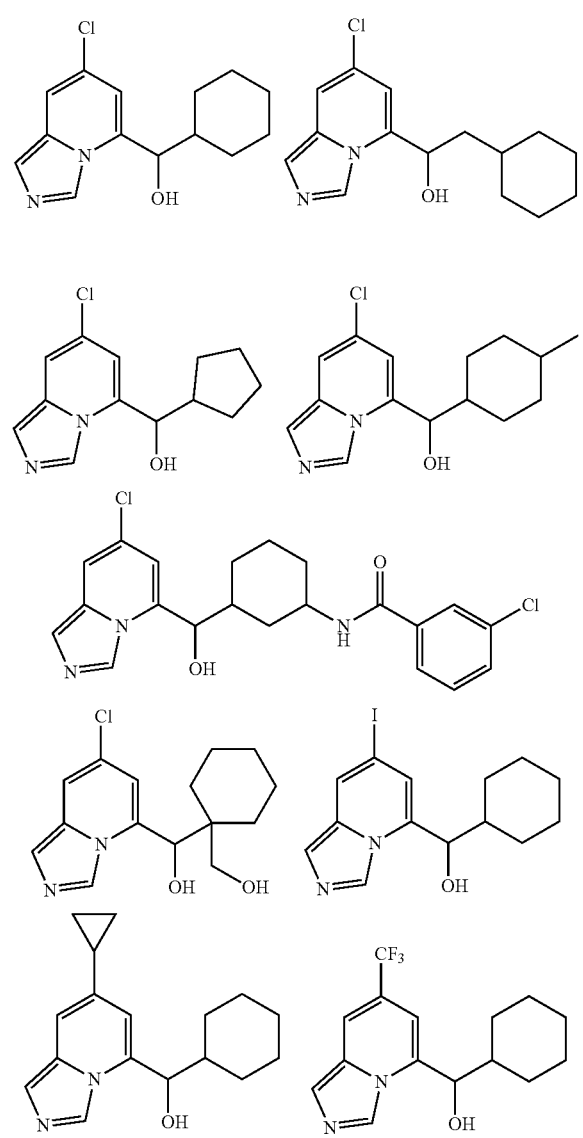

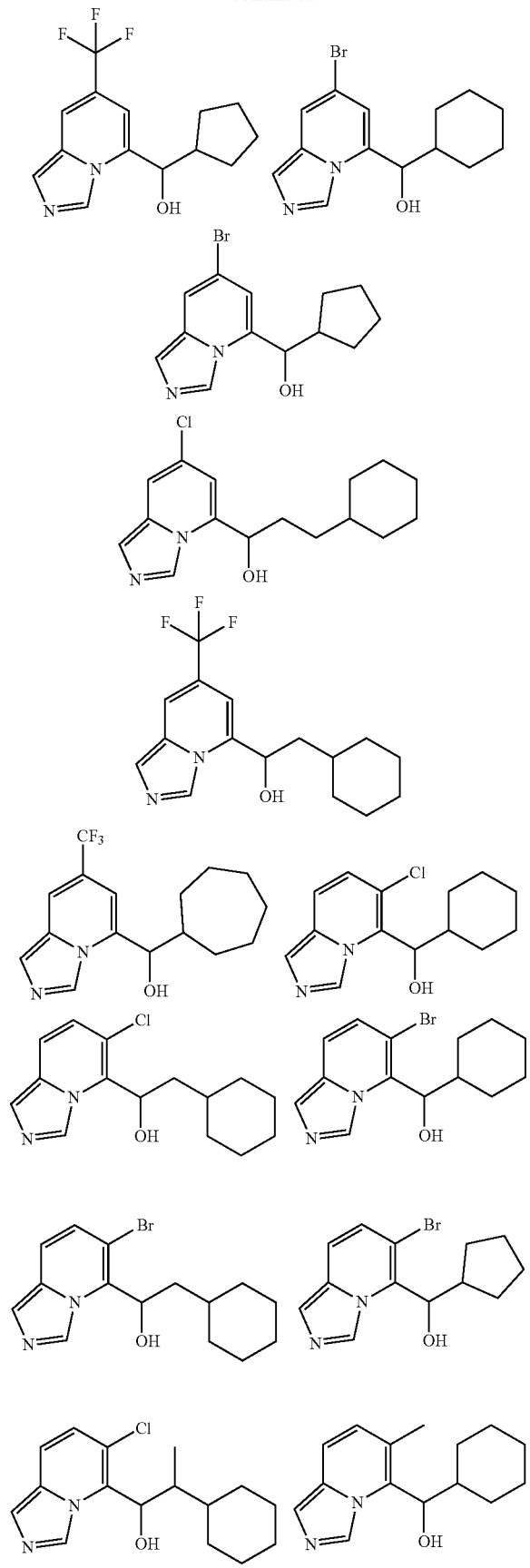
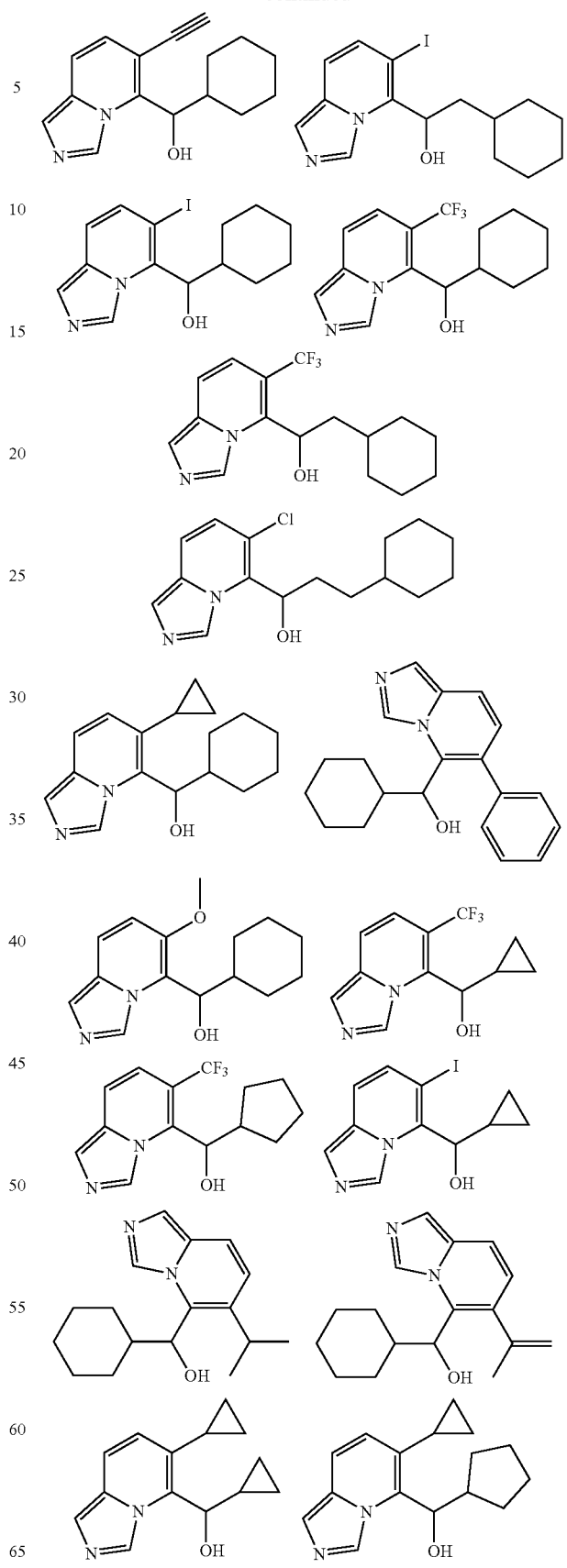

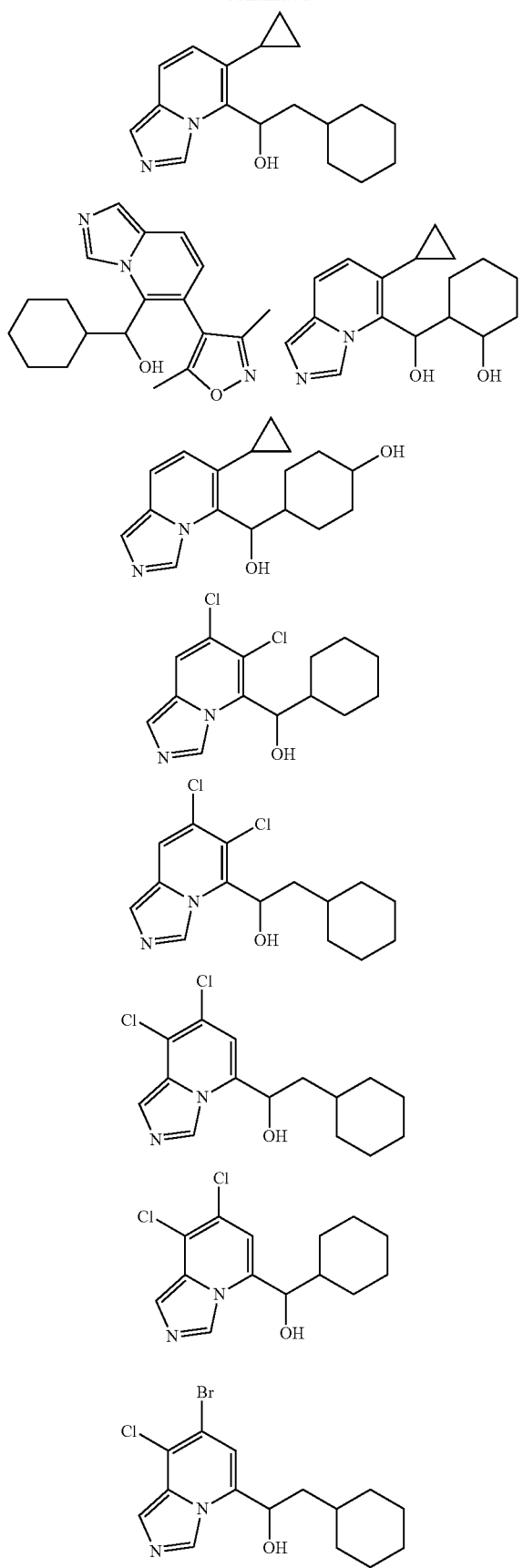
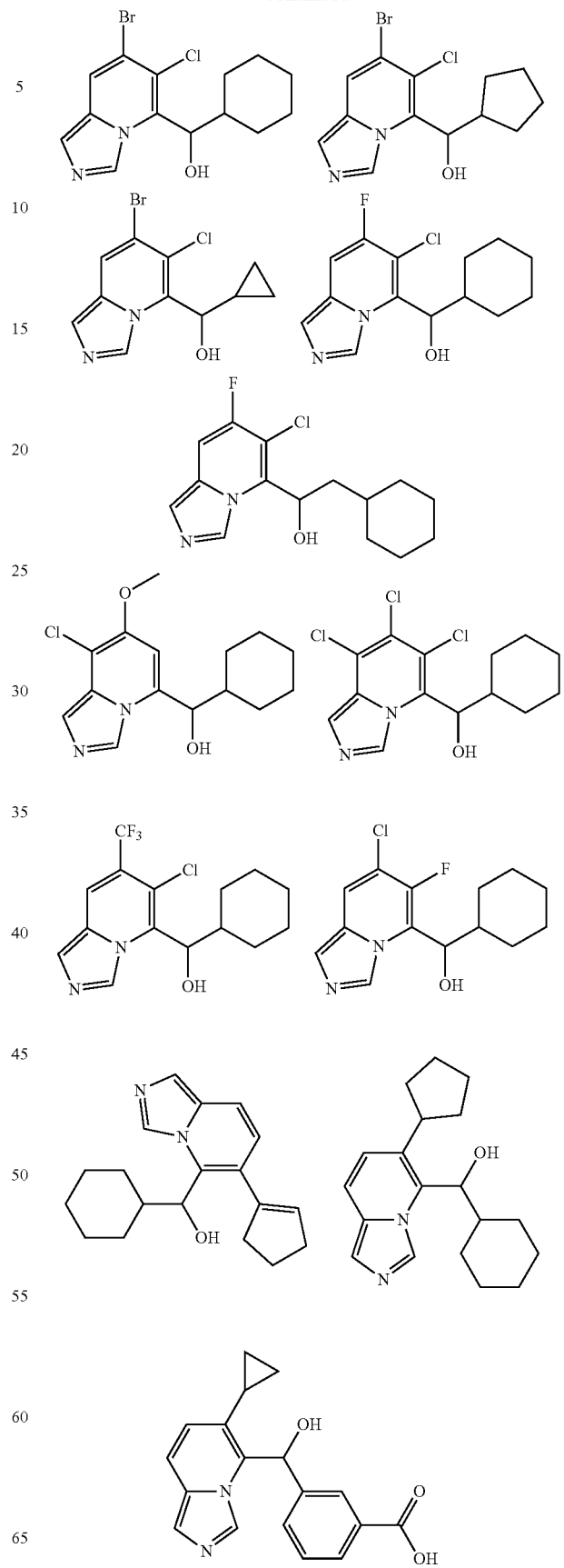

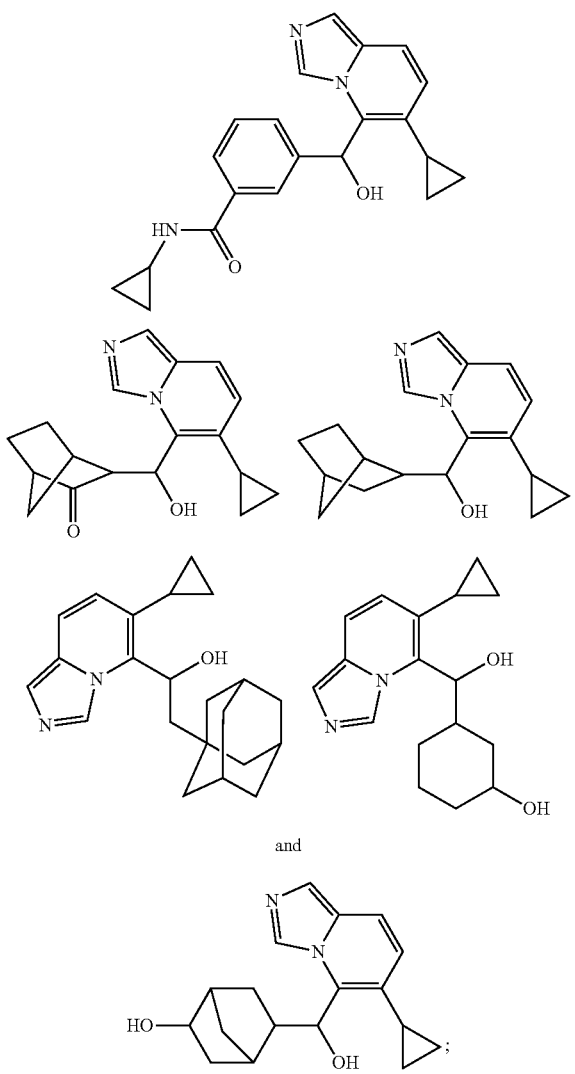
or a stereoisomer thereof, or a pharmaceutically acceptable salt thereof.
25. A compound selected from the group consisting of:
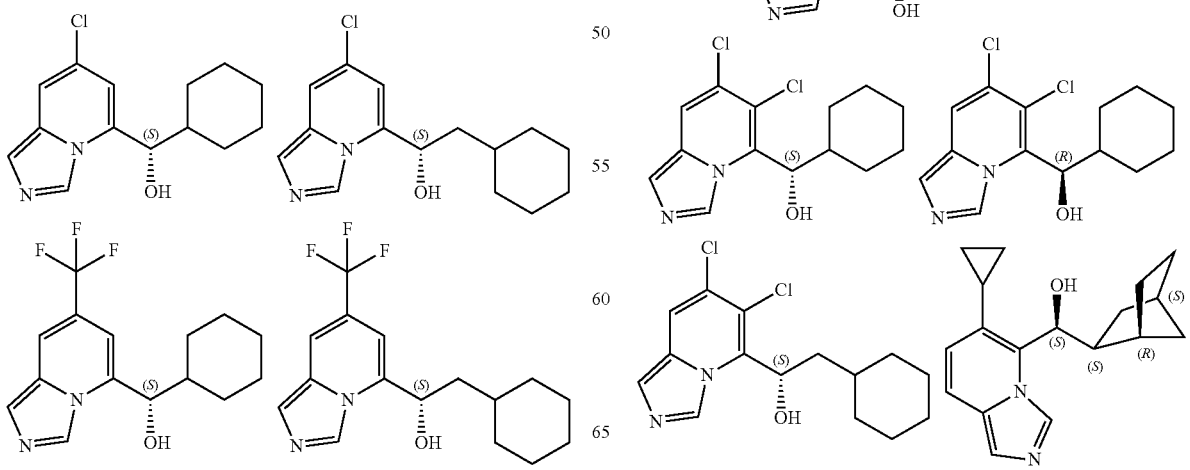

-continued

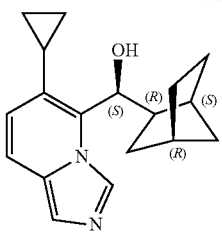

First isomer on normal HPLC
Two isomers

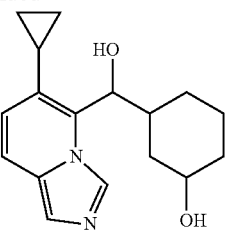

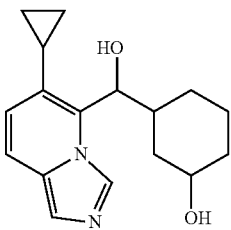

Second isomer on normal HPLC
Four isomers and

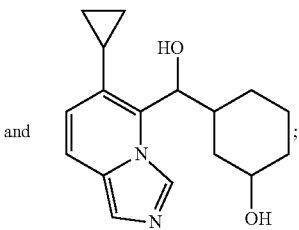

Third isomer on normal HPLC
Two isomers or a pharmaceutically acceptable salt thereof.

26. A pharmaceutical composition comprising at least one pharmaceutically acceptable carrier and as an active ingredient a therapeutically effective amount of a compound of claim 1, or a stereoisomer thereof, or a pharmaceutically acceptable salt thereof.

27. A method for treating cancer responsive to inhibition of indoleamine 2,3-dioxygenase (IDO) and/or tryptophane 2,3-dioxygenase (TDO) comprising administering to a subject in recognized need thereof a compound of claim 1, or a stereoisomer thereof, or a pharmaceutically acceptable salt thereof in an amount effective to inhibit said IDO and/or TDO;

wherein the cancer is melanomas, thyroid cancer, Barret's adenocarcinoma, breast cancer, cervical cancer, colorectal cancer, gastric cancer, lung cancer, renal carcinoma, head and neck cancer, liver cancer, stomach cancer, esophageal cancer, ovarian cancer, pancreatic cancer, prostate cancer, hematologic cancers, cancer of biliary tract, non-small cell lung cancer, endometrium cancer, blood cancer, large intestinal colon carcinoma, histiocytic lymphoma, or lung adenocarcinoma.

28. The compound according to claim 7, wherein $R^6$ is halogen, $C_{1-6}$ alkyl, or $C_{1-6}$ haloalkyl.

29. The compound according to claim 10, wherein $R^6$ is halogen, $C_{1-6}$ alkyl, or $C_{1-6}$ haloalkyl.

30. A pharmaceutical composition comprising at least one pharmaceutically acceptable carrier and as an active ingredient a therapeutically effective amount of a compound of claim 24, or a stereoisomer thereof, or a pharmaceutically acceptable salt thereof.

* * * * *